United States Patent
Klaerner et al.

(10) Patent No.: US 11,266,684 B2
(45) Date of Patent: Mar. 8, 2022

(54) COMPOSITIONS FOR AND METHOD OF TREATING ACID-BASE DISORDERS

(71) Applicant: Tricida, Inc., South San Francisco, CA (US)

(72) Inventors: Gerrit Klaerner, Hillsborough, CA (US); Jerry M. Buysse, Los Altos, CA (US); Jun Shao, Fremont, CA (US); Dawn Parsell Otto, Cedar Park, TX (US)

(73) Assignee: Tricida, Inc., South San Francisco, CA (US)

(*) Notice: Subject to any disclaimer, the term of this patent is extended or adjusted under 35 U.S.C. 154(b) by 0 days.

(21) Appl. No.: 16/756,721

(22) PCT Filed: Nov. 3, 2018

(86) PCT No.: PCT/US2018/059092
§ 371 (c)(1),
(2) Date: Apr. 16, 2020

(87) PCT Pub. No.: WO2019/090176
PCT Pub. Date: May 9, 2019

(65) Prior Publication Data
US 2020/0289551 A1    Sep. 17, 2020

Related U.S. Application Data

(60) Provisional application No. 62/748,371, filed on Oct. 19, 2018, provisional application No. 62/581,325, filed on Nov. 3, 2017.

(51) Int. Cl.
*A61K 31/785* (2006.01)
*C08F 226/02* (2006.01)

(52) U.S. Cl.
CPC .......... *A61K 31/785* (2013.01); *C08F 226/02* (2013.01)

(58) Field of Classification Search
None
See application file for complete search history.

(56) References Cited

U.S. PATENT DOCUMENTS

| 5,496,545 A | 3/1996 | Holmes-Farley et al. |
| 5,643,951 A | 7/1997 | Stacpoole et al. |

(Continued)

FOREIGN PATENT DOCUMENTS

| CN | 1503676 A | 6/2004 |
| CN | 1878822 A | 12/2006 |

(Continued)

OTHER PUBLICATIONS

Gonzalez et al., Sevelamer carbonate increases serum bicarbonate in pediatric dialysis patients, Pediatr Nephrol., 25: 373-375 2010.
(Continued)

*Primary Examiner* — Brian Gulledge
(74) *Attorney, Agent, or Firm* — Bryan Cave Leighton Paisner LLP

(57) ABSTRACT

The present disclosure provides, inter alia, pharmaceutical compositions for and methods of treating an animal, including a human, and methods of preparing such compositions. In certain embodiments, the pharmaceutical compositions contain nonabsorbable pharmaceutical composition and may be used, for example, to treat eubicarbonatemic metabolic acidosis.

7 Claims, 24 Drawing Sheets

(56) References Cited

U.S. PATENT DOCUMENTS

| | | |
|---|---|---|
| 5,648,355 A | 7/1997 | Theoharides |
| 5,667,775 A | 9/1997 | Holmes-Farley et al. |
| 5,679,717 A | 10/1997 | Mandeville, III et al. |
| 5,753,706 A | 5/1998 | Hsu |
| 6,271,264 B1 | 8/2001 | Dhal et al. |
| 6,444,221 B1 | 9/2002 | Shapiro |
| 6,468,964 B1 | 10/2002 | Rowe |
| 6,485,703 B1 | 11/2002 | Cote et al. |
| 6,726,905 B1 | 4/2004 | Mandeville, III et al. |
| 6,733,780 B1 | 5/2004 | Tyler et al. |
| 6,877,408 B2 | 4/2005 | Kubota et al. |
| 7,335,795 B2 | 2/2008 | Chang et al. |
| 7,342,083 B2 | 3/2008 | Chang et al. |
| 7,449,605 B2 | 11/2008 | Chang et al. |
| 7,459,502 B2 | 12/2008 | Connor et al. |
| 7,608,674 B2 | 10/2009 | Connor et al. |
| 7,754,199 B2 | 7/2010 | Chang et al. |
| 7,767,229 B1 | 8/2010 | Milne et al. |
| 7,767,768 B2 | 8/2010 | Chang et al. |
| 7,767,851 B2 | 8/2010 | Kwok et al. |
| 7,815,898 B2 | 10/2010 | Savica |
| 7,846,425 B2 | 12/2010 | Hedge et al. |
| 7,964,182 B2 | 6/2011 | Omray et al. |
| 7,985,418 B2 | 7/2011 | Bhagat et al. |
| 8,003,600 B2 | 8/2011 | Hageman |
| 8,084,397 B2 | 12/2011 | Li et al. |
| 8,163,799 B2 | 4/2012 | Dhal et al. |
| 8,187,634 B2 | 5/2012 | Hedge et al. |
| 8,273,384 B2 | 9/2012 | Wurzberger |
| 8,349,305 B2 | 1/2013 | Chang et al. |
| 8,394,416 B2 | 3/2013 | Bianchi et al. |
| 8,399,025 B2 | 3/2013 | Roy et al. |
| 8,445,014 B2 | 5/2013 | Charmot et al. |
| 8,530,519 B2 | 9/2013 | Ueno |
| 8,586,097 B2 | 11/2013 | Liu et al. |
| 8,842,086 B2 | 9/2014 | Ogg |
| 8,986,669 B2 | 3/2015 | Huval et al. |
| 9,205,107 B2 | 12/2015 | Klaemer et al. |
| 9,925,214 B2 | 3/2018 | Klaemer et al. |
| 9,993,500 B2 | 6/2018 | Klaemer et al. |
| 10,363,268 B2 | 7/2019 | Klaemer et al. |
| 10,369,169 B1 | 8/2019 | Klaemer et al. |
| 10,391,118 B2 | 8/2019 | Klaemer et al. |
| 2002/0110560 A1 | 8/2002 | Demuth et al. |
| 2002/0159968 A1 | 10/2002 | Petersen et al. |
| 2003/0039627 A1 | 2/2003 | Holmes-Farley et al. |
| 2003/0091530 A1 | 5/2003 | Goto et al. |
| 2003/0092782 A1 | 5/2003 | Goto et al. |
| 2004/0059065 A1 | 3/2004 | Goto et al. |
| 2005/0090553 A1 | 4/2005 | Shapiro |
| 2005/0220750 A1 | 10/2005 | Robert et al. |
| 2005/0220751 A1 | 10/2005 | Charmot et al. |
| 2005/0220752 A1 | 10/2005 | Charmot et al. |
| 2005/0220889 A1 | 10/2005 | Charmot et al. |
| 2005/0220890 A1 | 10/2005 | Charmot et al. |
| 2005/0234129 A1 | 10/2005 | Sutton et al. |
| 2006/0024336 A1 | 2/2006 | Charmot et al. |
| 2006/0034847 A1 | 2/2006 | Yun et al. |
| 2007/0098678 A1 | 5/2007 | Bhagat et al. |
| 2007/0135335 A1 | 6/2007 | Collier et al. |
| 2007/0293429 A1 | 12/2007 | Nestor |
| 2008/0125394 A1 | 5/2008 | Savica |
| 2008/0200533 A1 | 8/2008 | Krishnan |
| 2008/0207766 A1 | 8/2008 | Devane |
| 2008/0214440 A1 | 9/2008 | Nestor |
| 2008/0248012 A1 | 10/2008 | Suematsu |
| 2008/0317729 A1 | 12/2008 | Kasch et al. |
| 2009/0053317 A1 | 2/2009 | Vigo et al. |
| 2009/0131338 A1 | 5/2009 | Saou et al. |
| 2009/0155368 A1 | 6/2009 | Holmes-Farley et al. |
| 2009/0155370 A1 | 6/2009 | Cope et al. |
| 2009/0156647 A1 | 6/2009 | Molino et al. |
| 2009/0162314 A1 | 6/2009 | Huval et al. |
| 2009/0325860 A1 | 12/2009 | Costantino et al. |
| 2010/0008988 A1 | 1/2010 | Mehta et al. |
| 2010/0035992 A1 | 2/2010 | Bhushan et al. |
| 2010/0080858 A1 | 4/2010 | Satou et al. |
| 2010/0104527 A1 | 4/2010 | Mansky et al. |
| 2010/0111891 A1 | 5/2010 | Albrecht et al. |
| 2010/0113479 A1 | 5/2010 | Choudhury et al. |
| 2010/0124542 A1 | 5/2010 | Dhal et al. |
| 2010/0129309 A1 | 5/2010 | Dhal et al. |
| 2010/0135950 A1 | 6/2010 | Huval et al. |
| 2010/0166696 A1 | 7/2010 | Dhal et al. |
| 2010/0166861 A1 | 7/2010 | Lynch |
| 2010/0189679 A1 | 7/2010 | Inoue et al. |
| 2010/0234309 A1 | 9/2010 | Cooper et al. |
| 2010/0316589 A1 | 12/2010 | Charmot et al. |
| 2011/0064820 A1 | 3/2011 | Omray et al. |
| 2011/0081413 A1 | 4/2011 | Omray |
| 2011/0142952 A1 | 6/2011 | Harris et al. |
| 2011/0189121 A1 | 8/2011 | Genth et al. |
| 2011/0263493 A1 | 10/2011 | Dugi et al. |
| 2011/0268666 A1 | 11/2011 | Friedman et al. |
| 2012/0219626 A1 | 8/2012 | Osinga |
| 2012/0259098 A1 | 10/2012 | Baker, Jr. et al. |
| 2012/0288471 A1 | 11/2012 | Huval et al. |
| 2013/0022570 A1 | 1/2013 | Kopping et al. |
| 2013/0130995 A1 | 5/2013 | Currie et al. |
| 2013/0131202 A1 | 5/2013 | Albrecht et al. |
| 2013/0137772 A1 | 5/2013 | Bergeron |
| 2013/0156720 A1 | 6/2013 | Currie |
| 2013/0189215 A1 | 7/2013 | Lees et al. |
| 2013/0189216 A1 | 7/2013 | Albrecht et al. |
| 2013/0251667 A1 | 9/2013 | Dhal et al. |
| 2013/0266533 A1 | 10/2013 | Dhal et al. |
| 2013/0345303 A1 | 12/2013 | Poradosu et al. |
| 2014/0105848 A1 | 4/2014 | Klaemer et al. |
| 2015/0056451 A1* | 2/2015 | Klaern ............... C08G 73/024 |
| | | 428/402 |
| 2016/0074430 A1 | 3/2016 | Klaemer et al. |
| 2017/0095441 A1 | 4/2017 | Kwok et al. |
| 2018/0021370 A1 | 1/2018 | Klaemer et al. |
| 2018/0280428 A1 | 10/2018 | Klaemer et al. |
| 2019/0134075 A1 | 5/2019 | Klaemer et al. |
| 2019/0209607 A1 | 7/2019 | Klaemer et al. |
| 2021/0187011 A1 | 6/2021 | Klaemer et al. |

FOREIGN PATENT DOCUMENTS

| | | |
|---|---|---|
| CN | 101687961 | 3/2010 |
| CN | 105377270 | 3/2016 |
| EP | 2168992 | 3/2010 |
| EP | 1931689 | 2/2015 |
| RU | 2160742 | 12/2000 |
| RU | 2008136081 | 3/2010 |
| RU | 2392926 | 6/2010 |
| WO | 9940990 | 8/1999 |
| WO | 2005041900 A2 | 5/2005 |
| WO | 2005041902 | 5/2005 |
| WO | 2005092039 | 10/2005 |
| WO | 2007022435 | 2/2007 |
| WO | 2007038801 | 4/2007 |
| WO | 2007056405 | 5/2007 |
| WO | 2008011047 | 1/2008 |
| WO | 2008027551 | 3/2008 |
| WO | 2008103368 | 8/2008 |
| WO | 2009023544 | 2/2009 |
| WO | 2009097127 | 8/2009 |
| WO | 2009125433 | 10/2009 |
| WO | 2012011063 A1 | 1/2012 |
| WO | 2014197725 | 12/2014 |
| WO | 2015066593 | 2/2015 |
| WO | 2016094685 A1 | 6/2016 |
| WO | 2017193024 | 11/2017 |
| WO | 2017193050 | 11/2017 |
| WO | 2017193064 | 11/2017 |
| WO | 2019090176 | 5/2019 |
| WO | 2019090177 | 5/2019 |
| WO | 2019236124 | 12/2019 |

(56) References Cited

FOREIGN PATENT DOCUMENTS

| WO | 2019236636 | 12/2019 |
|----|-----------|---------|
| WO | 2019236639 | 12/2019 |

OTHER PUBLICATIONS

Greene et al., Role of Aldosterone in the Remnant Kidney Model in the Rat, J. Clin. Invest., 98(4): 1063-1068 1996.
Halperin et al., Ammonium Excretion in Chronic Metabolic Acidosis: Benefits and Risks, American Journal of Kidney Diseases, 14(4): 267-271 1989.
Harris et al., Mechanism of Hyperkalemia-Induced Metabolic Acidosis, J Am Soc Nephrol, 29: 1411-1425 2018.
Jeong et al., Effect of Bicarbonate Supplementation on Renal Function and Nutritional Indices in Predialysis Advanced Chronic Kidney Disease, Electrolyte Blood Press, 12: 80-87 2014.
Ketteler Eler et al., Efficacy and Tolerability of Sevelamer Carbonate in Hyperphosphatemic Patients Who Have Chronic Kidney Disease and Are Not on Dialysis, Clin J Am Soc Nephrol, 3: 1125-1130 2008.
Kittiskulnam et al., Impact of Serum Bicarbonate Levels on Muscle Mass and Kidney Function in Pre-Dialysis Chronic Kidney Disease Patients, Am J Nephrol., 11 pgs 2019.
Kraut et al., Metabolic acidosis: pathophysiology, diagnosis and management, Nature Reviews Nephrology, 6: 274-285 2010.
Mathur et al., Effects of Correction of Metabolic Acidosis on Blood Urea and Bone Metabolism in Patients with Mild to Moderate Chronic Kidney Disease: A Prospective Randomized Single Blind Controlled Trial, Renal Failure, 28: 1-5, 2006.
Melamed et al., Effects of Sodium Bicarbonate in CKD Stages 3 and 4: A Randomized, Placebo-Controlled, Multicenter Clinical Trial, Am J Kidney Dis., 10pgs 2019.
Mircescu et al., Effects of a Supplemented Hypoproteic Diet in Chronic Kidney Disease, Journal of Renal Nutrition, 17(3): 179-188 2007.
Nath et al., Increased Ammoniagenesis as a Determinant of Progressive Renal Injury, Am. Jour. Kid. Dis. 17(6): 654-657 1991.
Nathan et al., The effect of intensive treatment of diabetes on the development and progression of long-term complications in insulin-dependent diabetes mellitus, New Eng. Jour. Med., 329(14): 977-986 1993.
Navaneethan et al., Effects of Treatment of Metabolic Acidosis in CKD A Systematic Review and Meta-Analysis, CJASN, 14: 10 pgs 2019.
Perry et al., Sevelamer Carbonate: A Review in Hyperphosphataemia in Adults with Chronic Kidney Disease, Drugs, 74: 771-792 2014.
Phisitkul et al., Amelioration of metabolic acidosis in patients with low GFR reduced kidney endothelin production and kidney injury, and better preserved GFR, Kidney International, 77: 617-623 2010.
Pisani et al., 6-tips diet: a simplified dietary approach in patients with chronic renal disease. A clinical randomized trial, Clin Exp Nephrol, 10 pgs 2015.
Mount, D. B., Potassium balance in acid-base disorders, retrieved from www.uptodate.com/contents/potassium-balance-in-acid-base-disorders?search=hyperkalemia%20and%20metabolic%20acidosis&source=search_result&selectedTitle=1~150&usage_type=default&display_rank, 5 pgs 2018.
Raphael et al., Higher serum bicarbonate levels within the normal range are associated with better survival and renal butcomes in African Americans Kidney International, 79: 356-362 2011.
Raphael et al., Bicarbonate Concentration, Acid-Base Status, and Mortality in the Health, Aging, and Body Composition Study, Clin J Am Soc Nephrol, 11:9 pgs 2016.
Raphael et al., Urine Ammonium Predicts Clinical Outcomes in Hypertensive Kidney Disease, J Am Soc Nephrol 28: 2483-2490 2017.
Raphael et al., A Randomized Trial Comparing the Safety, Adherence, and Pharmacodynamics Profiles of Two Doses of Sodium Bicarbonate in CKD: the BASE Pilot Trial, JASN 31: 14 pgs 2020.
Raphael K. L., Metabolic Acidosis in CKD: Core Curriculum 2019, AJKD, 13 pgs 2019.
Remuzzi G.., Role of Endothelin in the Development of Glomerulosclerosis, Kidney and Blodd Ress Res., 19: 182-183 1996.
Ruiz-Ortega et al., Involvement of angiotensin II and endothelin in matrix protein production and renal sclerosis, Jour Hypertension, 12: S51-S58 1994.
Seccia et al., Role of angiotensin II, endothelin-1 and L-type calcium channel in the development of glomerular, tubulointerstitial and perivascular fibrosis, Journal of Hypertension, 26:2022-2029 2008.
Shah et al., Serum Bicarbonate Levels and the Progression of Kidney Disease: A Cohort Study, Am J Kidney Dis 54:270-277 2009.
Stein et al., Role of an improvement in acid-base status and nutrition in CARD patients, Kidney International, 52: 1089-1095 1997.
Szeto et al., Oral Sodium Bicarbonate for the Treatment of Metabolic Acidosis in Peritoneal Dialysis Patients: A Randomized Placebo-Control Trial, J Am Soc Nephrol 14: 2119-2126 2003.
Tangri et al., A Predictive Model for Progression of Chronic Kidney Disease to Kidney Failure, JAMA, 305(15): 1553-1559 2011.
Wesson D. E., Endogenous Endothelins Mediate Increased Acidification in Remnant Kidneys, J Am Soc Nephrol 12: 1826-1835 2001.
Wesson et al., Angiotensin II receptors mediate increased distal nephron acidification caused by acid retention, Kidney International, 82: 1184-1194 2012.
Wesson et al., Angiotensin Il-mediated GFR decline in subtotal nephrectomy is due to acid retention associated with reduced GFR, Nephrol Dial Transplant, 30: 762-770 2015.
European Patent Office, Extended Search Report for EP App. 17793497.3, 11 pages dated Mar. 17, 2020.
Anonymous, Tricida Announces Positive Topline Phase ½ Clinical Trial Results for TRC101 in 135 Subjects with Chronic Kidney Disease and Metabolic Acidosis, Business Wire, 2 pages Jan. 9, 2017.
Steed et al., Supramolectular Chemistry, 2nd Edition, John Wiley & Sons, Ltd. West Sussex, United Kingdom, 216-279.
Adrogue et al., Respiratory Acidosis, Respiratory Alkalosis, and Mixed Disorders in Comprehensive Clinical Nephrology, 4th Edition, 2010, Elsevier Saunders, St. Louis, Missouri, Ch. 14, 176-189.
Ballmer et al., Chronic metabolic acidosis decreases albumin synthesis and induces negative nitrogen balance in humans. The Journal of Clinical Investigation, 1995, 95: 39-45.
Brezina et al., Acid loading during treatment with sevelamer hydrocholoride: Mechanisms and clinical implications, Kidney International, 2004, 66(90): S39-S45.
Chmelarova, Short chain fatty acids and colonic health, Bratisl Lek Listy, 2007, 108(8): 354-358.
D'Agostino et al., Alterations in the ionic composition of icotonic saline solutins instilled into the colon, The Journal of Clinical Investigation, 1953, 32(5): 444-448.
Davis et al., Evaluation of Chlorida/Biocarbonate exchange in the human colon in vivo, The Journal of Clinical Investigation, 1983, 71:201-207.
De Brito-Ashurst et al., Bicarbonate Supplementation Slows Progression of CKD and Improves Nutritional Status, J Am Soc Nephrol, 2009, 20(9): 2075-2084.
Dobre et al., Association of Serum Bicarbonate With Risk of Renal and Cardiovascular Outcomes in CKD: A Report From the Chronic Renal Insufficiency Cohort (CRIC) Study, American Journal of Kidney Diseases, 62(4): 670-678 2013.
Dubose, Jr., et al., Renal Tubular Acidosis in Acid Base and Electrolyte Disorders: A Companion to Brenner & Rector's The Kidney, Elsevier Health Sciences, 2002, Ch 11, 189-206.
Farwell et al., Serum anion gap, bicarbonate and biomarkers of inflammation in healthy individuals in a national survey, Canadian Medical Association Journal, 2010, 182(2): 137-141.
Fortran et al., Ionic constituents and osmolality of gastric and small-intestinal fluids after eating, New Series, 1966, 11(7):503-521.

(56) References Cited

OTHER PUBLICATIONS

Goldberg, Approach to Acid-Base Disorders, Ch 11, 2005, 104-109.
Heart Failure Society of America, HFSA 2010 Guideline Executive Summary Executive Summary: HFSA 2010 Comprehensive Heart Failure Practice Guideline, Journal of Cardiac Failure, 2010, 16(6), 259 pages.
Hospria Sodium Bicarb IV ANDA labels and packaging, 5 pages.
Kielland, J., Individual Activity Coefficients of Ions in Aqueous Solutions, 1937, 59, 1675-1678, retrieved from www.ufscar.br.
Lemann, Jr., et al., Bone buffering of acid and base in humans, Am J Physiol Renal Physiol, 2003, 285:F811-F832.
Lemann, Jr., et al., The Effects of Chronic Acid Loads in Normal Man: Further Evidence for the Participation of Bone Mineral in the Defense against Chronic Metabolic Acidosis, Journal of Clinical Investigation, 1966, 45(10):1608-1614.
Mitch, W. E., Influence of Metabolic Acidosis on Nutrition, American Journal of Kidney Diseases, 29(5):xlvi-xlviii.
National Kidney Foundation, K/DOQI Clinical Practice Guidelines for Bone Metabolism and Disease in Chronic Kidney Disease, 2003,42(4), Supp. 3.
National Kidney Foundation, K/Doqi Nutrition Guidelines, American Journal of Kidney Diseases, 2000, 35(6), Supp 2.
Phisitkul et al., Dietary protein causes a decline in the glomerular filtration rate of the remnant kidney mediated by metabolic acidosis and endothelin receptors, Kidney International, 73: 192-199 2008.
Raphael et al., Serum bicarbonate and mortality in adults in Nhanes III, Nephrol Dial Transplant, 28: 1207-1213 2013.
Shannon, R.D., Revised Effective Ionic Radii and Systematic Studies of Interatomie Distances in Halides and Chaleogenides, Acta Cryst., 1976, A32: 751-767.
Sullivan et al., Halogenated Solvents, Trichloroethylene, and Methylene Chloride in Clinical Environmental Health and Toxic Exposures, 2nd Ed., Ch. 58, 1999, Lippincott Williams & Wilkins, Philadelphia, PA.
Szerlip, Metabolic Acidosis, Ch. 8, p. 74-89.
Widmer et al., Serum Electrolyte and Acid Base Composition, Arch Intern Med, 1979, 139, 1099-1102.
Wrong et al., In Vivo dialysis of faeces as a method of stool analysis, Clinical Science, 1967, 33(1): 89-100.
Yaqoob, M. M., Acidosis and progression of chronic kidney disease, Current Opinion in Nephrology and Hypertension, 19:489-492 2010.
Remington, The Science and Practice of Pharmacy, 21st Ed., Edited by D. B. Troy, p. 317-318 and 745-775, Lippincott Williams & Wilkins, Baltimore, Maryland.
Patent Cooperation Treaty, International Search Report and Written Opinion for PCT/US2014/041152, dated Nov. 27, 2014, 10 pages.
Nakaki et al., Effect of fatty acids on the phosphate binding of TRK-390, a novel, highly selective phosphate-binding polymer, European Journal of Pharmacology, 2013, 714(1-3): 312-317.
Akizawa, et al., Long-Term Treatment of Hyperphosphatemia With Bixalomer in Japanese Hemodialysis Patients, Therapeutic Apheresis and Dialysis, 2013, 17(6): 612-619.
Ito et al., Treatment of Hyperphosphatemia With Bixalomer in Japanese Patients on Long-Term Hemodialysis With Gastrointestinal Symptoms, Therapeutic Apheresis and Dialysis, 2014; 18(Supplement 2):19-23.
Shima et al., Clinical Experiences of Bixalomer Usage at Our Hospital, Therapeutic Apheresis and Dialysis 2014; 18 (Supplement 2):13-18.
Kioussis et al., Reactive nitrogen and phosphorus removal from aquaculture wastewater effluents using polymer hydrogels, Aquacultural Engineering, 2000, 23: 315-332.
Kioussis et al., Phosphate binding polymeric hydrogels for aquaculture wastewater remediation, Aquacultural Engineering, 1999,19: 163-178.
Kioussis et al., Selective anion sorption and recovery from wastewater by polyelectrolyte hydrogels, Polymer Preprints, 2000, 41(2): 1679-1680.
Patent Cooperation Treaty, International Search Report for PCT/US2015/065041, dated Mar. 22, 2016, 5 pgs.
Patent Cooperation Treaty, International Search Report for PCT/US2017/031395, 6 pages dated Aug. 8, 2017.
Patent Cooperation Treaty, International Search Report for PCT/US2017/031344, 5 pages dated Aug. 8, 2017.
Noue et al., Highly selective and low-swelling phosphate-binding polymer for hyperphosphatema therapy, Chem. Letters, 41, 932-933 2012.
Franch et al., Catabolism in Uremia: The Impact of Metabolic Acidosis, J. Am. Soc. Nephrol., 9: S78-S81 1998.
Stevens et al., Electrolyte composition of endoscopically collected duodenal drainage fluid after synthetic porcine secretin stimulation in healthy subjects, Gastroentestinal Endoscopy, 60(3); 351-355 2004.
Patent Cooperation Treaty, International Search Report for PCT/US2017/031378, 5 pages dated Sep. 20, 2017.
European Patent Office, Extended European Search Report issued for U.S. Appl. No. 17/177,221 3, 8 pages dated Jan. 23, 2018.
Akizawa et al., Randomized Controlled Trial of Bixalomer Versus Sevelamer Hydrochloride in Hemodialysis Patients With Hyperphosphatemia, Therapeutic Aphreresis and Dialysis, 18(2):122-131 2014.
Akizawa et al., Bixalomer in Hyperphosphatemic Patients With Chronic Kidney Disease Not on Dialysis: Phase 3 Randomized Trial, Therapeutic Apheresis and Dialysis, 10 pages 2016.
Akizawa et al., Long-Term Safety and Efficacy of Bixalomer in Hyperphosphatemic Patients With Chronic Kidney Disease Noton Dialysis, Therapeutic Apheresis and Dialysis, 7pgs 2017.
Beaubien-Souligny et al., The effect of lanthanum carbonate on metabolic acidosis in patients with chronic kidney disease stage IV, V and V-D, Int Urol Nephrol, 7pg. 2015.
European Patent Office, Extended Search Report for EP App. 20154562.1, 6 pages dated Sep. 8, 2020.
Kovacic et al., Metabolic Acidosis of Chronically Hemodialyzed Patients, Am J Nephrol 23:158-164 Mar. 21, 2003.
Witham et al., Clinical and cost-effectiveness of oral sodium bicarbonate therapy for older patients with chronic kidney disease and low-grade acidosis (BiCARB): a pragmatic randomised, double-blind, placebo-controlled trial, BMC Medicine, 18:91, 16 pages 2020.
European Pattent Office, Extended European Search Report for App. No. 20204589.4, 12 pages dated Apr. 30, 2021.
Wesson, D. E., The Continuum of Acid Stress, Clinical Journal of the American Society of Nephrology, 16(8): 1292-1299 2021.
Madias, N. E., Metabolic Acidosis and CKD Progression, Clinical Journal of the American Society of Nephrology,16(2): 310-312 2021.
Bezzaoucha et al., The role of sevelamer carbonate in increasing serum bicarbonate in hyperphosphatemic pre-dialysis patients who have metabolic acidosis, Intern. Journal of Clinical Pharmacology and Therapeutics, 51(Dec. 2013) 989-990 2013.
Bushinsky et al., Randomized, Controlled Trial of TRC101 to Increase Serum Bicarbonate in Patients with CKD, Clin J Am Soc Nephrol, 10pg. 2018.
Chen et al., Epidemiology of Acid-Base Derangements in CKD, Adv Chronic Kidney Dis., 24(5):280-288 2017.
Garneata et al., Ketoanalogue-Supplemented Vegetarian Very Low-Protein Diet and CKD Progression, J Am Soc Nephrol 27:2164-2176 2016.
Pai et al., Comparison of Sevelamer Hydrochloride and Sevelamer Carbonate: Risk of Metabolic Acidosis and Clinical Implications, Pharmacotherapy, 29(5):554-561 2009.
Mahajan et al., Daily oral sodium bicarbonate preserves glomerular filtration rate by slowing its decline in early hypertensive nephropathy, Kidney International, 78, 303-309 2010.
Raphael, K.L., Metabolic Acidosis and Subclinical Metabolic Acidosis in CKD, J Am Soc Nephrol 29, 7pg 2017.
Rombola et al., Lanthanum carbonate: a postmarketing observational study of efficacy and safety, Jour Nephrol, 25(4): 490-496 2012.

(56) References Cited

OTHER PUBLICATIONS

Susantitaphong et al., Short- and Long-Term Effects of Alkali Therapy in Chronic Kidney Disease: A Systematic Review. Am J Nephrol, 35:540-547 2012.
Thet et al., Differential effects of phosphate binders on pre-dialysis serum bicarbonate in end-stage kidney disease patients on maintenance haemodialysis, BMC Nephrology, 14:205-215 2013.
Goraya et al., A Comparison of Treating Metabolic Acidosis in CKD Stage 4 Hypertensive Kidney Disease with Fruits and Vegetables or Sodium Bicarbonate, Clin J Am Soc Nephrol 8: 371-381 2013.
Goraya et al., Treatment of metabolic acidosis in patients with stage 3 chronic kidney disease with fruits and vegetables or oral bicarbonate reduces urine angiotensinogen and preserves glomerular filtration rate, Kidney International, 86:1031-1038 2014.
Goraya et al., Management of the Metabolic Acidosis of Chronic Kidney Disease, Adv Chronic Kidney Dis., 24(5):298-304 2017.
Hatakeyama et al., Switching hemodialysis patients from sevelamer hydrochloride to bixalomer: a single-center, non-randomized analysis of efficacy and effects on gastrointestinal symptoms and metabolic acidosis, BMC Nephrology, 14:222-229 2013.
Husted et al., NaHC03 and NaCl tolerance in chronic renal failure II, Clinical Nephrology, 7(1):21-25 1977.
Lindley et al., Correction of metabolic acidosis after conversion from sevelamer hydrochloride to lanthanum carbonate, NDT Plus, 3:196 2008.
Navaneethan et al., Serum Bicarbonate and Mortality in Stage 3 and Stage 4 Chronic Kidney Disease, Clinical Journal of the American Society of Nephrology, 6(10): 2395-2402 2011.
Russian Federal Institute of Industrial Property, Search Report for 2015155596, 2 pages dated May 8, 2018.
Patent Cooperation Treaty, International Search Report for PCT/US2018/059092, 3pgs. dated Jan. 8, 2019.
Kraut, Disturbances in Acid-Base, Potassium, and Sodium Balance in Patients With CKD: New Insights and Novel Therapies, Adv Chronic Kidney Dis., 2017, 24(5): 272-273 2017.
Patent Cooperation Treaty, International Search Report for PCT/US2018/059093, 3pgs. dated Jan. 8, 2019.
Wesson et al., Veverimer versus placebo in patients with metabolic acidosis associated with chronic kidney disease a multicentre, randomised, double-blind, controlled, phase 3 trial, The Lancet, 11 pgs. 2019.
European Patent Office, Extended Search Report for EP App. 19169259.9, 12 pages dated Oct. 10, 2019.
Abramowitz et al., Effects of Oral Sodium Bicarbonate in Patients with CKD, Clin J Am Soc Nephrol, 8: 714-720 2013.
Abramowitz, M.K., Acid-Base Balance and Physical Function, Clin J Am Soc Nephrol, 9: 2030-2032 2014.
Abramowitz, M.K., Metabolic Acidosis and Cardiovascular Disease Risk in CKD, Clin J Am Soc Nephrol, 13, 2 pgs. 2018.
Aronson et al., Effects of pH on Potassium: New Explanations for Old Observations, J Am Soc Nephrol, 22: 1981-1989 2011.
Ballasi et al., Correction of metabolic acidosis improves insulin resistance in chronic kidney disease, BMC Nephrology, 17:158-167 2016.
Wolf et al., The Renin-Angiotensin System and Progression of Renal Disease: From Hemodynamics to Cell Biology, Nephron Physiol, 93: 3-13 2003.
Witham, BiCARB results, 9 pgs. 2019.
Williams et al., Failure of Dietary Protein and Phosphate Restriction to Retard the Rate of Progression of Chronic Renal Failure: A Prospective, Randomized, Controlled Trial, 81(294): 837-855 1991.
Wesson et al., Long-term safety and efficacy of veverimer in patients with metabolic acidosis in chronic kidney disease: a multicentre, randomised, blinded, placebo-controlled, 40-week extension, Lancet, 11 pgs. 2019.
Biggar et al., Sevelamer carbonate for the treatment of hyperphosphatemia in patients with kidney failure (CKD III-V), Expert Opin. Pharmacother, 11(16): 2739-2750 2010.
Bushinsky, D. A., Tolerance to Sodium in Patients With CKD-lnduced Metabolic Acidosis: Does the Accompanying Anion Matter?, 73(6): 858-865 2019.
Chen et al., Is an Increased Serum Bicarbonate Concentration during Hemodialysis Associated with an Increased Risk of Death?. Semin. Dial., 27(3): 259-262 2014.
Chen et al., Advances in management of chronic metabolic acidosis in chronic kidney disease, Pharm. Thera., 28: 8 pgs 2019.
Dawson-Hughes et al., Impact of supplementation with bicarbonate on lower-extremity muscle performance in older men and women, Osteoporos Int, 21(7): 1171-1179 2010.
De Brito-Ashurst et al., Acidosis: progression of chronic kidney disease and quality of life, Pediatr Nephrol, 30: 873-879 2015.
De Iorio et al., Very Low-Protein Diet (VLPD) Reduces Metabolic Acidosis in Subjects with Chronic Kidney Disease: The "Nutritional Light Signal" of the Renal Acid Load, Nutrients, 9: 69-82 2017.
De Iorio et al., Treatment of metabolic acidosis with sodium bicarbonate delays progression of chronic kidney disease: the UBI Study, Journal of Nephrology, 32: 989-1001 2019.
Disthabanchong et al., Oral Sodium Bicarbonate Improves Thyroid Function in Predialysis Chronic Kidney Disease, Am J Nephrol., 32: 549-556 2010.
Dobre et al., Serum bicarbonate and cardiovascular events in hypertensive adults: results from the Systolic Blood Pressure Intervention Trial, Nephrol Dial Transplant, 1-8 2019.
Dobre et al., Current Status of Bicarbonate in CKD, J Am Soc Nephrol., 26(3): 515-523 2015.
Dobre et al., Persistent High Serum Bicarbonate and the Risk of Heart Failure in Patients With Chronic Kidney Disease (CKD): A Report From the Chronic Renal Insufficiency Cohort (CRIC) Study, J Am Heart Assoc., 17 pgs. 2015.
Dobre et al., Serum Bicarbonate and Structural and Functional Cardiac Abnormalities in Chronic Kidney Disease—A Report from the Chronic Renal Insufficiency Cohort Study, Am J Nephrol., 43: 411-420 2016.
Dobre et al., Serum Bicarbonate Concentration and Cognitive Function in Hypertensive Adults, Clin J Am Soc Nephrol., 13(4): 596-603 2018.
Domrongkitchaipron et al., Bone histology and bone mineral density after correction of acidosis in distal renal tubular acidosis, Kidney International, 62: 2160-2166 2002.
Dubey et al., Correction of metabolic acidosis improves muscle mass and renal function in chronic kidney disease stages 3 and 4: a randomized controlled trial, Nephrol Dial Transplant, 9 pgs 2018.
Fan et al., A randomized, crossover design study of sevelamer carbonate powder and sevelamer hydrochloride tablets in chronic kidney disease patients on haemodialysis, European Renal Association European, 5 pgs. 2011.
Gennari et al., Effect of Dietary Protein Intake on Serum Total CO2 Concentration in Chronic Kidney Disease Modification of Diet in Renal Disease Study Findings, Clin J Am Soc Nephrol., 1: 52-57 2006.
Kovesdy et al., Association of serum bicarbonate levels with mortality in patients with non-dialysis-dependent CKD, Nephrology Dialysis Transplantation, 4(24): 1232-1237 2008.
Inker et al., GFR Decline as an Alternative End Point to Kidney Failure in Clinical Trials: A Meta-analysis of Treatment Effects From 37 Randomized Trials, American Journal of Kidney Diseases, 64(4): 848-859 2014.

\* cited by examiner

Subpopulations used in Cox Regression Analyses

Analysis 1:

Analysis 2:

Analysis 3:

The following items are about activities you might do during a typical day. <u>Does your health now limit</u> you in these activities? If so, how much? [Mark an ☒ in a box on each line.]

|   | Yes, limited a lot ▼ | Yes, limited a little ▼ | No, not limited at all ▼ |
|---|---|---|---|
| a <u>Vigorous activities</u>, such as running, lifting heavy objects, participating in strenuous sports | ☐ 1 | ☐ 2 | ☐ 3 |
| b <u>Moderate activities</u>, such as moving a table, pushing a vacuum cleaner, bowling, or playing golf | ☐ 1 | ☐ 2 | ☐ 3 |
| c Lifiting or carrying groceries | ☐ 1 | ☐ 2 | ☐ 3 |
| d Climbing <u>several</u> flights of stairs | ☐ 1 | ☐ 2 | ☐ 3 |
| e Climbing <u>one</u> flight of stairs | ☐ 1 | ☐ 2 | ☐ 3 |
| f Bending, kneeling, or stooping | ☐ 1 | ☐ 2 | ☐ 3 |
| g Walking <u>more than a mile</u> | ☐ 1 | ☐ 2 | ☐ 3 |
| h Walking <u>several blocks</u> | ☐ 1 | ☐ 2 | ☐ 3 |
| i Walking <u>one block</u> | ☐ 1 | ☐ 2 | ☐ 3 |
| j Bathing or dressing yourself | ☐ 1 | ☐ 2 | ☐ 3 |

FIG. 21

Chair Stand Protocols

Required Equipment
- A chair without cushions that has a straight back without arm rests. The following chair dimensions (or close to these) are recommended: seat 44.5 cm (17 1/2 inches) high and 38 cm (15 inches) deep.
- A Stopwatch.

Instructions
Instructions to the subject are shown in _bold italic_ and should be given exactly as they are written in this script. The subject must be able to stand unassisted without the use of a cane or walker.

> _Now let's begin the repeated chair stand evaluation. I will first describe and show the movement to you. Then I'd like you to try to do it. If you cannot do sit-stand movement, or if you feel it would be unsafe to try to do it, please tell me. Let me emphasize that I do not want you to try to do this exercise if you feel it might be unsafe. Do you have any questions before we begin?_

Single Chair Stand (Practice Test)
1. _Do you think it would be safe for you to try to stand up from a chair without using your arms?_
2. _This test measures the strength in your legs_
3. (Demonstrate and explain the procedure.) _First, fold your arms across your chest and sit so that your feet are on the floor; then stand up keeping your arms folded across your chest_
4. _Please stand up keeping your arms folded across your chest._ (Record result).
5. If subject cannot rise without using arms, say: _"Okay, try to stand up using your arms."_ This is the end of their test. Record result and go to the scoring page.

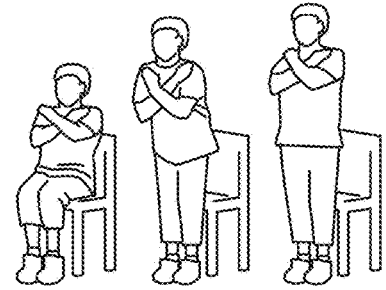

Repeated Chair Stand Test
1. _Do you think it would be safe for you to try to stand up from a chair five times without using your arms?_
2. (Demonstrate and explain the procedure.) _Please stand up straight as QUICKLY as you can five times, without stopping in between. After standing up each time, sit down and then stand up again. Keep your arms folded across your chest. I will be timing you with a stopwatch._
3. When the subject is properly seated, say _"Ready? Stand"_, and begin timing using a stopwatch.
4. Count out loud as the subject arises each time, up to five times.
5. Stop if subject becomes tired or short of breath during repeated chair stands.
6. Stop the stopwatch when subject has straightened up completely for the fifth time.
7. Also stop:
   - If subject uses his/her arms
   - After 1 minute, if subject has not completed five rises
   - At your discretion, if concerned for subject's safety
8. If the subject stops and appears to be fatigued before completing the five stands, confirm this by asking: _"Can you continue?"_
9. If subject says "Yes", continue timing. If subject says "No", stop and reset the stopwatch.

FIG. 22A

Single Chair Stand — SCORING

| | YES | NO |
|---|---|---|
| A. Safe to stand without help | ☐ | ☐ |
| | | |
| B. Results: | | |
|    Subject stood without using arms | ☐ | → Go to Repeated Chair Stand Test |
|    Subject used arms to stand | ☐ | → End test: score as 0 points |
|    Test not completed | ☐ | → End test: score as 0 points |
| | | |
| C. If subject did not attempt test or failed, circle why: | | |
|    Tried but unable | 1 | |
|    Subject could not stand unassisted | 2 | |
|    Not attempted, you felt unsafe | 3 | |
|    Not attempted, subject felt unsafe | 4 | |
|    Subject unable to understand instructions | 5 | |
|    Other (Specify) | 6 | |
|    Subject refused | 7 | |

Repeated Chair Stand Test

| | YES | NO |
|---|---|---|
| A. Safe to stand five times | ☐ | ☐ |
| | | |
| B. If five stands done successfully, record time in seconds. | | |
| | | |
|    Time to complete five stands __ . __ seconds | | |
| | | |
| C. If subject did not attempt test or failed, circle why: | | |
|    Tried but unable | 1 | |
|    Subject could not stand unassisted | 2 | |
|    Not attempted, you (person administering test) felt unsafe | 3 | |
|    Not attempted, subject felt unsafe | 4 | |
|    Subject unable to understand instructions | 5 | |
|    Other (Specify) | 6 | |
|    Subject refused | 7 | |

Scoring the Repeated Chair Stand Test

| | |
|---|---|
| Subject unable to complete 5 chair stands or completes stands in >60 sec: | ☐ 0 points |
| If chair stand time is 16.70 sec or more: | ☐ 1 points |
| If chair stand time is 13.70 to 16.69 sec: | ☐ 2 points |
| If chair stand time is 11.20 to 13.69 sec: | ☐ 3 points |
| If chair stand time is 11.19 sec or less: | ☐ 4 points |

FIG. 22B

|  | Placebo (N=93) | TRC101 (N=123) |
|---|---|---|
| Baseline | | |
| n | 93 | 123 |
| Mean (SD) | 54.14 (27.073) | 53.33 (23.597) |
| Median | 55.00 | 50.00 |
| Min, Max | 0.0, 100.0 | 10.0, 100.0 |
| Week 12/ET | | |
| n | 90 | 121 |
| Mean (SD) | 55.56 (25.367) | 59.71 (22.139) |
| Median | 55.00 | 60.00 |
| Min, Max | 0.0, 100.0 | 0.0, 100.0 |
| Week 12/ET Change from Baseline[a] | | |
| n | 90 | 121 |
| Mean (SD) | 0.89 (15.169) | 6.45 (16.259) |
| Median | 0.00 | 5.00 |
| Min, Max | -40.0, 35.0 | -50.0, 60.0 |
| Within Group CFB | | |
| LS Mean (SE) | 1.10 (1.549) | 6.29 (1.334) |
| 95% CI of LS Mean | -1.95, 4.15 | 3.66, 8.92 |
| p-value | 0.4787 | <.0001 |
| Between Group CFB Difference (TRC101 Treated - Placebo) | | |
| LS Mean (SE) | NA | 5.19 (2.053) |
| 95% CI of LS Mean | NA | 1.14, 9.24 |
| p-value | NA | 0.0122 |

CFB = change from baseline; CI = confidence interval; eGFR = estimated glomerular filtration rate; ET = Early termination; LS = least squares; Max = maximum; Min = minimum; NA = not applicable; SD = standard deviation; SE = standard error of LS mean.

[a]LS mean, SE, 95% CI of LSmean, and p-values are based on the analysis of covariance model with the CFB in total score as the dependent variable; treatment (Placebo or TRC101) as a fixed effect; as well as baseline total score, baseline eGFR, and baseline serum bicarbonate as continuous covariates.

FIG. 23

|  | Placebo (N=82) | TRC101 (N=115) |
|---|---|---|
| Baseline | | |
| n | 79 | 111 |
| Mean (SD) | 15.47 (8.850) | 17.39 (11.616) |
| Median | 13.08 | 14.32 |
| Min, Max | 6.7, 50.0 | 7.5, 100.0 |
| Week 12/ET | | |
| n | 79 | 113 |
| Mean (SD) | 16.03 (9.175) | 16.54 (8.928) |
| Median | 13.80 | 13.68 |
| Min, Max | 7.7, 53.8 | 7.8, 56.1 |
| Week 12/ET Change from Baseline[a] | | |
| n | 76 | 109 |
| Mean (SD) | 0.64 (2.836) | -1.37 (8.559) |
| Median | 0.03 | -0.40 |
| Min, Max | -6.9, 17.9 | -85.0, 10.9 |
| Within Group CFB | | |
| LS Mean (SE) | 0.35 (0.619) | -1.17 (0.515) |
| 95% CI of LS Mean | -0.87, 1.57 | -2.18, -0.15 |
| p-value | 0.5727 | 0.0249 |
| Between Group CFB Difference (TRC101 Treated - Placebo) | | |
| LS Mean (SE) | NA | -1.52 (0.810) |
| 95% CI of LS Mean | NA | -3.11, 0.08 |
| p-value | NA | 0.0630 |

CFB = change from baseline; CI = confidence interval; eGFR = estimated glomerular filtration rate; ET = Early termination; LS = least squares; Max = maximum; Min = minimum; NA = not applicable; SD = standard deviation; SE = standard error of LS mean.

[a]LS mean, SE, 95% CI of LSmean, and p-values are based on the analysis of covariance model with the CFB in time of completing 5 chair stands as the dependent variable; treatment (Placebo or TRC101) as fixed effect; as well as baseline value (time to complete 5 stands), baseline eGFR, and baseline serum bicarbonate as continuous covariates.

FIG. 24

COMPOSITIONS FOR AND METHOD OF TREATING ACID-BASE DISORDERS

CROSS REFERENCE TO RELATED APPLICATIONS

This application is a U.S. National Phase application of International Application PCT Application No. PCT/US18/59092 filed on Nov. 3, 2018, which claims benefit of U.S. Provisional Patent Application Ser. No. 62/748,371, filed on Oct. 19, 2018, and U.S. Provisional Patent Application Ser. No. 62/581,325, filed on Nov. 3, 2017, which applications are incorporated by reference herein in their entireties.

The present invention generally relates to methods of treating acid-base disorders. These methods may be used, for example, in the treatment of patients with chronic kidney disease (CKD) who have a serum bicarbonate value of at least 22 mEq/l. These methods may also be used in the treatment of eubicarbonatemic metabolic acidosis.

Acid-base disorders are common in chronic kidney disease and heart failure patients. Chronic kidney disease (CKD) progressively impairs renal excretion of the approximately 1 mmol/kg body weight of hydrogen ions generated in healthy adults (Yaqoob, M M. 2010, Acidosis and progression of chronic kidney disease, Curr. Opin. Nephrol. Hyperten. 19:489-492.). Metabolic acidosis, resulting from the accumulation of acid ($H^+$) or depletion of base ($HCO_3^-$) in the body, is a common complication of patients with CKD, particularly when the glomerular filtration rate (GFR, a measure of renal function) falls below 30 ml/min/1.73 m². Metabolic acidosis has profound long-term effects on protein and muscle metabolism, bone turnover and the development of renal osteodystrophy. In addition, metabolic acidosis influences a variety of paracrine and endocrine functions, again with long term consequences such as increased inflammatory mediators, reduced leptin, insulin resistance, and increased corticosteroid and parathyroid hormone production (Mitch W E, 1997, Influence of metabolic acidosis on nutrition, Am. J. Kidney Dis. 29:46-48.). The net effect of sustained metabolic acidosis in the CKD patient is loss of bone and muscle mass, a negative nitrogen balance, and the acceleration of chronic renal failure due to hormonal and cellular abnormalities (De Brito-Ashurst I, Varagunam M, Raftery M J, et al, 2009, Bicarbonate supplementation slows progression of CKD and improves nutritional status, J. Am. Soc. Nephrol. 20: 2075-2084). Conversely, the potential concerns with alkali therapy in CKD patients include expansion of extracellular fluid volume associated with sodium ingestion, resulting in the development or aggravation of hypertension, facilitation of vascular calcification, and the decompensation of existing heart failure. CKD patients of moderate degree (GFR at 20-25% of normal) first develop hyperchloremic acidosis with a normal anion gap due to the inability to reclaim filtered bicarbonate and excrete proton and ammonium cations. As they progress toward the advanced stages of CKD the anion gap typically increases, reflective of the continuing degradation of the kidney's ability to excrete the anions that were associated with the unexcreted protons. Serum bicarbonate in these patients rarely goes below 15 mmol/L with a maximum elevated anion gap of approximately 20 mmol/L. The non-metabolizable anions that accumulate in CKD are buffered by alkaline salts from bone (Lemann J Jr, Bushinsky D A, Hamm L L Bone buffering of acid and base in humans. Am. J. Physiol Renal Physiol. 2003 November, 285(5):F811-32).

The majority of patients with chronic kidney disease have underlying diabetes (diabetic nephropathy) and hypertension, leading to deterioration of renal function. In almost all patients with hypertension a high sodium intake will worsen the hypertension. Accordingly, kidney, heart failure, diabetes and hypertensive guidelines strictly limit sodium intake in these patients to less than 1.5 g or 65 mEq per day (HFSA 2010 guidelines, Lindenfeld 2010, J. Cardiac Failure V16 No 6 P475). Chronic anti-hypertensive therapies often induce sodium excretion (diuretics) or modify the kidney's ability to excrete sodium and water (such as, for example, Renin Angiotensin Aldosterone System inhibiting "RAASi" drugs). However, as kidney function deteriorates, diuretics become less effective due to an inability of the tubule to respond. The RAASi drugs induce life-threatening hyperkalemia as they inhibit renal potassium excretion. Given the additional sodium load, chronically treating metabolic acidosis patients with amounts of sodium-containing base that often exceed the total daily recommended sodium intake is not a reasonable practice. As a consequence, oral sodium bicarbonate is not commonly prescribed chronically in these diabetic nephropathy patients. Potassium bicarbonate is also not acceptable as patients with CKD are unable to readily excrete potassium, leading to severe hyperkalemia.

Despite these shortcomings, the role of oral sodium bicarbonate has been studied in the small subpopulation of non-hypertensive CKD patients. As part of the Kidney Research National Dialogue, alkali therapy was identified as having the potential to slow the progression of CKD, as well as to correct metabolic acidosis. The annual age-related decline in glomerular filtration rate (GFR) after the age of 40 is 0.75-1.0 ml/min/1.73 m² in normal individuals. In CKD patients with fast progression, a steeper decline of >4 ml/min/1.73 m² annually can be seen. Glomerular filtration rate or estimated glomerular filtration rate is typically used to characterize kidney function and the stage of chronic kidney disease. The five stages of chronic kidney disease and the GFR for each stage is as follows:

Stage 1 with normal or high GFR (GFR>90 mL/min/1.73 m²)
Stage 2 Mild CKD (GFR=60-89 mL/min/1.73 m²)
Stage 3A Moderate CKD (GFR=45-59 mL/min/1.73 m²)
Stage 3B Moderate CKD (GFR=30-44 mL/min/1.73 m²)
Stage 4 Severe CKD (GFR=15-29 mL/min/1.73 m²)
Stage 5 End Stage CKD (GFR<15 mL/min/1.73 m²).

In one aspect, the invention relates to a method of treating a patient with chronic kidney disease, wherein the patient has a serum bicarbonate (SBC) value of at least 22 mEq/l and exhibits symptoms of an acid-base prior to the treatment. The method comprises oral administration of a pharmaceutical composition comprising a nonabsorbable proton-binding polymer. As described in greater detail elsewhere herein, such patients have an increased risk of adverse events when their baseline serum bicarbonate value is at the lower end of what is currently considered the "normal" range (i.e., 22-24 mEq/l). Without wishing to be bound by theory, it is believed that this risk is associated with acid/base imbalances that precede chronic metabolic acidosis. Using a nonabsorbable protein binding polymer as disclosed herein can absorb and remove protons, a strong acid, and/or the conjugate base of a strong acid. The treatment is further defined in the appended claims.

Chronic metabolic acidosis is a process characterized by excessive acid generation or diminished acid removal, resulting in an accumulation of nonvolatile acids in the body (as described in more detail below). Chronic metabolic acidosis is a common feature of progressive renal disease, owing to altered homeostatic mechanisms that regulate acid-base balance, however normal aging and excessive protein intake are also conditions that can be associated with metabolic acidosis. However, prior to the onset of chronic metabolic acidosis, patients may suffer from eubicarbonatemic metabolic acidosis, a condition in which the patient does not necessarily show the reduced serum bicarbonate levels associated with chronic metabolic acidosis (e.g., a SBC value of less than 22 mEq/l), but there is a raised level of acid production/retention with the potential to have serious physiological consequences. In short, the acid-base disorder is masked by the body's homeostatic mechanisms, but these are a finite resource. As these homeostatic mechanisms are depleted, (e.g., bone dissolves in order to buffer the blood pH), eubicarbonatemic metabolic acidosis leads to increased risk factors and can develop into chronic metabolic acidosis.

Because the body's homeostatic response to these acid-generating processes is efficient, serum bicarbonate and blood pH are frequently maintained within the "normal" range, despite the accumulation of acid in the body. This eubicarbonatemic metabolic acidosis nonetheless triggers responses that have pathologic consequences, such as nephrolithiasis, bone loss, muscle protein breakdown and renal hypertrophy. There are animal and human subject studies that have identified eubicarbonatemic acidosis as a clinical entity (Alpern R J and K Sakhaee (1997). The clinical spectrum of chronic metabolic acidosis: homeostasis mechanisms produce significant morbidity. Am. J. Kidney Dis. 29 (2): 291-302.). Therefore, eubicarbonatemic metabolic acidosis can be defined based on a raised level of acid production/retention where the serum bicarbonate and/or blood pH are maintained within the "normal" range.

In a study by Wesson ((1998), Dietary acid increases blood and renal cortical acid content in rats. Am. J. Physiol. 274: F97-F103) dietary acid was shown to increase blood and renal cortical acid content in normal renal function rats. In this study, dietary acid in the form of $(NH_4)_2SO_4$ was given in drinking water such that no measurable decrease in plasma pH or serum bicarbonate was evident, while measuring net acid excretion (NAE) in the urine. Compared to control animals ($Na_2SO_4$), animals fed the acid diet increased NAE in the urine; blood base excess decreased and renal cortical $H^+$ content increased because of the additional acid load. The data show that dietary acid sufficient to increase NAE without decreasing plasma $tCO_2$ or pH nevertheless decreases blood base excess and increases renal cortical acid content, consistent with net acid retention in an apparently "normal" setting.

Sodium bicarbonate has been shown to be effective in slowing the progression of kidney disease in patients with stage 2 chronic kidney disease (CKD) due to hypertensive nephropathy (Mahajan et al. 2010. Daily Oral Sodium Bicarbonate Preserves Glomerular Filtration Rate by Slowing its Decline in Early Hypertensive Nephropathy. Kidney Int 78(3): 303-309). It is notable in this study that the enrolled patients had normal serum total $CO_2$ of ~26 mM. After 5 years of treatment with sodium bicarbonate (0.5 mEq/kg/day), sodium chloride (0.5 mEq/kg/day) or placebo, the sodium bicarbonate group had slowed the rate of eGFR decline, reduced urine ET-1 excretion and reduced tubulointerstitial injury as measured by urine NAG.

It has been postulated that metabolic acidosis can mediate eGFR decline through endothelin and mineralocorticoid receptors. To test this hypothesis, Wesson et al. (2011. Acid retention accompanies reduced GFR in humans and increases plasma levels of endothelin and aldosterone. Am. J. Physiol. Renal Physiol. 300(4): F830-F837.) compared eubicarbonatemic, macroalbuminuric (UACR>200 mg/g) hypertensive nephropathy subjects with moderately reduced eGFR (CKD stage 2) or normal eGFR (CKD stage 1), to determine if CKD stage 2 subjects have: (1) $H^+$ retention, (2) higher plasma ET-1 and aldosterone levels and (3) whether chronic daily $NaHCO_3$ lowers H+ retention and levels of ET-1 and aldosterone. Baseline dietary H+ and urine NAE were not different between the groups. However, an acute oral $NaHCO_3$ bolus reduced urine NAE less (i.e., postbolus urine NAE was higher) in CKD stage 2 than in CKD stage 1 subjects, consistent with greater acid retention in the CKD stage 2 subjects, despite no apparent chronic metabolic acidosis as reflected by serum bicarbonate (i.e., the patient has a serum bicarbonate value of at least 22 mEq/l). Additionally, the daily $NaHCO_3$ decreased urinary ET-1 and plasma aldosterone in the CKD stage 2 subjects. This study demonstrated that subjects with CKD stage 2 and no apparent metabolic acidosis as reflected by serum bicarbonate (i.e., the patient has a serum bicarbonate value of at least 22 mEq/l) have significant acid retention, as measured by NAE response to an alkali bolus, and decreased urinary ET-1 and plasma aldosterone levels on administration of daily $NaHCO_3$.

A recent study by Goroya, et al. (2016 Urine citrate excretion might identify eubicarbonatemic CKD patients with acid retention and assess their response to therapy. Am. Soc. Nephrol. National Meeting) has proposed that urine citrate excretion might be used to identify eubicarbonatemic CKD patients with acid retention, and so assess response to alkali therapy. As noted above, CKD stage 2 patients with no apparent metabolic acidosis as reflected by serum bicarbonate (i.e., the patient has a serum bicarbonate value of at least 22 mEq/l) retain acid, while dietary acid reduction slows their eGFR decline. To determine if urine excretion of citrate (a measure of excess base) might identify CKD patients with acid retention and assess response to therapy, the authors measured acid retention and urine citrate excretion in CKD stage 2 and stage 1 patients ($tCO_2$ 24.5 mM) before and after 30 days of dietary acid reduction with base-producing fruits and vegetables (F+V). Baseline acid retention was higher in CKD stage 2 than CKD stage 1 (28.1±9.4 vs. 5.2±12.0 mmol, respectively, p<0.01) but baseline 8 hour urine citrate excretion was lower in CKD 2 than CKD 1 (187±40 vs. 335±125 mg, p<0.01). Thirty days of F+V reduced acid retention in CKD 2 (to 18.4±17.4 mmol, p<0.01) but not in CKD 1 (to 4.7±15.6 mmol, p=0.88) and acid retention remained higher in CKD 2 than CKD 1 (p<0.01). By contrast, 30 days of F+V increased urine citrate excretion in both CKD 2 (to 245±70 mg, p<0.01 vs. baseline) and CKD 1 (to 369±125 mg, p<0.02, vs. baseline) yet overall urine citrate excretion remained lower in CKD 2 than CKD 1 (p<0.01). These results show that acid retention in CKD patients with eubicarbonatemic metabolic acidosis was associated with low urine citrate excretion, which increased after dietary acid reduction with F+V (corresponding to an increased level of base equivalents in the blood). Thus, low urine citrate excretion might identify CKD patients with acid retention and might also be used to assess their response to therapy.

Other urine markers of eubicarbonatemic metabolic acidosis are being evaluated, particularly as risk factors for predicting progression to ESRD and mortality. Because urine ammonium excretion is critical for the maintenance of normal serum bicarbonate levels and reduced urine ammonium excretion plays an important role in the development of metabolic acidosis in CKD, it is being evaluated as an earlier indicator of risk than bicarbonate or $pCO_2$ measures. An initial study by Vallet, et al. (2015, Urinary ammonia and long-term outcomes in chronic kidney disease, kidney international Volume 88, Issue 1, Pages 137-145) suggested that lower urinary ammonium excretion was a risk factor for ESRD in >1000 patients with CKD in the NephroTest cohort. However, this preliminary study did not adjust for serum $tCO_2$ or nutritional indicators of acid-alkali content in the main analysis, thus it is uncertain whether the trend with reduced urinary ammonium excretion was prognostic for ESRD or if the excess risk of ESRD was because of poor nutritional status. A recently published study (Raphael, 2017. Urine ammonium predicts clinical outcomes in hypertensive kidney disease. J. Am. Soc. Nephrol. 28: 2483-2490) has re-examined the association of urine ammonium excretion with long-term clinical end points, adjusting for serum $tCO_2$, net endogenous acid production (NEAP), GFR and other potential confounders. In this study of 1,044 patients within the African American Study of Kidney Disease and Hypertension (AASK) database, urinary ammonium excretion decreased with lower mGFR, as expected. Event free survival was highest in the CKD patients with the highest urine ammonium excretion rate (tertile 3, >20 mEq/day) and was significantly lower in those patients with compromised urine ammonium excretion (tertiles 1 and 2, <20 mEq/day).

When the dataset was adjusted for age, sex, randomized group, mGFR, proteinuria, NEAP, and serum potassium, urine ammonium excretion below 20 mEq/day was associated with an increased HR of the composite endpoint of death and dialysis. Thus, lower urine ammonium excretion is a risk factor for acidosis and poor renal and survival outcomes among this African American hypertensive CKD population, after adjustment for potential confounding factors. With the increased interest in the potential use of alkaline therapy to slow CKD progression in patients without overt acidosis (e.g., Mahajan, 2010), the observation that lower daily urine ammonium excretion signals a higher risk of death or ESRD in this patient population suggests that early markers of kidney failure effecting acid-base balance may be helpful in identifying at-risk individuals, even when serum bicarbonate levels appear normal.

In another aspect, the present invention relates to treating or preventing eubicarbonatemic metabolic acidosis using a polymer as set out herein to reduce the amount of protons, a strong acid, and/or the conjugate base of a strong acid in a patient (i.e., reduce the overall acid load). Such polymers can also treat metabolic acidosis characterized by a baseline serum bicarbonate value of less than 22 mEq/l (sometimes referred to herein "chronic metabolic acidosis") by the same mechanism, as defined below for completeness. However, in this aspect, the polymer is administered before the onset of chronic metabolic acidosis in order to treat or prevent eubicarbonatemic metabolic acidosis. The treatment is further defined in the appended claims.

The various methods of treatment or prevention disclosed herein can be measured by a range of markers suitable for assessing the progression of eubicarbonatemic metabolic acidosis. The following table summarizes some of these markers, and shows the values expected for healthy individuals compared to those suffering from eubicarbonatemic metabolic acidosis:

| Marker | normal level | Typical Levels in patients with eubicarbonatemic metabolic acidosis |
|---|---|---|
| Serum bicarbonate | 22-31 mEq/L | 22-24 mEq/L |
| Urine citrate excretion | 640 mg/day | 180-370 mg/day |
| Urine ammonium excretion | 30-40 mmol/day | 200 mmol/day |
| Net acid excretion (NAE) | 30-300 mEq/day | <50 mEq/day |
| Plasma Endothelin (ET-1) levels | 0.91-1.91 pg/mL | 2-5 pg/mL |
| Urine Endothelin (ET-1) levels as a ratio of creatinine (ET-1/creatinine) | 3-3.5 | >4 |
| Plasma aldosterone levels | 3-16 ng/dL in adults, 3-35 ng/dL in children - lying down | 9-64 ng/dL in adults, 9-140 ng/dL in children - lying down |

The treatment disclosed herein involves the treatment or prevention of eubicarbonatemic metabolic acidosis in subjects afflicted with chronic kidney disease and exhibiting one or more symptoms of an acid base disorder (e.g., exhibiting a serum bicarbonate, urine citrate excretion, urine ammonium excretion, net acid excretion, plasma Endothelin (ET-1) and/or plasma aldosterone level that is typical of a patient with eubicarbonatemic metabolic acidosis; see table immediately preceding this paragraph). Successful treatment or prevention can be defined by changes in one or more of the markers disclosed herein, for example one or more or any combination of the markers listed in the table above. The presence of eubicarbonatemic metabolic acidosis may be defined by improvements in any one, or any combination of, the markers disclosed herein or listed in the table above. Successful treatment may involve increasing the serum bicarbonate value from a value in the range of 22-24 mEq/l to a value of at least 25 mEq/l or a change in any of the other markers defined in the table above that marker towards the normal level. The treatment goal, therefore, includes any change in any one of the markers listed above (or any combination thereof) such that the marker returns to the normal level specified in the table. Prevention includes maintaining an individual in the normal range for any one of the markers specified in the above table (or any combination thereof).

Metabolic acidosis is the result of metabolic and dietary processes that in various disease states create a condition in which non-volatile acids accumulate in the body, causing a net addition of protons ($H^+$) or the loss of bicarbonate ($HCO_3^-$). Metabolic acidosis occurs when the body accumulates acid from metabolic and dietary processes and the excess acid is not completely removed from the body by the kidneys. Chronic kidney disease is often accompanied by metabolic acidosis due to the reduced capacity of the kidney to excrete hydrogen ions secondary to an inability to reclaim filtered bicarbonate ($HCO_3^-$), synthesize ammonia (ammoniagenesis), and excrete titratable acids. Clinical practice guidelines recommend initiation of alkali therapy in patients with non-dialysis-dependent chronic kidney disease (CKD)

when the serum bicarbonate level is <22 mEq/L to prevent or treat complications of metabolic acidosis. (Clinical practice guidelines for nutrition in chronic renal failure, K/DOQI, National Kidney Foundation, Am. J. Kidney Dis. 2000; 35:S1-140; Raphael, K L, Zhang, Y, Wei, G, et al. 2013, Serum bicarbonate and mortality in adults in NHANES III, Nephrol. Dial. Transplant 28: 1207-1213). These complications include malnutrition and growth retardation in children, exacerbation of bone disease, increased muscle degradation, reduced albumin synthesis, and increased inflammation. (Leman, J, Litzow, J R, Lennon, E J. 1966. The effects of chronic acid loads in normal man: further evidence for the participation of bone mineral in the defense against chronic metabolic acidosis, J. Clin. Invest. 45: 1608-1614; Franch H A, Mitch W E, 1998, Catabolism in uremia: the impact of metabolic acidosis, J. Am. Soc. Nephrol. 9: S78-81; Ballmer, P E, McNurlan, M A, Hulter, H N, et al., 1995, Chronic metabolic acidosis decreases albumin synthesis and induces negative nitrogen balance in humans, J. Clin. Invest. 95: 39-45; Farwell, W R, Taylor, E N, 2010, Serum anion gap, bicarbonate and biomarkers of inflammation in healthy individuals in a national survey, CMAJ 182:137-141). Overt metabolic acidosis is present in a large proportion of patients when the estimated glomerular filtration rate is below 30 ml/min/1.73 m$^2$. (KDOQI bone guidelines: American Journal of Kidney Diseases (2003) 42:S1-S201. (suppl); Widmer B, Gerhardt R E, Harrington J T, Cohen J J, Serum electrolyte and acid base composition: The influence of graded degrees of chronic renal failure, Arch Intern Med139:1099-1102, 1979; Dobre M, Yang, W, Chen J, et. al., Association of serum bicarbonate with risk of renal and cardiovascular outcomes in CKD: a report from the chronic renal insufficiency cohort (CRIC) study. Am. J. Kidney Dis. 62: 670-678, 2013; Yaqoob, M M. Acidosis and progression of chronic kidney disease. Curr. Opin. Nephrol. Hypertens. 19: 489-492, 2010).

Metabolic acidosis, regardless of etiology, lowers extracellular fluid bicarbonate and, thus, decreases extracellular pH. The relationship between serum pH and serum bicarbonate is described by the Henderson-Hasselbalch equation $$pH=pK'+\log[HCO_3^-]/[(0.03 \times P_aCO_2)]$$

where 0.03 is the physical solubility coefficient for $CO_2$, $[HCO_3]$ and $P_aCO_2$ are the concentrations of bicarbonate and the partial pressure of carbon dioxide, respectively.

There are several laboratory tests that can be used to define metabolic acidosis. The tests fundamentally measure either bicarbonate ($HCO_3^-$) or proton ($H^+$) concentration in various biological samples, including venous or arterial blood. These tests can measure either bicarbonate ($HCO_3$) or proton ($H^+$) concentration by enzymatic methodology, by ion selective electrodes or by blood gas analysis. In both the enzymatic and ion selective electrode methods, bicarbonate is "measured." Using blood gas analysis, bicarbonate level can be calculated using the Henderson-Hasselbalch equation.

Arterial blood gas (ABG) analysis is commonly performed for clinical evaluation, but the procedure has certain limitations in the form of reduced patient acceptability because of painful procedure and the potential to cause complications such as arterial injury, thrombosis with distal ischaemia, haemorrhage, aneurysm formation, median nerve damage and reflex sympathetic dystrophy. Venous blood gas (VBG) analysis is a relatively safer procedure as fewer punctures are required thus reducing the risk of needle stick injury to the health care workers. Therefore, as set out below, when the invention requires assessment of metabolic acidosis, it is preferred to complete this assessment using VBG analysis. Any measurements specified herein are preferably achieved by VBG analysis where possible, for example measurements of blood or serum bicarbonate levels.

The most useful measurements for the determination of acidosis rely on a measurement of the venous plasma bicarbonate (or total carbon dioxide [$tCO_2$]), or arterial plasma bicarbonate (or total carbon dioxide [$tCO_2$]), serum electrolytes $Cl^-$, $K^+$, and $Na^+$, and a determination of the anion gap. In the clinical laboratory, measurement of venous plasma or serum electrolytes includes an estimation of the $tCO_2$. This measurement reflects the sum of circulating $CO_2$ [i.e., the total $CO_2$ represented by bicarbonate ($HCO_3^-$), carbonic acid, ($H_2CO_3$) and dissolved $CO_2$ ($0.03 \times PCO_2$)]. $tCO_2$ can also be related to $HCO_3^-$ by using a simplified and standardized form of the Henderson-Hasselbalch equation: $tCO_2=HCO_3^-+0.03\ PCO_2$, where $PCO_2$ is the measured partial pressure of $CO_2$. Since $HCO_3^-$ concentration is greater than 90% of the $tCO_2$, and there are small amounts of $H_2CO_3$, then venous $tCO_2$ is often used as a reasonable approximation of the venous $HCO_3$ concentration in the blood. Especially during chronic kidney disease, an abnormal plasma $HCO_3$ value <22 mEq/L generally indicates metabolic acidosis.

Changes in serum $Cl^-$ concentration can provide additional insights into possible acid-base disorders, particularly when they are disproportionate to changes in serum $Na^+$ concentration. When this occurs, the changes in serum $Cl^-$ concentration are typically associated with reciprocal changes in serum bicarbonate. Thus, in metabolic acidosis with normal anion gap, serum $Cl^-$ increases >105 mEq/L as serum bicarbonate decreases <22 mEq/L.

Calculation of the anion gap [defined as the serum $Na^+$—$(Cl^+ + HCO_3)$] is an important aspect of the diagnosis of metabolic acidosis. Metabolic acidosis may be present with a normal or an elevated anion gap. However, an elevated anion gap commonly signifies the presence of metabolic acidosis, regardless of the change in serum $HCO_3^-$. An anion gap greater than 20 mEq/L (normal anion gap is 8 to 12 mEq/L) is a typical feature of metabolic acidosis.

Arterial blood gases are used to identify the type of an acid-base disorder and to determine if there are mixed disturbances. In general, the result of arterial blood gas measures should be coordinated with history, physical exam and the routine laboratory data listed above. An arterial blood gas measures the arterial carbon dioxide tension ($P_aCO_2$), acidity (pH), and the oxygen tension ($P_aO_2$). The $HCO_3^-$ concentration is calculated from the pH and the $P_aCO_2$. Hallmarks of metabolic acidosis are a pH<7.35, $P_aCO_2$<35 mm Hg and $HCO_3^-$<22 mEq/L. The value of $P_aO_2$ (normal 80-95 mmHg) is not used in making the diagnosis of metabolic acidosis but may be helpful in determining the cause. Acid-base disturbance are first classified as respiratory or metabolic. Respiratory disturbances are those caused by abnormal pulmonary elimination of $CO_2$, producing an excess (acidosis) or deficit (alkalosis) of $CO_2$ (carbon dioxide) in the extracellular fluid. In respiratory acid-base disorders, changes in serum bicarbonate ($HCO_3$) are initially a direct consequence of the change in $PCO_2$ with a greater increase in $PCO_2$ resulting in an increase in $HCO_3^-$. (Adrogue H J, Madias N E, 2003, Respiratory acidosis, respiratory alkalosis, and mixed disorders, in Johnson R J, Feehally J (eds): Comprehensive Clinical Nephrology. London, C V Mosby, pp. 167-182). Metabolic disturbances are those caused by excessive intake of, or metabolic production or losses of, nonvolatile acids or bases in the extracellular fluid. These changes are reflected by changes in the concentration of bicarbonate anion ($HCO_3$) in the blood; adaptation in this case involves both buffering (immediate), respiratory (hours to days) and renal (days) mechanisms. (DuBose T D, MacDonald G A: renal tubular acidosis, 2002, in DuBose T D, Hamm L L (eds): Acid-base and electrolyte disorders: A companion to Brenners and Rector's the Kidney, Philadelphia, W B Saunders, pp. 189-206).

The overall hydrogen ion concentration in the blood is defined by the ratio of two quantities, the serum $HCO_3$ content (regulated by the kidneys) and the $PCO_2$ content (regulated by the lungs) and is expressed as follows:

$$[H^+] \propto (PCO_2/[HCO_3^-])$$

The consequence of an increase in the overall hydrogen ion concentration is a decline in the major extracellular buffer, bicarbonate. Normal blood pH is between 7.38 and 7.42, corresponding to a hydrogen ion ($H^+$) concentration of 42 to 38 nmol/L (Goldberg M: Approach to Acid-Base Disorders. 2005. In Greenberg A, Cheung A K (eds) Primer on Kidney Diseases, National Kidney Foundation, Philadelphia, Elsevier-Saunders, pp. 104-109.). Bicarbonate ($HCO_3$) is an anion that acts to buffer against pH disturbances in the body, and normal levels of plasma bicarbonate range from 22-26 mEq/L (Szerlip H M: Metabolic Acidosis, 2005, in Greenberg A, Cheung A K (eds) Primer on Kidney Diseases, National Kidney Foundation, Philadelphia, Elsevier-Saunders, pp. 74-89.). Acidosis is the process which causes a reduction in blood pH (acidemia) and reflects the accumulation of hydrogen ion ($H^+$) and its consequent buffering by bicarbonate ion ($HCO_3^-$) resulting in a decrease in serum bicarbonate. Metabolic acidosis can be represented as follows:

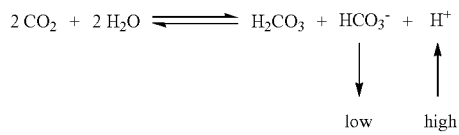

(Clinical practice guidelines for nutrition in chronic renal failure. K/DOQI, National Kidney Foundation. Am. J. Kidney Dis. 2000; 35:S1-140). Using this balance equation, the loss of one $HCO_3^-$ is equivalent to the addition of one $H^+$ and conversely, the gain of one $HCO_3^-$ is equivalent to the loss of one $H^+$. Thus, changes in blood pH, particularly increases in $H^+$ (lower pH, acidosis) can be corrected by increasing serum $HCO_3^-$ or, equivalently, by decreasing serum $H^+$.

In order to maintain extracellular pH within the normal range, the daily production of acid must be excreted from the body. Acid production in the body results from the metabolism of dietary carbohydrates, fats and amino acids. Complete oxidation of these metabolic substrates produces water and $CO_2$. The carbon dioxide generated by this oxidation (20,000 mmol/day) is efficiently exhaled by the lungs, and represents the volatile acid component of acid-base balance.

In contrast, nonvolatile acids (~50-100 mEq/day) are produced by the metabolism of sulfate- and phosphate-containing amino acids and nucleic acids. Additional nonvolatile acids (lactic acid, butyric acid, acetic acid, other organic acids) arise from the incomplete oxidation of fats and carbohydrates, and from carbohydrate metabolism in the colon, where bacteria residing in the colon lumen convert the substrates into small organic acids that are then absorbed into the bloodstream. The impact of short chain fatty acids on acidosis is somewhat minimized by anabolism, for example into long-chain fatty acids, or catabolism to water and $CO_2$.

The kidneys maintain pH balance in the blood through two mechanisms: reclaiming filtered $HCO_3^-$ to prevent overall bicarbonate depletion and the elimination of non-volatile acids in the urine. Both mechanisms are necessary to prevent bicarbonate depletion and acidosis.

In the first mechanism, the kidneys reclaim $HCO_3^-$ that is filtered by the glomerulus. This reclamation occurs in the proximal tubule and accounts for ~4500 mEq/day of reclaimed $HCO_3^-$. This mechanism prevents $HCO_3^-$ from being lost in the urine, thus preventing metabolic acidosis. In the second mechanism, the kidneys eliminate enough $H^+$ to equal the daily nonvolatile acid production through metabolism and oxidation of protein, fats and carbohydrates. Elimination of this acid load is accomplished by two distinct routes in the kidney, comprising active secretion of $H^+$ ion and ammoniagenesis. The net result of these two interconnected processes is the elimination of the 50-100 mEq/day of nonvolatile acid generated by normal metabolism.

Thus, normal renal function is needed to maintain acid-base balance. During chronic kidney disease, filtration and reclamation of $HCO_3^-$ is impaired as is generation and secretion of ammonia. These deficits rapidly lead to chronic metabolic acidosis which is, itself, a potent antecedent to end-stage renal disease. With continued acid production from metabolism, a reduction in acid elimination will disturb the $H^+/HCO_3^-$ balance such that blood pH falls below the normal value of pH=7.38-7.42.

Treatment of metabolic acidosis by alkali therapy is usually indicated to raise and maintain the plasma pH to greater than 7.20. Sodium bicarbonate ($NaHCO_3$) is the agent most commonly used to correct metabolic acidosis. $NaHCO_3$ can be administered intravenously to raise the serum $HCO_3^-$ level adequately to increase the pH to greater than 7.20. Further correction depends on the individual situation and may not be indicated if the underlying process is treatable or the patient is asymptomatic. This is especially true in certain forms of metabolic acidosis. For example, in high-anion gap (AG) acidosis secondary to accumulation of organic acids, lactic acid, and ketones, the cognate anions are eventually metabolized to $HCO_3^-$. When the underlying disorder is treated, the serum pH corrects; thus, caution should be exercised in these patients when providing alkali to raise the pH much higher than 7.20, to prevent an increase in bicarbonate above the normal range (>26 mEq/L).

Citrate is an appropriate alkali therapy to be given orally or IV, either as the potassium or sodium salt, as it is metabolized by the liver and results in the formation of three moles of bicarbonate for each mole of citrate. Potassium citrate administered IV should be used cautiously in the presence of renal impairment and closely monitored to avoid hyperkalemia.

Intravenous sodium bicarbonate ($NaHCO_3$) solution can be administered if the metabolic acidosis is severe or if correction is unlikely to occur without exogenous alkali administration. Oral alkali administration is the preferred route of therapy in persons with chronic metabolic acidosis. The most common alkali forms for oral therapy include $NaHCO_3$ tablets where 1 g of $NaHCO_3$ is equal to 11.9 mEq of $HCO_3^-$. However, the oral form of $NaHCO_3$ is not approved for medical use and the package insert of the intravenous sodium bicarbonate solution includes the following contraindications, warnings and precautions (Hospira label for NDC 0409-3486-16):

Contraindications: Sodium Bicarbonate Injection, USP is contraindicated in patients who are losing chloride by vomiting or from continuous gastrointestinal suction, and in patients receiving diuretics known to produce a hypochloremic alkalosis.

Warnings: Solutions containing sodium ions should be used with great care, if at all, in patients with congestive heart failure, severe renal insufficiency and in clinical states in which there exists edema with sodium retention. In patients with diminished renal function, administration of solutions containing sodium ions may result in sodium retention. The intravenous administration of these solutions can cause fluid and/or solute overloading resulting in dilution of serum electrolyte concentrations, overhydration, congested states or pulmonary edema.

Precautions: [ . . . ] The potentially large loads of sodium given with bicarbonate require that caution be exercise in the use of sodium bicarbonate in patients with congestive heart failure or other edematous or sodium-retaining states, as well as in patients with oliguria or anuria.

In one outcome study, De Brito-Ashurst et al showed that bicarbonate supplementation preserves renal function in CKD (De Brito-Ashurst I, Varagunam M, Raftery M J, et al, 2009, Bicarbonate supplementation slows progression of CKD and improves nutritional status, J. Am. Soc. Nephrol. 20: 2075-2084). The study randomly assigned 134 adult patients with CKD (creatinine clearance [CrCl] 15 to 30 ml/min per 1.73 m$^2$) and serum bicarbonate 16 to 20 mmol/L to either supplementation with oral sodium bicarbonate or standard of care for 2 years. The average dose of bicarbonate in this study was 1.82 g/day, which provides 22 mEq of bicarbonate per day. The primary end points were rate of CrCl decline, the proportion of patients with rapid decline of CrCl (>3 ml/min per 1.73 m$^2$/yr), and end-stage renal disease ("ESRD") (CrCl<10 ml/min). Compared with the control group, decline in CrCl was slower with bicarbonate supplementation (decrease of 1.88 ml/min per 1.73 m$^2$ for patients receiving bicarbonate versus a decrease of 5.93 ml/min per 1.73 m$^2$ for control group; P<0.0001). Patients supplemented with bicarbonate were significantly less likely to experience rapid progression (9% versus 45%; relative risk 0.15; 95% confidence interval 0.06 to 0.40; P<0.0001). Similarly, fewer patients supplemented with bicarbonate developed ESRD (6.5% versus 33%; relative risk 0.13; 95% confidence interval 0.04 to 0.40; P<0.001).

Hyperphosphatemia is a common co-morbidity in patients with CKD, particularly in those with advanced or end-stage renal disease. Sevelamer hydrochloride is a commonly used ion-exchange resin that reduces serum phosphate concentration. However, reported drawbacks of this agent include metabolic acidosis apparently due to the net absorption of HCl in the process of binding phosphate in the small intestine. Several studies in patients with CKD and hyperphosphatemia who received hemodialysis or peritoneal dialysis found decreases in serum bicarbonate concentrations with the use of sevelamer hydrochloride (Brezina, 2004 Kidney Int. V66 S90 (2004) S39-S45; Fan, 2009 Nephrol Dial Transplant (2009) 24:3794).

Among the various aspects of the present disclosure, the following is a useful guide for one method for treating metabolic acidosis (without wishing to be bound by theory). When an H$^+$ is pumped into the stomach a HCO$_3$ enters the systemic circulation and raises the serum bicarbonate concentration. The initial binding of gastric H$^+$ to a nonabsorbable composition as described herein results in HCO$_3$ entering the systemic circulation and raising the serum bicarbonate concentration. The more H$^+$ bound the greater the increase in systemic HCO$_3^-$. The binding of Cl$^-$ the nonabsorbable composition prevents subsequent exchange of luminal Cl$^-$ for HCO$_3$ which would counteract the initial rise in HCO$_3^-$. The analogous clinical situation to administering the composition is vomiting. Administration of the composition is essentially causing the loss of gastric HCl as in vomiting. If a person vomits they lose gastric HCl and have an increase in serum bicarbonate. The increase in serum bicarbonate persists only if they are not given a lot of oral for example as NaCl, which would allow subsequent exchange of intestinal Cl$^-$ for HCO$_3$ and dissipate the increase in serum bicarbonate concentration. The disclosure is not limited by these requirements, and instead they are set out in full below.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

binding capacities of TRC101 and bixalomer in a pig with normal renal function in the study described in Example 2.

Figure 7:
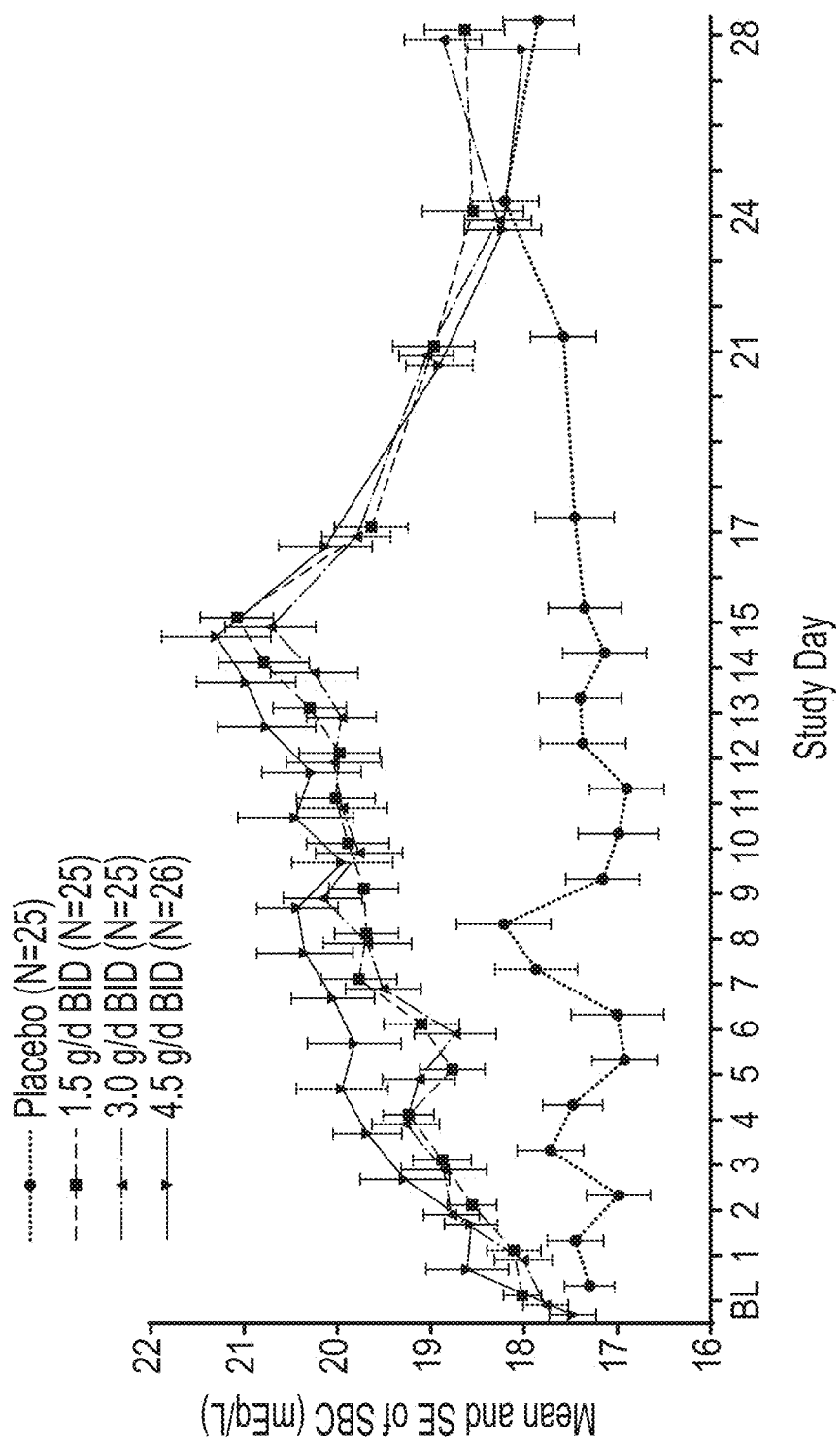

FIG. 7 is a line graph showing the mean change in serum bicarbonate (SBC) from baseline (BL) and standard error (SE) by treatment group over time in a human study as described more fully in Example 3 (Part 1).

Figure 8:
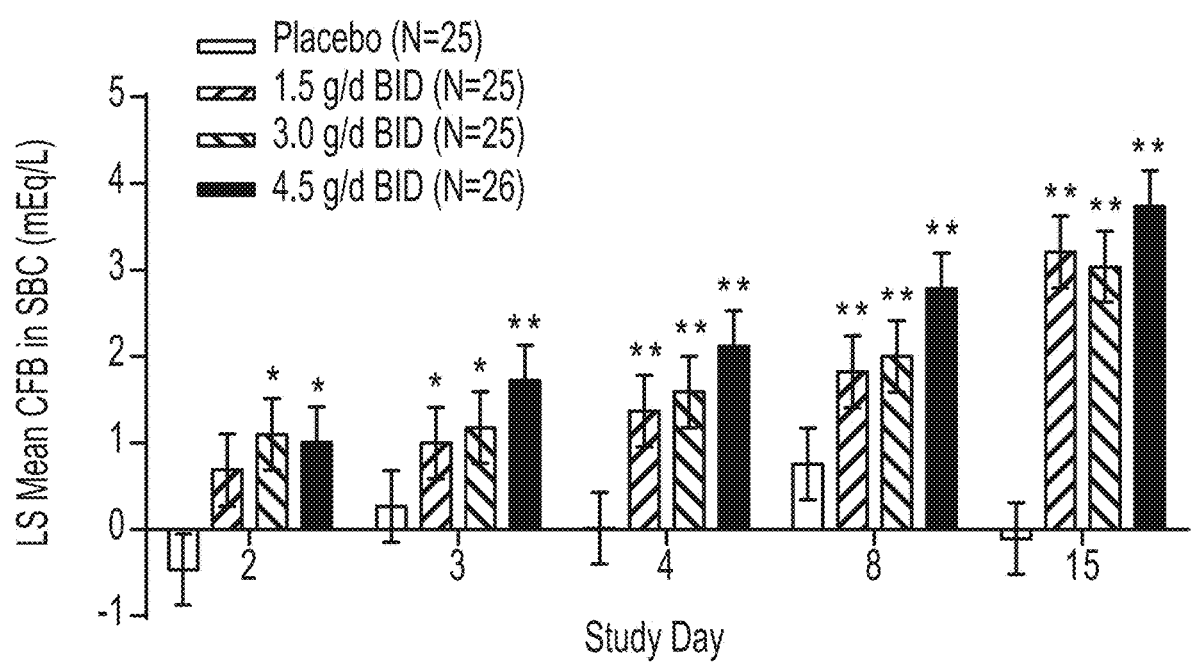

FIG. 8 is a bar graph showing the least squares mean (LS Mean) change from baseline (CFB) to end of treatment in serum bicarbonate (SBC) by treatment group in a human study as described more fully in Example 3 (Part 1). Single asterisk ("*") indicates statistically significant difference ($p<0.5$) and double asterisk ("**") indicates highly statistically significant difference ($p<0.0001$).

Figure 9:
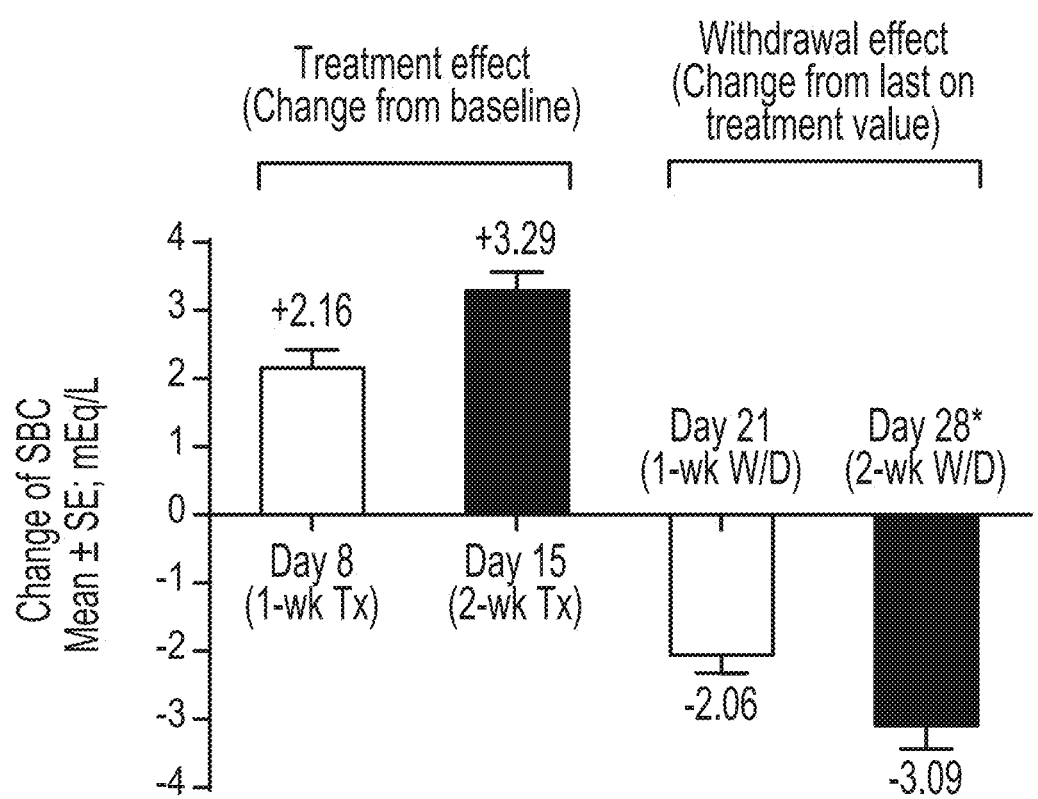

FIG. 9 is a bar graph showing the effect on serum bicarbonate (SBC) levels and standard error (SE) at days 8 and 15 resulting from treatment (Tx=treatment) and upon withdrawal of TRC101 in a human study as described more fully in Example 3 (Part 1).

Figure 10:
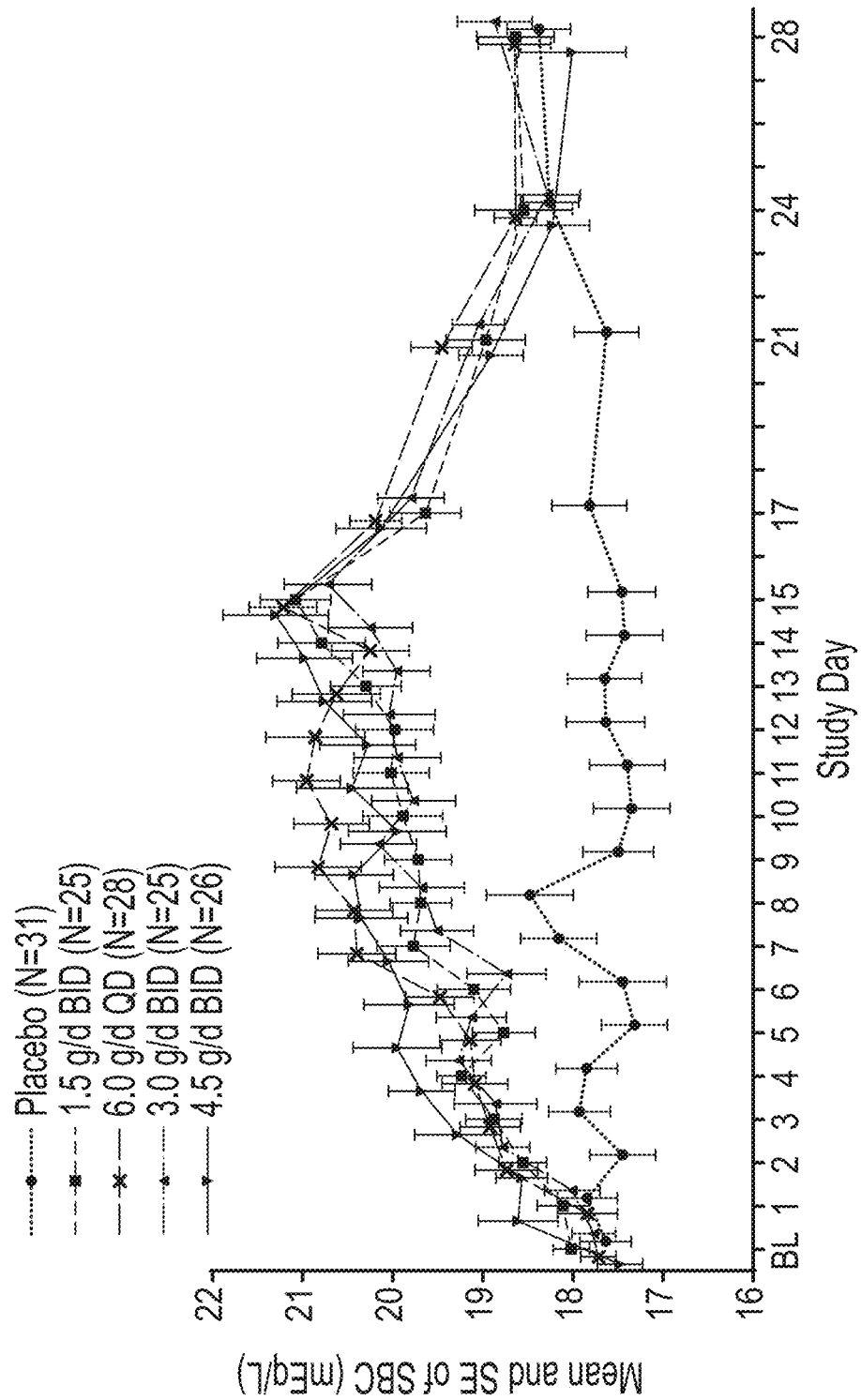

FIG. 10 is a line graph showing the mean change in serum bicarbonate (SBC) and standard error (SE) for the four TRC101 active arms and the two placebo arms (pooled) of the study described more fully in Example 3 (Parts 1 and 2).

Figure 11:
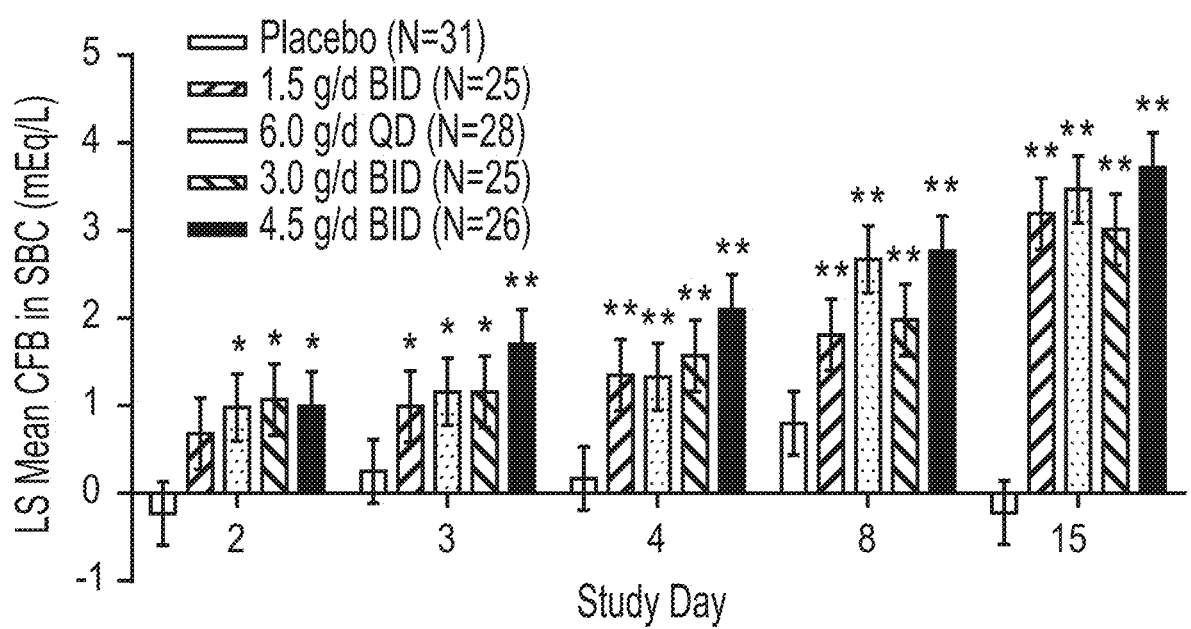

FIG. 11 is a bar graph showing the least squares mean (LS Mean) change from baseline (CFB) in serum bicarbonate (SBC) by treatment group over time for the four TRC101 active arms and the two placebo arms (pooled) of the study described more fully in Example 3 (Parts 1 and 2). Single asterisk ("*") indicates statistically significant difference ($p<0.5$) and double asterisk ("**") indicates highly statistically significant difference ($p<0.0001$).

Figure 12:
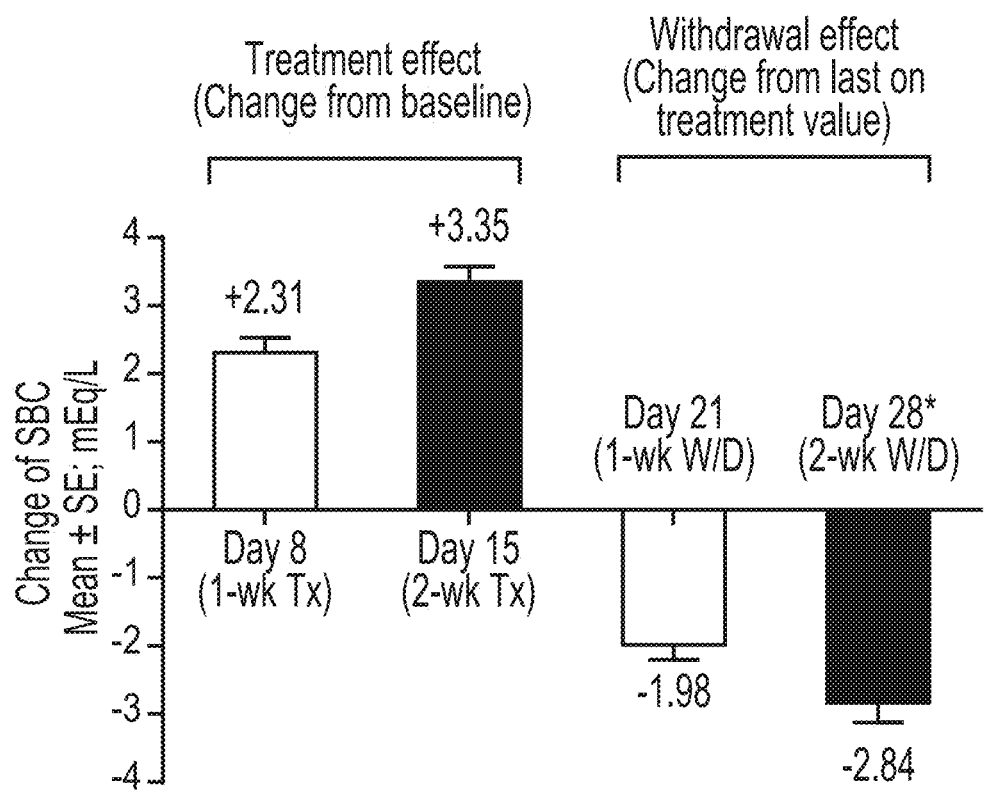
Figure 13A:
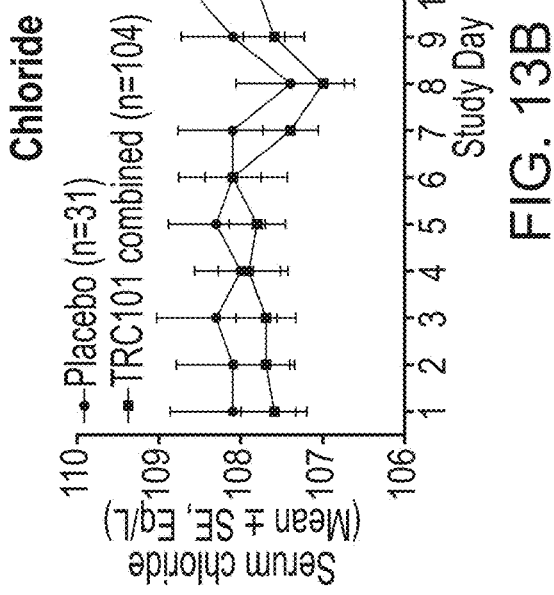
Figure 13B:
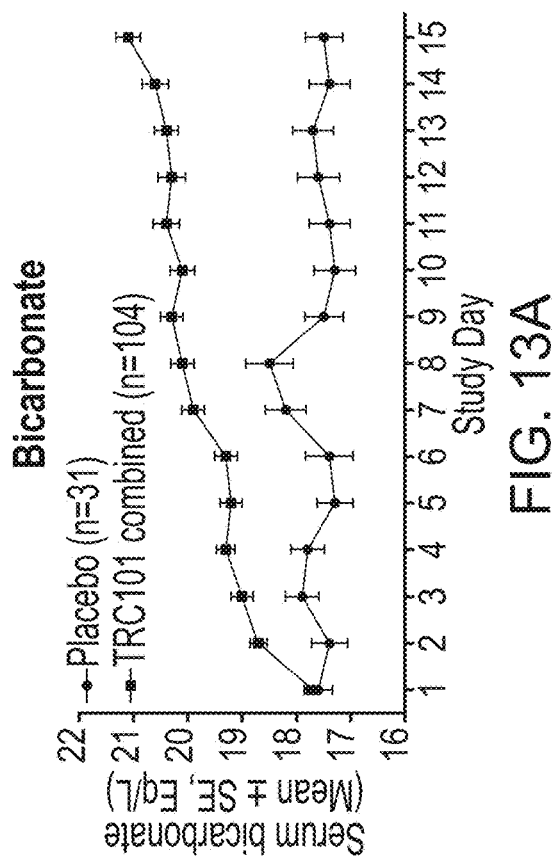
Figure 13C:
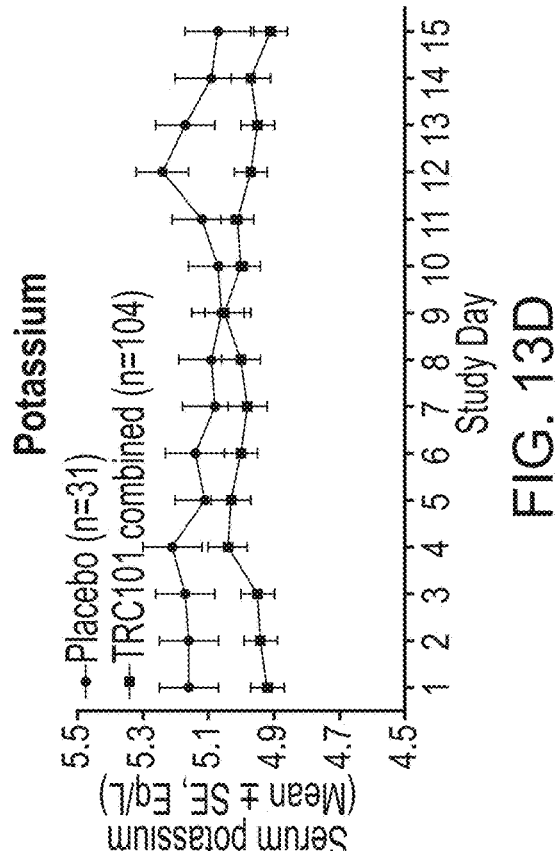
Figure 13D:
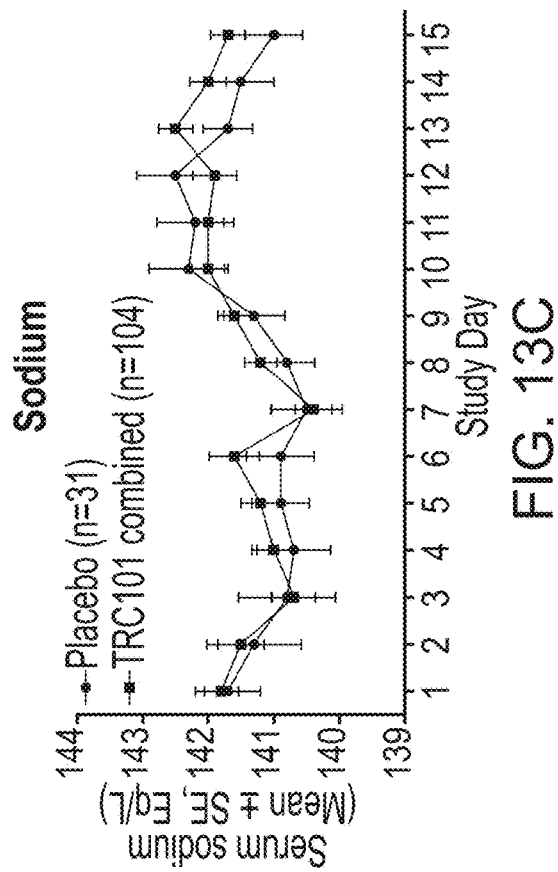

FIG. 12 is a bar graph showing the treatment effect on serum bicarbonate (SBC) levels and standard error (SE) at days 8 and 15 resulting from treatment (Tx=treatment) with and upon withdrawal of TRC101 in a human study as described more fully in Example 3 (Parts 1 and 2).

FIGS. 13A, 13B, 13C and 13D are graphs showing the changes in serum bicarbonate (FIG. 13A), serum chloride (FIG. 13B), serum sodium (FIG. 13C) and serum potassium (FIG. 13D) for the four TRC101 active arms (combined) vs the two placebo arms (pooled) over time for the study described more fully in Example 3 (Parts 1 and 2).

Figure 14:
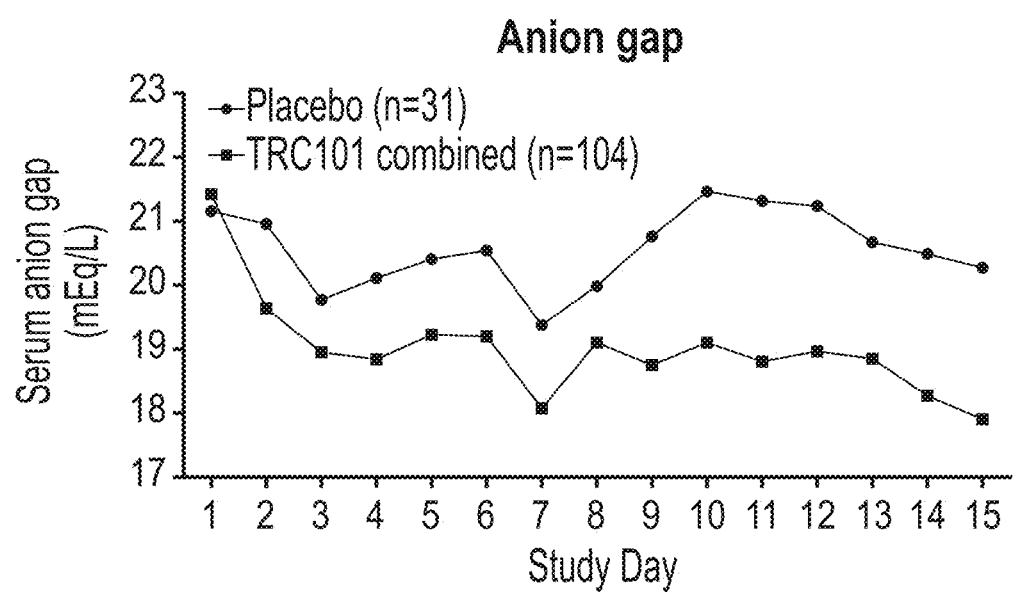

FIG. 14 is a graph showing the changes in the calculated anion gap for the four TRC101 active arms (combined) vs the two placebo arms (pooled) over time for the study described more fully in Example 3 (Parts 1 and 2).

Figure 15:
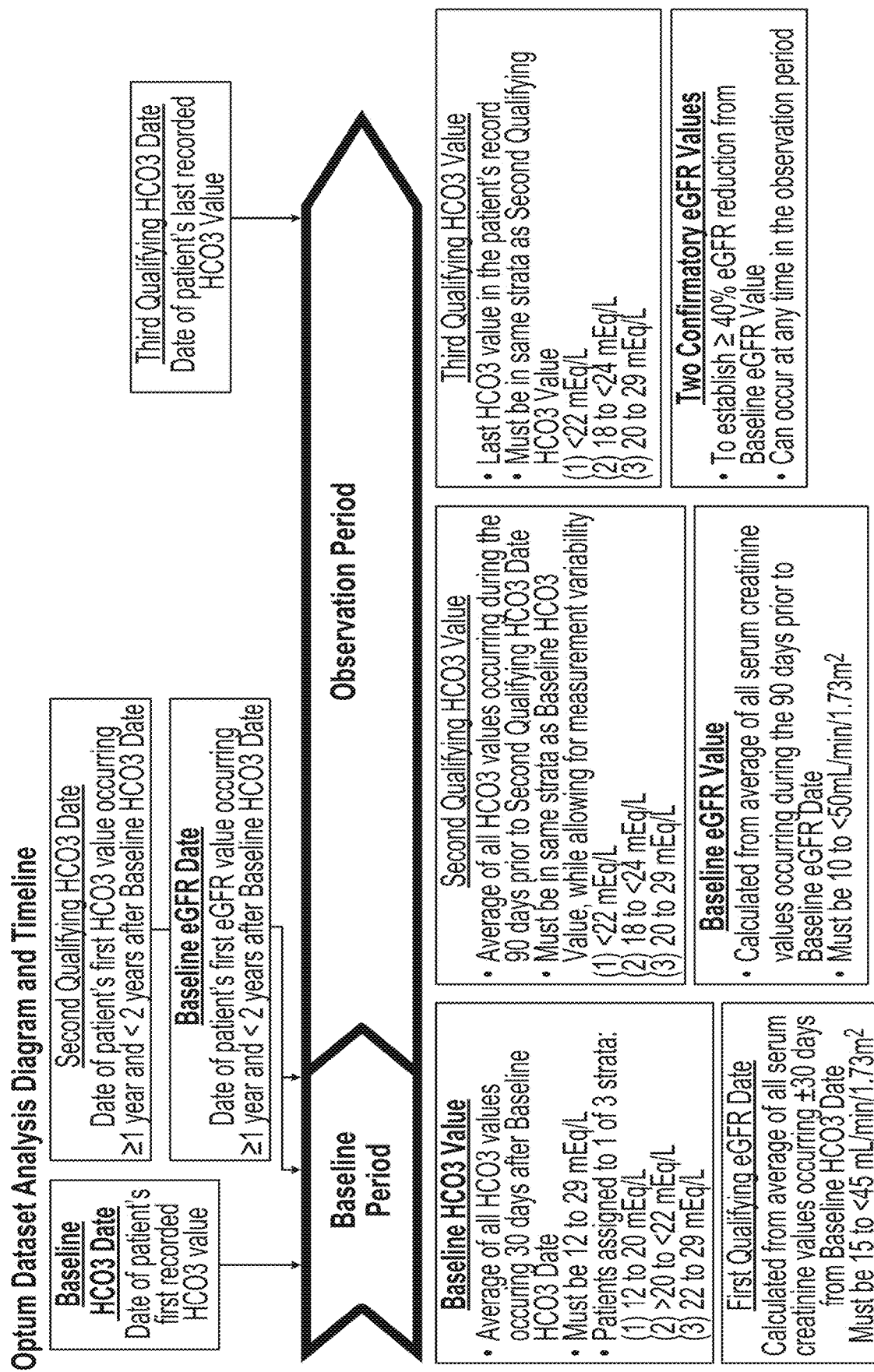

FIG. 15 is a dataset analysis diagram and timeline, as described in greater detail in Example 4.

Figure 16:
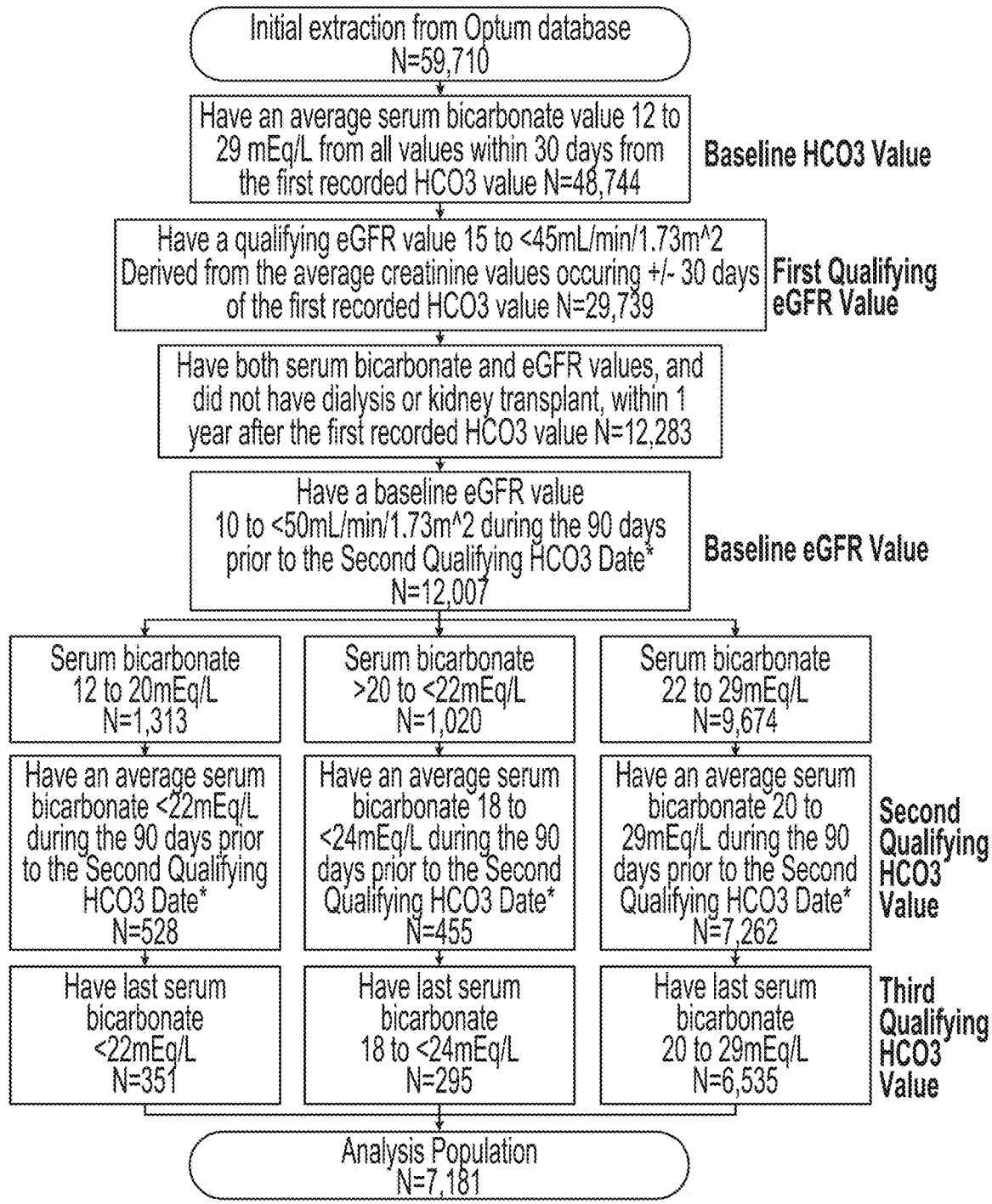

FIG. 16 is a population analysis flow chart, as described in greater detail in Example 4.

Figure 17:
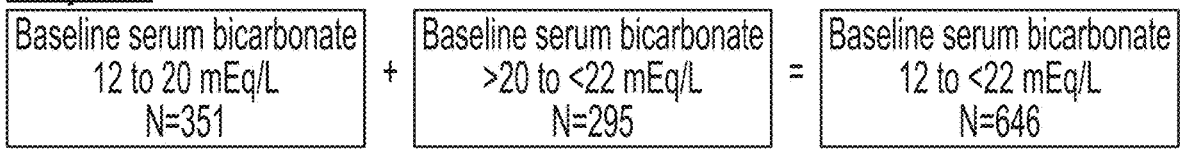
Figure 17:
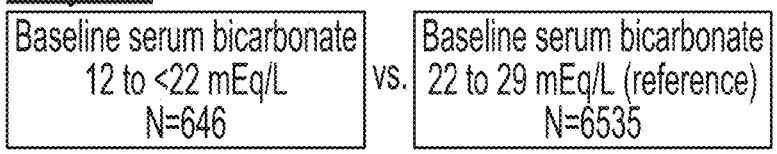
Figure 17:
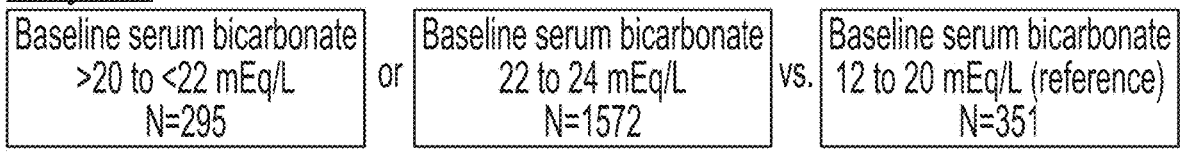

FIG. 17 is an illustration of the subpopulation used in the Cox Regression Analysis, as described in greater detail in Example 4.

Figure 18:
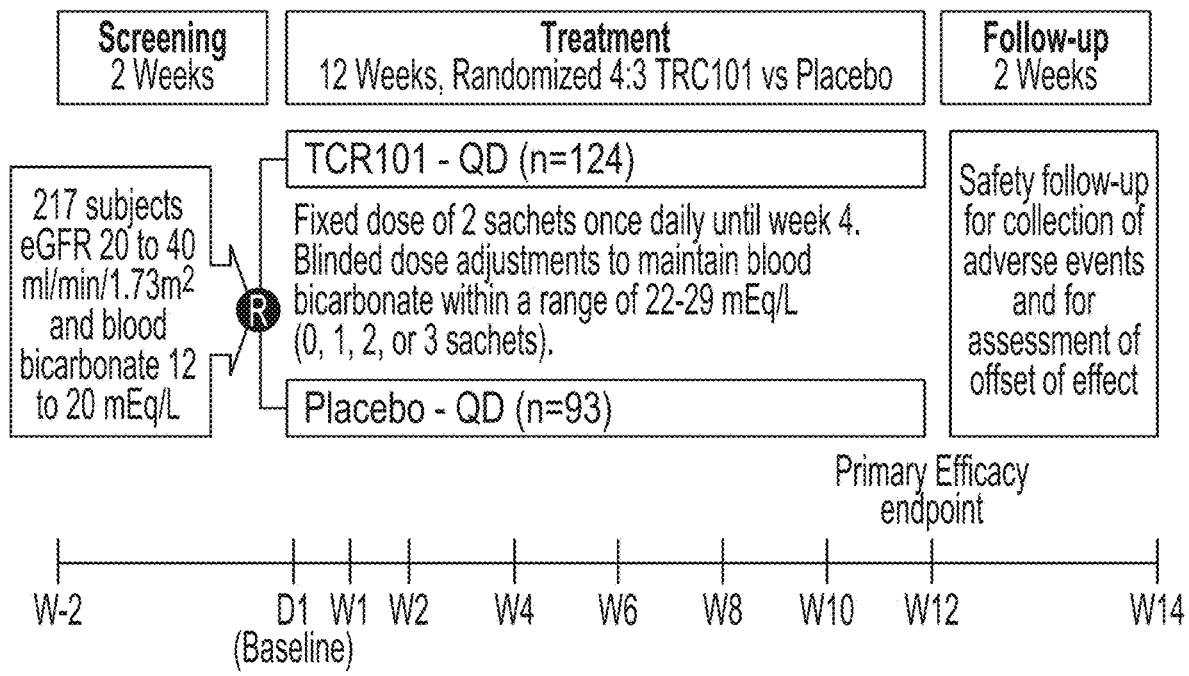

FIG. 18 is an analysis diagram and timeline for the clincial trial as described in more detail in Example 5.

Figure 19A:
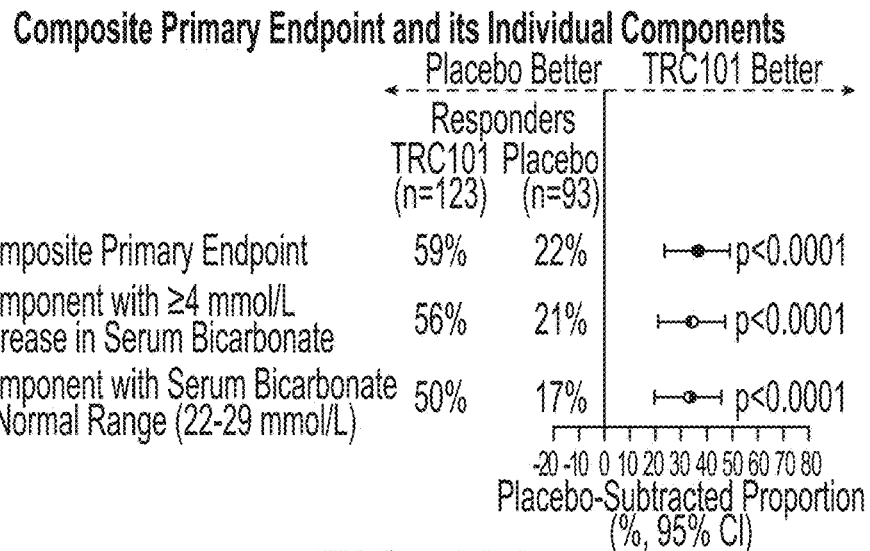

FIG. 19A is a graph showing the composite primary endpoint at the end of the treatment period for the clinical study described in more detail in Example 5.

Figure 19B:
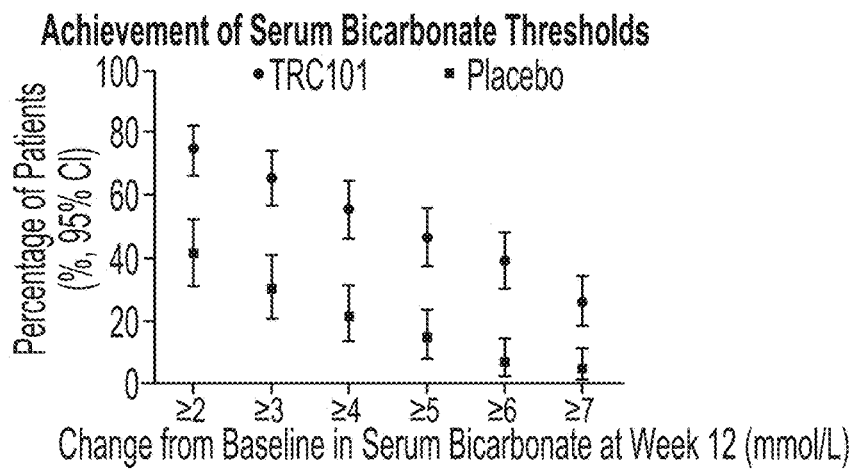

FIG. 19B is a graph showing the achievement of serum bicarbonate thresholds at various time points for the clinical study described in more detail in Example 5.

Figure 19C:
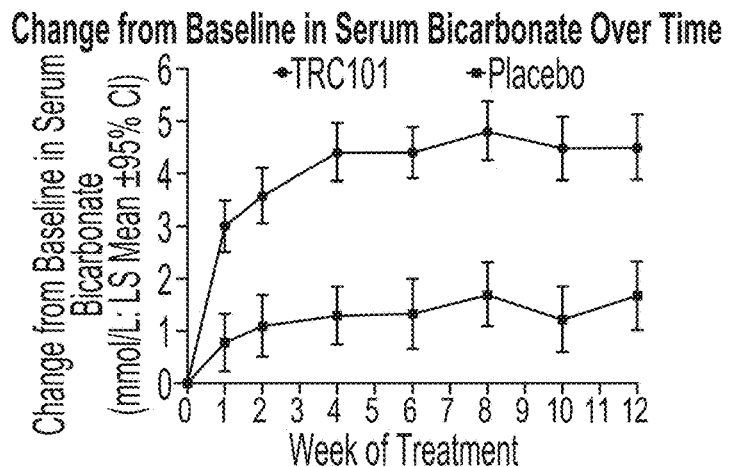

FIG. 19C is a graph showing the change from baseline in serum bicarbonate over time at various time points for the clinical study described in more detail in Example 5.

Figure 20A:
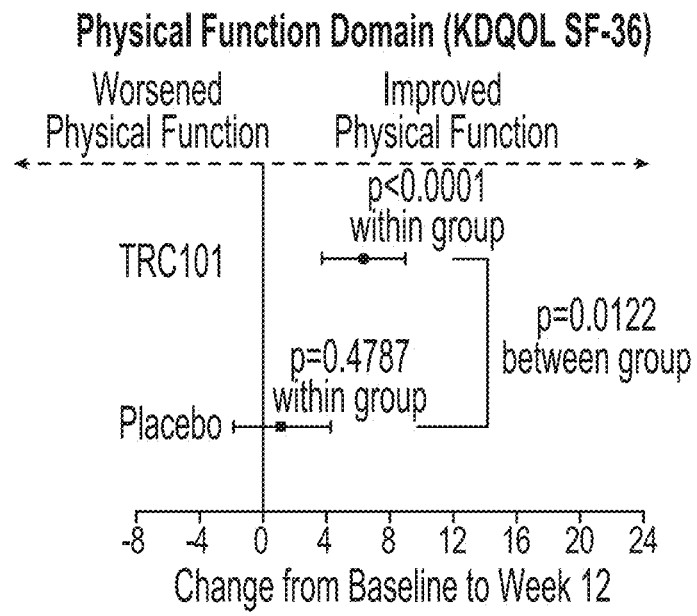
Figure 20B:
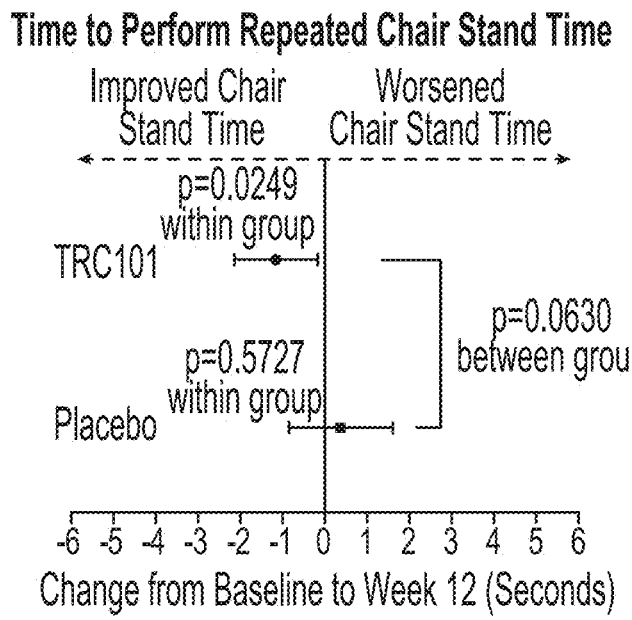

FIGS. 20A-20B are graphs showing that TRC101-treated subjects experienced a statistically significant improvement in quality of life, particularly, in physical function, based on results from Question #3 of the KDQOL-SF survey for the clinical study described in more detail in Example 5.

FIG. 21 is a copy of Question #3 of the KDQOL-SF survey for the clinical study described in Example 5. The score conversion is as follows: 1 (limited a lot)=0; 2 (limited a little)=50; 3 (not limited)=100. Total score=sum of all 10, divided by 10.

FIG. 22A is a copy of the Single Chair Stand and Repeated Chair Stand protocols, including the scoring criteria (FIG. 22B), as described in more detail in Example 5.

FIG. 23 is table showing the analysis from baseline in total score in kidney disease and quality of life (Question 3) at week 12, as described in more detail in Example 5.

FIG. 24 is a table showing the analysis from baseline in time (seconds) of completing repeated chair stand at the end of week 12, as described in more detail in Example 5.

DETAILED DESCRIPTION OF THE INVENTION

Abbreviations and Definitions

The following definitions and methods are provided to better define the present invention and to guide those of ordinary skill in the art in the practice of the present invention. Unless otherwise noted, terms are to be understood according to conventional usage by those of ordinary skill in the relevant art.

The term "absorption capacity" as used herein in connection with a polymer and a swelling agent (or in the case of a mixture of swelling agents, the mixture of swelling agents) is the amount of the swelling agent (or such mixture) absorbed during a period of at least 16 hours at room temperature by a given amount of a dry polymer (e.g., in the form of a dry bead) immersed in an excess amount of the swelling agent (or such mixture).

The term "acrylamide" denotes a moiety having the structural formula $H_2C=CH-C(O)NR-$*, where * denotes the point of attachment of the moiety to the remainder of the molecule and R is hydrogen, hydrocarbyl, or substituted hydrocarbyl.

The term "acrylic" denotes a moiety having the structural formula $H_2C=CH-C(O)O-$*, where * denotes the point of attachment of the moiety to the remainder of the molecule.

The term "adult" refers to an individual over 18 years of age.

The term "alicyclic", "alicyclo" or "alicyclyl" means a saturated monocyclic group of 3 to 8 carbon atoms and includes cyclopentyl, cyclohexyl, cycloheptyl, and the like.

The term "aliphatic" denotes saturated and non-aromatic unsaturated hydrocarbyl moieties having, for example, one to about twenty carbon atoms or, in specific embodiments, one to about twelve carbon atoms, one to about ten carbon atoms, one to about eight carbon atoms, or even one to about four carbon atoms. The aliphatic groups include, for example, alkyl moieties such as methyl, ethyl, n-propyl, isopropyl, n-butyl, isobutyl, sec-butyl, tert-butyl, pentyl, iso-amyl, hexyl and the like, and alkenyl moieties of comparable chain length.

The term "alkanol" denotes an alkyl moiety that has been substituted with at least one hydroxyl group. In some embodiments, alkanol groups are "lower alkanol" groups comprising one to six carbon atoms, one of which is attached to an oxygen atom. In other embodiments, lower alkanol groups comprise one to three carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In certain embodiments, alkenyl groups are "lower alkenyl" groups having two to about four carbon atoms. Examples of alkenyl groups include, but are not limited thereto, ethenyl, propenyl, allyl, vinyl, butenyl and 4-methylbutenyl. The terms "alkenyl group" and "lower alkenyl group", encompass groups having "cis" or "trans" orientations, or alternatively, "E" or "Z" orientations.

The term "alkyl group" as used, either alone or within other terms such as "haloalkyl group," "aminoalkyl group" and "alkylamino group", encompasses saturated linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkylamino group" refers to amino groups directly attached to the remainder of the molecule via the nitrogen atom of the amino group and wherein the nitrogen atom of the alkylamino group is substituted by one or two alkyl groups. In some embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino, pentamethyleneamine and the like.

The term "allyl" denotes a moiety having the structural formula $H_2C=CH-CH_2-*_1$ where * denotes the point of attachment of the moiety to the remainder of the molecule and the point of attachment is to a heteroatom or an aromatic moiety.

The term "allylamine" denotes a moiety having the structural formula $H_2C=CH-CH_2N(X_8)(X_9)$, wherein $X_8$ and $X_9$ are independently hydrogen, hydrocarbyl, or substituted hydrocarbyl, or $X_8$ and $X_9$ taken together form a substituted or unsubstituted alicyclic, aryl, or heterocyclic moiety, each as defined in connection with such term, typically having from 3 to 8 atoms in the ring.

The term "amine" or "amino" as used alone or as part of another group, represents a group of formula $—N(X_8)(X_9)$, wherein $X_8$ and $X_9$ are independently hydrogen, hydrocarbyl, or substituted hydrocarbyl, heteroaryl, or heterocyclo, or $X_8$ and $X_9$ taken together form a substituted or unsubstituted alicyclic, aryl, or heterocyclic moiety, each as defined in connection with such term, typically having from 3 to 8 atoms in the ring.

The term "aminoalkyl group" encompasses linear or branched alkyl groups having one to about ten carbon atoms, any one of which may be substituted with one or more amino groups, directly attached to the remainder of the molecule via an atom other than a nitrogen atom of the amine group(s). In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The terms "anion exchange material" and "cation exchange material" take their normal meaning in the art. For example, the terms "anion exchange material" and "cation exchange material" refer to materials that exchange anions and cations, respectively. Anion and cation exchange materials are typically water-insoluble substances which can exchange some of their cations or anions, respectively, for similarly charged anions or cations contained in a medium with which they are in contact. Anion exchange materials may contain positively charged groups, which are fixed to the backbone materials and allow passage of anions but reject cations. A non-exhaustive list of such positively charged groups includes: amino group, alkyl substituted phosphine, and alkyl substituted sulphides. A non-exhaustive list of cation or anion exchange materials includes: clays (e.g., bentonite, kaolinite, and illite), vermiculite, zeolites (e.g., analcite, chabazite, sodalite, and clinoptilolite), synthetic zeolites, polybasic acid salts, hydrous oxides, metal ferrocyanides, and heteropolyacids. Cation exchange materials can contain negatively charged groups fixed to the backbone material, which allow the passage of cations but reject anions. A non-exhaustive list of such negatively charged groups includes: sulphate, carboxylate, phosphate, and benzoate.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 5 to 10 carbon atoms, typically 5 to 7 carbon atoms, and more typically 5 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "bead" is used to describe a crosslinked polymer that is substantially spherical in shape.

The term "bicarbonate equivalent" is used to describe an organic acid or anion that yields bicarbonate when metabolized. Citrate and succinate are exemplary bicarbonate equivalents.

The term "binds" as used herein in connection with a polymer and one or more ions, that is, a cation (e.g. "proton-binding" polymer) and an anion, is an "ion-binding" polymer and/or when it associates with the ion, generally though not necessarily in a non-covalent manner, with sufficient association strength that at least a portion of the ion remains bound under the in vitro or in vivo conditions in which the polymer is used for sufficient time to effect a removal of the ion from solution or from the body.

The term "ceramic material" takes its normal meaning in the art. In certain embodiments, the term "ceramic material" refers to an inorganic, nonmetallic, solid material comprising metal, nonmetal or metalloid atoms primarily held in ionic and covalent bonds. A non-exhaustive list of examples of ceramic materials includes: barium titanate, bismuth strontium calcium copper oxide, boron oxide, earthenware, ferrite, lanthanum carbonate, lead zirconate, titanate, magnesium diboride, porcelain, sialon, silicon carbide, silicon nitride, titanium carbide, yttrium barium copper oxide, zinc oxide, zirconium dioxide, and partially stabilised zirconia. In certain embodiments, the term "clinically significant increase" as used herein in connection with a treatment refers to a treatment that improves or provides a worthwhile change in an individual from a dysfunctional state back to a relatively normal functioning state, or moves the measurement of that state in the direction of normal functioning, or at least a marked improvement to untreated. A number of methods can be used to calculate clinical significance. A non-exhaustive list of methods for calculating clinical significance includes: Jacobson-Truax, Gulliksen-Lord-Novick, Edwards-Nunnally, Hageman-Arrindell, and Hierarchical Linear Modeling (HLM).

The term "crosslink density" denotes the average number of connections of the amine containing repeat unit to the rest of the polymer. The number of connections can be 2, 3, 4 and higher. Repeat units in linear, non-crosslinked polymers are incorporated via 2 connections. To form an insoluble gel, the number of connections should be greater than 2. Low crosslinking density materials such as sevelamer have on average about 2.1 connections between repeat units. More crosslinked systems such as bixalomer have on average about 4.6 connections between the amine-containing repeat units. "Crosslinking density" represents a semi-quantitative measure based on the ratios of the starting materials used. Limitations include the fact that it does not account for different crosslinking and polymerization methods. For example, small molecule amine systems require higher amounts of crosslinker as the crosslinker also serves as the monomer to form the polymer backbone whereas for radical polymerizations the polymer chain is formed independent from the crosslinking reaction. This can lead to inherently higher crosslinking densities under this definition for the substitution polymerization/small molecule amines as compared to radical polymerization crosslinked materials.

The term "crosslinker" as used, either alone or within other terms, encompasses hydrocarbyl or substituted hydrocarbyl, linear or branched molecules capable of reacting with any of the described monomers, or the infinite polymer network, as described in Formula 1, more than one time. The reactive group in the crosslinker can include, but is not limited to alkyl halide, epoxide, phosgene, anhydride, carbamate, carbonate, isocyanate, thioisocyanate, esters, activated esters, carboxylic acids and derivatives, sulfonates and derivatives, acyl halides, aziridines, α,β-unsaturated carbonyls, ketones, aldehydes, pentafluoroaryl groups, vinyl, allyl, acrylate, methacrylate, acrylamide, methacrylamide, styrenic, acrylonitriles and combinations thereof. In one exemplary embodiment, the crosslinker's reactive group will include alkyl halide, epoxide, anhydrides, isocyanates, allyl, vinyl, acrylamide, and combinations thereof. In one such embodiment, the crosslinker's reactive group will be alkyl halide, epoxide, or allyl.

The term "diallylamine" denotes an amino moiety having two allyl groups.

The terms "dry bead" and "dry polymer" refer to beads or polymers that contain no more than 5% by weight of a non-polymer swelling agent or solvent. Often the swelling agent/solvent is water remaining at the end of a purification. This is generally removed by lyophilization or oven drying before storage or further crosslinking of a preformed amine polymer. The amount of swelling agent/solvent can be measured by heating (e.g., heating to 100-200° C.) and measuring the resulting change in weight. This is referred to a "loss on drying" or "LOD."

The term "estimated glomerular filtration rate" or eGFR refers to an estimate of the glomerular filtration rate and is estimated from the serum level of an endogenous filtration marker. Creatinine is a commonly used endogenous filtration marker in clinical practice and several equations have been proposed for estimating the glomerular filtration rate. As used herein, all eGFR values may be determined according to the CKD-EPI equation (Levey et al., A New Equation to Estimate Glomerular Filtration Rate. Ann Intern Med. 2009; 150:604-612):

$$GFR=141*min(Scr/\kappa,1)^{\alpha}*max(Scr/\kappa,1)^{-1.209}*0.993^{Age}*1.018[\text{if female}]*1.159[\text{if black}]$$

wherein Scr is serum creatinine (mg/dL), $\kappa$ is 0.7 for females and 0.9 for males, $\alpha$ is -0.329 for females and -0.411 for males, min indicates the minimum of Scr/$\kappa$ or 1, and max indicates the maximum of Scr/$\kappa$ or 1.

The term "ethereal" denotes a moiety having an oxygen bound to two separate carbon atoms as depicted the structural formula *—$H_xC$—O—$CH_x$—*, where *denotes the point of attachment to the remainder of the moiety and x independently equals 0, 1, 2, or 3.

The term "gel" is used to describe a crosslinked polymer that has an irregular shape.

The term "glomerular filtration rate" or GFR is the volume of fluid filtered from the renal (kidney) glomerular capillaries into the Bowman's capsule per unit time. GFR cannot be measured directly; instead, it is measured indirectly (mGFR) as the clearance of an exogenous filtration marker (e.g., inulin, iothalamate, iohexol, etc.) or estimated (eGFR) using an endogenous filtration marker.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "heteroaliphatic" describes a chain of 1 to 25 carbon atoms, typically 1 to 12 carbon atoms, more typically 1 to 10 carbon atoms, and most typically 1 to 8 carbon atoms, and in some embodiments 1 to 4 carbon atoms that can be saturated or unsaturated (but not aromatic), containing one or more heteroatoms, such as halogen, oxygen, nitrogen, sulfur, phosphorus, or boron. A heteroatom atom may be a part of a pendant (or side) group attached to a chain of atoms (e.g., —CH(OH)— —CH($NH_2$)— where the carbon atom is a member of a chain of atoms) or it may be one of the chain atoms (e.g., —ROR— or —RNHR— where each R is aliphatic). Heteroaliphatic encompasses heteroalkyl and heterocyclo but does not encompass heteroaryl.

The term "heteroalkyl" describes a fully saturated heteroaliphatic moiety.

The term "heteroaryl" means a monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. "Heteroarylene" means a divalent heteroaryl radical.

The term "heteroatom" means an atom other than carbon and hydrogen. Typically, but not exclusively, heteroatoms are selected from the group consisting of halogen, sulfur, phosphorous, nitrogen, boron and oxygen atoms. Groups containing more than one heteroatom may contain different heteroatoms.

The term "heterocyclo," "heterocyclic," or heterocyclyl means a saturated or unsaturated group of 4 to 8 ring atoms in which one or two ring atoms are heteroatom such as N, O, B, P and $S(O)_n$, where n is an integer from 0 to 2, the remaining ring atoms being carbon. Additionally, one or two ring carbon atoms in the heterocyclyl ring can optionally be replaced by a —C(O)— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

"Initiator" is a term used to describe a reagent that initiates a polymerization.

The term "measured glomerular filtration rate" or "mGFR" refers to a measurement of the glomerular filtration rate using any chemical (e.g., inulin, iothalamate, iohexol, etc.) that has a steady level in the blood, and is freely filtered but neither reabsorbed nor secreted by the kidneys according to standard technique.

The term "Michael acceptor" takes its normal meaning in the art. In certain embodiments the term "Michael acceptor" refers to activated olefins, such as $\alpha,\beta$-unsaturated carbonyl compounds. A Michael acceptor can be a conjugated system with an electron withdrawing group, such as cyano, keto or ester. A non-exhaustive list of examples of Michael acceptors includes: vinyl ketones, alkyl acrylates, acrylo nitrile, and fumarates.

The term "molecular weight per nitrogen" or "MW/N" represents the calculated molecular weight in the polymer per nitrogen atom. It represents the average molecular weight to present one amine function within the crosslinked polymer. It is calculated by dividing the mass of a polymer sample by the moles of nitrogen present in the sample. "MW/N" is the inverse of theoretical capacity, and the calculations are based upon the feed ratio, assuming full reaction of crosslinker and monomer. The lower the molecular weight per nitrogen the higher the theoretical capacity of the crosslinked polymer.

The term "nonabsorbable" as used herein takes its normal meaning in the art. Therefore, if something is nonabsorbable it is not absorbed during its passage through the human GI tract. This could be measured by any appropriate means. One option known to the skilled person would be to examine faeces to see if the nonabsorbable material is recovered after passing through the GI tract. As a practical matter, the amount of a nonabsorbable material recovered in this scenario will never be 100% of the material administered. For example, about 90-99% of the material might be recovered from the faeces. Another option known to the skilled person would be to look for the presence of the material in the lymph, blood, interstitial fluid, secretions from various organs (e.g., pancreas, liver, gut, etc.) or in the body of organs (e.g., liver, kidney, lungs, etc.) as oral administration of a nonabsorbable material would not result in an increase in the amount of that material in these matrices and tissues. Nonabsorbable compositions may be particulate compositions that are essentially insoluble in the human GI tract and have a particle size that is large enough to avoid passive or active absorption through the human GI tract. As an example, nonabsorbable compositions is meant to imply that the substance does not enter the lymph, blood, interstitial fluids or organs through the main entry points of the human GI tract, namely by paracellular entry between gut epithelial cells, by endocytic uptake through gut epithelial cells, or through entry via M cells comprising the gut epithelial antigen sampling and immune surveillance system (Jung, 2000), either through active or passive transport processes. There is a known size limit for a particulate to be absorbed in the human GI tract (Jung et al., European Journal of Pharmaceutics and Biopharmaceutics 50 (2000) 147-160; Jani et al., Internation. Journal of Pharmaceutics, 84 (1992) 245-252; and Jani et al., J. Pharm. Pharmacol. 1989, 41:809-812), so the skilled person would know that materials that, when in the GI tract, have a size of at least 1 micrometers would be nonabsorbable.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes embodiments in which the heterocyclyl group is substituted with an alkyl group and embodiments in which the heterocyclyl group is not substituted with alkyl.

"Particle size" is measured by wet laser diffraction using Mie theory. Particles are dispersed in an appropriate solvent, such as water or methanol, and added to the sample chamber to achieve red channel obscuration of 10-20%. Sonication may be performed, and a dispersing agent, such as a surfactant (e.g. Tween-80), may be added in order to disrupt weak particle-particle interactions. The refractive index setting of the particles used for size distribution calculation is selected to minimize artifacts in the results and the R parameter value, determined by the laser diffraction software. The D(0.1), D(0.5), and D(0.9) values characterizing the particle size distribution by volume-basis are recorded.

"Pharmaceutically acceptable" as used in connection with a carrier, diluent or excipient means a carrier, diluent or an excipient, respectively, that is useful in preparing a pharmaceutical composition that is generally safe, non-toxic and neither biologically nor otherwise undesirable for veterinary use and/or human pharmaceutical use.

The term "physical function" as used herein in connection with a patient afflicted with chronic kidney disease and an acid-base disorder may be assessed using (i) the Kidney Disease and Quality of Life (KDQOL) Short Form-36, Question 3 (Physical Functioning Domain) as illustrated in FIGS. 22A & 22B and Example 5, or (iii) both the KDQOL Short Form-36 Question 3 and the standardized repeated chair stand test (i.e., "i" and "ii" of this paragraph).

The term "post polymerization crosslinking" is a term that describes a reaction to an already formed bead or gel, where more crosslinking is introduced to the already formed bead or gel to create a bead or gel that has an increased amount of crosslinking.

The term "post polymerization modification" is a term that describes a modification to an already formed bead or gel, where a reaction or a treatment introduces an additional functionality. This functionality can be linked either covalently or non-covalently to the already formed bead.

The term "quaternized amine assay" ("QAA") describes a method to estimate the amount of quaternary amines present in a given crosslinked polymer sample. This assay measures chloride binding of a crosslinked polymer at a pH of 11.5. At this pH, primary, secondary and tertiary amines are not substantially protonated and do not substantially contribute to chloride binding. Therefore, any binding observed under these conditions can be attributed to the presence of permanently charged quaternary amines. The test solution used for QAA assay is 100 mM sodium chloride at a pH of 11.5. The concentration of chloride ions is similar to that in the SGF assay which is used to assess total binding capacity of crosslinked polymers. Quaternary amine content as a percentage of total amines present is calculated as follows:

$$\% \text{ Quaternary amines} = \frac{\text{Chloride bound (mmol/g) in } QAA}{\text{Chloride bound (mmol/g) in } SGF} \times 100$$

To perform the QAA assay, the free-amine polymer being tested is prepared at a concentration of 2.5 mg/ml (e.g. 25 mg dry mas) in 10 mL of QAA buffer. The mixture is incubated at 37° C. for ~16 hours with agitation on a rotisserie mixer. After incubation and mixing, 600 microliters of supernatant is removed and filtered using a 800 microliter, 0.45 micrometer pore size, 96-well poly propylene filter plate. With the samples arrayed in the filter plate and the collection plate fitted on the bottom, the unit is centrifuged at 1000×g for 1 minute to filter the samples. After filtration into the collection plate, the respective filtrates are diluted appropriately before measuring for chloride content. The IC method (e.g. ICS-2100 Ion Chromatography, Thermo Fisher Scientific) used for the analysis of chloride content in the filtrates consists of a 15 mM KOH mobile phase, an injection volume of 5 microliters, with a run time of three minutes, a washing/rinse volume of 1000 microliters, and flow rate of 1.25 mL/min. To determine the chloride bound to the polymer, the following calculation is completed:

Binding capacity expressed as mmol chloride/g dry polymer =

$$\frac{(\text{Cl start} - \text{Cl } eq)}{2.5}$$

where Cl start corresponds to the starting concentration of chloride in the QAA buffer, Cl eq corresponds to the equilibrium value of chloride in the measured filtrates after exposure to the test polymer, and 2.5 is the polymer concentration in mg/ml.

The terms "short chain carboxylic acid" or "short chain fatty acid" take their normal meaning in the art. In certain embodiments, the terms "short chain carboxylic acid" or "short chain fatty acid" refer to carboxylic acids having a chain length of 0, 1, 2, 3, 4, 5 or 6 carbon atoms long. A non-exhaustive list of examples of short chain carboxylic acids includes: formic acid, acetic acid, propionic acid, butyric acid, isobutyric acid, valeric acid, isovaleric acid, and lactic acid.

"Simulated Gastric Fluid" or "SGF" Assay describes a test to determine total chloride binding capacity for a test polymer using a defined buffer that simulates the contents of gastric fluid as follows: Simulated gastric fluid (SGF) consists of 35 mM NaCl, 63 mM HCl, pH 1.2. To perform the assay, the free-amine polymer being tested is prepared at a concentration of 2.5 mg/ml (25 mg dry mass) in 10 mL of SGF buffer. The mixture is incubated at 37° C. overnight for ~12-16 hours with agitation on a rotisserie mixer. Unless another time period is otherwise stated, SGF binding data or binding capacities recited herein are determined in a time period of this duration. After incubation and mixing, the tubes containing the polymer are centrifuged for 2 minutes at 500-1000×g to pellet the test samples. Approximately 750 microliters of supernatant are removed and filtered using an appropriate filter, for example a 0.45 micrometer pore-size syringe filter or an 800 microliter, 1 micrometer pore-size, 96-well, glass filter plate that has been fitted over a 96-well 2 mL collection plate. With the latter arrangement, multiple samples tested in SGF buffer can be prepared for analysis, including the standard controls of free amine sevelamer, free amine bixalomer and a control tube containing blank buffer that is processed through all of the assay steps. With the samples arrayed in the filter plate and the collection plate fitted on the bottom, the unit is centrifuged at 1000×g for 1 minute to filter the samples. In cases of small sample sets, a syringe filter may be used in lieu of the filter plate, to retrieve ~2-4 mL of filtrate into a 15 mL container. After filtration, the respective filtrates are diluted 4× with water and the chloride content of the filtrate is measured via ion chromatography (IC). The IC method (e.g. Dionex ICS-2100, Thermo Scientific) consists of an AS11 column and a 15 mM KOH mobile phase, an injection volume of 5 microliters, with a run time of 3 minutes, a washing/rinse volume of 1000 microliters, and flow rate of 1.25 mL/min. To determine the chloride bound to the polymer, the following calculation is completed:

$$\frac{(\text{Cl start} - \text{Cl } eq) \times 4}{2.5}.$$

Binding capacity expressed as mmol chloride/g polymer: where Cl start corresponds to the starting concentration of chloride in the SGF buffer, Cl eq corresponds to the equilibrium value of chloride in the diluted measured filtrates after exposure to the test polymer, 4 is the dilution factor and 2.5 is the polymer concentration in mg/ml.

"Simulated Small Intestine Inorganic Buffer" or "SIB" is a test to determine the chloride and phosphate binding capacity of free amine test polymers in a selective specific interfering buffer assay (SIB). The chloride and phosphate binding capacity of free amine test polymers, along with the chloride and phosphate binding capacity of free amine sevelamer and bixalomer control polymers, was determined using the selective specific interfering buffer assay (SIB) as follows: The buffer used for the SIB assay comprises 36 mM NaCl, 20 mM NaH$_2$PO$_4$, 50 mM 2-(N-morpholino)ethanesulfonic acid (MES) buffered to pH 5.5. The SIB buffer contains concentrations of chloride, phosphate and pH that are present in the human duodenum and upper gastrointestinal tract (Stevens T, Conwell D L, Zuccaro G, Van Lente F, Khandwala F, Purich E, et al. Electrolyte composition of endoscopically collected duodenal drainage fluid after synthetic porcine secretin stimulation in healthy subjects. Gastrointestinal endoscopy. 2004; 60(3):351-5, Fordtran J, Locklear T. Ionic constituents and osmolality of gastric and small-intestinal fluids after eating. Digest Dis Sci. 1966; 11(7):503-21) and is an effective measure of the selectivity of chloride binding compared to phosphate binding by a polymer. To perform the assay, the free amine polymer being tested is prepared at a concentration of 2.5 mg/ml (25 mg dry mass) in 10 mL of SIB buffer. The mixture is incubated at 37° C. for 1 hour with agitation on a rotisserie mixer. Unless another time period is otherwise stated, SIB binding data or binding capacities recited herein are determined in a time period of this duration. After incubation and mixing, the tubes containing the polymer are centrifuged for 2 minutes at 1000×g to pellet the test samples. 750 microliter of supernatant is removed and filtered using an 800 microliter, 1 micrometer pore-size, 96-well, glass filter plate that has been fitted over a 96-well 2 mL collection plate; with this arrangement multiple samples tested in SIB buffer can be prepared for analysis, including the standard controls of free amine sevelamer, free amine bixalomer and a control tube containing blank buffer that is processed through all of the assay steps. With the samples arrayed in the filter plate and the collection plate fitted on the bottom, the unit is centrifuged at 1000×g for 1 minute to filter the samples. In cases of small sample sets, a syringe filter (0.45 micrometer) may be used in lieu of the filter plate, to retrieve ~2-4 mL of filtrate into a 15 mL vial. After filtration into the collection plate, the respective filtrates are diluted before measuring for chloride or phosphate content. For the measurement of chloride and phosphate, the filtrates under analysis are diluted 4× with water. The chloride and phosphate content of the filtrate is measured via ion chromatography (IC). The IC method (e.g. Dionex ICS-2100, Thermo Scientific) consists of an AS24A column, a 45 mM KOH mobile phase, an injection volume of 5 microliters, with a run time of about 10 minutes, a washing/rinse volume of 1000 microliter, and flow rate of 0.3 m L/m in. To determine the chloride bound to the polymer, the following calculation is completed:

Binding capacity expressed as mmol chloride/g polymer =
$$\frac{(Cl_{start} - Cl_{final}) \times 4}{2.5}$$

where $Cl_{start}$ corresponds to the starting concentration of chloride in the SIB buffer, $Cl_{final}$ corresponds to the final value of chloride in the measured diluted filtrates after exposure to the test polymer, 4 is the dilution factor and 2.5 is the polymer concentration in mg/ml. To determine the phosphate bound to the polymer, the following calculation is completed:

Binding capacity expressed as mmol phosphate/g polymer =
$$\frac{(P_{start} - P_{final}) \times 4}{2.5}$$

where $P_{start}$ corresponds to the starting concentration of phosphate in the SIB buffer, $P_{final}$ corresponds to the final value of phosphate in the measured diluted filtrates after exposure to the test polymer, 4 is the dilution factor and 2.5 is the polymer concentration in mg/ml.

In certain embodiments, the term "statistically significant" refers to the likelihood that a relationship between two or more variables is caused by something other than random chance. More precisely, the significance level, a, defined for a study is the probability of the study rejecting the null hypothesis, given that it were true, and the p-value, p, of a result is the probability of obtaining a result at least as extreme, given that the null hypothesis were true. The result is statistically significant, by the standards of the study, when p<α. The significance level for a study is chosen before data collection, and typically set to 5%

The term "substituted hydrocarbyl," "substituted alkyl," "substituted alkenyl," "substituted aryl," "substituted heterocyclo," or "substituted heteroaryl" as used herein denotes hydrocarbyl, alkyl, alkenyl, aryl, heterocyclo, or heteroaryl moieties which are substituted with at least one atom other than carbon and hydrogen, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, keto, acyl, acyloxy, nitro, amino, amido, nitro, cyano, thiol, ketals, acetals, esters and ethers.

"Swelling Ratio" or simply "Swelling" describes the amount of water absorbed by a given amount of polymer divided by the weight of the polymer aliquot. The Swelling Ratio is expressed as: swelling=(g swollen polymer—g dry polymer)/g dry polymer. The method used to determine the Swelling Ratio for any given polymer comprised the following:
 a. 50-100 mg of dry (less than 5 wt % water content) polymer is placed into an 11 mL sealable test tube (with screw cap) of known weight (weight of tube=Weight A).
 b. Deionized water (10 mL) is added to the tube containing the polymer. The tube is sealed and tumbled for 16 hours (overnight) at room temperature. After incubation, the tube is centrifuged at 3000×g for 3 minutes and the supernatant is carefully removed by vacuum suction. For polymers that form a very loose sediment, another step of centrifugation is performed.
 c. After step (b), the weight of swollen polymer plus tube (Weight B) is recorded.
 d. Freeze at –40° C. for 30 minutes. Lyophilize for 48 h. Weigh dried polymer and test tube (recorded as Weight C).
 e. Calculate g water absorbed per g of polymer, defined as: [(Weight B–Weight A)–(Weight C–Weight A)]/(Weight C–Weight A).

A "target ion" is an ion to which the polymer binds, and usually refers to the major ions bound by the polymer, or the ions whose binding to the polymer is thought to produce the therapeutic effect of the polymer (e.g., proton and chloride binding which leads to net removal of HCl).

The term "theoretical capacity" represents the calculated, expected binding of hydrochloric acid in an "SGF" assay, expressed in mmol/g. The theoretical capacity is based on the assumption that 100% of the amines from the monomer(s) and crosslinker(s) are incorporated in the cross-linked polymer based on their respective feed ratios. Theoretical capacity is thus equal to the concentration of amine functionalities in the polymer (mmol/g). The theoretical capacity assumes that each amine is available to bind the respective anions and cations and is not adjusted for the type of amine formed (e.g. it does not subtract capacity of quaternary amines that are not available to bind proton).

"Therapeutically effective amount" means the amount of a proton-binding crosslinked polymer that, when administered to a patient for treating a disease, is sufficient to effect such treatment for the disease. The amount constituting a "therapeutically effective amount" will vary depending on the polymer, the severity of the disease and the age, weight, etc., of the mammal to be treated.

"Treating" or "treatment" of a disease includes (i) inhibiting the disease, i.e., arresting or reducing the development of the disease or its clinical symptoms; or (ii) relieving the disease, i.e., causing regression of the disease or its clinical symptoms. Inhibiting the disease, for example, would include prophylaxis.

The term "triallylamine" denotes an amino moiety having three allyl groups.

The term "vinyl" denotes a moiety having the structural formula $R_xH_yC=CH-*$, where * denotes the point of attachment of the moiety to the remainder of the molecule wherein the point of attachment is a heteroatom or aryl, X and Y are independently 0, 1 or 2, such that X+Y=2, and R is hydrocarbyl or substituted hydrocarbyl.

The term "weight percent crosslinker" represents the calculated percentage, by mass, of a polymer sample that is derived from the crosslinker. Weight percent crosslinker is calculated using the feed ratio of the polymerization, and assumes full conversion of the monomer and crosslinker(s). The mass attributed to the crosslinker is equal to the expected increase of molecular weight in the infinite polymer network after reaction (e.g., 1,3-dichloropropane is 113 amu, but only 42 amu are added to a polymer network after crosslinking with DCP because the chlorine atoms, as leaving groups, are not incorporated into the polymer network).

When introducing elements of the present invention or the preferred embodiments(s) thereof, the articles "a", "an", "the" and "said" are intended to mean that there are one or more of the elements. The terms "comprising", "including" and "having" are intended to be inclusive and not exclusive (i.e., there may be other elements in addition to the recited elements).

While the methods described above refer to daily dose, a further aspect of the disclosure include the methods disclosed herein in which the dose is administered less frequently than once per day (while still being administered on a regular basis). In any of the disclosure, the daily dose specified may, instead, be administrated on a less frequent basis. For example, the doses disclosed here may be administered once every two or three days. Or the doses disclosed here may be administered once, twice or three times a week.

The various aspects and embodiments disclosed in the claims may have a range of advantages, such as improved or successful treatment of eubicarbonatemic metabolic acidosis. Such improvements may also include reduced side effects, increased patient compliance, reduced drug loads, increased speed of treatment, increased magnitude of treatment, avoiding unwanted changes to other electrolytes and/ or reduced drug-drug interactions. Further useful features of the disclosed aspects can be found in the examples.

Embodiments

In accordance with the present disclosure, acid-base disorders associated with chronic kidney disease and characterized by a marker of eubicarbonatemic metabolic acidosis may be treated using pharmaceutical compositions comprising a nonabsorbable composition having the capacity to remove clinically significant quantities of protons, the conjugate base of one or more strong acids, and/or one or more strong acids. An individual afflicted with chronic kidney disease and having a baseline serum bicarbonate value of at least 22 mEq/l and at least one marker of eubicarbonatemic metabolic acidosis may thus be treated by oral administration of a pharmaceutical composition comprising the nonabsorbable composition which then transits the individual's digestive system, binds a target species (protons, one or more conjugate base(s) of a strong acid and/or one or more strong acid(s)) as it transits the digestive system, and removes the bound target species by normal biological function (defecation).

In general, the individual afflicted with acid/base disorder may be at any stage of chronic kidney disease. For example, in one embodiment the afflicted individual has not yet reached end stage renal disease ("ESRD") sometimes also referred to as end stage chronic kidney disease and is not yet on dialysis (i.e., the individual has a mGFR (or eGFR) of at least 15 mL/min/1.73 m$^2$). In some embodiments, the afflicted individual will be Stage 3B CKD (i.e., the individual has a mGFR (or eGFR) in the range of 30-44 mL/min/1.73 m$^2$ for at least three months). In some embodiments, the afflicted individual will be Stage 3A CKD (i.e., the individual has a mGFR (or eGFR) in the range of 45-59 mL/min/1.73 m$^2$ for at least three months). Thus, for example, in some embodiments the afflicted individual has a mGFR or an eGFR of less than 60 mL/min/1.73 m$^2$ for at least three months. By way of further example, in some embodiments the afflicted individual has a mGFR or an eGFR of less than 45 mL/min/1.73 m$^2$ for at least three months. By way of further example, in some embodiments the afflicted individual has a mGFR or an eGFR of less than 30 mL/min/1.73 m$^2$ for at least three months. By way of further example, in some embodiments the afflicted individual has a mGFR or an eGFR of 15-30, 15-45, 15-60, 30-45 or even 30-60 mL/min/1.73 m$^2$ for at least three months.

The baseline serum bicarbonate value may be the serum bicarbonate concentration determined at a single time point or may be the mean or median value of two or more serum bicarbonate concentrations determined at two or more time-points. For example, in one embodiment the baseline serum bicarbonate value may be the value of the serum bicarbonate concentration determined at a single time point and the baseline serum bicarbonate value is used as a basis to determine an acute acidic condition requiring immediate treatment. In another embodiment, the baseline serum bicarbonate treatment value is the mean value of the serum bicarbonate concentration for serum samples drawn at different time points (e.g., different days). By way of further example, in one such embodiment the baseline serum bicarbonate treatment value is the mean value of the serum bicarbonate concentration for serum samples drawn on different days (e.g., at least 2, 3, 4, 5 or more days, that may be consecutive or separated by one or more days or even weeks). By way of further example, in one such embodiment the baseline serum bicarbonate treatment value is the mean value of the serum bicarbonate concentration for serum samples drawn on two consecutive days preceding the initiation of treatment.

In one embodiment, the acid-base disorder being treated is characterized by a baseline serum bicarbonate value that is at least 22 mEq/l but not in excess of 24 mEq/l. For example, in one such embodiment the acid-base disorder being treated is characterized by a baseline serum bicarbonate value of at least 22 mEq/l. By way of further example, in one such embodiment the acid-base disorder being treated is characterized by a baseline serum bicarbonate value of at least 23 mEq/l.

In certain embodiments, the acid-base disorder being treated is characterized by a baseline serum bicarbonate value in the range of 22 to 24 mEq/l. By way of further example, in one such embodiment the acid-base disorder is characterized by a baseline serum bicarbonate value in the range of 22 to 23 mEq/l. By way of further example, in one such embodiment the acid-base disorder is characterized by a baseline serum bicarbonate value in the range of 23 to 24 mEq/l.

In certain embodiments, oral administration of a pharmaceutical composition containing a nonabsorbable composition increases the individual's serum bicarbonate value from baseline to an increased serum bicarbonate value that exceeds the baseline serum bicarbonate value by at least 1 mEq/l. For example, in one such embodiment the treatment increases the individual's serum bicarbonate value to an increased serum bicarbonate value that exceeds the baseline serum bicarbonate value by at least 1.5 mEq/l. By way of further example in one such embodiment the treatment increases the individual's serum bicarbonate value to an increased serum bicarbonate value that exceeds the baseline serum bicarbonate value by at least 2 mEq/l. By way of further example in one such embodiment the treatment the individual's serum bicarbonate value to an increased serum bicarbonate value that exceeds the baseline serum bicarbonate value by at least 2.5 mEq/l. By way of further example in one such embodiment the treatment increases the individual's serum bicarbonate value to an increased serum bicarbonate value that exceeds the baseline serum bicarbonate value by at least at least 3 mEq/l. By way of further example in one such embodiment the treatment increases the baseline serum bicarbonate value to an increased serum bicarbonate value that exceeds the baseline serum bicarbonate value by at least 3.5 mEq/l. By way of further example in one such embodiment the treatment increases the individual's serum bicarbonate value to an increased serum bicarbonate value that exceeds the baseline serum bicarbonate value by at least 4 mEq/l. By way of further example in one such embodiment the treatment increases the individual's serum bicarbonate value to an increased serum bicarbonate value that exceeds the baseline serum bicarbonate value by at least 5 mEq/l but does not exceed 29 mEq/l. By way of further example in one such embodiment the treatment increases the individual's serum bicarbonate value to an increased serum bicarbonate value that exceeds the baseline serum bicarbonate value by at least 5 mEq/l but does not exceed 28 mEq/l. By way of further example in one such embodiment the treatment increases the individual's serum bicarbonate value to an increased serum bicarbonate value that exceeds the baseline serum bicarbonate value by at least 5 mEq/l but does not exceed 27 mEq/l. By way of further example in one such embodiment the treatment increases the individual's serum bicarbonate value to an increased serum bicarbonate value that exceeds the baseline serum bicarbonate value by at least 6 mEq/l but does not exceed 29 mEq/l. By way of further example in one such embodiment the treatment increases the individual's serum bicarbonate value to an increased serum bicarbonate value that exceeds the baseline serum bicarbonate value by at least 6 mEq/l but does not exceed 28 mEq/l. By way of further example in one such embodiment the treatment increases the individual's serum bicarbonate value to an increased serum bicarbonate value that exceeds the baseline serum bicarbonate value by at least 7 mEq/l but does not exceed 29 mEq/l. In each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, treatment with the nonabsorbable composition increases the individual's serum bicarbonate value from a baseline serum bicarbonate value in the range of 22 to 24 mEq/l by at least 1 mEq/l. For example, in one such embodiment the treatment increases the individual's serum bicarbonate value from a baseline serum bicarbonate value in the range of 22 to 24 mEq/l by at least 1.5 mEq/l. By way of further example, in one such embodiment the treatment increases the individual's serum bicarbonate value from a baseline serum bicarbonate value in the range of 22 to 24 mEq/l by at least 2 mEq/l. By way of further example, in one such embodiment the treatment increases the individual's serum bicarbonate value from a baseline serum bicarbonate value in the range of 22 to 24 mEq/l by at least 2.5 mEq/l. By way of further example, in one such embodiment the treatment increases the individual's serum bicarbonate value from a baseline serum bicarbonate value in the range of 22 to 24 mEq/l by at least 3 mEq/l. By way of further example, in one such embodiment the treatment increases the individual's serum bicarbonate value from a baseline serum bicarbonate value in the range of 22 to 24 mEq/l by at least 3.5 mEq/l. By way of further example, in one such embodiment the treatment increases the individual's serum bicarbonate value from a baseline serum bicarbonate value in the range of 22 to 24 mEq/l by at least 4 mEq/l. By way of further example, in one such embodiment the treatment increases the individual's serum bicarbonate value from a baseline serum bicarbonate value in the range of 22 to 24 mEq/l by at least 4.5 mEq/l. By way of further example, in one such embodiment the treatment increases the individual's serum bicarbonate value from a baseline serum bicarbonate value in the range of 22 to 24 mEq/l by at least 5 mEq/l. In each of the foregoing exemplary embodiments recited in this paragraph, the increased serum bicarbonate value preferably does not exceed 29 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, the acid-base disorder is treated with a pharmaceutical composition comprising the nonabsorbable composition and the treatment increases the individual's serum bicarbonate value from a baseline serum bicarbonate value in the range of 22 to 23 mEq/l by at least 1 mEq/l. For example, in one such embodiment the treatment increases the individual's serum bicarbonate value from a baseline serum bicarbonate value in the range of 22 to 23 mEq/l by at least 1.5 mEq/l. By way of further example, in one such embodiment the treatment increases the individual's serum bicarbonate value from a baseline serum bicarbonate value in the range of 22 to 23 mEq/l by at least 2 mEq/l. By way of further example, in one such embodiment the treatment increases the individual's serum bicarbonate value from a baseline serum bicarbonate value in the range of 22 to 23 mEq/l by at least 2.5 mEq/l. By way of further example, in one such embodiment the treatment increases the individual's serum bicarbonate value from a baseline serum bicarbonate value in the range of 22 to 23 mEq/l by at least 3 mEq/l. By way of further example, in one such embodiment the treatment increases the individual's serum bicarbonate value from a baseline serum bicarbonate value in the range of 22 to 23 mEq/l by at least 3.5 mEq/l. By way of further example, in one such embodiment the treatment increases the individual's serum bicarbonate value from a baseline serum bicarbonate value in the range of 22 to 23 mEq/l by at least 4 mEq/l. By way of further example, in one such embodiment the treatment increases the individual's serum bicarbonate value from a baseline serum bicarbonate value in the range of 22 to 23 mEq/l by at least 4.5 mEq/l. By way of further example, in one such embodiment the treatment increases the individual's serum bicarbonate value from a baseline serum bicarbonate value in the range of 22 to 23 mEq/l by at least 5 mEq/l. By way of further example, in one such embodiment the treatment increases the individual's serum bicarbonate value from a baseline serum bicarbonate value in the range of 22 to 23 mEq/l by at least 6 mEq/l. In each of the foregoing exemplary embodiments recited in this paragraph, the increased serum bicarbonate value preferably does not exceed 29 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, the treatment increases the individual's serum bicarbonate value from a baseline serum bicarbonate value in the range of 22 to 24 mEq/l to an increased value in the range of 25 mEq/l to 30 mEq/l. For example, in one such embodiment the treatment increases the individual's serum bicarbonate value from a baseline serum bicarbonate value in the range of 22 to 24 mEq/l to an increased value in the range of 25 mEq/l to 29 mEq/l. By way of further example, in one such embodiment the treatment increases the individual's serum bicarbonate value from a baseline serum bicarbonate value in the range of 22 to 24 mEq/l to an increased value in the range of 25 mEq/l to 28 mEq/l. By way of further example, in one such embodiment the treatment increases the individual's serum bicarbonate value from a baseline serum bicarbonate value in the range of 22 to 24 mEq/l to an increased value in the range of 25 mEq/l to 30 mEq/l. By way of further example, in one such embodiment the treatment increases the individual's serum bicarbonate value from a baseline serum bicarbonate value in the range of 22 to 24 mEq/l to an increased value in the range of 25 mEq/l to 29 mEq/l. By way of further example, in one such embodiment the treatment increases the individual's serum bicarbonate value from a baseline serum bicarbonate value in the range of 22 to 24 mEq/l to an increased value in the range of 25 mEq/l to 28 mEq/l. In each of the foregoing embodiments recited in this paragraph, the treatment enables the increased serum bicarbonate value to be sustained over a prolonged period of at least one week, at least one month, at least two months, at least three months, at least six months, or even at least one year.

In certain embodiments, the treatment achieves a clinically significant increase is achieved within a treatment period of less than one month. For example, in one such embodiment, the treatment achieves a clinically significant increase within a treatment period of 25 days. By way of further example, in one such embodiment the treatment achieves the clinically significant increase is achieved within a treatment period of 3 weeks. By way of further example, in one such embodiment the treatment achieves the clinically significant increase is achieved within a treatment period of 15 days. By way of further example, in one such embodiment the treatment achieves the clinically significant increase is achieved within a treatment period of 2 weeks. By way of further example, in one such embodiment the treatment achieves the clinically significant increase is achieved within a treatment period of 10 days. By way of further example, in one such embodiment the treatment achieves the clinically significant increase is achieved within a treatment period of 1 week. By way of further example, in one such embodiment the treatment achieves the clinically significant increase is achieved within a treatment period of 6 days. By way of further example, in one such embodiment the treatment achieves the clinically significant increase is achieved within a treatment period of 5 days. By way of further example, in one such embodiment the treatment achieves the clinically significant increase is achieved within a treatment period of 4 days. By way of further example, in one such embodiment the treatment achieves the clinically significant increase is achieved within a treatment period of 3 days. By way of further example, in one such embodiment the treatment achieves the clinically significant increase is achieved within a treatment period of 2 days. By way of further example, in one such embodiment the treatment achieves the clinically significant increase is achieved within a treatment period of 1 day. By way of further example, in one such embodiment the treatment achieves the clinically significant increase is achieved within a treatment period of 12 hours.

In certain embodiments, the treatment achieves a clinically significant increase is achieved without any change in the individual's diet or dietary habits relative to the period immediately preceding the initiation of treatment. For example, in one such embodiment the clinically significant increase is achieved independent of the individual's diet or dietary habits.

In certain embodiments, the individual's serum bicarbonate value returns to the baseline value±2.5 mEq/l within 1 month of the cessation of treatment. For example, in one such embodiment the individual's serum bicarbonate value returns to the baseline value±2.5 mEq/l within 3 weeks of the cessation of treatment. By way of further example, in one such embodiment the individual's serum bicarbonate value returns to the baseline value±2.5 mEq/l within 2 weeks of the cessation of treatment. By way of further example, in one such embodiment the individual's serum bicarbonate value returns to the baseline value±2.5 mEq/l within 10 days of the cessation of treatment. By way of further example, in one such embodiment the individual's serum bicarbonate value returns to the baseline value±2.5 mEq/l within 9 days of the cessation of treatment. By way of further example, in one such embodiment the individual's serum bicarbonate value returns to the baseline value±2.5 mEq/l within 8 days of the cessation of treatment. By way of further example, in one such embodiment the individual's serum bicarbonate value returns to the baseline value±2.5 mEq/l within 7 days of the cessation of treatment. By way of further example, in one such embodiment the individual's serum bicarbonate value returns to the baseline value±2.5 mEq/l within 6 days of the cessation of treatment. By way of further example, in one such embodiment the individual's serum bicarbonate value returns to the baseline value±2.5 mEq/l within 5 days of the cessation of treatment. By way of further example, in one such embodiment the individual's serum bicarbonate value returns to the baseline value±2.5 mEq/l within 4 days of the cessation of treatment. By way of further example, in one such embodiment the individual's serum bicarbonate value returns to the baseline value±2.5 mEq/l within 3 days of the cessation of treatment. By way of further example, in one such embodiment the individual's serum bicarbonate value returns to the baseline value±2.5 mEq/l within 2 days of the cessation of treatment. By way of further example, in one such embodiment the individual's serum bicarbonate value returns to the baseline value±2.5 mEq/l within 1 day of the cessation of treatment.

In certain embodiments, the individual's serum bicarbonate value returns to the baseline value±2 mEq/l within 1 month of the cessation of treatment. For example, in one such embodiment the individual's serum bicarbonate value returns to the baseline value±2 mEq/l within 3 weeks of the cessation of treatment. By way of further example, in one such embodiment the individual's serum bicarbonate value returns to the baseline value±2 mEq/l within 2 weeks of the cessation of treatment. By way of further example, in one such embodiment the individual's serum bicarbonate value returns to the baseline value±2 mEq/l within 10 days of the cessation of treatment. By way of further example, in one such embodiment the individual's serum bicarbonate value returns to the baseline value±2 mEq/l within 9 days of the cessation of treatment. By way of further example, in one such embodiment the individual's serum bicarbonate value returns to the baseline value±2 mEq/l within 8 days of the cessation of treatment. By way of further example, in one such embodiment the individual's serum bicarbonate value returns to the baseline value±2 mEq/l within 7 days of the cessation of treatment. By way of further example, in one such embodiment the individual's serum bicarbonate value returns to the baseline value±2 mEq/l within 6 days of the cessation of treatment. By way of further example, in one such embodiment the individual's serum bicarbonate value returns to the baseline value±2 mEq/l within 5 days of the cessation of treatment. By way of further example, in one such embodiment the individual's serum bicarbonate value returns to the baseline value±2 mEq/l within 4 days of the cessation of treatment. By way of further example, in one such embodiment the individual's serum bicarbonate value returns to the baseline value±2 mEq/l within 3 days of the cessation of treatment. By way of further example, in one such embodiment the individual's serum bicarbonate value returns to the baseline value±2 mEq/l within 2 days of the cessation of treatment. By way of further example, in one such embodiment the individual's serum bicarbonate value returns to the baseline value±2 mEq/l within 1 day of the cessation of treatment.

In certain embodiments, the individual's serum bicarbonate value returns to the baseline value±1.5 mEq/l within 1 month of the cessation of treatment. For example, in one such embodiment the individual's serum bicarbonate value returns to the baseline value±1.5 mEq/l within 3 weeks of the cessation of treatment. By way of further example, in one such embodiment the individual's serum bicarbonate value returns to the baseline value±1.5 mEq/l within 2 weeks of the cessation of treatment. By way of further example, in one such embodiment the individual's serum bicarbonate value returns to the baseline value±1.5 mEq/l within 10 days of the cessation of treatment. By way of further example, in one such embodiment the individual's serum bicarbonate value returns to the baseline value±1.5 mEq/l within 9 days of the cessation of treatment. By way of further example, in one such embodiment the individual's serum bicarbonate value returns to the baseline value±1.5 mEq/l within 8 days of the cessation of treatment. By way of further example, in one such embodiment the individual's serum bicarbonate value returns to the baseline value±1.5 mEq/l within 7 days of the cessation of treatment. By way of further example, in one such embodiment the individual's serum bicarbonate value returns to the baseline value±1.5 mEq/l within 6 days of the cessation of treatment. By way of further example, in one such embodiment the individual's serum bicarbonate value returns to the baseline value±1.5 mEq/l within 5 days of the cessation of treatment. By way of further example, in one such embodiment the individual's serum bicarbonate value returns to the baseline value±1.5 mEq/l within 4 days of the cessation of treatment. By way of further example, in one such embodiment the individual's serum bicarbonate value returns to the baseline value±1.5 mEq/l within 3 days of the cessation of treatment. By way of further example, in one such embodiment the individual's serum bicarbonate value returns to the baseline value±1.5 mEq/l within 2 days of the cessation of treatment. By way of further example, in one such embodiment the individual's serum bicarbonate value returns to the baseline value±1.5 mEq/l within 1 day of the cessation of treatment.

In certain embodiments, the individual's serum bicarbonate value returns to the baseline value±1 mEq/l within 1 month of the cessation of treatment. For example, in one such embodiment the individual's serum bicarbonate value returns to the baseline value±1 mEq/l within 3 weeks of the cessation of treatment. By way of further example, in one such embodiment the individual's serum bicarbonate value returns to the baseline value±1 mEq/l within 2 weeks of the cessation of treatment. By way of further example, in one such embodiment the individual's serum bicarbonate value returns to the baseline value±1 mEq/l within 10 days of the cessation of treatment. By way of further example, in one such embodiment the individual's serum bicarbonate value returns to the baseline value±1 mEq/l within 9 days of the cessation of treatment. By way of further example, in one such embodiment the individual's serum bicarbonate value returns to the baseline value±1 mEq/l within 8 days of the cessation of treatment. By way of further example, in one such embodiment the individual's serum bicarbonate value returns to the baseline value±1 mEq/l within 7 days of the cessation of treatment. By way of further example, in one such embodiment the individual's serum bicarbonate value returns to the baseline value±1 mEq/l within 6 days of the cessation of treatment. By way of further example, in one such embodiment the individual's serum bicarbonate value returns to the baseline value±1 mEq/l within 5 days of the cessation of treatment. By way of further example, in one such embodiment the individual's serum bicarbonate value returns to the baseline value±1 mEq/l within 4 days of the cessation of treatment. By way of further example, in one such embodiment the individual's serum bicarbonate value returns to the baseline value±1 mEq/l within 3 days of the cessation of treatment. By way of further example, in one such embodiment the individual's serum bicarbonate value returns to the baseline value±1 mEq/l within 2 days of the cessation of treatment. By way of further example, in one such embodiment the individual's serum bicarbonate value returns to the baseline value±1 mEq/l within 1 day of the cessation of treatment.

In certain embodiments, upon the cessation of treatment the individual's serum bicarbonate value decreases by at least 1 mEq/l within 1 month of the cessation of treatment. For example, in one such embodiment. For example, in one such embodiment the individual's serum bicarbonate value decreases by at least 1 mEq/l within 3 weeks of the cessation of treatment. By way of further example, in one such embodiment the individual's serum bicarbonate value decreases by at least 1 mEq/l within 2 weeks of the cessation of treatment. By way of further example, in one such embodiment the individual's serum bicarbonate value decreases by at least 1 mEq/l within 10 days of the cessation of treatment. By way of further example, in one such embodiment the individual's serum bicarbonate value decreases by at least 1 mEq/l within 9 days of the cessation of treatment. By way of further example, in one such embodiment the individual's serum bicarbonate value decreases by at least 1 mEq/l within 8 days of the cessation of treatment. By way of further example, in one such embodiment the individual's serum bicarbonate value decreases by at least 1 mEq/l within 7 days of the cessation of treatment. By way of further example, in one such embodiment the individual's serum bicarbonate value decreases by at least 1 mEq/l within 6 days of the cessation of treatment. By way of further example, in one such embodiment the individual's serum bicarbonate value decreases by at least 1 mEq/l within 5 days of the cessation of treatment. By way of further example, in one such embodiment the individual's serum bicarbonate value decreases by at least 1 mEq/l within 4 days of the cessation of treatment. By way of further example, in one such embodiment the individual's serum bicarbonate value decreases by at least 1 mEq/l within 3 days of the cessation of treatment. By way of further example, in one such embodiment the individual's serum bicarbonate value decreases by at least 1 mEq/l within 2 days of the cessation of treatment. By way of further example, in one such embodiment the individual's serum bicarbonate value decreases by at least 1 mEq/l within 1 day of the cessation of treatment. By way of further example, in one such embodiment the individual's serum bicarbonate value decreases by at least 1 mEq/l within 12 hours of the cessation of treatment.

In certain embodiments, upon the cessation of treatment the individual's serum bicarbonate value decreases by at least 1.5 mEq/l within 1 month of the cessation of treatment. For example, in one such embodiment. For example, in one such embodiment the individual's serum bicarbonate value decreases by at least 1.5 mEq/l within 3 weeks of the cessation of treatment. By way of further example, in one such embodiment the individual's serum bicarbonate value decreases by at least 1.5 mEq/l within 2 weeks of the cessation of treatment. By way of further example, in one such embodiment the individual's serum bicarbonate value decreases by at least 1.5 mEq/l within 10 days of the cessation of treatment. By way of further example, in one such embodiment the individual's serum bicarbonate value decreases by at least 1.5 mEq/l within 9 days of the cessation of treatment. By way of further example, in one such embodiment the individual's serum bicarbonate value decreases by at least 1.5 mEq/l within 8 days of the cessation of treatment. By way of further example, in one such embodiment the individual's serum bicarbonate value decreases by at least 1.5 mEq/l within 7 days of the cessation of treatment. By way of further example, in one such embodiment the individual's serum bicarbonate value decreases by at least 1.5 mEq/l within 6 days of the cessation of treatment. By way of further example, in one such embodiment the individual's serum bicarbonate value decreases by at least 1.5 mEq/l within 5 days of the cessation of treatment. By way of further example, in one such embodiment the individual's serum bicarbonate value decreases by at least 1.5 mEq/l within 4 days of the cessation of treatment. By way of further example, in one such embodiment the individual's serum bicarbonate value decreases by at least 1.5 mEq/l within 3 days of the cessation of treatment. By way of further example, in one such embodiment the individual's serum bicarbonate value decreases by at least 1.5 mEq/l within 2 days of the cessation of treatment. By way of further example, in one such embodiment the individual's serum bicarbonate value decreases by at least 1.5 mEq/l within 1 day of the cessation of treatment. By way of further example, in one such embodiment the individual's serum bicarbonate value decreases by at least 1.5 mEq/l within 12 hours of the cessation of treatment.

In certain embodiments, upon the cessation of treatment the individual's serum bicarbonate value decreases by at least 2 mEq/l within 1 month of the cessation of treatment. For example, in one such embodiment. For example, in one such embodiment the individual's serum bicarbonate value decreases by at least 2 mEq/l within 3 weeks of the cessation of treatment. By way of further example, in one such embodiment the individual's serum bicarbonate value decreases by at least 2 mEq/l within 2 weeks of the cessation of treatment. By way of further example, in one such embodiment the individual's serum bicarbonate value decreases by at least 2 mEq/l within 10 days of the cessation of treatment. By way of further example, in one such embodiment the individual's serum bicarbonate value decreases by at least 2 mEq/l within 9 days of the cessation of treatment. By way of further example, in one such embodiment the individual's serum bicarbonate value decreases by at least 2 mEq/l within 8 days of the cessation of treatment. By way of further example, in one such embodiment the individual's serum bicarbonate value decreases by at least 2 mEq/l within 7 days of the cessation of treatment. By way of further example, in one such embodiment the individual's serum bicarbonate value decreases by at least 2 mEq/l within 6 days of the cessation of treatment. By way of further example, in one such embodiment the individual's serum bicarbonate value decreases by at least 2 mEq/l within 5 days of the cessation of treatment. By way of further example, in one such embodiment the individual's serum bicarbonate value decreases by at least 2 mEq/l within 4 days of the cessation of treatment. By way of further example, in one such embodiment the individual's serum bicarbonate value decreases by at least 2 mEq/l within 3 days of the cessation of treatment. By way of further example, in one such embodiment the individual's serum bicarbonate value decreases by at least 2 mEq/l within 2 days of the cessation of treatment. By way of further example, in one such embodiment the individual's serum bicarbonate value decreases by at least 2 mEq/l within 1 day of the cessation of treatment. By way of further example, in one such embodiment the individual's serum bicarbonate value decreases by at least 2 mEq/l within 12 hours of the cessation of treatment.

In certain embodiments, upon the cessation of treatment the individual's serum bicarbonate value decreases by at least 2.5 mEq/l within 1 month of the cessation of treatment. For example, in one such embodiment. For example, in one such embodiment the individual's serum bicarbonate value decreases by at least 2.5 mEq/l within 3 weeks of the cessation of treatment. By way of further example, in one such embodiment the individual's serum bicarbonate value decreases by at least 2.5 mEq/l within 2 weeks of the cessation of treatment. By way of further example, in one such embodiment the individual's serum bicarbonate value decreases by at least 2.5 mEq/l within 10 days of the cessation of treatment. By way of further example, in one such embodiment the individual's serum bicarbonate value decreases by at least 2.5 mEq/l within 9 days of the cessation of treatment. By way of further example, in one such embodiment the individual's serum bicarbonate value decreases by at least 2.5 mEq/l within 8 days of the cessation of treatment. By way of further example, in one such embodiment the individual's serum bicarbonate value decreases by at least 2.5 mEq/l within 7 days of the cessation of treatment. By way of further example, in one such embodiment the individual's serum bicarbonate value decreases by at least 2.5 mEq/l within 6 days of the cessation of treatment. By way of further example, in one such embodiment the individual's serum bicarbonate value decreases by at least 2.5 mEq/l within 5 days of the cessation of treatment. By way of further example, in one such embodiment the individual's serum bicarbonate value decreases by at least 2.5 mEq/l within 4 days of the cessation of treatment. By way of further example, in one such embodiment the individual's serum bicarbonate value decreases by at least 2.5 mEq/l within 3 days of the cessation of treatment. By way of further example, in one such embodiment the individual's serum bicarbonate value decreases by at least 2.5 mEq/l within 2 days of the cessation of treatment. By way of further example, in one such embodiment the individual's serum bicarbonate value decreases by at least 2.5 mEq/l within 1 day of the cessation of treatment. By way of further example, in one such embodiment the individual's serum bicarbonate value decreases by at least 2.5 mEq/l within 12 hours of the cessation of treatment.

In certain embodiments, upon the cessation of treatment the individual's serum bicarbonate value decreases by at least 3 mEq/l within 1 month of the cessation of treatment. For example, in one such embodiment. For example, in one such embodiment the individual's serum bicarbonate value decreases by at least 3 mEq/l within 3 weeks of the cessation of treatment. By way of further example, in one such embodiment the individual's serum bicarbonate value decreases by at least 3 mEq/l within 2 weeks of the cessation of treatment. By way of further example, in one such embodiment the individual's serum bicarbonate value decreases by at least 3 mEq/l within 10 days of the cessation of treatment. By way of further example, in one such embodiment the individual's serum bicarbonate value decreases by at least 3 mEq/l within 9 days of the cessation of treatment. By way of further example, in one such embodiment the individual's serum bicarbonate value decreases by at least 3 mEq/l within 8 days of the cessation of treatment. By way of further example, in one such embodiment the individual's serum bicarbonate value decreases by at least 3 mEq/l within 7 days of the cessation of treatment. By way of further example, in one such embodiment the individual's serum bicarbonate value decreases by at least 3 mEq/l within 6 days of the cessation of treatment. By way of further example, in one such embodiment the individual's serum bicarbonate value decreases by at least 3 mEq/l within 5 days of the cessation of treatment. By way of further example, in one such embodiment the individual's serum bicarbonate value decreases by at least 3 mEq/l within 4 days of the cessation of treatment. By way of further example, in one such embodiment the individual's serum bicarbonate value decreases by at least 3 mEq/l within 3 days of the cessation of treatment. By way of further example, in one such embodiment the individual's serum bicarbonate value decreases by at least 3 mEq/l within 2 days of the cessation of treatment. By way of further example, in one such embodiment the individual's serum bicarbonate value decreases by at least 3 mEq/l within 1 day of the cessation of treatment. By way of further example, in one such embodiment the individual's serum bicarbonate value decreases by at least 3 mEq/l within 12 hours of the cessation of treatment.

In certain embodiments, upon the cessation of treatment the individual's serum bicarbonate value decreases by at least 3.5 mEq/l within 1 month of the cessation of treatment. For example, in one such embodiment. For example, in one such embodiment the individual's serum bicarbonate value decreases by at least 3.5 mEq/l within 3 weeks of the cessation of treatment. By way of further example, in one such embodiment the individual's serum bicarbonate value decreases by at least 3.5 mEq/l within 2 weeks of the cessation of treatment. By way of further example, in one such embodiment the individual's serum bicarbonate value decreases by at least 3.5 mEq/l within 10 days of the cessation of treatment. By way of further example, in one such embodiment the individual's serum bicarbonate value decreases by at least 3.5 mEq/l within 9 days of the cessation of treatment. By way of further example, in one such embodiment the individual's serum bicarbonate value decreases by at least 3.5 mEq/l within 8 days of the cessation of treatment. By way of further example, in one such embodiment the individual's serum bicarbonate value decreases by at least 3.5 mEq/l within 7 days of the cessation of treatment. By way of further example, in one such embodiment the individual's serum bicarbonate value decreases by at least 3.5 mEq/l within 6 days of the cessation of treatment. By way of further example, in one such embodiment the individual's serum bicarbonate value decreases by at least 3.5 mEq/l within 5 days of the cessation of treatment. By way of further example, in one such embodiment the individual's serum bicarbonate value decreases by at least 3.5 mEq/l within 4 days of the cessation of treatment. By way of further example, in one such embodiment the individual's serum bicarbonate value decreases by at least 3.5 mEq/l within 3 days of the cessation of treatment. By way of further example, in one such embodiment the individual's serum bicarbonate value decreases by at least 3.5 mEq/l within 2 days of the cessation of treatment. By way of further example, in one such embodiment the individual's serum bicarbonate value decreases by at least 3.5 mEq/l within 1 day of the cessation of treatment. By way of further example, in one such embodiment the individual's serum bicarbonate value decreases by at least 3.5 mEq/l within 12 hours of the cessation of treatment.

In certain embodiments, upon the cessation of treatment the individual's serum bicarbonate value decreases by at least 4 mEq/l within 1 month of the cessation of treatment. For example, in one such embodiment. For example, in one such embodiment the individual's serum bicarbonate value decreases by at least 4 mEq/l within 3 weeks of the cessation of treatment. By way of further example, in one such embodiment the individual's serum bicarbonate value decreases by at least 4 mEq/l within 2 weeks of the cessation of treatment. By way of further example, in one such embodiment the individual's serum bicarbonate value decreases by at least 4 mEq/l within 10 days of the cessation of treatment. By way of further example, in one such embodiment the individual's serum bicarbonate value decreases by at least 4 mEq/l within 9 days of the cessation of treatment. By way of further example, in one such embodiment the individual's serum bicarbonate value decreases by at least 4 mEq/l within 8 days of the cessation of treatment. By way of further example, in one such embodiment the individual's serum bicarbonate value decreases by at least 4 mEq/l within 7 days of the cessation of treatment. By way of further example, in one such embodiment the individual's serum bicarbonate value decreases by at least 4 mEq/l within 6 days of the cessation of treatment. By way of further example, in one such embodiment the individual's serum bicarbonate value decreases by at least 4 mEq/l within 5 days of the cessation of treatment. By way of further example, in one such embodiment the individual's serum bicarbonate value decreases by at least 4 mEq/l within 4 days of the cessation of treatment. By way of further example, in one such embodiment the individual's serum bicarbonate value decreases by at least 4 mEq/l within 3 days of the cessation of treatment. By way of further example, in one such embodiment the individual's serum bicarbonate value decreases by at least 4 mEq/l within 2 days of the cessation of treatment. By way of further example, in one such embodiment the individual's serum bicarbonate value decreases by at least 4 mEq/l within 1 day of the cessation of treatment. By way of further example, in one such embodiment the individual's serum bicarbonate value decreases by at least 4 mEq/l within 12 hours of the cessation of treatment.

In certain embodiments, upon the cessation of treatment the individual's serum bicarbonate value decreases by at least 4.5 mEq/l within 1 month of the cessation of treatment. For example, in one such embodiment. For example, in one such embodiment the individual's serum bicarbonate value decreases by at least 4.5 mEq/l within 3 weeks of the cessation of treatment. By way of further example, in one such embodiment the individual's serum bicarbonate value decreases by at least 4.5 mEq/l within 2 weeks of the cessation of treatment. By way of further example, in one such embodiment the individual's serum bicarbonate value decreases by at least 4.5 mEq/l within 10 days of the cessation of treatment. By way of further example, in one such embodiment the individual's serum bicarbonate value decreases by at least 4.5 mEq/l within 9 days of the cessation of treatment. By way of further example, in one such embodiment the individual's serum bicarbonate value decreases by at least 4.5 mEq/l within 8 days of the cessation of treatment. By way of further example, in one such embodiment the individual's serum bicarbonate value decreases by at least 4.5 mEq/l within 7 days of the cessation of treatment. By way of further example, in one such embodiment the individual's serum bicarbonate value decreases by at least 4.5 mEq/l within 6 days of the cessation of treatment. By way of further example, in one such embodiment the individual's serum bicarbonate value decreases by at least 4.5 mEq/l within 5 days of the cessation of treatment. By way of further example, in one such embodiment the individual's serum bicarbonate value decreases by at least 4.5 mEq/l within 4 days of the cessation of treatment. By way of further example, in one such embodiment the individual's serum bicarbonate value decreases by at least 4.5 mEq/l within 3 days of the cessation of treatment. By way of further example, in one such embodiment the individual's serum bicarbonate value decreases by at least 4.5 mEq/l within 2 days of the cessation of treatment. By way of further example, in one such embodiment the individual's serum bicarbonate value decreases by at least 4.5 mEq/l within 1 day of the cessation of treatment. By way of further example, in one such embodiment the individual's serum bicarbonate value decreases by at least 4.5 mEq/l within 12 hours of the cessation of treatment.

In certain embodiments, upon the cessation of treatment the individual's serum bicarbonate value decreases by at least 5 mEq/l within 1 month of the cessation of treatment. For example, in one such embodiment. For example, in one such embodiment the individual's serum bicarbonate value decreases by at least 5 mEq/l within 3 weeks of the cessation of treatment. By way of further example, in one such embodiment the individual's serum bicarbonate value decreases by at least 5 mEq/l within 2 weeks of the cessation of treatment. By way of further example, in one such embodiment the individual's serum bicarbonate value decreases by at least 5 mEq/l within 10 days of the cessation of treatment. By way of further example, in one such embodiment the individual's serum bicarbonate value decreases by at least 5 mEq/l within 9 days of the cessation of treatment. By way of further example, in one such embodiment the individual's serum bicarbonate value decreases by at least 5 mEq/l within 8 days of the cessation of treatment. By way of further example, in one such embodiment the individual's serum bicarbonate value decreases by at least 5 mEq/l within 7 days of the cessation of treatment. By way of further example, in one such embodiment the individual's serum bicarbonate value decreases by at least 5 mEq/l within 6 days of the cessation of treatment. By way of further example, in one such embodiment the individual's serum bicarbonate value decreases by at least 5 mEq/l within 5 days of the cessation of treatment. By way of further example, in one such embodiment the individual's serum bicarbonate value decreases by at least 5 mEq/l within 4 days of the cessation of treatment. By way of further example, in one such embodiment the individual's serum bicarbonate value decreases by at least 5 mEq/l within 3 days of the cessation of treatment. By way of further example, in one such embodiment the individual's serum bicarbonate value decreases by at least 5 mEq/l within 2 days of the cessation of treatment. By way of further example, in one such embodiment the individual's serum bicarbonate value decreases by at least 5 mEq/l within 1 day of the cessation of treatment. By way of further example, in one such embodiment the individual's serum bicarbonate value decreases by at least 5 mEq/l within 12 hours of the cessation of treatment.

In one embodiment, the baseline serum bicarbonate value is the value of the serum bicarbonate concentration determined at a single time point. In another embodiment, the baseline serum bicarbonate value is the mean value of at least two serum bicarbonate concentrations determined at different time-points. For example, in one such embodiment the baseline serum bicarbonate value is the mean value of at least two serum bicarbonate concentrations for serum samples drawn on different days. By way of further example, the baseline serum bicarbonate value is the mean or median value of at least two serum bicarbonate concentrations for serum samples drawn on non-consecutive days. By way of further example, in one such method the non-consecutive days are separated by at least two days. By way of further example, in one such method the non-consecutive days are separated by at least one week. By way of further example, in one such method the non-consecutive days are separated by at least two weeks. By way of further example, in one such method the non-consecutive days are separated by at least three weeks.

In certain embodiments, the daily dose is no more than 100 g/day of the nonabsorbable composition. For example, in one such embodiment the daily dose is no more than 90 g/day of the nonabsorbable composition. By way of further example, in one such embodiment the daily dose is no more than 75 g/day of the nonabsorbable composition. By way of further example, in one such embodiment the daily dose is no more than 65 g/day of the nonabsorbable composition. By way of further example, in one such embodiment the daily dose is no more than 50 g/day of the nonabsorbable composition. By way of further example, in one such embodiment the daily dose is no more than 40 g/day of the nonabsorbable composition. By way of further example, in one such embodiment the daily dose is no more than 30 g/day of the nonabsorbable composition. By way of further example, in one such embodiment the daily dose is no more than 25 g/day of the nonabsorbable composition. By way of further example, in one such embodiment the daily dose is no more than 20 g/day of the nonabsorbable composition. By way of further example, in one such embodiment the daily dose is no more than 15 g/day of the nonabsorbable composition. By way of further example, in one such embodiment the daily dose is no more than 10 g/day of the nonabsorbable composition. By way of further example, in one such embodiment the daily dose is no more than 5 g/day of the nonabsorbable composition.

In certain embodiments, the individual is treated with the daily dose for a period of at least one day. For example, in one such embodiment the individual is treated with the daily dose for a period of at least one week. By way of further example, in one such embodiment the individual is treated with the daily dose for a period of at least one month. By way of further example, in one such embodiment the individual is treated with the daily dose for a period of at least two months. By way of further example, in one such embodiment the individual is treated with the daily dose for a period of at least three months. By way of further example, in one such embodiment the individual is treated with the daily dose for a period of at least several months. By way of further example, in one such embodiment the individual is treated with the daily dose for a period of at least six months. By way of further example, in one such embodiment the individual is treated with the daily dose for a period of at least one year.

In certain embodiments of the method of the present disclosure, the daily dose of the nonabsorbable composition has the capacity to remove at least about 5 mEq/day of the target species. For example, in one such embodiment the daily dose of the nonabsorbable composition has the capacity to remove at least about 6 mEq/day of the target species. By way of further example, in one such embodiment the daily dose of the nonabsorbable composition has the capacity to remove at least about 7 mEq/day of the target species. By way of further example, in one such embodiment the daily dose of the nonabsorbable composition has the capacity to remove at least about 8 mEq/day of the target species. By way of further example, in one such embodiment the daily dose of the nonabsorbable composition has the capacity to remove at least about 9 mEq/day of the target species. By way of further example, in one such embodiment the daily dose of the nonabsorbable composition has the capacity to remove at least about 10 mEq/day of the target species. By way of further example, in one such embodiment the daily dose of the nonabsorbable composition has the capacity to remove at least about 11 mEq/day of the target species. By way of further example, in one such embodiment the daily dose of the nonabsorbable composition has the capacity to remove at least about 12 mEq/day of the target species. By way of further example, in one such embodiment the daily dose of the nonabsorbable composition has the capacity to remove at least about 13 mEq/day of the target species. By way of further example, in one such embodiment the daily dose of the nonabsorbable composition has the capacity to remove at least about 14 mEq/day of the target species. By way of further example, in one such embodiment the daily dose of the nonabsorbable composition has the capacity to remove at least about 15 mEq/day of the target species. By way of further example, in one such embodiment the daily dose of the nonabsorbable composition has the capacity to remove at least about 16 mEq/day of the target species. By way of further example, in one such embodiment the daily dose of the nonabsorbable composition has the capacity to remove at least about 17 mEq/day of the target species. By way of further example, in one such embodiment the daily dose of the nonabsorbable composition has the capacity to remove at least about 18 mEq/day of the target species. By way of further example, in one such embodiment the daily dose of the nonabsorbable composition has the capacity to remove at least about 19 mEq/day of the target species. By way of further example, in one such embodiment the daily dose of the nonabsorbable composition has the capacity to remove at least about 20 mEq/day of the target species. By way of further example, in one such embodiment the daily dose of the nonabsorbable composition has the capacity to remove at least about 21 mEq/day of the target species. By way of further example, in one such embodiment the daily dose of the nonabsorbable composition has the capacity to remove at least about 22 mEq/day of the target species. By way of further example, in one such embodiment the daily dose of the nonabsorbable composition has the capacity to remove at least about 23 mEq/day of the target species. By way of further example, in one such embodiment the daily dose of the nonabsorbable composition has the capacity to remove at least about 24 mEq/day of the target species. By way of further example, in one such embodiment the daily dose of the nonabsorbable composition has the capacity to remove at least about 25 mEq/day of the target species. By way of further example, in one such embodiment the daily dose of the nonabsorbable composition has the capacity to remove at least about 26 mEq/day of the target species. By way of further example, in one such embodiment the daily dose of the nonabsorbable composition has the capacity to remove at least about 27 mEq/day of the target species. By way of further example, in one such embodiment the daily dose of the nonabsorbable composition has the capacity to remove at least about 28 mEq/day of the target species. By way of further example, in one such embodiment the daily dose of the nonabsorbable composition has the capacity to remove at least about 29 mEq/day of the target species. By way of further example, in one such embodiment the daily dose of the nonabsorbable composition has the capacity to remove at least about 30 mEq/day of the target species. By way of further example, in one such embodiment the daily dose of the nonabsorbable composition has the capacity to remove at least about 31 mEq/day of the target species. By way of further example, in one such embodiment the daily dose of the nonabsorbable composition has the capacity to remove at least about 32 mEq/day of the target species. By way of further example, in one such embodiment the daily dose of the nonabsorbable composition has the capacity to remove at least about 33 mEq/day of the target species. By way of further example, in one such embodiment the daily dose of the nonabsorbable composition has the capacity to remove at least about 34 mEq/day of the target species. By way of further example, in one such embodiment the daily dose of the nonabsorbable composition has the capacity to remove at least about 35 mEq/day of the target species. By way of further example, in one such embodiment the daily dose of the nonabsorbable composition has the capacity to remove at least about 36 mEq/day of the target species. By way of further example, in one such embodiment the daily dose of the nonabsorbable composition has the capacity to remove at least about 37 mEq/day of the target species. By way of further example, in one such embodiment the daily dose of the nonabsorbable composition has the capacity to remove at least about 38 mEq/day of the target species. By way of further example, in one such embodiment the daily dose of the nonabsorbable composition has the capacity to remove at least about 39 mEq/day of the target species. By way of further example, in one such embodiment the daily dose of the nonabsorbable composition has the capacity to remove at least about 40 mEq/day of the target species. By way of further example, in one such embodiment the daily dose of the nonabsorbable composition has the capacity to remove at least about 41 mEq/day of the target species. By way of further example, in one such embodiment the daily dose of the nonabsorbable composition has the capacity to remove at least about 42 mEq/day of the target species. By way of further example, in one such embodiment the daily dose of the nonabsorbable composition has the capacity to remove at least about 43 mEq/day of the target species. By way of further example, in one such embodiment the daily dose of the nonabsorbable composition has the capacity to remove at least about 44 mEq/day of the target species. By way of further example, in one such embodiment the daily dose of the nonabsorbable composition has the capacity to remove at least about 45 mEq/day of the target species. By way of further example, in one such embodiment the daily dose of the nonabsorbable composition has the capacity to remove at least about 46 mEq/day of the target species. By way of further example, in one such embodiment the daily dose of the nonabsorbable composition has the capacity to remove at least about 47 mEq/day of the target species. By way of further example, in one such embodiment the daily dose of the nonabsorbable composition has the capacity to remove at least about 48 mEq/day of the target species. By way of further example, in one such embodiment the daily dose of the nonabsorbable composition has the capacity to remove at least about 49 mEq/day of the target species. By way of further example, in one such embodiment the daily dose of the nonabsorbable composition has the capacity to remove at least about 50 mEq/day of the target species.

In certain embodiments of the method of the present disclosure, the daily dose of the nonabsorbable composition removes at least about 5 mEq/day of the target species. For example, in one such embodiment the daily dose of the nonabsorbable composition removes at least about 6 mEq/day of the target species. By way of further example, in one such embodiment the daily dose of the nonabsorbable composition removes at least about 7 mEq/day of the target species. By way of further embodiment the daily dose of the nonabsorbable composition removes at least about 8 mEq/day of the target species. By way of further example, in one such embodiment the daily dose of the nonabsorbable composition removes at least about 9 mEq/day of the target species. By way of further example, in one such embodiment the daily dose of the nonabsorbable composition removes at least about 10 mEq/day of the target species. By way of further example, in one such embodiment the daily dose of the nonabsorbable composition removes at least about 11 mEq/day of the target species. By way of further example, in one such embodiment the daily dose of the nonabsorbable composition removes at least about 12 mEq/day of the target species. By way of further example, in one such embodiment the daily dose of the nonabsorbable composition removes at least about 13 mEq/day of the target species. By way of further example, in one such embodiment the daily dose of the nonabsorbable composition removes at least about 14 mEq/day of the target species. By way of further example, in one such embodiment the daily dose of the nonabsorbable composition removes at least about 15 mEq/day of the target species. By way of further example, in one such embodiment the daily dose of the nonabsorbable composition removes at least about 16 mEq/day of the target species. By way of further example, in one such embodiment the daily dose of the nonabsorbable composition removes at least about 17 mEq/day of the target species. By way of further example, in one such embodiment the daily dose of the nonabsorbable composition removes at least about 18 mEq/day of the target species. By way of further example, in one such embodiment the daily dose of the nonabsorbable composition removes at least about 19 mEq/day of the target species. By way of further example, in one such embodiment the daily dose of the nonabsorbable composition removes at least about 20 mEq/day of the target species. By way of further example, in one such embodiment the daily dose of the nonabsorbable composition removes at least about 21 mEq/day of the target species. By way of further example, in one such embodiment the daily dose of the nonabsorbable composition removes at least about 22 mEq/day of the target species. By way of further example, in one such embodiment the daily dose of the nonabsorbable composition removes at least about 23 mEq/day of the target species. By way of further example, in one such embodiment the daily dose of the nonabsorbable composition removes at least about 24 mEq/day of the target species. By way of further example, in one such embodiment the daily dose of the nonabsorbable composition removes at least about 25 mEq/day of the target species. By way of further example, in one such embodiment the daily dose of the nonabsorbable composition removes at least about 26 mEq/day of the target species. By way of further example, in one such embodiment the daily dose of the nonabsorbable composition removes at least about 27 mEq/day of the target species. By way of further example, in one such embodiment the daily dose of the nonabsorbable composition removes at least about 28 mEq/day of the target species. By way of further example, in one such embodiment the daily dose of the nonabsorbable composition removes at least about 29 mEq/day of the target species. By way of further example, in one such embodiment the daily dose of the nonabsorbable composition removes at least about 30 mEq/day of the target species. By way of further example, in one such embodiment the daily dose of the nonabsorbable composition removes at least about 31 mEq/day of the target species. By way of further example, in one such embodiment the daily dose of the nonabsorbable composition removes at least about 32 mEq/day of the target species. By way of further example, in one such embodiment the daily dose of the nonabsorbable composition removes at least about 33 mEq/day of the target species. By way of further example, in one such embodiment the daily dose of the nonabsorbable composition removes at least about 34 mEq/day of the target species. By way of further example, in one such embodiment the daily dose of the nonabsorbable composition removes at least about 35 mEq/day of the target species. By way of further example, in one such embodiment the daily dose of the nonabsorbable composition removes at least about 36 mEq/day of the target species. By way of further example, in one such embodiment the daily dose of the nonabsorbable composition removes at least about 37 mEq/day of the target species. By way of further example, in one such embodiment the daily dose of the nonabsorbable composition removes at least about 38 mEq/day of the target species. By way of further example, in one such embodiment the daily dose of the nonabsorbable composition removes at least about 39 mEq/day of the target species. By way of further example, in one such embodiment the daily dose of the nonabsorbable composition removes at least about 40 mEq/day of the target species. By way of further example, in one such embodiment the daily dose of the nonabsorbable composition removes at least about 41 mEq/day of the target species. By way of further example, in one such embodiment the daily dose of the nonabsorbable composition removes at least about 42 mEq/day of the target species. By way of further example, in one such embodiment the daily dose of the nonabsorbable composition removes at least about 43 mEq/day of the target species. By way of further example, in one such embodiment the daily dose of the nonabsorbable composition removes at least about 44 mEq/day of the target species. By way of further example, in one such embodiment the daily dose of the nonabsorbable composition removes at least about 45 mEq/day of the target species. By way of further example, in one such embodiment the daily dose of the nonabsorbable composition removes at least about 46 mEq/day of the target species. By way of further example, in one such embodiment the daily dose of the nonabsorbable composition removes at least about 47 mEq/day of the target species. By way of further example, in one such embodiment the daily dose of the nonabsorbable composition removes at least about 48 mEq/day of the target species. By way of further example, in one such embodiment the daily dose of the nonabsorbable composition removes at least about 49 mEq/day of the target species. By way of further example, in one such embodiment the daily dose of the nonabsorbable composition removes at least about 50 mEq/day of the target species.

In certain embodiments of the method of the present disclosure, the daily dose of the nonabsorbable composition removes less than 60 mEq/day of the target species. For example, in one such method the daily dose removes less than 55 mEq/day of the target species. By way of further example, in one such embodiment the daily dose removes less than 50 mEq/day of the target species. By way of further example, in one such embodiment the daily dose removes less than 45 mEq/day of the target species. By way of further example, in one such embodiment the daily dose removes less than 40 mEq/day of the target species. By way of further example, in one such embodiment the daily dose removes less than 35 mEq/day of the target species. By way of further example, in one such embodiment the daily dose removes less than 34 mEq/day of the target species. By way of further example, in one such embodiment the daily dose removes less than 33 mEq/day of the target species. By way of further example, in one such embodiment the daily dose removes less than 32 mEq/day of the target species. By way of further example, in one such embodiment the daily dose removes less than 31 mEq/day of the target species. By way of further example, in one such embodiment the daily dose removes less than 30 mEq/day of the target species. By way of further example, in one such embodiment the daily dose removes less than 29 mEq/day of the target species. By way of further example, in one such embodiment the daily dose removes less than 28 mEq/day of the target species. By way of further example, in one such embodiment the daily dose removes less than 27 mEq/day of the target species. By way of further example, in one such embodiment the daily dose removes less than 26 mEq/day of the target species. By way of further example, in one such embodiment the daily dose removes less than 25 mEq/day of the target species. By way of further example, in one such embodiment the daily dose removes less than 24 mEq/day of the target species. By way of further example, in one such embodiment the daily dose removes less than 23 mEq/day of the target species. By way of further example, in one such embodiment the daily dose removes less than 22 mEq/day of the target species. By way of further example, in one such embodiment the daily dose removes less than 21 mEq/day of the target species. By way of further example, in one such embodiment the daily dose removes less than 20 mEq/day of the target species. By way of further example, in one such embodiment the daily dose removes less than 19 mEq/day of the target species. By way of further example, in one such embodiment the daily dose removes less than 18 mEq/day of the target species. By way of further example, in one such embodiment the daily dose removes less than 17 mEq/day of the target species. By way of further example, in one such embodiment the daily dose removes less than 16 mEq/day of the target species. By way of further example, in one such embodiment the daily dose removes less than 15 mEq/day of the target species. By way of further example, in one such embodiment the daily dose removes less than 14 mEq/day of the target species. By way of further example, in one such embodiment the daily dose removes less than 13 mEq/day of the target species. By way of further example, in one such embodiment the daily dose removes less than 12 mEq/day of the target species. By way of further example, in one such embodiment the daily dose removes less than 11 mEq/day of the target species. By way of further example, in one such embodiment the daily dose removes less than 10 mEq/day of the target species. By way of further example, in one such embodiment the daily dose removes less than 9 mEq/day of the target species. By way of further example, in one such embodiment the daily dose removes less than 8 mEq/day of the target species. By way of further example, in one such embodiment the daily dose removes less than 7 mEq/day of the target species. By way of further example, in one such embodiment the daily dose removes less than 6 mEq/day of the target species.

In certain embodiments of the method of the present disclosure, the daily dose of the nonabsorbable composition has insufficient capacity to remove more than 60 mEq/day of the target species. For example, in one such method the daily dose has insufficient capacity to remove more than 55 mEq/day of the target species. By way of further example, in one such embodiment the daily dose has insufficient capacity to remove more than 50 mEq/day of the target species. By way of further example, in one such embodiment the daily dose has insufficient capacity to remove more than 45 mEq/day of the target species. By way of further example, in one such embodiment the daily dose has insufficient capacity to remove more than 40 mEq/day of the target species. By way of further example, in one such embodiment the daily dose has insufficient capacity to remove more than 35 mEq/day of the target species. By way of further example, in one such embodiment the daily dose has insufficient capacity to remove more than 34 mEq/day of the target species. By way of further example, in one such embodiment the daily dose has insufficient capacity to remove more than 33 mEq/day of the target species. By way of further example, in one such embodiment the daily dose has insufficient capacity to remove more than 32 mEq/day of the target species. By way of further example, in one such embodiment the daily dose has insufficient capacity to remove more than 31 mEq/day of the target species. By way of further example, in one such embodiment the daily dose has insufficient capacity to remove more than 30 mEq/day of the target species. By way of further example, in one such embodiment the daily dose has insufficient capacity to remove more than 29 mEq/day of the target species. By way of further example, in one such embodiment the daily dose has insufficient capacity to remove more than 28 mEq/day of the target species. By way of further example, in one such embodiment the daily dose has insufficient capacity to remove more than 27 mEq/day of the target species. By way of further example, in one such embodiment the daily dose has insufficient capacity to remove more than 26 mEq/day of the target species. By way of further example, in one such embodiment the daily dose has insufficient capacity to remove more than 25 mEq/day of the target species. By way of further example, in one such embodiment the daily dose has insufficient capacity to remove more than 24 mEq/day of the target species. By way of further example, in one such embodiment the daily dose has insufficient capacity to remove more than 23 mEq/day of the target species. By way of further example, in one such embodiment the daily dose has insufficient capacity to remove more than 22 mEq/day of the target species. By way of further example, in one such embodiment the daily dose has insufficient capacity to remove more than 21 mEq/day of the target species. By way of further example, in one such embodiment the daily dose has insufficient capacity to remove more than 20 mEq/day of the target species. By way of further example, in one such embodiment the daily dose has insufficient capacity to remove more than 19 mEq/day of the target species. By way of further example, in one such embodiment the daily dose has insufficient capacity to remove more than 18 mEq/day of the target species. By way of further example, in one such embodiment the daily dose has insufficient capacity to remove more than 17 mEq/day of the target species. By way of further example, in one such embodiment the daily dose has insufficient capacity to remove more than 16 mEq/day of the target species. By way of further example, in one such embodiment the daily dose has insufficient capacity to remove more than 15 mEq/day of the target species. By way of further example, in one such embodiment the daily dose has insufficient capacity to remove more than 14 mEq/day of the target species. By way of further example, in one such embodiment the daily dose has insufficient capacity to remove more than 13 mEq/day of the target species. By way of further example, in one such embodiment the daily dose has insufficient capacity to remove more than 12 mEq/day of the target species. By way of further example, in one such embodiment the daily dose has insufficient capacity to remove more than 11 mEq/day of the target species. By way of further example, in one such embodiment the daily dose has insufficient capacity to remove more than 10 mEq/day of the target species. By way of further example, in one such embodiment the daily dose has insufficient capacity to remove more than 9 mEq/day of the target species. By way of further example, in one such embodiment the daily dose has insufficient capacity to remove more than 8 mEq/day of the target species. By way of further example, in one such embodiment the daily dose has insufficient capacity to remove more than 7 mEq/day of the target species. By way of further example, in one such embodiment the daily dose has insufficient capacity to remove more than 6 mEq/day of the target species.

In certain embodiments of the method of the present disclosure, the method comprises oral administration of a pharmaceutical composition to increase the individual's serum bicarbonate levels wherein: (i) the pharmaceutical composition binds a target species in the individual's digestive system when given orally, the target species being selected from the group consisting of protons, strong acids, and conjugate bases of strong acids; and (ii) the pharmaceutical composition increases the serum bicarbonate level by at least 1 mEq/l in a placebo controlled study, said increase being the difference between the cohort average serum bicarbonate level in a first cohort at the end of the study, relative to the cohort average serum bicarbonate level in a second cohort at the end of the study, wherein the first cohort's subjects receive the pharmaceutical composition and the second cohort's subjects receive a placebo, wherein the first and second cohorts each comprise at least 25 subjects, each cohort is prescribed the same diet during the study and the study lasts at least two weeks. In one embodiment, the first cohort receives a daily dose of the pharmaceutical composition that does not exceed 100 g/day. In one embodiment, the first cohort receives a daily dose of the pharmaceutical composition that does not exceed 50 g/day. In one embodiment, the first cohort receives a daily dose of the pharmaceutical composition that does not exceed 30 g/day. In one embodiment, the first cohort receives a daily dose of the pharmaceutical composition that does not exceed 25 g/day. In one embodiment, the first cohort receives a daily dose of the pharmaceutical composition that does not exceed 20 g/day. In one embodiment, the first cohort receives a daily dose of the pharmaceutical composition that does not exceed 15 g/day. In one embodiment, the first cohort receives a daily dose of the pharmaceutical composition that does not exceed 10 g/day. In one embodiment, the first cohort receives a daily dose of the pharmaceutical composition that does not exceed 5 g/day. In one embodiment, the target species is protons. In one embodiment, the target species is chloride ions. In one embodiment, the target species is a strong acid. In one embodiment, the target species is HCl. In one embodiment, the pharmaceutical composition is not absorbed when ingested.

In one embodiment, the individual or adult human patient has chronic kidney disease (CKD Stage 3-4; eGFR 20-<60 mL/min/1.73 m$^2$) and a baseline serum bicarbonate value at the start of the study between 12 and 20 mEq/L. In one embodiment, the pharmaceutical composition increases the serum bicarbonate level of the individual or adult human patient by at least 2 mEq/l in the placebo controlled study. In one embodiment, the pharmaceutical composition increases the serum bicarbonate level of the individual or adult human patient by at least 3 mEq/l in the placebo controlled study. In one embodiment, the individual or adult human patient is not yet in need for kidney replacement therapy (dialysis or transplant). In one embodiment, the individual or adult human patient has not yet reached end stage renal disease ("ESRD").

In one embodiment, the individual or adult human patient has a mGFR of at least 15 mL/min/1.73 m$^2$. In one embodiment, the individual or adult human patient has an eGFR of at least 15 mL/min/1.73 m$^2$. In one embodiment, the individual or adult human patient has a mGFR of at least 30 mL/min/1.73 m$^2$. In one embodiment, the individual or adult human patient has an eGFR of at least 30 mL/min/1.73 m². In one embodiment, the individual or adult human patient has a mGFR of less than 45 mL/min/1.73 m² for at least three months. In one embodiment, the individual or adult human patient has an eGFR of less than 45 mL/min/1.73 m² for at least three months. In one embodiment, the individual or adult human patient has a mGFR of less than 60 mL/min/1.73 m² for at least three months. In one embodiment, the individual or adult human patient has an eGFR of less than 60 mL/min/1.73 m² for at least three months. In one embodiment, the individual or adult human patient has Stage 3A CKD, Stage 3B CKD, or Stage 4 CKD.

While the methods described above refer to daily dose, a further aspect of the disclosure include the methods disclosed herein in which the dose is administered less frequently than once per day (while still being administered on a regular basis). In any of the disclosure, the daily dose specified may, instead, be administrated on a less frequent basis. For example, the doses disclosed here may be administered once every two or three days. Or the doses disclosed here may be administered once, twice or three times a week.

In addition to (or as a surrogate for) serum bicarbonate, other biomarkers of acid-base imbalance may be used as a measure of acid-base status. For example, blood (serum or plasma) pH, total $CO_2$, anion gap, and/or the concentration of other electrolytes (e.g., sodium, potassium, calcium, magnesium, chloride and/or sulfate) may be used as an indicator of acid-base imbalance. Similarly, net acid excretion ("NAE"), urine pH, urine ammonium concentration, and/or the concentration of other electrolytes in the urine (e.g., sodium, potassium, calcium, magnesium, chloride and/or sulfate) may be used as an indicator of acid-base imbalance.

| Fluid | Biomarker of interest | Normal/Target Value | Analytical Technique |
|---|---|---|---|
| Blood (serum or plasma) | Total $CO_2$ | 23-29 mmol/L | Blood gas analyzer; enzymatic assay; ion selective electrode |
| | Anion gap | 3-11 mEq/L | Obtained from standard chemistry electrolyte panel |
| | pH | 7.36 to 7.44 | Blood gas analyzer; enzymatic assay; ion selective electrode |
| | Electrolytes | Na = 135-145 mEq/L; K = 3.5-5 mEq/L; Total Ca = 8-10.5 mEq/L, depending on age and sex; Mg = 1.5-2.5 mEq/L, depending on age; Cl = 95-105 mEq/L; phosphate = 2.5-4.5 mEq/L; sulfate = 1 mEq/L | Obtained from standard chemistry electrolyte panel; ion selective electrodes can be used for Na, Cl and K |
| urine | pH | 4.5-8.0 | pH meter |
| | ammonium | 3-65 mmol/L | Enzymatic |
| | citrate | 150-1,191 mg/24-hour urine collection; ranges for 20 to 60 years of age | Enzymatic |
| | sodium | 20 mEq/L in spot samples, 41-227 mEq/L per day (depending upon salt and fluid intake) | Ion-selective electrode |
| | potassium | 17-77 mmol/24 hours; spot sample is ~45 mmol/L | Ion-selective electrode |
| | calcium | Urinary calcium is <250 mg/24 hours in males, <200 mg/24 hours in females | Enzymatic |
| | magnesium | Urinary magnesium is 51-269 mg/24 hours; spot values are usually reported as a ratio with creatinine and are >0.035 mg Mg/mg creatinine | Enzymatic |
| | chloride | Urinary chloride is 40-224 mmol/24 hours | Ion-selective electrode |
| | Urine Anion Gap ("UAG") | UAG = 0-10 mEq/L; Metabolic acidosis indicated when UAG > 20 mEq/L | UAG = $(Na^+ + K^+) - Cl^-$ in urine. It is a measure of ammonium excretion, the primary mechanism for acid excretion. |
| | Net Acid Excretion | Urinary net acid excretion is the total amount of acid excreted by the kidney per day; the NAE value depends on the age of the subject, gender, and protein intake; typical NAE values range from 9 mEq/day to 38 mEq/day | 24-hour urine collection required; Direct NAE measurement (mEq/day) = $[NH_4^+] + [TA] - [HCO_3^-]$, where TA is concentration of titratable acids Indirect NAE measurement (mEq/day) = (Cl + P + $SO_4$ + organic anions) − (Na + K + Ca + Mg). |

In one embodiment, treatment of an individual as described herein may improve an individuals' serum anion gap. For example, treating an acid base imbalance with a neutral composition having the capacity to bind both protons and anions (unaccompanied by the delivery of sodium or potassium ions) can increase serum bicarbonate without an accompanying increase in sodium or potassium (see Example 3 and FIGS. 13A, 13C and 13D). Consequently, the serum anion gap may be improved (decreased) by at least 1 mEq/l or more (e.g., at least 2 mEq/l) within a period as short as 2 weeks (see Example 3).

The various aspects and embodiments may have a range of advantages, such as improved or successful treatment of metabolic acidosis. Such improvements may also include reduced side effects, increased patient compliance, reduced drug loads, increased speed of treatment, increased magnitude of treatment, avoiding unwanted changes to other electrolytes and/or reduced drug-drug interactions. A further improvement may include reducing a patient's anion gap (as defined above) as part of the methods and other aspects disclosed herein. Further useful features of the disclosed aspects can be found in the examples.

Nonabsorbable Compositions

The nonabsorbable compositions having the medical uses described herein possess the capacity to remove clinically significant quantities of one or more target species: (i) protons, (ii) the conjugate base(s) of one or more strong acids (e.g., chloride, bisulfate ($HSO_4$) and/or sulfate ($SO_4$) ions) and/or (iii) one or more strong acids (e.g., HCl and/or $H_2SO_4$). To bind such target species, the nonabsorbable compositions may be selected from the group consisting of cation exchange compositions, anion exchange compositions, amphoteric ion exchange compositions, neutral compositions having the capacity to bind both protons and anions, composites thereof and mixtures thereof. However, as set out in the appended claims and further defined below, the active part of the nonabsorbable compositions may be a nonabsorbable proton binding polymer. These include all polymers disclosed in WO2014/197725 A1 and WO2016/094685 A1.

In general, the nonabsorbable composition has a preferred particle size range that is (i) large enough to avoid passive or active absorption through the GI tract and (ii) small enough to not cause grittiness or unpleasant mouth feel when ingested as a powder, sachet and/or chewable tablet/dosage form with a mean particle size of at least 3 microns. For example, in one such embodiment the nonabsorbable composition comprises a population of particles having a mean particle size (volume distribution) in the range of 5 to 1,000 microns. By way of further example, in one such embodiment the nonabsorbable composition comprises a population of particles having a mean particle size (volume distribution) in the range of 5 to 500 microns. By way of further example, in one such embodiment the nonabsorbable composition comprises a population of particles having a mean particle size (volume distribution) in the range of 10 to 400 microns. By way of further example, in one such embodiment the nonabsorbable composition comprises a population of particles having a mean particle size (volume distribution) in the range of 10 to 300 microns. By way of further example, in one such embodiment the nonabsorbable composition comprises a population of particles having a mean particle size (volume distribution) in the range of 20 to 250 microns. By way of further example, in one such embodiment the nonabsorbable composition comprises a population of particles having a mean particle size (volume distribution) in the range of 30 to 250 microns. By way of further example, in one such embodiment the nonabsorbable composition comprises a population of particles having a mean particle size (volume distribution) in the range of 40 to 180 microns. In certain embodiments, less than 7% of the particles in the population (volume distribution) have a diameter less than 10 microns. For example, in such embodiments less than 5% of the particles in the particles in the population (volume distribution) have a diameter less than 10 microns. By way of further example, in such embodiments less than 2.5% of the particles in the particles in the population (volume distribution) have a diameter less than 10 microns. By way of further example, in such embodiments less than 1% of the particles in the particles in the population (volume distribution) have a diameter less than 10 microns. In all embodiments, the particle size may be measured using the protocol set out in the abbreviations and definitions section (above).

To minimize GI side effects in patients that are often related to a large volume polymer gel moving through the GI tract, a low Swelling Ratio of the nonabsorbable composition is preferred (0.5 to 10 times its own weight in water). For example, in one such embodiment the nonabsorbable composition has a Swelling Ratio of less than 9. By way of further example, in one such embodiment the nonabsorbable composition has a Swelling Ratio of less than 8. By way of further example, in one such embodiment the nonabsorbable composition has a Swelling Ratio of less than 7. By way of further example, in one such embodiment the nonabsorbable composition has a Swelling Ratio of less than 6. By way of further example, in one such embodiment the nonabsorbable composition has a Swelling Ratio of less than 5. By way of further example, in one such embodiment the nonabsorbable composition has a Swelling Ratio of less than 4. By way of further example, in one such embodiment the nonabsorbable composition has a Swelling Ratio of less than 3. By way of further example, in one such embodiment the nonabsorbable composition has a Swelling Ratio of less than 2.

The amount of the target species (proton, conjugate base of a strong acid and/or strong acid) that is bound as the nonabsorbable composition transits the GI tract is largely a function of the binding capacity of the composition for the target species (protons, the conjugate base of a strong acid, and/or a strong acid) and the quantity of the nonabsorbable composition administered per day as a daily dose. In general, the theoretical binding capacity for a target species may be determined using a SGF assay and determining the amount of a species that appeared in or disappeared from the SGF buffer during the SGF assay. For example, the theoretical proton binding capacity of a cation exchange resin may be determined by measuring the increase in the amount of cations (other than protons) in the buffer during a SGF assay. Similarly, the theoretical anion binding capacity of an anion exchange resin (in a form other than the chloride form) may be determined by measuring the increase in the amount of anions (other than chloride ions) in the buffer during a SGF assay. Additionally, the theoretical anion binding capacity of a neutral composition for protons and the conjugate base of a strong acid may be determined by measuring the decrease in chloride concentration in the buffer during a SGF assay.

In general, the nonabsorbable composition will have a theoretical binding capacity for the target species of at least about 0.5 mEq/g (as determined in an SGF assay). For example, in some embodiments the nonabsorbable composition will have a theoretical binding capacity for the target species of at least about 1 mEq/g. By way of further example, in some embodiments the nonabsorbable composition will have a theoretical binding capacity for the target species of at least about 2 mEq/g. By way of further example, in some embodiments the nonabsorbable composition will have a theoretical binding capacity for the target species of at least about 3 mEq/g. By way of further example, in some embodiments the nonabsorbable composition will have a theoretical binding capacity for the target species of at least about 4 mEq/g. By way of further example, in some embodiments the nonabsorbable composition will have a theoretical binding capacity for the target species of at least about 5 mEq/g. By way of further example, in some embodiments the nonabsorbable composition will have a theoretical binding capacity for the target species of at least about 7.5 mEq/g. By way of further example, in some embodiments the nonabsorbable composition will have a theoretical binding capacity for the target species of at least about 10 mEq/g. By way of further example, in some embodiments the nonabsorbable composition will have a theoretical binding capacity for the target species of at least about 12.5 mEq/g. By way of further example, in some embodiments the nonabsorbable composition will have a theoretical binding capacity for the target species of at least about 15 mEq/g. By way of further example, in some embodiments the nonabsorbable composition will have a theoretical binding capacity for the target species of at least about 20 mEq/g. In general, the nonabsorbable composition will typically have a theoretical binding capacity for the target species that is not in excess of about 35 mEq/g. For example, in some embodiments, the theoretical binding capacity of the nonabsorbable compositions for the target species that is not be excess of 30 mEq/g. Thus, for example, the theoretical binding capacity of the nonabsorbable compositions for the target species may range from 2 to 25 mEq/g, 3 to 25 mEq/g, 5 to 25 mEq/g, 10 to 25 mEq/g, 5 to 20 mEq/g, 6 to 20 mEq/g, 7.5 to 20 mEq/g, or even 10 to 20 mEq/g. In those embodiments in which the target species comprises protons and at least one conjugate base, the binding capacities recited in this paragraph are the theoretical binding capacities for protons and the theoretical binding capacities for the conjugate base(s), independently and individually, and not the sum thereof.

In general, the nonabsorbable composition will have a theoretical binding capacity for protons of at least about 0.5 mEq/g (as determined in an SGF assay). For example, in some embodiments the nonabsorbable composition will have a theoretical binding capacity for protons of at least about 1 mEq/g. By way of further example, in some embodiments the nonabsorbable composition will have a theoretical binding capacity for protons of at least about 2 mEq/g. By way of further example, in some embodiments the nonabsorbable composition will have a theoretical binding capacity for protons of at least about 3 mEq/g. By way of further example, in some embodiments the nonabsorbable composition will have a theoretical binding capacity for protons of at least about 4 mEq/g. By way of further example, in some embodiments the nonabsorbable composition will have a theoretical binding capacity for protons of at least about 5 mEq/g. By way of further example, in some embodiments the nonabsorbable composition will have a theoretical binding capacity for protons of at least about 7.5 mEq/g. By way of further example, in some embodiments the nonabsorbable composition will have a theoretical binding capacity for protons of at least about 10 mEq/g. By way of further example, in some embodiments the nonabsorbable composition will have a theoretical binding capacity for protons of at least about 12.5 mEq/g. By way of further example, in some embodiments the nonabsorbable composition will have a theoretical binding capacity for protons of at least about 15 mEq/g. By way of further example, in some embodiments the nonabsorbable composition will have a theoretical binding capacity for protons of at least about 20 mEq/g. In general, the nonabsorbable composition will typically have a theoretical binding capacity for protons that is not in excess of about 35 mEq/g. For example, in some embodiments, the theoretical binding capacity of the nonabsorbable compositions for protons that is not be excess of 30 mEq/g. Thus, for example, the theoretical binding capacity of the nonabsorbable compositions for protons may range from 2 to 25 mEq/g, 3 to 25 mEq/g, 5 to 25 mEq/g, 10 to 25 mEq/g, 5 to 20 mEq/g, 6 to 20 mEq/g, 7.5 to 20 mEq/g, or even 10 to 20 mEq/g. In those embodiments in which the target species comprises protons and at least one conjugate base, the binding capacities recited in this paragraph are the theoretical binding capacities for protons and the theoretical binding capacities for the conjugate base(s), independently and individually, and not the sum thereof.

Phosphate, bicarbonate, bicarbonate equivalents, the conjugate bases of bile and fatty acids are potential interfering anions for chloride or other conjugate bases of strong acids (e.g., $HSO_4^-$ and $SO_4^{2-}$) in the stomach and small intestine. Therefore, rapid and preferential binding of chloride over phosphate, bicarbonate equivalents, and the conjugate bases of bile and fatty acids in the small intestine is desirable and the SIB assay may be used to determine kinetics and preferential binding. Since the transit time of the colon is slow (2-3 days) relative to the small intestine, and since conditions in the colon will not be encountered by an orally administered nonabsorbable composition until after stomach and small intestine conditions have been encountered, kinetics of chloride binding by a nonabsorbable composition do not need to be as rapid in the colon or under in vitro conditions designed to mimic the late small intestine/colon. It is, however, desirable that chloride binding and selectivity over other interfering anions is high, for example, at 24 and/or 48 hours or longer.

In one embodiment, the nonabsorbable composition is characterized by a chloride ion binding capacity of at least 1 mEq/g in a Simulated Small Intestine Inorganic Buffer ("SIB") assay. For example, in one such embodiment the nonabsorbable composition is characterized by a chloride ion binding capacity of at least 1.5 mEq/g in a SIB assay. By way of further example, in one such embodiment the nonabsorbable composition is characterized by a chloride ion binding capacity of at least 2 mEq/g in a SIB assay. By way of further example, in one such embodiment the nonabsorbable composition is characterized by a chloride ion binding capacity of at least 2.5 mEq/g in a SIB assay. By way of further example, in one such embodiment the nonabsorbable composition is characterized by a chloride ion binding capacity of at least 3 mEq/g in a SIB assay. By way of further example, in one such embodiment the nonabsorbable composition is characterized by a chloride ion binding capacity of at least 3.5 mEq/g in a SIB assay. By way of further example, in one such embodiment the nonabsorbable composition is characterized by a chloride ion binding capacity of at least 4 mEq/g in a SIB assay. By way of further example, in one such embodiment the nonabsorbable composition is characterized by a chloride ion binding capacity of at least 4.5 mEq/g in a SIB assay. By way of further example, in one such embodiment the nonabsorbable composition is characterized by a chloride ion binding capacity of at least 5 mEq/g in a SIB assay. By way of further example, in one such embodiment the nonabsorbable composition is characterized by a chloride ion binding capacity of at least 5.5 mEq/g in a SIB assay. By way of further example, in one such embodiment the nonabsorbable composition is characterized by a chloride ion binding capacity of at least 6 mEq/g in a SIB assay.

In one embodiment, the nonabsorbable composition binds a significant amount of chloride relative to phosphate as exhibited, for example, in a SIB assay. For example, in one embodiment the ratio of the amount of bound chloride to bound phosphate in a SIB assay is at least 0.1:1, respectively. By way of further example, in one such embodiment the ratio of the amount of bound chloride to bound phosphate in a SIB assay is at least 0.2:1, respectively. By way of further example, in one such embodiment the ratio of the amount of bound chloride to bound phosphate in a SIB assay is at least 0.25:1, respectively. By way of further example, in one such embodiment the ratio of the amount of bound chloride to bound phosphate in a SIB assay is at least 0.3:1, respectively. By way of further example, in one such embodiment the ratio of the amount of bound chloride to bound phosphate in a SIB assay is at least 0.35:1, respectively. By way of further example, in one such embodiment the ratio of the amount of bound chloride to bound phosphate in a SIB assay is at least 0.4:1, respectively. By way of further example, in one such embodiment the ratio of the amount of bound chloride to bound phosphate in a SIB assay is at least 0.45:1, respectively. By way of further example, in one such embodiment the ratio of the amount of bound chloride to bound phosphate in a SIB assay is at least 0.5:1, respectively. By way of further example, in one such embodiment the ratio of the amount of bound chloride to bound phosphate in a SIB assay is at least 2:3, respectively. By way of further example, in one such embodiment the ratio of the amount of bound chloride to bound phosphate in a SIB assay is at least 0.75:1, respectively. By way of further example, in one such embodiment the ratio of the amount of bound chloride to bound phosphate in a SIB assay is at least 0.9:1, respectively. By way of further example, in one such embodiment the ratio of the amount of bound chloride to bound phosphate in a SIB assay is at least 1:1, respectively. By way of further example, in one such embodiment the ratio of the amount of bound chloride to bound phosphate in a SIB assay is at least 1.25:1, respectively. By way of further example, in one such embodiment the ratio of the amount of bound chloride to bound phosphate in a SIB assay is at least 1.5:1, respectively. By way of further example, in one such embodiment the ratio of the amount of bound chloride to bound phosphate in a SIB assay is at least 1.75:1, respectively. By way of further example, in one such embodiment the ratio of the amount of bound chloride to bound phosphate in a SIB assay is at least 2:1, respectively. By way of further example, in one such embodiment the ratio of the amount of bound chloride to bound phosphate in a SIB assay is at least 2.25:1, respectively. By way of further example, in one such embodiment the ratio of the amount of bound chloride to bound phosphate in a SIB assay is at least 2.5:1, respectively. By way of further example, in one such embodiment the ratio of the amount of bound chloride to bound phosphate in a SIB assay is at least 2.75:1, respectively. By way of further example, in one such embodiment the ratio of the amount of bound chloride to bound phosphate in a SIB assay is at least 3:1, respectively. By way of further example, in one such embodiment the ratio of the amount of bound chloride to bound phosphate in a SIB assay is at least 4:1, respectively. By way of further example, in one such embodiment the ratio of the amount of bound chloride to bound phosphate in a SIB assay is at least 5:1, respectively.

In one embodiment, the orally administered nonabsorbable composition is characterized by a proton-binding capacity and a chloride binding capacity in Simulated Gastric Fluid of at least 1 mEq/g in a SGF assay. For example, in one such embodiment the nonabsorbable composition is characterized by a proton-binding capacity and a chloride binding capacity in a SGF assay of at least 2 mEq/g. By way of further example, in one such embodiment the nonabsorbable composition is characterized by a proton-binding capacity and a chloride binding capacity in a SGF assay of at least 3 mEq/g. By way of further example, in one such embodiment the nonabsorbable composition is characterized by a proton-binding capacity and a chloride binding capacity in a SGF assay of at least 4 mEq/g. By way of further example, in one such embodiment the nonabsorbable composition is characterized by a proton-binding capacity and a chloride binding capacity in a SGF assay of at least 5 mEq/g. By way of further example, in one such embodiment the nonabsorbable composition is characterized by a proton-binding capacity and a chloride binding capacity in a SGF assay of at least 6 mEq/g. By way of further example, in one such embodiment the nonabsorbable composition is characterized by a proton-binding capacity and a chloride binding capacity in a SGF assay of at least 7 mEq/g. By way of further example, in one such embodiment the nonabsorbable composition is characterized by a proton-binding capacity and a chloride binding capacity in a SGF assay of at least 8 mEq/g. By way of further example, in one such embodiment the nonabsorbable composition is characterized by a proton-binding capacity and a chloride binding capacity in a SGF assay of at least 9 mEq/g. By way of further example, in one such embodiment the nonabsorbable composition is characterized by a proton-binding capacity and a chloride binding capacity in a SGF assay of at least 10 mEq/g. By way of further example, in one such embodiment the nonabsorbable composition is characterized by a proton-binding capacity and a chloride binding capacity in a SGF assay of at least 11 mEq/g. By way of further example, in one such embodiment the nonabsorbable composition is characterized by a proton-binding capacity and a chloride binding capacity in a SGF assay of at least 12 mEq/g. By way of further example, in one such embodiment the nonabsorbable composition is characterized by a proton-binding capacity and a chloride binding capacity in a SGF assay of at least 13 mEq/g. By way of further example, in one such embodiment the nonabsorbable composition is characterized by a proton-binding capacity and a chloride binding capacity in a SGF assay of at least 14 mEq/g. By way of further example, in one such embodiment the nonabsorbable composition is characterized by a proton-binding capacity and a chloride binding capacity after 1 hour in SGF that is at least 50% of the proton-binding capacity and the chloride binding capacity, respectively, of the nonabsorbable composition at 24 hours in SGF. By way of further example, in one such embodiment the nonabsorbable composition is characterized by a proton-binding capacity and a chloride binding capacity after 1 hour in SGF that is at least 60% of the proton-binding capacity and the chloride binding capacity, respectively, of the nonabsorbable composition at 24 hours in SGF. By way of further example, in one such embodiment the nonabsorbable composition is characterized by a proton-binding capacity and a chloride binding capacity after 1 hour in SGF that is at least 70% of the proton-binding capacity and the chloride binding capacity, respectively, of the nonabsorbable composition at 24 hours in SGF. By way of further example, in one such embodiment the nonabsorbable composition is characterized by a proton-binding capacity and a chloride binding capacity after 1 hour in SGF that is at least 80% of the proton-binding capacity and the chloride binding capacity, respectively, of the nonabsorbable composition at 24 hours in SGF. By way of further example, in one such embodiment the nonabsorbable composition is characterized by a proton-binding capacity and a chloride binding capacity after 1 hour in SGF that is at least 90% of the proton-binding capacity and the chloride binding capacity, respectively, of the nonabsorbable composition at 24 hours in SGF.

In one embodiment, the nonabsorbable composition is a cation exchange material comprising an insoluble (in the gastric environment) support structure and exchangeable cations. The cation exchange material may be organic (e.g., polymeric), inorganic (e.g., a zeolite) or a composite thereof. The exchangeable cations may be selected, for example, from the group consisting of lithium, sodium, potassium, calcium, magnesium, iron and combinations thereof, and more preferably from the group consisting of sodium, potassium, calcium, magnesium, and combinations thereof. In such embodiments it is generally preferred that the nonabsorbable composition contain a combination of exchangeable cations that establish or maintain electrolyte homeostasis. For example, in one such embodiment the nonabsorbable composition optionally contains exchangeable sodium ions, but when included, the amount of the sodium ions in a daily dose is insufficient to increase the patient's serum sodium ion concentration to a value outside the range of 135 to 145 mEq/l. By way of further example, in one such embodiment the nonabsorbable composition optionally contains exchangeable potassium ions, but when included, the amount of the potassium ions in a daily dose is insufficient to increase the patient's serum potassium ion concentration to a value outside the range of 3.7 to 5.2 mEq/L. By way of further example, in one such embodiment the nonabsorbable composition optionally contains exchangeable magnesium ions, but when included, the amount of the magnesium ions in a daily dose is insufficient to increase the patient's serum magnesium ion concentration to a value outside the range of 1.7 to 2.2 mg/dL. By way of further example, in one such embodiment the nonabsorbable composition optionally contains exchangeable calcium ions, but when included, the amount of the calcium ions in a daily dose is insufficient to increase the patient's serum calcium ion concentration to a value outside the range of 8.5 to 10.2 mg/dL. By way of further example, in one such embodiment the nonabsorbable composition contains a combination of exchangeable cations selected from the group consisting of sodium, potassium, calcium, magnesium, and combinations thereof, designed to maintain serum $Na^+$ levels within the range of 135 to 145 mEq/l, serum $K^+$ levels within the range of 3.7 to 5.2 mEq/L, serum $Mg^{2+}$ levels within the range of 1.7 to 2.2 mg/dL and serum $Ca^{2+}$ levels within the range of 8.5 to 10.2 mg/dL.

In one embodiment, the nonabsorbable composition is a cation exchange material comprising an insoluble (in the gastric environment) support structure, optionally containing exchangeable sodium ions cations. The cation exchange material may be organic (e.g., polymeric), inorganic (e.g., a molecular sieve) or a composite thereof. In one such embodiment, the nonabsorbable composition contains less than 12% by weight sodium. For example, in one such embodiment the nonabsorbable composition contains less than 9% by weight sodium. By way of further example, in one such embodiment the nonabsorbable composition contains less than 6% by weight sodium. By way of further example, in one such embodiment the nonabsorbable composition contains less than 3% by weight sodium. By way of further example, in one such embodiment the nonabsorbable composition contains less than 1% by weight sodium. By way of further example, in one such embodiment the nonabsorbable composition contains less than 0.1% by weight sodium. By way of further example, in one such embodiment the nonabsorbable composition contains less than 0.01% by weight sodium. By way of further example, in one such embodiment the nonabsorbable composition contains between 0.05 and 3% by weight sodium.

In one exemplary embodiment, the nonabsorbable composition is a resin comprising any of a wide range of crosslinked polymeric materials that are able to bind protons in aqueous solutions. Exemplary crosslinked polymeric material comprises a polyanion crosslinked material selected from poly(carboxylic acids), poly(acrylic acids), poly(sulfonic acids), poly(maleic acids), poly(phenols), functionalized polyols and poly(alcohols), poly(hydroxamic acids), poly(imides) and copolymers thereof. In one embodiment, the polyanion is coordinated to exchangeable monovalent cations, divalent cations, or a combination thereof. Exemplary monovalent cations include lithium, sodium, and potassium, or any combination thereof. Exemplary divalent cations include magnesium and calcium or combinations thereof.

In one exemplary embodiment, the nonabsorbable composition is a cation exchange resin comprising a polyanion backbone that exchanges cations for protons and has an average pKa of at least 4. For example, in one embodiment, the polyanion backbone has an average pKa of 4-5. By way of further example, in one such embodiment the polyanion backbone has an average pKa of 5-6. By way of further example, in one such embodiment the polyanion backbone has an average pKa of 6-7. By way of further example, in one such embodiment the polyanion backbone has an average pKa of greater than 7. Exemplary cation exchange resins include poly(carboxylic acids), poly(acrylic acids), poly(sulfonic acids), poly(maleic acids), poly(phenols), functionalized polyols and poly(alcohols), poly(hydroxamic acids), poly(imides) and copolymers thereof. In one embodiment, these polyanion backbones are further functionalized with functional groups to affect the pKa. These functional groups can increase pKa when electron donating, or decrease pKa when electron withdrawing. Exemplary electron donating groups include amino, hydroxyl, methyl ether, ether, phenyl, and amido. Exemplary electron withdrawing groups include fluoro, chloro, halo, sulphonyl, nitroxyl, trifluoromethyl, and cyano. Further exemplary cation exchange resins include resins modified with protonable functional groups including carboxylic acids and functionalized alcohols.

Polymeric cation exchanger resins may be prepared using a range of chemistries, including for example, (i) substitution polymerization of polyfunctional reagents at least one of which comprises basic anionic or conjugate-acid moieties, (2) radical polymerization of a monomer comprising at least one acid or conjugate-acid containing moiety, and (3) crosslinking of a basic anionic or conjugate-acid containing intermediate with a polyfunctional crosslinker, optionally containing basic anionic or conjugate-acid moieties. The resulting crosslinked polymers may thus, for example, be crosslinked homopolymers or crosslinked copolymers. By way of further example, the resulting crosslinked polymers will typically possess repeat units comprising basic anionic or conjugate-acid, separated by the same or varying lengths of repeating linker (or intervening) units. In some embodiments, the polymers comprise repeat units comprising a basic anionic or conjugate-acid moiety and an intervening linker unit. In other embodiments, multiple basic anionic or conjugate-acid containing repeat units are separated by one or more linker units. Additionally, the polyfunctional crosslinkers may comprise proton binding functional groups, e.g. basic anionic, ("active crosslinkers") or may lack proton binding functional groups such as acrylates ("passive crosslinkers").

In some embodiments, a basic anion or conjugate-acid monomer is polymerized and the polymer is concurrently crosslinked in a substitution polymerization reaction. The basic anion or conjugate-acid reactant (monomer) in the concurrent polymerization and crosslinking reaction can react more than one time for the substitution polymerization. In one such embodiment, the basic anion or conjugate-acid monomer is a branched basic anion or conjugate-acid possessing at least two reactive moieties to participate in the substitution polymerization reaction.

In one embodiment, the nonabsorbable composition is an anion exchange material comprising at least 1 mEq/g of an anion selected from the group consisting of hydroxide, carbonate, citrate or other bicarbonate equivalent anion, or a combination thereof. In this embodiment, the nonabsorbable composition has the capacity to induce an increase in the individual's serum bicarbonate value, at least in part, by delivering a physiologically significant amount of hydroxide, carbonate, citrate or other bicarbonate equivalent, or a combination thereof. Exemplary bicarbonate equivalent anions include acetate, lactate and the conjugate bases of other short chain carboxylic acids. In one such embodiment, the nonabsorbable composition comprises at least 2 mEq/g of an anion selected from the group consisting of hydroxide, carbonate, citrate or other bicarbonate equivalent anion. By way of further example, in one such embodiment the nonabsorbable composition comprises at least 3 mEq/g of an anion selected from the group consisting of hydroxide, carbonate, citrate or other bicarbonate equivalent anion. By way of further example, in one such embodiment the nonabsorbable composition comprises at least 4 mEq/g of an anion selected from the group consisting of hydroxide, carbonate, citrate or other bicarbonate equivalent anion. By way of further example, in one such embodiment the nonabsorbable composition comprises at least 5 mEq/g of an anion selected from the group consisting of hydroxide, carbonate, citrate or other bicarbonate equivalent anion.

In one embodiment, the nonabsorbable composition is an anion exchange material comprising less than 10 mEq/g of an anion selected from the group consisting of hydroxide, carbonate, citrate or other bicarbonate equivalent anion, or a combination thereof. In one such embodiment, the nonabsorbable composition comprises less than 7.5 mEq/g of an anion selected from the group consisting of hydroxide, carbonate, citrate or other bicarbonate equivalent anion. By way of further example, in one such embodiment the nonabsorbable composition comprises less than 5 mEq/g of an anion selected from the group consisting of hydroxide, carbonate, citrate or other bicarbonate equivalent anion. By way of further example, in one such embodiment the nonabsorbable composition comprises less than 2.5 mEq/g of an anion selected from the group consisting of hydroxide, carbonate, citrate or other bicarbonate equivalent anion. By way of further example, in one such embodiment the nonabsorbable composition comprises less than 1 mEq/g of an anion selected from the group consisting of hydroxide, carbonate, citrate or other bicarbonate equivalent anion. By way of further example, in one such embodiment the nonabsorbable composition comprises less than 0.1 mEq/g of an anion selected from the group consisting of hydroxide, carbonate, citrate or other bicarbonate equivalent anion.

In one embodiment, the nonabsorbable composition comprises an amphoteric ion exchange resin. Exemplary amphoteric ion-exchange resins include crosslinked polystyrene, polyethylene or the like as a base material and quaternary ammonium group, carboxylic acid group and the like in (i) the same pendant groups (e.g., betaine-containing pendant groups) such as the amphoteric resin sold under the trade designation DIAION AMP03 (Mitsubishi Chemical Corporation) or (ii) different pendant groups (e.g., mixed charged copolymers containing the residues of at least two different monomers, one containing ammonium groups and one containing carboxylic acid groups), to provide a function of ion-exchanging the both of cations and negative ions. Exemplary amphoteric ion-exchange resins containing a mixture of cation and anion exchange sites also include resins in which a linear polymer is trapped inside a crosslinked ion exchange resin, such as the amphoteric resin sold under the trade designation DOWEX™ Retardion 11A8 (Dow Chemical Company).

In one embodiment, the nonabsorbable composition comprises a neutral composition having the capacity to bind both protons and anions. Exemplary neutral nonabsorbable compositions that bind both protons and anions include polymers functionalized with propylene oxide, polymers functionalized with Michael acceptors, expanded porphyrins, covalent organic frameworks, and polymers containing amine and/or phosphine functional groups.

In those embodiments in which the nonabsorbable composition binds chloride ions, it is generally preferred that the nonabsorbable composition selectively bind chloride ions relative to other counter ions such as bicarbonate equivalent anions, phosphate anions, and the conjugate bases of bile and fatty acids. Stated differently, it is generally preferred in these embodiments that the nonabsorbable composition (i) remove more chloride ions than bicarbonate equivalent anions (ii) remove more chloride ions than phosphate anions, and (iii) remove more chloride ions than the conjugate bases of bile and fatty acids. Advantageously, therefore, treatment with the nonabsorbable composition does not induce or exacerbate hypophosphatemia (i.e., a serum phosphorous concentration of less than about 2.4 mg/dL, does not significantly elevate low density lipoproteins ("LDL"), or otherwise negatively impact serum or colon levels of metabolically relevant anions.

In some embodiments, the pharmaceutical composition comprises a crosslinked polymer containing the residue of an amine corresponding to Formula 1:

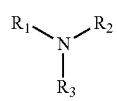

Formula 1 wherein $R_1$, $R_2$ and $R_3$ are independently hydrogen, hydrocarbyl, substituted hydrocarbyl provided, however, at least one of $R_1$, $R_2$ and $R_3$ is other than hydrogen. Stated differently, at least one of $R_1$, $R_2$ and $R_3$ is hydrocarbyl or substituted hydrocarbyl, and the others of $R_1$, $R_2$ and $R_3$ are independently hydrogen, hydrocarbyl, or substituted hydrocarbyl. In one embodiment, for example, $R_1$, $R_2$ and $R_3$ are independently hydrogen, aryl, aliphatic, heteroaryl, or heteroaliphatic provided, however, each of $R_1$, $R_2$ and $R_3$ are not hydrogen. By way of further example, in one such embodiment $R_1$, $R_2$ and $R_3$ are independently hydrogen, saturated hydrocarbons, unsaturated aliphatic, unsaturated heteroaliphatic, heteroalkyl, heterocyclic, aryl or heteroaryl, provided, however, each of $R_1$, $R_2$ and $R_3$ are not hydrogen. By way of further example, in one such embodiment $R_1$, $R_2$ and $R_3$ are independently hydrogen, alkyl, alkenyl, allyl, vinyl, aryl, aminoalkyl, alkanol, haloalkyl, hydroxyalkyl, ethereal, heteroaryl or heterocyclic provided, however, each of $R_1$, $R_2$ and $R_3$ are not hydrogen. By way of further example, in one such embodiment $R_1$, $R_2$ and $R_3$ are independently hydrogen, alkyl, aminoalkyl, alkanol, aryl, haloalkyl, hydroxyalkyl, ethereal, heteroaryl or heterocyclic provided, however, each of $R_1$, $R_2$ and $R_3$ are not hydrogen. By way of further example, in one such embodiment $R_1$ and $R_2$ (in combination with the nitrogen atom to which they are attached) together constitute part of a ring structure, so that the monomer as described by Formula 1 is a nitrogen-containing heterocycle (e.g., piperidine) and $R_3$ is hydrogen, or heteroaliphatic. By way of further example, in one embodiment $R_1$, $R_2$ and $R_3$ are independently hydrogen, aliphatic or heteroaliphatic provided, however, at least one of $R_1$, $R_2$ and $R_3$ is other than hydrogen. By way of further example, in one embodiment $R_1$, $R_2$ and $R_3$ are independently hydrogen, allyl, or aminoalkyl.

In one embodiment, the crosslinked polymer comprises the residue of an amine corresponding to Formula 1 wherein $R_1$, $R_2$, and $R_3$ are independently hydrogen, heteroaryl, aryl, aliphatic or heteroaliphatic provided, however, at least one of $R_1$, $R_2$, and $R_3$ is aryl or heteroaryl. For example, in this embodiment $R_1$ and $R_2$, in combination with the nitrogen atom to which they are attached, may form a saturated or unsaturated nitrogen-containing heterocyclic ring. By way of further example, $R_1$ and $R_2$, in combination with the nitrogen atom to which they are attached may constitute part of a pyrrolidino, pyrole, pyrazolidine, pyrazole, imidazolidine, imidazole, piperidine, pyridine, piperazine, diazine, or triazine ring structure. By way of further example, $R_1$ and $R_2$, in combination with the nitrogen atom to which they are attached may constitute part of a piperidine ring structure.

In one embodiment, the crosslinked polymer comprises the residue of an amine corresponding to Formula 1 wherein $R_1$, $R_2$, and $R_3$ are independently hydrogen, aliphatic, or heteroaliphatic provided, however, at least one of $R_1$, $R_2$, and $R_3$ is other than hydrogen. For example, in this embodiment $R_1$, $R_2$, and $R_3$ may independently be hydrogen, alkyl, alkenyl, allyl, vinyl, aminoalkyl, alkanol, haloalkyl, hydroxyalkyl, ethereal, or heterocyclic provided, however, at least one of $R_1$, $R_2$, and $R_3$ is other than hydrogen. By way of further example, in one such embodiment $R_1$ and $R_2$, in combination with the nitrogen atom to which they are attached, may form a saturated or unsaturated nitrogen-containing heterocyclic ring. By way of further example, in one such embodiment $R_1$ and $R_2$, in combination with the nitrogen atom to which they are attached may constitute part of a pyrrolidino, pyrole, pyrazolidine, pyrazole, imidazolidine, imidazole, piperidine, piperazine, or diazine ring structure. By way of further example, in one such embodiment $R_1$ and $R_2$, in combination with the nitrogen atom to which they are attached may constitute part of a piperidine ring structure. By way of further example, in one such embodiment the amine corresponding to Formula 1 is acyclic and at least one of $R_1$, $R_2$, and $R_3$ is aliphatic or heteroaliphatic. By way of further example, in one such embodiment $R_1$, $R_2$, and $R_3$ are independently hydrogen, alkyl, allyl, vinyl, alicyclic, aminoalkyl, alkanol, or heterocyclic, provided at least one of $R_1$, $R_2$, and $R_3$ is other than hydrogen.

In one embodiment, the crosslinked polymer comprises the residue of an amine corresponding to Formula 1 and the crosslinked polymer is prepared by substitution polymerization of the amine corresponding to Formula 1 with a polyfunctional crosslinker (optionally also comprising amine moieties) wherein $R_1$, $R_2$, and $R_3$ are independently hydrogen, alkyl, aminoalkyl, or alkanol, provided at least one of $R_1$, $R_2$, and $R_3$ is other than hydrogen.

In some embodiments, the molecular weight per nitrogen of the polymers of the present disclosure may range from about 40 to about 1000 Daltons. In one embodiment, the molecular weight per nitrogen of the polymer is from about 40 to about 500 Daltons. In another embodiment, the molecular weight per nitrogen of the polymer is from about 50 to about 170 Daltons. In another embodiment, the molecular weight per nitrogen of the polymer is from about 60 to about 110 Daltons.

In some embodiments, an amine-containing monomer is polymerized and the polymer is concurrently crosslinked in a substitution polymerization reaction in the first reaction step. The amine reactant (monomer) in the concurrent polymerization and crosslinking reaction can react more than one time for the substitution polymerization. In one such embodiment, the amine monomer is a linear amine possessing at least two reactive amine moieties to participate in the substitution polymerization reaction. In another embodiment, the amine monomer is a branched amine possessing at least two reactive amine moieties to participate in the substitution polymerization reaction. Crosslinkers for the concurrent substitution polymerization and crosslinking typically have at least two amine-reactive moieties such as alkyl-chlorides, and alkyl-epoxides. In order to be incorporated into the polymer, primary amines react at least once and potentially may react up to three times with the crosslinker, secondary amines can react up to twice with the crosslinkers, and tertiary amines can only react once with the crosslinker. In general, however, the formation of a significant number of quaternary nitrogens/amines is generally not preferred because quaternary amines cannot bind protons.

Exemplary amines that may be used in substitution polymerization reactions described herein include 1,3-Bis[bis(2-aminoethyl)amino]propane, 3-Amino-1-{[2-(bis{2-[bis(3-aminopropyl)amino]ethyl}amino)ethyl](3-aminopropyl)amino}propane, 2-[Bis(2-aminoethyl)amino]ethanamine, Tris(3-aminopropyl)amine, 1,4-Bis[bis(3-aminopropyl)amino]butane, 1,2-Ethanediamine, 2-Amino-1-(2-aminoethylamino)ethane, 1,2-Bis(2-aminoethylamino)ethane, 1,3-Propanediamine, 3,3'-Diaminodipropylamine, 2,2-dimethyl-1,3-propanediamine, 2-methyl-1,3-propanediamine, N,N'-dimethyl-1,3-propanediamine, N-methyl-1,3-diaminopropane, 3,3'-diamino-N-methyldipropylamine, 1,3-diaminopentane, 1,2-diamino-2-methylpropane, 2-methyl-1,5-diaminopentane, 1,2-diaminopropane, 1,10-diaminodecane, 1,8-diaminooctane, 1,9-diaminooctane, 1,7-diaminoheptane, 1,6-diaminohexane, 1,5-diaminopentane, 3-bromopropylamine hydrobromide, N,2-dimethyl-1,3-propanediamine, N-isopropyl-1,3-diaminopropane, N,N'-bis(2-aminoethyl)-1,3-propanediamine, N,N'-bis(3-aminopropyl)ethylenediamine, N,N'-bis(3-aminopropyl)-1,4-butanediamine tetrahydrochloride, 1,3-diamino-2-propanol, N-ethylethylenediamine, 2,2'-diamino-N-methyldiethylamine, N,N'-diethylethylenediamine, N-isopropylethylenediamine, N-methylethylenediamine, N,N'-di-tert-butylethylenediamine, N,N'-diisopropylethylenediamine, N,N'-dimethylethylenediamine, N-butylethylenediamine, 2-(2-aminoethylamino)ethanol, 1,4,7,10,13,16-hexaazacyclooctadecane, 1,4,7,10-tetraazacyclododecane, 1,4,7-triazacyclononane, N,N'-bis(2-hydroxyethyl)ethylenediamine, piperazine, bis(hexamethylene)triamine, N-(3-hydroxypropyl)ethylenediamine, N-(2-Aminoethyl)piperazine, 2-Methylpiperazine, Homopiperazine, 1,4,8,11-Tetraazacyclotetradecane, 1,4,8,12-Tetraazacyclopentadecane, 2-(Aminomethyl)piperidine, 3-(Methylamino)pyrrolidine.

Exemplary crosslinking agents that may be used in substitution polymerization reactions and post-polymerization crosslinking reactions include, but are not limited to, one or more multifunctional crosslinking agents such as: dihaloalkanes, haloalkyloxiranes, alkyloxirane sulfonates, di(haloalkyl)amines, tri(haloalkyl) amines, diepoxides, triepoxides, tetraepoxides, bis(halomethyl)benzenes, tri(halomethyl)benzenes, tetra(halomethyl)benzenes, epihalohydrins such as epichlorohydrin and epibromohydrin poly(epichlorohydrin), (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1,3-dichloropropane, 1,2-dichloroethane, 1-bromo-2-chloroethane, 1,3-dibromopropane, bis(2-chloroethyl)amine, tris(2-chloroethyl)amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, 1,2 ethanedioldiglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol digylcidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis(glycidyloxy)diphenylmethane, bisphenol F diglycidyl ether, 1,4-bis(2',3'epoxypropyl)perfluoro-n-butane, 2,6-di(oxiran-2-ylmethyl)-1,2,3,5,6,7-hexahydropyrrolo[3,4-f]isoindol-1,3,5,7-tetraone, bisphenol A diglycidyl ether, ethyl 5-hydroxy-6,8-di(oxiran-2-ylmethyl)-4-oxo-4-h-chromene-2-carboxylate, bis[4-(2,3-epoxy-propylthio)phenyl]-sulfide, 1,3-bis(3-glycidoxypropyl) tetramethyldisiloxane, 9,9-bis[4-(glycidyloxy)phenyl]fluorine, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris [[3-(epoxypropoxy)propyl]dimethylsilyloxy]-1,3,5,7,9,11,14-heptacyclopentyltricyclo [7,3,3,15, 11]heptasiloxane, 4,4'methylenebis(N, N-diglycidylaniline), bis(halomethyl) benzene, bis(halomethyl)biphenyl and bis(halomethyl) naphthalene, toluene diisocyanate, acrylol chloride, methyl acrylate, ethylene bisacrylamide, pyrometallic dianhydride, succinyl dichloride, dimethylsuccinate, 3-chloro-1-(3-chloropropylamino-2-propanol, 1,2-bis(3-chloropropylamino) ethane, Bis(3-chloropropyl)amine, 1,3-Dichloro-2-propanol, 1,3-Dichloropropane, 1-chloro-2,3-epoxypropane, tris [(2-oxiranyl)methyl]amine.

In some embodiments, the carbon to nitrogen ratio of the polymers of the present disclosure may range from about 2:1 to about 6:1, respectively. For example, in one such embodiment, the carbon to nitrogen ratio of the polymers of the present disclosure may range from about 2.5:1 to about 5:1, respectively. By way of further example, in one such embodiment, the carbon to nitrogen ratio of the polymers of the present disclosure may range from about 3:1 to about 4.5:1, respectively. By way of further example, in one such embodiment, the carbon to nitrogen ratio of the polymers of the present disclosure may range from about 3.25:1 to about 4.25:1, respectively. By way of further example, in one such embodiment, the carbon to nitrogen ratio of the polymers of the present disclosure may range from about 3.4:1 to about 4:1, respectively. In another embodiment, the molecular weight per nitrogen of the polymer is from about 60 to about 110 Daltons.

In some embodiments, the crosslinked polymer comprises the residue of an amine corresponding to Formula 1a and the crosslinked polymer is prepared by radical polymerization of an amine corresponding to Formula 1a:

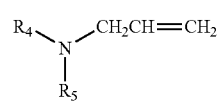

Formula 1a wherein $R_4$ and $R_5$ are independently hydrogen, hydrocarbyl, or substituted hydrocarbyl. In one embodiment, for example, $R_4$ and $R_5$ are independently hydrogen, saturated hydrocarbon, unsaturated aliphatic, aryl, heteroaryl, unsaturated heteroaliphatic, heterocyclic, or heteroalkyl. By way of further example, in one such embodiment $R_4$ and $R_5$ are independently hydrogen, aliphatic, heteroaliphatic, aryl, or heteroaryl. By way of further example, in one such embodiment $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic. By way of further example, in one such embodiment $R_4$ and $R_5$ are independently hydrogen, alkyl, allyl, aminoalkyl, alkanol, aryl, haloalkyl, hydroxyalkyl, ethereal, or heterocyclic. By way of further example, in one such embodiment $R_4$ and $R_5$ (in combination with the nitrogen atom to which they are attached) together constitute part of a ring structure, so that the monomer as described by Formula 1a is a nitrogen-containing heterocycle (e.g., piperidine). By way of further example, in one embodiment $R_4$ and $R_5$ are independently hydrogen, aliphatic or heteroaliphatic. By way of further example, in one embodiment $R_4$ and $R_5$ are independently hydrogen, allyl, or aminoalkyl.

In some embodiments, the crosslinked polymer comprises the residue of an amine corresponding to Formula 1b and the crosslinked polymer is prepared by substitution polymerization of the amine corresponding to Formula 1b with a polyfunctional crosslinker (optionally also comprising amine moieties):

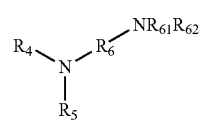

Formula 1b wherein $R_4$ and $R_5$ are independently hydrogen, hydrocarbyl, or substituted hydrocarbyl, $R_6$ is aliphatic and $R_{61}$ and $R_{62}$ are independently hydrogen, aliphatic, or heteroaliphatic. In one embodiment, for example, $R_4$ and $R_5$ are independently hydrogen, saturated hydrocarbon, unsaturated aliphatic, aryl, heteroaryl, heteroalkyl, or unsaturated heteroaliphatic. By way of further example, in one such embodiment $R_4$ and $R_5$ are independently hydrogen, aliphatic, heteroaliphatic, aryl, or heteroaryl. By way of further example, in one such embodiment $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic. By way of further example, in one such embodiment $R_4$ and $R_5$ are independently hydrogen, alkyl, alkenyl, aminoalkyl, alkanol, aryl, haloalkyl, hydroxyalkyl, ethereal, heteroaryl or heterocyclic. By way of further example, in one such embodiment $R_4$ and $R_5$ (in combination with the nitrogen atom to which they are attached) together constitute part of a ring structure, so that the monomer as described by Formula 1a is a nitrogen-containing heterocycle (e.g., piperidine). By way of further example, in one embodiment $R_4$ and $R_5$ are independently hydrogen, aliphatic or heteroaliphatic. By way of further example, in one embodiment $R_4$ and $R_5$ are independently hydrogen, allyl, or aminoalkyl. By way of further example, in each of the embodiments recited in this paragraph, $R_6$ may be methylene, ethylene or propylene, and $R_{61}$ and $R_{62}$ may independently be hydrogen, allyl or aminoalkyl.

In some embodiments, the crosslinked polymer comprises the residue of an amine corresponding to Formula 1c:

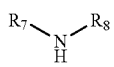

Formula 1c wherein $R_7$ is hydrogen, aliphatic or heteroaliphatic and $R_8$ is aliphatic or heteroaliphatic. For example, in one such embodiment, for example, $R_7$ is hydrogen and $R_8$ is aliphatic or heteroaliphatic. By way of further example, in one such embodiment $R_7$ and $R_8$ are independently aliphatic or heteroaliphatic. By way of further example, in one such embodiment at least one of $R_7$ and $R_8$ comprises an allyl moiety. By way of further example, in one such embodiment at least one of $R_7$ and $R_8$ comprises an aminoalkyl moiety. By way of further example, in one such embodiment $R_7$ and $R_8$ each comprise an allyl moiety. By way of further example, in one such embodiment $R_7$ and $R_8$ each comprise an aminoalkyl moiety. By way of further example, in one such embodiment $R_7$ comprises an allyl moiety and $R_8$ comprises an aminoalkyl moiety.

In some embodiments, the crosslinked polymer comprises the residue of an amine corresponding to Formula 2:

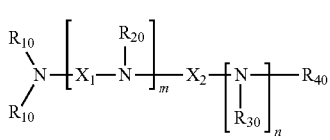

Formula 2 wherein
m and n are independently non-negative integers;
$R_{10}$, $R_{20}$, $R_{30}$, and $R_{40}$ are independently hydrogen, hydrocarbyl, or substituted hydrocarbyl;
$X_1$ is

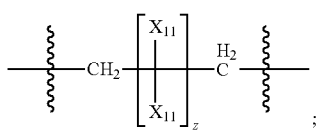

;

$X_2$ is hydrocarbyl or substituted hydrocarbyl;
each $X_{11}$ is independently hydrogen, hydrocarbyl, substituted hydrocarbyl, hydroxyl, amino, boronic acid, or halo; and
z is a non-negative number.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and m and n are independently 0, 1, 2 or 3 and n is 0 or 1.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and $R_{10}$, $R_{20}$, $R_{30}$, and $R_{40}$ are independently hydrogen, aliphatic, aryl, heteroaliphatic, or heteroaryl. By way of further example, in one such embodiment $R_{10}$, $R_{20}$, $R_{30}$, and $R_{40}$ are independently hydrogen, aliphatic, or heteroaliphatic. By way of further example, in one such embodiment $R_{10}$, $R_{20}$, $R_{30}$, and $R_{40}$ are independently hydrogen, alkyl, allyl, vinyl, or aminoalkyl. By way of further example, in one such embodiment $R_{10}$, $R_{20}$, $R_{30}$, and $R_{40}$ are independently hydrogen, alkyl, allyl, vinyl, $-(CH_2)_d NH_2$, $-(CH_2)_d N[(CH_2)_e NH_2)]_2$ where d and e are independently 2-4. In each of the foregoing exemplary embodiments of this paragraph, m and z may independently be 0, 1, 2 or 3 and n is 0 or 1.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and $X_2$ is aliphatic or heteroaliphatic. For example, in one such embodiment $X_2$ is aliphatic or heteroaliphatic and $R_{10}$, $R_{20}$, $R_{30}$, and $R_{40}$ are independently hydrogen, aliphatic, heteroaliphatic. By way of further example, in one such embodiment $X_2$ is alkyl or aminoalkyl and $R_{10}$, $R_{20}$, $R_{30}$, and $R_{40}$ are independently hydrogen, aliphatic, or heteroaliphatic. By way of further example, in one such embodiment $X_2$ is alkyl or aminoalkyl and $R_{10}$, $R_{20}$, $R_{30}$, and $R_{40}$ are independently hydrogen, alkyl, allyl, vinyl, or aminoalkyl. In each of the foregoing exemplary embodiments of this paragraph, m and z may independently be 0, 1, 2 or 3 and n is 0 or 1.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and m is a positive integer. For example, in one such embodiment m is a positive integer, z is zero and $R_{20}$ is hydrogen, aliphatic or heteroaliphatic. By way of further example, in one such embodiment m is a positive integer (e.g., 1 to 3), z is a positive integer (e.g., 1 to 2), $X_{11}$ is hydrogen, aliphatic or heteroaliphatic, and $R_{20}$ is hydrogen, aliphatic or heteroaliphatic. By way of further example, in one such embodiment m is a positive integer, z is zero, one or two, $X_{11}$ is hydrogen alkyl, alkenyl, or aminoalkyl, and $R_{20}$ is hydrogen, alkyl, alkenyl, or aminoalkyl.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and n is a positive integer and $R_{30}$ is hydrogen, aliphatic or heteroaliphatic. By way of further example, in one such embodiment n is 0 or 1, and $R_{30}$ is hydrogen, alkyl, alkenyl, or aminoalkyl.

In one embodiment, the crosslinked polymer comprises the residue of an amine corresponding to Formula 2, the crosslinked polymer is prepared by (i) substitution polymerization of the amine corresponding to Formula 2 with a polyfunctional crosslinker (optionally also comprising amine moieties) or (2) radical polymerization of an amine corresponding to Formula 2, and m and n are independently non-negative integers and $X_2$ is aliphatic or heteroaliphatic. For example, in one such embodiment m is 0 to 2, n is 0 or 1, $X_2$ is aliphatic or heteroaliphatic, and $R_{10}$, $R_{20}$, $R_{30}$, and $R_{40}$ are independently hydrogen, aliphatic, or heteroaliphatic. By way of further example, in one such embodiment m is 0 to 2, n is 0 or 1, $X_2$ is alkyl or aminoalkyl, and $R_{10}$, $R_{20}$, $R_{30}$, and $R_{40}$ are independently hydrogen, aliphatic, or heteroaliphatic. By way of further example, in one such embodiment m is 0 to 2, n is 0 or 1, $X_2$ is alkyl or aminoalkyl, and $R_{10}$, $R_{20}$, $R_{30}$, and $R_{40}$ are independently hydrogen, alkyl, alkenyl, or aminoalkyl.

In some embodiments, the crosslinked polymer comprises the residue of an amine corresponding to Formula 2a and the crosslinked polymer is prepared by substitution polymerization of the amine corresponding to Formula 2a with a polyfunctional crosslinker (optionally also comprising amine moieties):

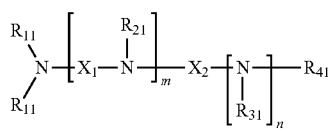

Formula 2a wherein m and n are independently non-negative integers;

each $R_{11}$ is independently hydrogen, hydrocarbyl, heteroaliphatic, or heteroaryl;

$R_{21}$ and $R_{31}$, are independently hydrogen or heteroaliphatic;

$R_{41}$ is hydrogen, substituted hydrocarbyl, or hydrocarbyl;

$X_1$ is

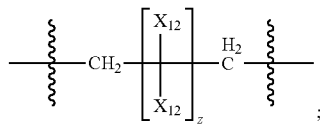

$X_2$ is alkyl or substituted hydrocarbyl;

each $X_{12}$ is independently hydrogen, hydroxy, amino, aminoalkyl, boronic acid or halo; and z is a non-negative number.

In one embodiment, the crosslinked polymer comprises the residue of an amine corresponding to Formula 2a, the crosslinked polymer is prepared by substitution polymerization of the amine corresponding to Formula 1 with a polyfunctional crosslinker (optionally also comprising amine moieties). For example, in one such embodiment, m and z are independently 0, 1, 2 or 3, and n is 0 or 1.

In one embodiment, the crosslinked polymer comprises the residue of an amine corresponding to Formula 2a, the crosslinked polymer is prepared by substitution polymerization of the amine corresponding to Formula 2a with a polyfunctional crosslinker (optionally also comprising amine moieties), and each $R_{11}$ is independently hydrogen, aliphatic, aminoalkyl, haloalkyl, or heteroaryl, $R_{21}$ and $R_{31}$ are independently hydrogen or heteroaliphatic and $R_{41}$ is hydrogen, aliphatic, aryl, heteroaliphatic, or heteroaryl. For example, in one such embodiment each $R_{11}$ is hydrogen, aliphatic, aminoalkyl, or haloalkyl, $R_{21}$ and $R_{31}$ are independently hydrogen or heteroaliphatic and $R_{41}$ is hydrogen, alkylamino, aminoalkyl, aliphatic, or heteroaliphatic. By way of further example, in one such embodiment each $R_{11}$ is hydrogen, aliphatic, aminoalkyl, or haloalkyl, $R_{21}$ and $R_{31}$ are hydrogen or aminoalkyl, and $R_{41}$ is hydrogen, aliphatic, or heteroaliphatic. By way of further example, in one such embodiment each $R_{11}$ and $R_{41}$ is independently hydrogen, alkyl, or aminoalkyl, and $R_{21}$ and $R_{31}$ are independently hydrogen or heteroaliphatic. By way of further example, in one such embodiment each $R_{11}$ and $R_{41}$ is independently hydrogen, alkyl, $—(CH_2)_d NH_2$, $—(CH_2)_d N[(CH_2)_3 NH_2]_2$ where d and e are independently 2-4, and $R_{21}$ and $R_{31}$ are independently hydrogen or heteroaliphatic. In each of the foregoing exemplary embodiments of this paragraph, m and z may independently be 0, 1, 2 or 3, and n is 0 or 1.

Exemplary amines for the synthesis of polymers comprising repeat units corresponding to Formula 2a include, but are not limited to, amines appearing in Table A.

TABLE A

| Abbreviation | IUPAC name | Other names | | MW (g/mol) |
|---|---|---|---|---|
| C2A3BTA | 1,3-Bis[bis(2-aminoethyl)amino]propane | | 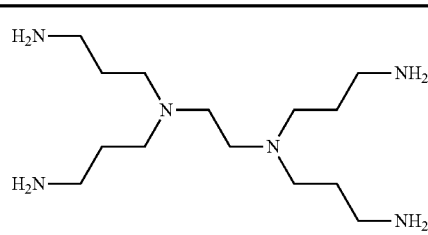 | 288.48 |

TABLE A-continued

| Abbreviation | IUPAC name | Other names | | MW (g/mol) |
|---|---|---|---|---|
| C2A3G2 | 3-Amino-1{[2-(bis{2-[bis(3-aminopropyl)amino]ethyl}amino)ethyl](3-aminopropyl)amino}propane | | | 488.81 |
| C2PW | 2-[Bis(2-aminoethyl)amino]ethanamine | 2,2',2"-Triaminotriethylamine or 2,2',2"-Nitrilotriethylamine | | 146.24 |
| C3PW | Tris(3-aminopropyl)amine | | | 188.32 |
| C4A3BTA | 1,4-Bis[bis(3-aminopropyl)amino]butane | | | 316.54 |
| EDA1 | 1,2-Ethanediamine | | | 60.1 |
| EDA2 | 2-Amino-1-(2-aminoethylamino)ethane | Bis(2-aminoethyl)amine or 2,2'-Diaminodiethylamine | | 103.17 |
| EDA3 | 1,2-Bis(2-aminoethylamino)ethane | N,N'-Bis(2-aminoethyl)ethane-1,2-diamine | | 146.24 |

TABLE A-continued

| Abbreviation | IUPAC name | Other names | | MW (g/mol) |
|---|---|---|---|---|
| PDA1 | 1,3-Propanediamine | | $H_2N\frown\frown NH_2$ | 74.3 |
| PDA2 | 3,3'-Diaminodipropylamine | | $H_2N\frown\frown N(H)\frown\frown NH_2$ | 131.22 |

Exemplary crosslinkers for the synthesis of polymers comprising the residue of amines corresponding to Formula 2a include but are not limited to crosslinkers appearing in Table B.

TABLE B

| Abbreviation | Common name | IUPAC name | | MW (g/mol) |
|---|---|---|---|---|
| BCPA | Bis(3-chloropropyl)amine | Bis(3-chloropropyl)amine | Cl–CH₂CH₂CH₂–NH·HCl–CH₂CH₂CH₂–Cl | 206.54 |
| DC2OH | 1,3-dichloroisopropanol | 1,3-Dichloro-2-propanol | Cl–CH₂–CH(OH)–CH₂–Cl | 128.98 |
| DCE | dichloroethane | 1,2-dichloroethane | Cl–CH₂CH₂–Cl | 98.96 |
| DCP | Dichloropropane | 1,3-Dichloropropane | Cl–CH₂CH₂CH₂–Cl | 112.98 |
| ECH | Epichlorohydrin | 1-chloro-2,3-epoxypropane | epoxide–CH₂–Cl | 92.52 |
| TGA | Triglycidyl amine | Tris[(2-oxiranyl)methyl]amine | N(CH₂-epoxide)₃ | 185.22 |
| BCPOH | Bis(3-chloropropyl)amine-OH | 3-Chloro-1-(3-chloropropylamino)-2-propanol | Cl–CH₂CH₂CH₂–NH–CH₂–CH(OH)–CH₂–Cl | 186.08 |
| BCPEDA | Bis(chloropropyl)ethylenediamine | 1,2-Bis(3-chloropropylamino)ethane | Cl–CH₂CH₂CH₂–NH–CH₂CH₂–NH–CH₂CH₂CH₂–Cl | 213.15 |

In some embodiments, the crosslinked polymer comprises the residue of an amine corresponding to Formula 2b and the crosslinked polymer is prepared by radical polymerization of an amine corresponding to Formula 2b:

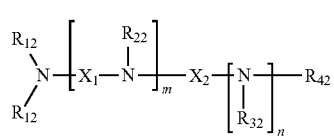

Formula 2b wherein m and n are independently non-negative integers;

each $R_{12}$ is independently hydrogen, substituted hydrocarbyl, or hydrocarbyl;

$R_{22}$ and $R_{32}$ are independently hydrogen substituted hydrocarbyl, or hydrocarbyl;

$R_{42}$ is hydrogen, hydrocarbyl or substituted hydrocarbyl;

$X_1$ is

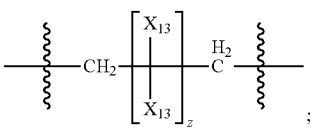

$X_2$ is alkyl, aminoalkyl, or alkanol;

each $X_{13}$ is independently hydrogen, hydroxy, alicyclic, amino, aminoalkyl, halogen, alkyl, heteroaryl, boronic acid or aryl;

z is a non-negative number, and the amine corresponding to Formula 2b comprises at least one allyl group.

In one embodiment, the crosslinked polymer comprises the residue of an amine corresponding to Formula 2b, the crosslinked polymer is prepared by radical polymerization of an amine corresponding to Formula 2b, and m and z are independently 0, 1, 2 or 3, and n is 0 or 1.

In one embodiment, the crosslinked polymer comprises the residue of an amine corresponding to Formula 2b, the crosslinked polymer is prepared by radical polymerization of an amine corresponding to Formula 1, and (i) $R_{12}$ or $R_{42}$ independently comprise at least one allyl or vinyl moiety, (ii) m is a positive integer and $R_{22}$ comprises at least one allyl or vinyl moiety, and/or (iii) n is a positive integer and $R_{32}$ comprises at least one allyl moiety. For example, in one such embodiment, m and z are independently 0, 1, 2 or 3 and n is 0 or 1. For example, in one such embodiment $R_{12}$ or $R_{42}$, in combination comprise at least two allyl or vinyl moieties. By way of further example, in in one such embodiment, m is a positive integer and $R_{12}$, $R_{22}$ and $R_{42}$, in combination comprise at least two allyl or vinyl moieties. By way of further example, in in one such embodiment, n is a positive integer and $R_{12}$, $R_{32}$ and $R_{42}$, in combination comprise at least two allyl or vinyl moieties. By way of further example, in in one such embodiment, m is a positive integer, n is a positive integer and $R_{12}$, $R_{22}$, $R_{32}$ and $R_{42}$, in combination, comprise at least two allyl or vinyl moieties.

In one embodiment, the crosslinked polymer comprises the residue of an amine corresponding to Formula 2b, the crosslinked polymer is prepared by radical polymerization of an amine corresponding to Formula 2b, and each $R_{12}$ is independently hydrogen, aminoalkyl, allyl, or vinyl, $R_{22}$ and $R_{32}$ are independently hydrogen, alkyl, aminoalkyl, haloalkyl, alkenyl, alkanol, heteroaryl, alicyclic heterocyclic, or aryl, and $R_{42}$ is hydrogen or substituted hydrocarbyl. For example, in one such embodiment each $R_{12}$ is aminoalkyl, allyl or vinyl, $R_{22}$ and $R_{32}$ are independently hydrogen, alkyl, aminoalkyl, haloalkyl, alkenyl, or alkanol, and $R_{42}$ is hydrogen or substituted hydrocarbyl. By way of further example, in one such embodiment each $R_{12}$ and $R_{42}$ is independently hydrogen, alkyl, allyl, vinyl, —$(CH_2)_d NH_2$ or —$(CH_2)_d N[(CH_2)_3 NH_2]_2$ where d and e are independently 2-4, and $R_{22}$ and $R_{32}$ are independently hydrogen or heteroaliphatic.

Exemplary amines and crosslinkers (or the salts thereof, for example the hydrochloric acid, phosphoric acid, sulfuric acid, or hydrobromic acid salts thereof) for the synthesis of polymers described by Formula 2b include but are not limited to the ones in Table C.

TABLE C

| Abbreviation | Common name | IUPAC name | Structure | MW (g/mol) |
|---|---|---|---|---|
| DABDA1 | Diallylbutyldiamine | 1,4-Bis(allylamino)butane | (structure with two allylamine groups connected by butane chain, 2 HCl) | 241.2 |
| DAEDA1 | Diallylethyldiamine | 1,2-Bis(allylamino)ethane | (structure with two allylamine groups connected by ethane chain, 2 HCl) | 213.15 |
| DAEDA2 | Diallyldiethylenetriamine | 2-(Allylamino)-1-[2-(allylamino)ethylamino]ethane | (structure with three amine groups, 3 HCl) | 292.67 |
| DAPDA | Diallylpropyldiamine | 1,3-Bis(allylamino)propane | (structure with two allylamine groups connected by propane chain, 2 HCl) | 227.17 |
| POHDA | Diallylamineisopropanol | 1,3-Bis(allylamino)-2-propanol | (structure with two allylamine groups connected by 2-hydroxypropane, 2 HCl) | 243.17 |
| AAH | Allylamine | 2-Propen-1-ylamine | (allylamine·HCl) | 93.5 |
| AEAAH | Aminoethylallylamine | 1-(Allylamino)-2-aminoethane | (structure with allylamine-ethylamine, 2 HCl) | 173.08 |
| BAEAAH | Bis(2-aminoethyl)allylamine | 1-[N-Allyl(2-aminoethyl)amino]-2-aminoethane | (structure with allyl group and two aminoethyl groups, 3 HCl) | 252.61 |

TABLE C-continued

| Abbreviation | Common name | IUPAC name | | MW (g/mol) |
|---|---|---|---|---|
| TAA | Triallylamine | N,N,N-triallylamine | 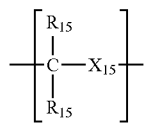 | 137.22 |

In some embodiments, the crosslinked polymer is derived from a reaction of the resulting polymers that utilize monomers described in any of Formulae 1, 1a, 1b, 1c, 2, 2a and 2b or a linear polymer comprised of a repeat unit described by Formula 3 with external crosslinkers or pre-existing polymer functionality that can serve as crosslinking sites. Formula 3 can be a repeat unit of a copolymer or terpolymer where $X_{15}$ is either a random, alternating, or block copolymer. The repeating unit in Formula 3 can also represent the repeating unit of a polymer that is branched, or hyperbranched, wherein the primary branch point can be from any atom in the main chain of the polymer:

Formula 3

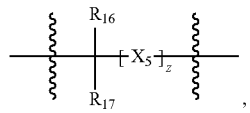

wherein $R_{15}$, $R_{16}$ and $R_{17}$ are independently hydrogen, hydrocarbyl, substituted hydrocarbyl, hydroxyl, amino, boronic acid or halo;

$X_{15}$ is $X_5$ is hydrocarbyl, substituted hydrocarbyl, oxo (—O—), or amino and z is a non-negative number.

In one embodiment, $R_{15}$, $R_{16}$ and $R_{17}$ are independently hydrogen, aryl, or heteroaryl, $X_5$ is hydrocarbyl, substituted hydrocarbyl, oxo or amino, and m and z are non-negative integers. In another embodiment, $R_{15}$, $R_{16}$ and $R_{17}$ are independently aliphatic or heteroaliphatic, $X_5$ is hydrocarbyl, substituted hydrocarbyl, oxo (—O—) or amino, and m and z are non-negative integers. In another embodiment, $R_{15}$, $R_{16}$ and $R_{17}$ are independently unsaturated aliphatic or unsaturated heteroaliphatic, $X_5$ is hydrocarbyl, substituted hydrocarbyl, oxo, or amino, and z is a non-negative integer. In another embodiment, $R_{15}$, $R_{16}$ and $R_{17}$ are independently alkyl or heteroalkyl, $X_5$ is hydrocarbyl, substituted hydrocarbyl, oxo, or amino, and z is a non-negative integer. In another embodiment, $R_{15}$, $R_{16}$ and $R_{17}$ are independently alkylamino, aminoalkyl, hydroxyl, amino, boronic acid, halo, haloalkyl, alkanol, or ethereal, $X_5$ is hydrocarbyl, substituted hydrocarbyl, oxo, or amino, and z is a non-negative integer. In another embodiment, $R_{15}$, $R_{16}$ and $R_{17}$ are independently hydrogen, hydrocarbyl, substituted hydrocarbyl, hydroxyl, amino, boronic acid or halo, $X_5$ is oxo, amino, alkylamino, ethereal, alkanol, or haloalkyl, and z is a non-negative integer.

Exemplary crosslinking agents that may be used in radical polymerization reactions include, but are not limited to, one or more multifunctional crosslinking agents such as: 1,4-bis(allylamino)butane, 1,2-bis(allylamino)ethane, 2-(allylamino)-1-[2-(allylamino)ethylamino]ethane, 1,3-bis(allylamino)propane, 1,3-bis(allylamino)-2-propanol, triallylamine, diallylamine, divinylbenzene, 1,7-octadiene, 1,6-heptadiene, 1,8-nonadiene, 1,9-decadiene, 1,4-divinyloxybutane, 1,6-hexamethylenebisacrylamide, ethylene bisacrylamide, N,N'-bis(vinylsulfonylacetyl)ethylene diamine, 1,3-bis(vinylsulfonyl) 2-propanol, vinylsulfone, N,N'-methylenebisacrylamide polyvinyl ether, polyallylether, divinylbenzene, 1,4-divinyloxybutane, and combinations thereof.

Crosslinked polymers derived from the monomers and polymers in formulas 1 through 3 may be synthesized either in solution or bulk or in dispersed media. Examples of solvents that are suitable for the synthesis of polymers of the present disclosure include, but are not limited to water, low boiling alcohols (methanol, ethanol, propanol, butanol), dimethylformamide, dimethylsulfoxide, heptane, chlorobenzene, toluene.

Alternative polymer processes may include, a lone polymerization reaction, stepwise addition of individual starting material monomers via a series of reactions, the stepwise addition of blocks of monomers, combinations or any other method of polymerization such as living polymerization, direct polymerization, indirect polymerization, condensation, radical, emulsion, precipitation approaches, spray dry polymerization or using some bulk crosslinking reaction methods and size reduction processes such as grinding, compressing, extrusion. Processes can be carried out as a batch, semi-continuous and continuous processes. For processes in dispersed media, the continuous phase can be non-polar solvents, such as toluene, benzene, hydrocarbon, halogenated solvents, super critical carbon dioxide. With a direct suspension reaction, water can be used and salt can be used to tune the properties of the suspension.

The starting molecules described in formulas 1 through 3 may be copolymerized with one or more other monomers of the invention, oligomers or other polymerizable groups. Such copolymer architectures can include, but are not limited to, block or block-like polymers, graft copolymers, and random copolymers. Incorporation of monomers described by formulas 1 through 3 can range from 1')/0 to 99%. In some embodiments, the incorporation of comonomer is between 20% and 80%.

Non-limiting examples of comonomers which may be used alone or in combination include: styrene, allylamine hydrochloride, substituted allylamine hydrochloride, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, N-vinyl amide, maleic acid derivatives, vinyl ether, allyle, methallyl monomers and combinations thereof. Functionalized versions of these monomers may also be used. Additional specific monomers or comonomers that may be used in this invention include, but are not limited to, 2-propen-1-ylamine, 1-(allylamino)-2-aminoethane, 1-[N-allyl(2-aminoethyl)amino]-2-aminoethane, methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, amethylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N—N-butylmethacrylamide, N-methylolmethacrylamide, N-ethylolmethacrylamide, N-tert-butylacryl amide, N—N-butylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamino a-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, N-vinylformamide, N-vinyl acetamide, allylamine, methallylamine, allylalcohol, methyl-vinylether, ethylvinyether, butylvinytether, butadiene, isoprene, chloroprene, ethylene, vinyl acetate, and combinations thereof.

Additional modification to the preformed crosslinked polymer can be achieved through the addition of modifiers, including but not limited to amine monomers, additional crosslinkers, and polymers. Modification can be accomplished through covalent or non-covalent methods. These modifications can be evenly or unevenly dispersed throughout the preformed polymer material, including modifications biased to the surface of the preformed crosslinked polymer. Furthermore, modifications can be made to change the physical properties of the preformed crosslinked polymer, including but not limited to reactions that occur with remaining reactive groups such as haloalkyl groups and allyl groups in the preformed polymer. Reactions and modifications to the preformed crosslinked polymer can include but are not limited to acid-base reactions, nucleophilic substitution reactions, Michael reactions, non-covalent electrostatic interactions, hydrophobic interactions, physical interactions (crosslinking) and radical reactions.

In one embodiment, the post-polymerization crosslinked amine polymer is a crosslinked amine polymer comprising a structure corresponding to Formula 4:

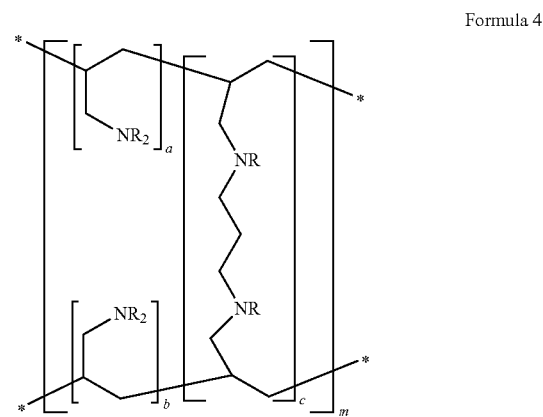

Formula 4 wherein each R is independently hydrogen or an ethylene crosslink between two nitrogen atoms of the crosslinked amine polymer

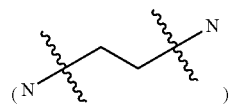

and a, b, c, and m are integers. Typically, m is a large integer indicating an extended polymer network. In one such embodiment, a ratio of the sum of a and b to c (i.e., a+b:c) is in the range of about 1:1 to 5:1. For example, in one such embodiment a ratio of the sum of a and b to c (i.e., a+b:c) is in the range of about 1.5:1 to 4:1. By way of further example, in one such embodiment a ratio of the sum of a and b to c (i.e., a+b:c) is in the range of about 1.75:1 to 3:1. For example, in one such embodiment a ratio of the sum of a and b is 57, c is 24 and m is large integer indicating an extended polymer network. In each of the foregoing embodiments a ratio of the sum of a and b to c (i.e., a+b:c) may be in the range of about 2:1 to 2.5:1. For example, in such embodiments the ratio of the sum of a and b to c (i.e., a+b:c) may be in the range of about 2.1:1 to 2.2:1. By way of further example, in such embodiments the ratio of the sum of a and b to c (i.e., a+b:c) may be in the range of about 2.2:1 to 2.3:1. By way of further example, in such embodiments the ratio of the sum of a and b to c (i.e., a+b:c) may be in the range of about 2.3:1 to 2.4:1. By way of further example, in such embodiments the ratio of the sum of a and b to c (i.e., a+b:c) may be in the range of about 2.4:1 to 2.5:1. In each of the foregoing embodiments, each R may independently be hydrogen or an ethylene crosslink between two nitrogen atoms. Typically, however, 35-95% of the R substituents will be hydrogen and 5-65% will be an ethylene crosslink

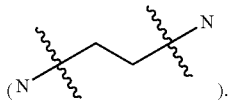

For example, in one such embodiment, 50-95% of the R substituents will be hydrogen and 5-50% will be an ethylene crosslink

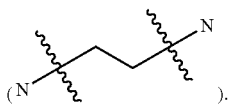

For example, in one such embodiment. 55-90% of the R substituents are hydrogen and 10-45% are an ethylene crosslink

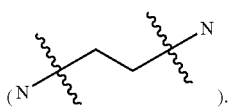

By way of further example, in one such embodiment, 60-90% of the R substituents are hydrogen and 10-40% are an ethylene crosslink. By way of further example, in one such embodiment, 65-90% of the R substituents are hydrogen and 10-35% are an ethylene crosslink

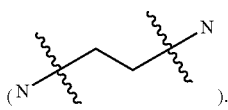

By way of further example, in one such embodiment, 70-90% of the R substituents are hydrogen and 10-30% are an ethylene crosslink. By way of further example, in one such embodiment, 75-85% of the R substituents are hydrogen and 15-25% are an ethylene crosslink. By way of further example, in one such embodiment, 65-75% of the R substituents are hydrogen and 25-35% are an ethylene crosslink. By way of further example, in one such embodiment, 55-65% of the R substituents are hydrogen and 35-45% are an ethylene crosslink. In some embodiments, a, b, c and R are such that the carbon to nitrogen ratio of the polymer of Formula 4 may range from about 2:1 to about 6:1, respectively. For example, in one such embodiment, the carbon to nitrogen ratio of the polymer of Formula 4 may range from about 2.5:1 to about 5:1, respectively. By way of further example, in one such embodiment, the carbon to nitrogen ratio of the polymer of Formula 4 may range from about 3:1 to about 4.5:1, respectively. By way of further example, in one such embodiment, the carbon to nitrogen ratio of the polymer of Formula 4 may range from about 3.25:1 to about 4.25:1, respectively. By way of further example, in one such embodiment, the carbon to nitrogen ratio of the polymer of Formula 4 may range from about 3.4:1 to about 4:1, respectively. By way of further example, in one such embodiment, the carbon to nitrogen ratio of the polymer of Formula 4 may range from about 3.5:1 to about 3.9:1, respectively. By way of further example, in one such embodiment, the carbon to nitrogen ratio of the polymer of Formula 4 may range from about 3.55:1 to about 3.85:1, respectively. In each of the foregoing embodiments recited in this paragraph, the polymer of Formula 4 is derived from monomers and cross-linkers, each of which comprise less than 5 wt % oxygen.

In certain embodiments, polymers in which crosslinking and/or entanglement were increased were found to have lower swelling than those with lower crosslinking and/or entanglement, yet also had a binding capacity for target ion (e.g., chloride) that was as great as or greater than the lower crosslinking and/or entanglement polymers while binding of interfering ions such as phosphate were significantly reduced. The selectivity effect may be introduced in two different manners: 1) Overall capacity was sacrificed for chloride specificity. Crosslinkers that don't include chloride binding sites (e.g., epichlorohydrin) allow for increased crosslinking while overall capacity is decreased proportional to the amount of crosslinker incorporated into the polymer. 2) Overall capacity is preserved for chloride specificity: Crosslinkers that include chloride binding sites (e.g., diallylamines) allow for increased crosslinking while overall capacity is staying the same or is reduced by only a small amount.

As previously noted, crosslinked polymers having a high capacity for chloride binding and high selectivity for chloride over other competing anions such as phosphate may be prepared in a two-step process in accordance with one embodiment of the present disclosure. In general, the selectivity of the polymer is a function of its crosslinking density and the capacity of the polymer is a function of the free amine density of the crosslinked polymer. Advantageously, the two-step process disclosed herein provides both, high capacity for chloride binding, and high selectivity for chloride over other competing ions by relying primarily upon carbon-carbon crosslinking in the first step, and nitrogen-nitrogen crosslinking in the second step.

In the first step, the crosslinking is preferably capacity-sparing, i.e., free amine sparing, crosslinking from carbon to carbon. In the second step, the crosslinking is amine-consuming and is directed towards tuning for selectivity. Based on the desired high capacity, the C—N ratio is preferably optimized to maximize amine functionalities for HCl binding, while still maintaining a spherical polymer particle of controlled particle size to ensure nonabsorption and acceptable mouth feel that is stable under GI conditions. The preferred extent of carbon-carbon crosslinking achieved after the first step is sufficient to permit the resulting bead to swell between 4× and 6× in water (i.e., a Swelling Ratio of 4 to 6).

In one embodiment, crosslinked polymers having a high capacity for chloride binding and high selectivity for chloride over other competing anions such as phosphate may be prepared in a two-step process, and the product of the first polymerization step is preferably in the form of beads whose diameter is controlled in the 5 to 1000 micromer range, preferably 10 to 500 micrometers and most preferred 40-180 micrometers.

The product of the first polymerization step is preferably in the form of beads whose Swelling Ratio in water is between 2 and 10, more preferably about 3 to about 8, and most preferably about 4 to about 6.

Additionally, if the crosslinked polymer beads resulting from the first polymerization step are protonated, this may reduce the amount of nitrogen-nitrogen crosslinking in the second crosslinking step. Accordingly, in certain embodiments the preformed amine polymer is at least partially deprotonated by treatment with a base, preferably a strong base such as a hydroxide base. For example, in one embodiment the base may be NaOH, KOH, NH$_4$OH, NaHCO$_3$, Na$_2$CO$_3$, K$_2$CO$_3$, LiOH, Li$_2$CO$_3$, CsOH or other metal hydroxides. If the charges are removed from the preformed crosslinked amine polymer bead by deprotonation, the bead will tend to collapse and the crosslinking agent used in the second step may not be able to access binding sites on the polymer unless the bead is prevented from collapsing. One means of preventing the crosslinked polymer bead from collapsing is the use of a swelling agent such as water to swell the bead, thereby allowing the second-step crosslinker to access binding sites.

The preformed polymer may be crosslinked to form the post-polymerization crosslinked polymer using any of a range of crosslinking compounds containing at least two amine-reactive functional groups. In one such embodiment, the crosslinker is a compound containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups. The crosslinker may be, for example, any of the crosslinkers disclosed herein, including a crosslinker selected from Table B. By way of further example, in one such embodiment the crosslinker is a dihalide such as a dichloroalkane.

As noted above, in certain embodiments a swelling agent for the preformed amine polymer may be included in the reaction mixture for the second polymerization step along with the crosslinking agent. In general, the swelling agent and the crosslinking agent may be miscible or immiscible and the swelling agent may be any composition or combination of compositions that have the capacity to swell the preformed amine polymer. Exemplary swelling agents include polar solvents such as water, methanol, ethanol, n-propanol, isopropanol, n-butanol, formic acid, acetic acid, acetonitrile, dimethylformamide, dimethylsulfoxide, nitromethane, propylene carbonate, or a combination thereof. Additionally, the amount of swelling agent included in the reaction mixture will typically be less than absorption capacity of the preformed amine polymer for the swelling agent. For example, it is generally preferred that the weight ratio of swelling agent to preformed polymer in the reaction mixture be less than 4:1. By way of further example, in some embodiments the weight ratio of swelling agent to preformed polymer in the reaction mixture will be less than 3:1. By way of further example, in some embodiments the weight ratio of swelling agent to preformed polymer in the reaction mixture will be less than 2:1. By way of further example, in some embodiments the weight ratio of swelling agent to preformed polymer in the reaction mixture will be less than 1:1. By way of further example, in some embodiments the weight ratio of swelling agent to preformed polymer in the reaction mixture will be less than 0.5:1. By way of further example, in some embodiments the weight ratio of swelling agent to preformed polymer in the reaction mixture will be less than 0.4:1. By way of further example, in some embodiments the weight ratio of swelling agent to preformed polymer in the reaction mixture will be less than 0.3:1. In general, however, the weight ratio of swelling agent to preformed polymer in the reaction mixture will typically be at least 0.05:1, respectively.

In general, the crosslinked polymers may be crosslinked homopolymers or crosslinked copolymers comprising free amine moieties. The free amine moieties may be separated, for example, by the same or varying lengths of repeating linker (or intervening) units. In some embodiments, the polymers comprise repeat units containing an amine moiety and an intervening linker unit. In other embodiments, multiple amine-containing repeat units are separated by one or more linker units. Additionally, the polyfunctional crosslinkers may comprise HCl binding functional groups, e.g., amines, ("active crosslinkers") or may lack HCl binding functional groups such as amines ("passive crosslinkers").

In a preferred embodiment, the first polymerization (crosslinking) step yields preformed amine polymer beads having a target size and chloride binding capacity. For example, in one such embodiment the beads have a chloride binding capacity of at least 10 mmol/g in Simulated Gastric Fluid ("SGF") and a Swelling Ratio in the range of 1 to 6. The resulting preformed amine polymer is then preferably (at least partially) deprotonated with a base and combined with a non-protonating swelling agent to swell the free amine polymer without protonating the amine functions. Furthermore, the amount of the non-protonating swelling agent is selected to tune the subsequent degree of crosslinking effectively forming a template that is then locked into place via the amine consuming crosslinking step. In the second crosslinking step, the swollen, deprotonated preformed amine polymer is crosslinked with a crosslinker containing amine reactive moieties to form a post-polymerization crosslinked polymer.

In general, selectivity for chloride over other competing ions is achieved with highly crosslinked polymers. For example, relatively high chloride binding capacity maybe be attained by reacting a preformed amine polymer bead with neat crosslinker in the presence of a swelling agent (water). While this "non-dispersed" reaction provides access to high selectivity for chloride over competing ions in the SIB assay, it also results in macroscopically (and microscopically) aggregated polymer beads. Accordingly, it is advantageous to include a solvent (e.g., heptane) in the second crosslinking step to disperse the preformed crosslinked polymer beads so as to avoid inter-bead reactions and resulting aggregation. The use of too much solvent (dispersant), however, can dilute the reaction solution to the point where the resulting bead is not sufficiently crosslinked to have the desired selectivity for chloride over other competing anions. By using a crosslinking agent that also functions as a solvent (dispersant), however, sufficient solvent (dispersant) may be included in the reaction mixture to avoid inter-bead reactions and aggregation without diluting the mixture to the point where the degree of amine-consuming crosslinking is insufficient. For example, in an effort to utilize the dispersing properties of a solvent (to avoid aggregation during the reaction) while maintaining reactivity, DCE and DCP were used neat, thus performing a dual purpose role, as both solvent (dispersant) and crosslinker. Interestingly, DCE was discovered to have excellent dispersal properties as a solvent, when compared to similar reactions with DCP and/or heptane. Additionally, less aggregation was observed when the beads were first dispersed in DCE and then in a second operation, the water is added to swell the beads. If water is added to the preformed amine polymer before the bead is dispersed in the DCE, aggregation may occur.

The use of 1,2-dichloroethane ("DCE") as the crosslinking solvent also generates HCl molecules during the second step. These HCl molecules protonate some of the free amine sites which block the reaction sites for the crosslinking reaction and thereby limit the number of binding sites available for crosslinking. Consequently, the use of DCE creates a self-limiting effect on the secondary crosslinking.

In each of the foregoing embodiments, the reaction mixture may contain a wide range of amounts of crosslinking agents. For example, in one embodiment the crosslinker may be used in large excess relative to the amount of preformed amine polymer in the reaction mixtures. Stated differently, in such embodiments the crosslinking agent is a crosslinking solvent, i.e., it is both a solvent for the reaction mixture and a crosslinking agent for the preformed amine polymer. In such embodiments, other solvents may optionally be included in the reaction mixture but are not required. Alternatively, the preformed amine polymer, swelling agent and crosslinker may be dispersed in a solvent that is miscible with the crosslinker and immiscible with the swelling agent. For example, in some embodiments the swelling agent may be a polar solvent; in some such embodiments, for example, the swelling agent may comprise water, methanol, ethanol, n-propanol, isopropanol, formic acid, acetic acid, acetonitrile, N,N-dimethylformamide, dimethylsulfoxide, nitromethane, or a combination thereof. By way of further example, when the swelling agent comprises a polar solvent, the solvent system for the reaction mixture will typically comprise a non-polar solvent such as pentane, cyclopentane, hexane, cyclohexane, benzene, toluene, 1,4-dioxane, chloroform, diethyl ether, dichloromethane, dichloroethane, dichloropropane, dichlorobutane, or a combination thereof. In certain embodiments, the crosslinker and the solvent may be the same; i.e., the solvent is a crosslinking solvent such as 1,2-dichloroethane, 1,3-dichloropropane, 1,4-dichlorobutane or a combination thereof.

It is notable that in a crosslinking solvent (e.g., a DCE-dispersed reaction), there is a large excess of crosslinker regardless of the amount of crosslinking solvent (e.g., DCE) used to disperse the bead (e.g., both 1 g:3 mL::bead:DCE and 1 g:10 mL::bead:DCE are a large excess of crosslinker, most of which is not consumed during the reaction). Despite this, the relative degree of crosslinking, and the performance in SIB assay, are unaffected by changes in the ratio of reactive crosslinker to polymer bead. This is possible because the reaction is limited by the acid-neutralizing capacity of the polymer bead, rather than the amount of crosslinker (e.g., DCE).

To more efficiently react with DCE or other crosslinker, the amines of the preformed polymer bead preferably have a free electron pair (neutral, deprotonated). As the free amines of the preformed polymer bead react with the crosslinker (e.g., DCE), HCl is produced and the amines become protonated, thus limiting the reaction. For this reason, the preformed amine polymer beads preferably start as the free amine in the second crosslinking step. If the preformed amine polymer bead is protonated after the first step of carbon-carbon crosslinking, amine-consuming crosslinking in the second step will be limited, thus reducing the desired selectivity for chloride over other competing ions. This has been demonstrated by adding known quantities of HCl to preformed amine polymer beads immediately before second step crosslinking with DCE. When less than 3 mol % HCl (to amine in preformed polymer amine bead) is added prior to second step crosslinking, total chloride capacity (SGF) and chloride selectivity in SIB are similar to beads not treated with HCl in the second step. When greater than 5 mol % HCl (to amine in preformed polymer amine bead) is added prior to second step crosslinking, total chloride capacity (SGF) increases and chloride selectivity in SIB decreases, indicating lower incorporation of crosslinker.

The benefits of deprotonated preformed polymer beads in the second step crosslinking highlights the advantages of using two steps to achieve the final product. In the first step, to form the amine polymer bead, all monomers (e.g., allylamine and DAPDA) are protonated to remain in the aqueous phase and to avoid the radical transfer reactions that severely limit the polymerization of non-protonated allylamine (and derivatives). Once the bead is formed through carbon-carbon crosslinks, the bead can then be deprotonated and further crosslinked with an amine reactive crosslinker in a second step.

Given the large excess of dual crosslinker/solvent, mono-incorporation of this reagent can occur leading to alkyl chloride functional groups on the crosslinked polymer bead that are hydrophobic in nature and can increase non-specific interactions with undesirable solutes other than HCl that are more hydrophobic in nature. Washing with ammonium hydroxide solution converts the alkyl-chloride to alkyl-amine functions that are hydrophilic and minimize non-specific interactions with undesirable solutes. Other modifications that yield more hydrophilic groups than alkyl chloride such as —OH are suitable to quench mono-incorporated crosslinker/solvent.

Any of a range of polymerization chemistries may be employed in the first reaction step, provided that the crosslinking mechanism is primarily carbon-carbon crosslinking. Thus, in one exemplary embodiment, the first reaction step comprises radical polymerization. In such reactions, the amine monomer will typically be a mono-functional vinyl, allyl, or acrylamide (e.g., allylamine) and crosslinkers will have two or more vinyl, allyl or acrylamide functionalities (e.g., diallylamine). Concurrent polymerization and crosslinking occurs through radically initiated polymerization of a mixture of the mono- and multifunctional allylamines. The resulting polymer network is thusly crosslinked through the carbon backbone. Each crosslinking reaction forms a carbon-carbon bond (as opposed to substitution reactions in which a carbon-heteroatom bond is formed during crosslinking). During the concurrent polymerization and crosslinking, the amine functionalities of the monomers do not undergo crosslinking reactions and are preserved in the final polymer (i.e., primary amines remain primary, secondary amines remain secondary, and tertiary amines remain tertiary).

In those embodiments in which the first reaction step comprises radical polymerization, a wide range of initiators may be used including cationic and radical initiators. Some examples of suitable initiators that may be used include: the free radical peroxy and azo type compounds, such as azodiisobutyronitrile, azodiisovaleronitrile, dimethylazodiisobutyrate, 2,2'azo bis(isobutyronitrile), 2,2'-azobis(N,N'-dimethyl-eneisobutyramidine)dihydrochloride, 2,2'-azobis(2-amidinopropane)dihydrochloride, 2,2'-azobis(N,N'-dimethyleneisobutyramidine), 1,1'-azo bis(I-cyclohexanecarbo-nitrile), 4,4'-azobis(4-cyanopentanoic acid), 2,2'-azobis(isobutyramide)dihydrate, 2,2'-azobis(2-methylpropane), 2,2'-azobis(2-methylbutyronitrile), VAZO 67, cyanopentanoic acid, the peroxypivalates, dodecylbenzene peroxide, benzoyl peroxide, di-t-butyl hydroperoxide, t-butyl peracetate, acetyl peroxide, dicumyl peroxide, cumylhydroperoxide, dimethyl bis(butylperoxy)hexane.

Exemplary amine-containing polymers as described above are more fully disclosed and exemplified in WO2016/094685 A1 and WO2014/197725 A1, the entire contents of which are incorporated herein by reference.

In one embodiment, the pharmaceutical composition comprises a mixture of any of the previously-identified nonabsorbable materials. For example, in one embodiment the pharmaceutical composition comprises a mixture of a cation exchange composition with at least one anion exchange composition, amphoteric ion exchange composition, or neutral composition having the capacity to bind both protons and anions. In another embodiment, the pharmaceutical composition comprises a mixture of an anion exchange composition with at least one cation exchange composition, amphoteric ion exchange composition, or neutral composition having the capacity to bind both protons and anions. In yet another embodiment, the pharmaceutical composition comprises a mixture of a neutral composition having the capacity to bind both protons and anions with at least one cation exchange composition, amphoteric ion exchange composition, or anion exchange composition.

Figure 1A:
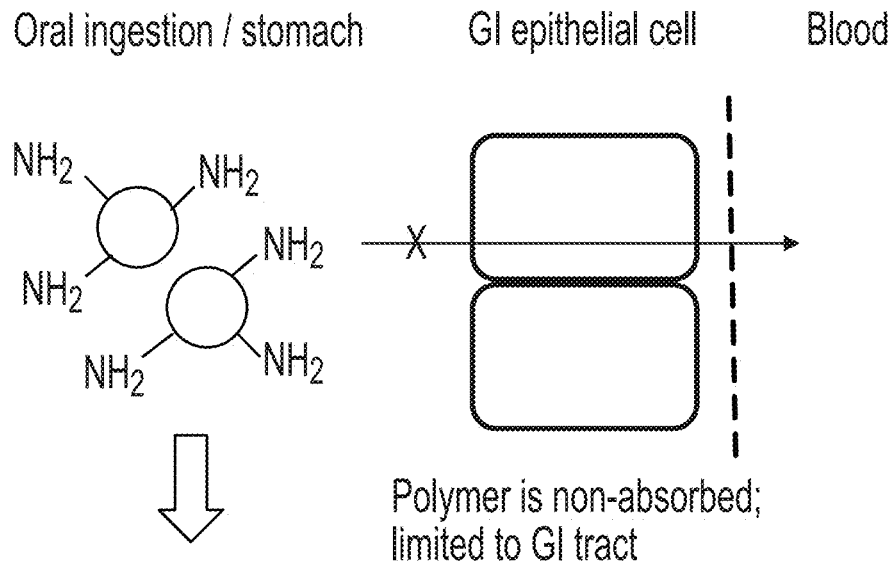
FIGS. 1A-1C is a flow chart schematically depicting the mechanism of action of the polymer when passing through the gastrointestinal tract of an individual from oral ingestion/stomach (FIG. 1A), to the upper GI tract (FIG. 1B) to the lower GI tract/colon (FIG. 1C).
Figure 1B:
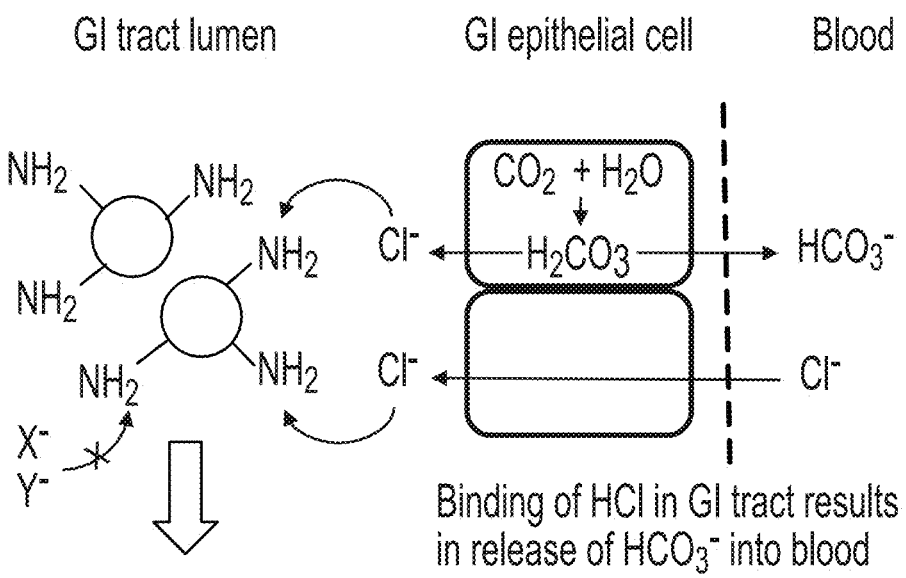
Figure 1C:
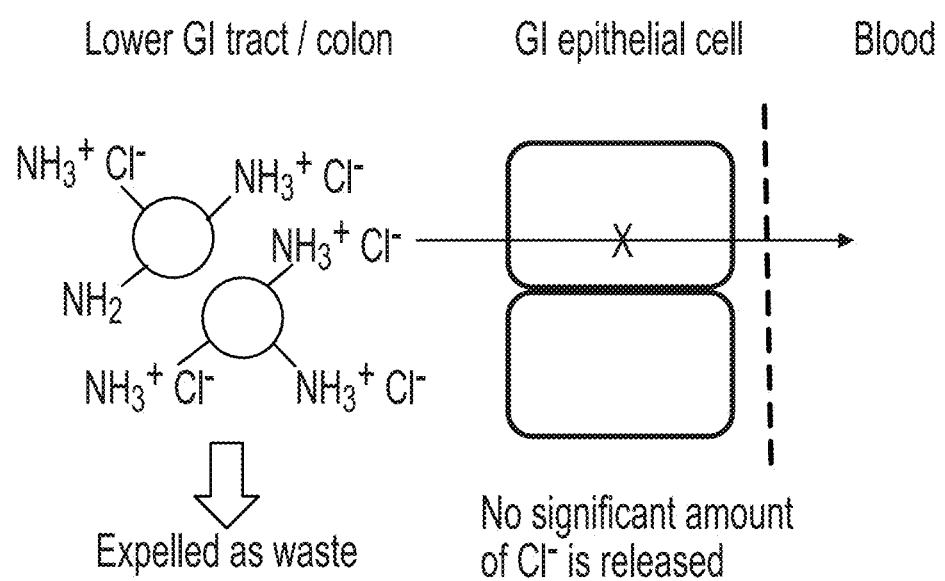

As schematically depicted in FIGS. 1A-1C and in accordance with one embodiment, a nonabsorbable free-amine polymer of the present disclosure is orally ingested and used to treat eubicarbonatemic metabolic acidosis by binding HCl in the gastrointestinal ("GI") tract and removing HCl through the feces. Free-amine polymer is taken orally (FIG. 1A) at compliance enhancing dose targeted to chronically bind sufficient amounts of HCl to enable clinically meaningful increase in serum bicarbonate of 3 mEq/L. In the stomach (FIG. 1B), free amine becomes protonated by binding $H^+$. Positive charge on polymer is then available to bind $Cl^-$; by controlling access of binding sites through crosslinking and hydrophilicity/hydrophobicity properties, other larger organic anions (e.g., acetate, propionate, butyrate, etc., depicted as $X^-$ and $Y^-$) are bound to a lesser degree, if at all. The net effect is therefore binding of HCl. In the lower GI tract/colon (FIG. 1C), $Cl^-$ is not fully released and HCl is removed from the body through regular bowel movement and fecal excretion, resulting in net alkalinization in the serum. $Cl^-$ bound in this fashion is not available for exchange via the $Cl^-/HCO_3^-$ antiporter system.

In one embodiment, the polymer is designed to simultaneously maximize efficacy (net HCl binding and excretion) and minimize GI side effects (through low swelling particle design and particle size distribution). Optimized HCl binding may be accomplished through a careful balance of capacity (number of amine binding sites), selectivity (preferred binding of chloride versus other anions, in particular organic anions in the colon) and retention (not releasing significant amounts of chloride in the lower GI tract to avoid the activity of the $Cl^-/HCO_3^-$ exchanger [antiporter] in the colon and intestine; if chloride is not tightly bound to the polymer the $Cl^-/HCO_3^-$ exchanger can mediate uptake of chloride ion from the intestinal lumen and reciprocal exchange for bicarbonate from the serum, thus effectively decreasing serum bicarbonate.

Competing anions that displace chloride lead to a decrease in net bicarbonate through the following mechanisms. First, displacement of chloride from the polymer in the GI lumen, particularly the colon lumen, provides for a facile exchange with bicarbonate in the serum. The colon has an anion exchanger (chloride/bicarbonate antiporter) that moves chloride from the luminal side in exchange for secreted bicarbonate. When free chloride is released from the polymer in the GI tract it will exchange for bicarbonate, which will then be lost in the stool and cause a reduction in total extracellular bicarbonate (Davis, 1983; D'Agostino, 1953). The binding of short chain fatty acids (SCFA) in exchange for bound chloride on the polymer, will result in the depletion of extracellular $HCO_3$ stores. Short chain fatty acids are the product of bacterial metabolism of complex carbohydrates that are not catabolized by normal digestive processes (Chemlarova, 2007). Short chain fatty acids that reach the colon are absorbed and distributed to various tissues, with the common metabolic fate being the generation of $H_2O$ and $CO_2$, which is converted to bicarbonate equivalents. Thus, binding of SCFA to the polymer to neutralize the proton charge would be detrimental to overall bicarbonate stores and buffering capacity, necessitating the design of chemical and physical features in the polymer that limit SCFA exchange. Finally, phosphate binding to the polymer should be limited as well, since phosphate represents an additional source of buffering capacity in the situation where ammoniagenesis and/or hydrogen ion secretion is compromised in chronic renal disease.

For each binding of proton, an anion is preferably bound as the positive charge seeks to leave the human body as a neutral polymer. "Binding" of an ion, is more than minimal binding, i.e., at least about 0.2 mmol of ion/g of polymer, at least about 1 mmol of ion/g of polymer in some embodiments, at least about 1.5 mmol of ion/g of polymer in some embodiments, at least about 3 mmol of ion/g of polymer in some embodiments, at least about 5 mmol of ion/g of polymer in some embodiments, at least about 10 mmol of ion/g of polymer in some embodiments, at least about 12 mmol of ion/g of polymer in some embodiments, at least about 13 mmol of ion/g of polymer in some embodiments, or even at least about 14 mmol of ion/g of polymer in some embodiments. In one embodiment, the polymers are characterized by their high capacity of proton binding while at the same time providing selectivity for anions; selectivity for chloride is accomplished by reducing the binding of interfering anions that include but are not limited to phosphate, citrate, acetate, bile acids and fatty acids. For example, in some embodiments, polymers of the present disclosure bind phosphate with a binding capacity of less than about 5 mmol/g, less than about 4 mmol/g, less than about 3 mmol/g, less than about 2 mmol/g or even less than about 1 mmol/g. In some embodiments, polymers of the invention bind bile and fatty acids with a binding capacity of less than about less than about 5 mmol/g, less than about 4 mmol/g, less than about 3 mmol/g, less than about 2 mmol/g, less than about 1 mmol/g in some embodiments, less than about 0.5 mmol/g in some embodiments, less than about 0.3 mmol/g in some embodiments, and less than about 0.1 mmol/g in some embodiments.

Pharmaceutical Compositions & Administration

In general, the dosage levels of the nonabsorbable compositions for therapeutic and/or prophylactic uses may range from about 0.1 g/day to about 100 g/day. To facilitate patient compliance, it is generally preferred that the dose be in the range of about 0.1 g/day to about 50 g/day. For example, in one such embodiment, the dose will be about 0.5 g/day to about 25 g/day. By way of further example, in one such embodiment, the dose will be about 1 g/day to about 25 g/day. By way of further example, in one such embodiment, the dose will be about 4 g/day to about 25 g/day. By way of further example, in one such embodiment, the dose will be about 5 g/day to about 25 g/day. By way of further example, in one such embodiment, the dose will be about 2.5 g/day to about 20 g/day. By way of further example, in one such embodiment, the dose will be about 2.5 g/day to about 15 g/day. By way of further example, in one such embodiment, the dose will be about 1 g/day to about 10 g/day. Optionally, the daily dose may be administered as a single dose (i.e., one time a day), or divided into multiple doses (e.g., two, three or more doses) over the course of a day. In general, the nonabsorbable compositions may be administered as a fixed daily dose or titrated based on the indicators of eubicarbonatemic metabolic acidosis as disclosed anywhere herein (in any combination). The titration may occur at the onset of treatment or throughout, as required, and starting and maintenance dosage levels may differ from patient to patient based on severity of the underlying disease.

The effectiveness of the nonabsorbable composition may be established in animal models, or in human volunteers and patients. In addition, in vitro, ex vivo and in vivo approaches are useful to establish HCl binding. In vitro binding solutions can be used to measure the binding capacity for proton, chloride and other ions at different pHs. Ex vivo extracts, such as the gastrointestinal lumen contents from human volunteers or from model animals can be used for similar purposes. The selectivity of binding and/or retaining certain ions preferentially over others can also be demonstrated in such in vitro and ex vivo solutions. In vivo models of metabolic acidosis and/or eubicarbonatemic metabolic acidosis can be used to test the effectiveness of the nonabsorbable composition in normalizing acid/base balance—for example 5/6 nephrectomized rats fed casein-containing chow (as described in Phisitkul S, Hacker C, Simoni J, Tran R M, Wesson D E. Dietary protein causes a decline in the glomerular filtration rate of the remnant kidney mediated by metabolic acidosis and endothelin receptors. Kidney international. 2008; 73(2):192-9), or adenine-fed rats (Terai K, K Mizukami and M Okada. 2008. Comparison of chronic renal failure rats and modification of the preparation protocol as a hyperphosphatemia model. Nephrol. 13: 139-146).

In one embodiment, the nonabsorbable compositions are provided (by oral administration) to an animal, including a human, in a dosing regimen of one, two or even multiple (i.e., at least three) doses per day to treat an acid-base disorder (e.g., eubicarbonatemic metabolic acidosis) and achieve a clinically significant and sustained increase of serum bicarbonate as previously described. For example, in one embodiment a daily dose of the nonabsorbable composition (whether orally administered in a single dose or multiple doses over the course of the day) has sufficient capacity to remove at least 5 mmol of protons, chloride ions or each per day. By way of further example, in one such embodiment a daily dose of the nonabsorbable composition has sufficient capacity to remove at least 10 mmol of protons, chloride ions or each per day. By way of further example, in one such embodiment a daily dose of the nonabsorbable composition has sufficient capacity to remove at least 20 mmol of protons, the conjugate base of a strong acid (e.g., $Cl^-$, $HSO_4^-$ and $SO_4^{2-}$) and/or a strong acid (e.g., HCl or $H_2SO_4$) each per day. By way of further example, in one such embodiment a daily dose of the nonabsorbable composition has sufficient capacity to remove at least 30 mmol of protons, the conjugate base of a strong acid, and/or a strong acid each per day. By way of further example, in one such embodiment a daily dose of the nonabsorbable composition has sufficient capacity to remove at least 40 mmol of protons, the conjugate base of a strong acid, and/or a strong acid each per day. By way of further example, in one such embodiment a daily dose of the nonabsorbable composition has sufficient capacity to remove at least 50 mmol of protons, the conjugate base of a strong acid, and/or a strong acid each per day.

The dosage unit form of the pharmaceutical comprising the nonabsorbable composition may be any form appropriate for oral administration. Such dosage unit forms include powders, tablets, pills, lozenges, sachets, cachets, elixirs, suspensions, syrups, soft or hard gelatin capsules, and the like. In one embodiment, the pharmaceutical composition comprises only the nonabsorbable composition. Alternatively, the pharmaceutical composition may comprise a carrier, a diluent, or excipient in addition to the nonabsorbable composition. Examples of carriers, excipients, and diluents that may be used in these formulations as well as others, include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, propylhydroxybenzoates, and talc. Pharmaceutical excipients useful in the pharmaceutical compositions further include a binder, such as microcrystalline cellulose, colloidal silica and combinations thereof (Prosolv 90), carbopol, providone and xanthan gum; a flavoring agent, such as sucrose, mannitol, xylitol, maltodextrin, fructose, or sorbitol; a lubricant, such as magnesium stearate, stearic acid, sodium stearyl fumurate and vegetable based fatty acids; and, optionally, a disintegrant, such as croscarmellose sodium, gellan gum, low-substituted hydroxypropyl ether of cellulose, sodium starch glycolate. Other additives may include plasticizers, pigments, talc, and the like. Such additives and other suitable ingredients are well-known in the art; see, e.g., Gennaro A R (ed), Remington's Pharmaceutical Sciences, 20th Edition.

In one embodiment, the nonabsorbable composition may be co-administered with other active pharmaceutical agents depending on the condition being treated. This co-administration may include simultaneous administration of the two agents in the same dosage form, simultaneous administration in separate dosage forms, and separate administration. For example, for the treatment of eubicarbonatemic metabolic acidosis, the nonabsorbable composition may be co-administered with common treatments that are required to treat underlying comorbidities including but not limited to edema, hypertension, diabetes, obesity, heart failure and complications of Chronic Kidney Disease. These medications and the nonabsorbable composition can be formulated together in the same dosage form and administered simultaneously as long as they do not display any clinically significant drug-drug-interactions. Alternatively, these treatments and the nonabsorbable composition may be separately and sequentially administered with the administration of one being followed by the administration of the other.

In one embodiment, the daily dose of the metabolic acidosis treatment is compliance enhancing (approximately 15 g or less per day) and optionally achieves a clinically significant and sustained increase of serum bicarbonate of approximately 3 mEq/L at these daily doses. The non-absorbed nature of the polymer and the lack of sodium load and/or introduction of other deleterious ions for such an oral drug enable for the first time a safe, chronic treatment of metabolic acidosis without worsening blood pressure/hypertension and/or without causing increased fluid retention and fluid overload. Another benefit is further slowing of the progression of kidney disease and time to onset of lifelong renal replacement therapy (End Stage Renal Disease "ESRD" including 3 times a week dialysis) or need for kidney transplants. Both are associated with significant mortality, low quality of life and significant burden to healthcare systems around the world. In the United States alone, approximately 20% of the 400,000 ESRD patients die and 100,000 new patients start dialysis every year.

A further aspect of the present disclosure is a pharmaceutical product comprising a sealed package and the nonabsorbable composition of the present disclosure within the sealed package. The sealed package is preferably substantially impermeable to moisture and oxygen to increase the stability of the pharmaceutical composition. For example, the dosage unit form may comprise a sealed container (e.g., a sealed sachet) that prevents or reduces ingress of moisture and oxygen upon packaging the nonabsorbable composition in the container. The container size can be optimized to reduce head space in the container after packaging and any head space may be filled with an inert gas such as nitrogen. Furthermore, container material of construction can be chosen to minimize the moisture and oxygen ingress inside the container after packaging. For example, the nonabsorbable composition may be packaged in a multilayer sachet containing at least one or more layer that serves as a barrier layer to moisture and oxygen ingress. In another example, the nonabsorbable composition may be packaged in a single layer or multilayer plastic, metal or glass container that has at least one or more barrier layers incorporated in the structure that limits oxygen and/or moisture ingress after packaging. For example, in one such embodiment the sachet (or other container or package) may comprise a multi-layer laminate of an inner contact layer, an outer layer; and a barrier layer disposed between the contact layer and outer layer. In one exemplary embodiment, the container includes one or more oxygen-scavenging layers.

Having described the invention in detail in the description and the appended claims, it will be apparent that modifications and variations are possible without departing the scope of the invention defined in the appended claims. Furthermore, it should be appreciated that all examples in the present disclosure are provided as non-limiting examples.

In further embodiments, enumerated as embodiments 1-404 below, the present disclosure includes:

Embodiment 1. A method of treating a patient with chronic kidney disease, wherein the patient has a serum bicarbonate value of at least 22 mEq/l prior to the treatment, wherein the method comprises oral administration of a nonabsorbable pharmaceutical composition that binds a target species, the target species being selected from the group consisting of protons, conjugate bases of strong acids, and/or strong acids.

Embodiment 2. A method of treating or preventing eubicarbonatemic metabolic acidosis in a patient wherein the method comprises oral administration of a nonabsorbable pharmaceutical composition that binds a target species, the target species being selected from the group consisting of protons, conjugate bases of strong acids, and/or strong acids, wherein said patient optionally has chronic kidney disease.

Embodiment 3. A method of treating a patient afflicted with chronic kidney disease characterized by a marker of eubicarbonatemic metabolic acidosis, the method comprising oral administration of a nonabsorbable pharmaceutical composition having the capacity to bind a target species as it transits the digestive system to maintain the patient's serum at a value of in excess of 24 mEq/l but not greater than 29 mEq/l, the target species being selected from the group consisting of protons, strong acids, and conjugate bases of strong acids.

Embodiment 4. A method of treating a patient afflicted with chronic kidney disease and a baseline serum bicarbonate value of at least 22 mEq/l but not greater than 24 mEq/l, the method comprising oral administration of a nonabsorbable pharmaceutical composition having the capacity to bind a target species as it transits the digestive system to increase the patient's serum bicarbonate value from baseline to a value in excess of 24 mEq/l but not greater than 29 mEq/l within a treatment period not greater than 1 month, the target species being selected from the group consisting of protons, strong acids, and conjugate bases of strong acids.

Embodiment 5. A method of treating a patient afflicted with chronic kidney disease and a baseline serum bicarbonate value of at least 22 mEq/l but not greater 24 mEq/l, the method comprising oral administration of a nonabsorbable pharmaceutical composition to bind a target species in the digestive system and increase the patient's serum bicarbonate value by at least 2 mEq/l from baseline within a treatment period not greater than 1 month, the target species being selected from the group consisting of protons, strong acids, and conjugate bases of strong acids.

Embodiment 6. The method of any preceding embodiment wherein the treatment enables the patient's serum bicarbonate value to be sustained at a value greater than 24 mEq/l but not greater than 29 mEq/l for a period of at least one week.

Embodiment 7. The method of any preceding embodiment wherein the treatment enables the patient's serum bicarbonate value to be sustained at a value greater than 24 mEq/l but not greater than 29 mEq/l for a period of at least one month.

Embodiment 8. The method of any preceding embodiment wherein the treatment enables the patient's serum bicarbonate value to be sustained at a value greater than 24 mEq/l but not greater than 29 mEq/l for a period of at least three months.

Embodiment 9. The method of any preceding embodiment wherein the treatment enables the patient's serum bicarbonate value to be sustained at a value greater than 24 mEq/l but not greater than 29 mEq/l for a period of at least six months.

Embodiment 10. The method of any preceding embodiment wherein the treatment enables the patient's serum bicarbonate value to be sustained at a value greater than 24 mEq/l but not greater than 29 mEq/l for a period of at least one year.

Embodiment 11. The method of any preceding embodiment wherein the oral administration is as frequent as at least weekly.

Embodiment 12. The method of any preceding embodiment wherein the oral administration is as frequent as at least semi-weekly.

Embodiment 13. The method of any preceding embodiment wherein the oral administration is as frequent as daily.

Embodiment 14. The method of any preceding embodiment wherein the oral administration is daily.

Embodiment 15. The method of any preceding embodiment wherein the oral administration is a daily dose and the daily dose of the nonabsorbable pharmaceutical composition has the capacity to remove at least about 5 mEq/day of the target species.

Embodiment 16. The method of any preceding embodiment wherein the oral administration is a daily dose and the daily dose of the nonabsorbable pharmaceutical composition has the capacity to remove at least about 10 mEq/day of the target species.

Embodiment 17. The method of any preceding embodiment wherein the oral administration is a daily dose and the daily dose of the nonabsorbable pharmaceutical composition has the capacity to remove at least about 15 mEq/day of the target species.

Embodiment 18. The method of any preceding embodiment wherein the oral administration is a daily dose and the daily dose of the nonabsorbable pharmaceutical composition has the capacity to remove at least about 20 mEq/day of the target species.

Embodiment 19. The method of any preceding embodiment wherein the oral administration is a daily dose and the daily dose of the nonabsorbable pharmaceutical composition has the capacity to remove at least about 25 mEq/day of the target species.

Embodiment 20. The method of any preceding embodiment wherein the oral administration is a daily dose and the daily dose of the nonabsorbable pharmaceutical composition has the capacity to remove at least about 30 mEq/day of the target species.

Embodiment 21. The method of any preceding embodiment wherein the oral administration is a daily dose and the daily dose of the nonabsorbable pharmaceutical composition has the capacity to remove at least about 35 mEq/day of the target species.

Embodiment 22. The method of any preceding embodiment wherein the oral administration is a daily dose and the daily dose of the nonabsorbable pharmaceutical composition has the capacity to remove at least about 40 mEq/day of the target species.

Embodiment 23. The method of any preceding embodiment wherein the oral administration is a daily dose and the daily dose of the nonabsorbable pharmaceutical composition has the capacity to remove at least about 45 mEq/day of the target species.

Embodiment 24. The method of any preceding embodiment wherein the oral administration is a daily dose and the daily dose of the nonabsorbable pharmaceutical composition has the capacity to remove at least about 50 mEq/day of the target species.

Embodiment 25. [intentionally omitted]

Embodiment 26. The method of any preceding embodiment wherein the target species comprises protons.

Embodiment 27. The method of any preceding embodiment wherein the target species comprises the conjugate base(s) of one or more strong acids.

Embodiment 28. The method of any preceding embodiment wherein the target species comprises chloride, bisulfate ($HSO_4^-$) and/or sulfate ($SO_4^-$) ions.

Embodiment 29. The method of any preceding embodiment wherein the target species comprises one or more strong acids.

Embodiment 30. The method of any preceding embodiment wherein the target species comprises HCl and/or $H_2SO_4$.

Embodiment 31. The method of any preceding embodiment, wherein the treatment delays the onset of chronic metabolic acidosis.

Embodiment 32. The method of any preceding embodiment, wherein the method prevents the onset of chronic metabolic acidosis.

Embodiment 33. The method of any preceding embodiment, wherein the method slows the progression of chronic kidney disease.

Embodiment 34. The method of any preceding embodiment, wherein the method halts the progression of chronic kidney disease.

Embodiment 35. The method of any preceding embodiment wherein the patient is not yet in need for kidney replacement therapy (dialysis or transplant).

Embodiment 36. The method of any preceding embodiment wherein the patient has not yet reached end stage renal disease ("ESRD").

Embodiment 37. The method of any preceding embodiment wherein the patient has a mGFR of at least 15 mL/min/1.73 m².

Embodiment 38. The method of any preceding embodiment wherein the patient has an eGFR of at least 15 mL/min/1.73 m².

Embodiment 39. The method of any preceding embodiment wherein the patient has a mGFR of at least 30 mL/min/1.73 m².

Embodiment 40. The method of any preceding embodiment wherein the patient has an eGFR of at least 30 mL/min/1.73 m².

Embodiment 41. The method of any preceding embodiment wherein the patient has a mGFR of less than 45 mL/min/1.73 m².

Embodiment 42. The method of any preceding embodiment wherein the patient has an eGFR of less than 45 mL/min/1.73 m².

Embodiment 43. The method of any preceding embodiment wherein the patient has a mGFR of less than 60 mL/min/1.73 m².

Embodiment 44. The method of any preceding embodiment wherein the patient has an eGFR of less than 60 mL/min/1.73 m².

Embodiment 45. The method of any preceding embodiment, wherein the patient has the specified eGFR and/or mGFR at least a month prior to the start of treatment with the nonabsorbable proton binding polymer.

Embodiment 46. The method of any preceding embodiment, wherein the patient has the specified eGFR and/or mGFR at least two months prior to the start of treatment with the nonabsorbable proton binding polymer.

Embodiment 47. The method of any preceding embodiment, wherein the patient has the specified eGFR and/or mGFR at least three months prior to the start of treatment with the nonabsorbable proton binding polymer.

Embodiment 48. The method of any preceding embodiment wherein the patient has Stage 3A CKD.

Embodiment 49. The method of any preceding embodiment wherein the patient has Stage 3B CKD.

Embodiment 50. The method of any preceding embodiment wherein the patient has Stage 4 CKD.

Embodiment 51. The method of any preceding embodiment wherein the nonabsorbable pharmaceutical composition comprises a proton-binding, crosslinked amine polymer comprising the residue of an amine corresponding to Formula 1:

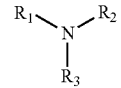

Formula 1 wherein $R_1$, $R_2$ and $R_3$ are independently hydrogen, hydrocarbyl, or substituted hydrocarbyl provided, however, at least one of $R_1$, $R_2$ and $R_3$ is other than hydrogen, and the crosslinked amine polymer has (i) an equilibrium proton binding capacity of at least 5 mmol/g and a chloride ion binding capacity of at least 5 mmol/g in an aqueous simulated gastric fluid buffer ("SGF") containing 35 mM NaCl and 63 mM HCl at pH 1.2 and 37° C., and (ii) an equilibrium swelling ratio in deionized water of about 2 or less.

Embodiment 52. The method of any preceding embodiment wherein the nonabsorbable pharmaceutical composition is a proton-binding, crosslinked amine polymer comprising the residue of an amine corresponding to Formula 1:

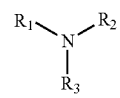

Formula 1 wherein $R_1$, $R_2$ and $R_3$ are independently hydrogen, hydrocarbyl, substituted hydrocarbyl provided, however, at least one of $R_1$, $R_2$ and $R_3$ is other than hydrogen, the crosslinked amine polymer has an equilibrium swelling ratio in deionized water of about 5 or less, and the crosslinked amine polymer binds a molar ratio of chloride ions to interfering ions of at least 0.35:1, respectively, in an interfering ion buffer at 37° C. wherein (i) the interfering ions are phosphate ions and the interfering ion buffer is a buffered solution at pH 5.5 of 36 mM chloride and 20 mM phosphate or (ii) the interfering ions are phosphate, citrate and taurocholate ions (combined amount) and the interfering ion buffer is a buffered solution at pH 6.2 including 36 mM chloride, 7 mM phosphate, 1.5 mM citrate, and 5 mM taurocholate.

Embodiment 53. The method of embodiment 51 wherein the crosslinked amine polymer has an equilibrium chloride binding capacity of at least 7.5 mmol/g in an aqueous simulated gastric fluid buffer ("SGF") containing 35 mM NaCl and 63 mM HCl at pH 1.2 and 37° C.

Embodiment 54. The method of embodiment 51 wherein the crosslinked amine polymer has an equilibrium chloride binding capacity of at least 10 mmol/g in an aqueous simulated gastric fluid buffer ("SGF") containing 35 mM NaCl and 63 mM HCl at pH 1.2 and 37° C.

Embodiment 55. The method of embodiment 52 wherein the crosslinked amine polymer binds more chloride than any one of the interfering anions in the interfering ion buffer, the interfering ions are phosphate, citrate and taurocholate ions and the interfering ion buffer is a buffered solution at pH 6.2 including 36 mM chloride, 7 mM phosphate, 1.5 mM citrate, and 5 mM taurocholate Embodiment 56. The method of embodiment 52 wherein at least 66% of the combined amount of chloride and interfering ions bound by the crosslinked amine polymer in the interfering ion buffer are chloride anions, the interfering ions are phosphate, citrate and taurocholate, and the interfering ion buffer is a buffered solution at pH 6.2 including 36 mM chloride, 7 mM phosphate, 1.5 mM citrate, and 5 mM taurocholate.

Embodiment 57. The method of embodiment 52 wherein 90% or more of the combined amount of chloride and interfering ions bound by the crosslinked amine polymer in the interfering ion buffer are chloride anions, the interfering ions are phosphate, citrate and taurocholate, and the interfering ion buffer is a buffered solution at pH 6.2 including 36 mM chloride, 7 mM phosphate, 1.5 mM citrate, and 5 mM taurocholate.

Embodiment 58. The method of embodiment 52 wherein the crosslinked amine polymer has an equilibrium swelling ratio in deionized water of about 4 or less.

Embodiment 59. The method of embodiment 52 wherein the crosslinked amine polymer has an equilibrium swelling ratio in deionized water of about 3 or less.

Embodiment 60. The method of embodiment 52 wherein the crosslinked amine polymer has an equilibrium swelling ratio in deionized water of about 2 or less.

Embodiment 61. The method of any of embodiments 28-37 wherein $R_1$, $R_2$ and $R_3$ are independently hydrogen, alkyl, alkenyl, allyl, vinyl, aryl, aminoalkyl, alkanol, haloalkyl, hydroxyalkyl, ethereal, heteroaryl or heterocyclic provided, however, each of $R_1$, $R_2$ and $R_3$ is not hydrogen.

Embodiment 62. The method of any of embodiments 51-61 wherein $R_1$, $R_2$ and $R_3$ are independently hydrogen, aliphatic or heteroaliphatic provided, however, at least one of $R_1$, $R_2$ and $R_3$ is other than hydrogen.

Embodiment 63. The method of any of embodiments 51-62 wherein the crosslinked amine polymer is prepared by substitution polymerization of the amine with a polyfunctional crosslinker, optionally also comprising amine moieties.

Embodiment 64. The method of any of embodiments 51-62 wherein the crosslinked amine polymer comprises the residue of an amine corresponding to Formula 1a and the crosslinked amine polymer is prepared by radical polymerization of an amine corresponding to Formula 1a:

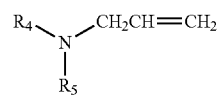

Formula 1a wherein $R_4$ and $R_5$ are independently hydrogen, hydrocarbyl, or substituted hydrocarbyl.

Embodiment 65. The method of embodiment 64 wherein $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic.

Embodiment 66. The method of embodiment 64 wherein $R_4$ and $R_5$ are independently hydrogen, aliphatic or heteroaliphatic.

Embodiment 67. The method of any of embodiments 51-62 wherein the crosslinked amine polymer comprises the residue of an amine corresponding to Formula 1b and the crosslinked amine polymer is prepared by substitution polymerization of the amine corresponding to Formula 1b with a polyfunctional crosslinker:

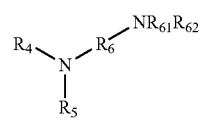

Formula 1b wherein $R_4$ and $R_5$ are independently hydrogen, hydrocarbyl, or substituted hydrocarbyl, $R_6$ is aliphatic and $R_{61}$ and $R_{62}$ are independently hydrogen, aliphatic, or heteroaliphatic.

Embodiment 68. The method of embodiment 67 wherein $R_4$ and $R_5$ are independently hydrogen, saturated hydrocarbon, unsaturated aliphatic, aryl, heteroaryl, heteroalkyl, or unsaturated heteroaliphatic.

Embodiment 69. The method of embodiment 67 wherein $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic.

Embodiment 70. The method of embodiment 67 wherein $R_4$ and $R_5$ are independently hydrogen, allyl, or aminoalkyl.

Embodiment 71. The method of any of embodiments 51-70 wherein the crosslinked amine polymer comprises the residue of an amine corresponding to Formula 1c:

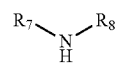

Formula 1c wherein $R_7$ is hydrogen, aliphatic or heteroaliphatic and $R_8$ is aliphatic or heteroaliphatic.

Embodiment 72. The method of any of embodiments 51-62 wherein the crosslinked amine polymer comprises the residue of an amine corresponding to Formula 2:

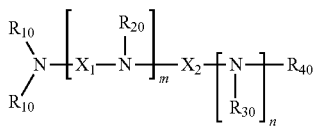

Formula 2 wherein
m and n are independently non-negative integers;
$R_{10}$, $R_{20}$, $R_{30}$, and $R_{40}$ are independently hydrogen, hydrocarbyl, or substituted hydrocarbyl;
$X_1$ is

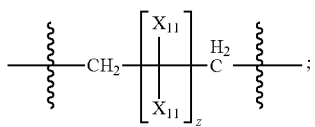

$X_2$ is hydrocarbyl or substituted hydrocarbyl;
each $X_{11}$ is independently hydrogen, hydrocarbyl, substituted hydrocarbyl, hydroxy, or amino; and
z is a non-negative number.

Embodiment 73. The method of embodiment 72 wherein $R_{10}$, $R_{20}$, $R_{30}$, and $R_{40}$ are independently hydrogen, aliphatic, aryl, heteroaliphatic, or heteroaryl, m and z are independently 0-3 and n is 0 or 1.

Embodiment 74. The method of embodiment 72 or 73 wherein $X_2$ is aliphatic or heteroaliphatic.

Embodiment 75. The method of embodiment 72, 73 or 74 wherein m is 1-3 and $X_{11}$ is hydrogen, aliphatic or heteroaliphatic.

Embodiment 76. The method of any of embodiments 51-62 wherein the crosslinked amine polymer comprises the residue of an amine corresponding to Formula 2a:

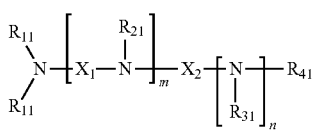

Formula 2a wherein
m and n are independently non-negative integers;
each $R_{11}$ is independently hydrogen, hydrocarbyl, heteroaliphatic, or heteroaryl;
$R_{21}$ and $R_{31}$, are independently hydrogen or heteroaliphatic;
$R_{41}$ is hydrogen, substituted hydrocarbyl, or hydrocarbyl;
$X_1$ is

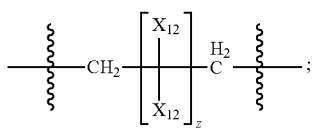

$X_2$ is alkyl or substituted hydrocarbyl;
each $X_{12}$ is independently hydrogen, hydroxy, amino, aminoalkyl, boronic acid or halo; and
z is a non-negative number.

Embodiment 77. The method of embodiment 76 wherein m and z are independently 0-3 and n is 0 or 1.

Embodiment 78. The method of embodiment 76 or 77 wherein $R_{11}$ is independently hydrogen, aliphatic, aminoalkyl, haloalkyl, or heteroaryl, $R_{21}$ and $R_{31}$ are independently hydrogen or heteroaliphatic and $R_{41}$ is hydrogen, aliphatic, aryl, heteroaliphatic, or heteroaryl.

Embodiment 79. The method of embodiment 76 or 77 wherein each $R_{11}$ is hydrogen, aliphatic, aminoalkyl, or haloalkyl, $R_{21}$ and $R_{31}$ are hydrogen or aminoalkyl, and $R_{41}$ is hydrogen, aliphatic, or heteroaliphatic.

Embodiment 80. The method of any of embodiments 51 to 62 wherein the crosslinked amine polymer comprises the residue of an amine corresponding to Formula 2b:

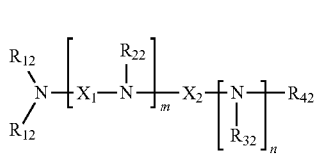

Formula 2b wherein
m and n are independently non-negative integers;
each $R_{12}$ is independently hydrogen, substituted hydrocarbyl, or hydrocarbyl;
$R_{22}$ and $R_{32}$ are independently hydrogen substituted hydrocarbyl, or hydrocarbyl;
$R_{42}$ is hydrogen, hydrocarbyl or substituted hydrocarbyl;
$X_1$ is

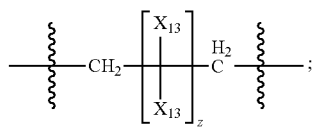

$X_2$ is alkyl, aminoalkyl, or alkanol;
each $X_{13}$ is independently hydrogen, hydroxy, alicyclic, amino, aminoalkyl, halogen, alkyl, heteroaryl, boronic acid or aryl;
z is a non-negative number; and the amine corresponding to Formula 2b comprises at least one allyl group.

Embodiment 81. The method of embodiment 80 wherein m and z are independently 0-3 and n is 0 or 1.

Embodiment 82. The method of embodiment 80 or 81 wherein $R_{12}$ or $R_{42}$ independently comprise at least one allyl or vinyl moiety.

Embodiment 83. The method of embodiment 80 or 81 wherein (i) m is a positive integer and $R_{12}$, $R_{22}$ and $R_{42}$, in combination comprise at least two allyl or vinyl moieties or (ii) n is a positive integer and $R_{12}$, $R_{32}$ and $R_{42}$, in combination, comprise at least two allyl or vinyl moieties.

Embodiment 84. The method of embodiment 80 or 81 wherein the crosslinked amine polymer comprises the residue of an amine appearing in Table C.

Embodiment 85. The method of embodiment 80, 81 or 84 57, 58 or 61 wherein the crosslinked amine polymer is crosslinked with a crosslinking agent appearing in Table B.

Embodiment 86. The method of any of embodiments 51 to 85 wherein the crosslinked amine polymer comprises a repeat unit corresponding to Formula 3:

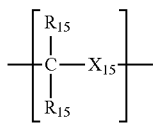

Formula 3 wherein $R_{15}$, $R_{16}$ and $R_{17}$ are independently hydrogen, hydrocarbyl, substituted hydrocarbyl, hydroxyl, amino, boronic acid or halo;

$X_{15}$ is

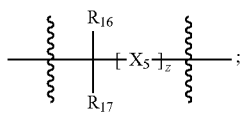

$X_5$ is hydrocarbyl, substituted hydrocarbyl, oxo (—O—), or amino; and z is a non-negative number.

Embodiment 87. The method of embodiment 86 wherein $R_{15}$, $R_{16}$ and $R_{17}$ are independently aliphatic or heteroaliphatic.

Embodiment 88. The method of embodiment 86 or 87 wherein $X_5$ is oxo, amino, alkylamino, ethereal, alkanol, or haloalkyl.

Embodiment 89. The method of any of embodiments 51-62 wherein the crosslinked amine polymer is prepared by (i) substitution polymerization of polyfunctional reagents at least one of which comprises amine moieties, (2) radical polymerization of a monomer comprising at least one amine moiety or nitrogen containing moiety, or (3) crosslinking of an amine-containing intermediate with a crosslinking agent, optionally containing amine moieties.

Embodiment 90. The method of embodiment 89 wherein the crosslinked amine polymer is a crosslinked homopolymer or a crosslinked copolymer.

Embodiment 91. The method of embodiment 89 wherein the crosslinked amine polymer comprises free amine moieties, separated by the same or varying lengths of repeating linker units.

Embodiment 92. The method of embodiment 89 wherein the crosslinked amine polymer is prepared by polymerizing an amine-containing monomer with a crosslinking agent in a substitution polymerization reaction.

Embodiment 93. The method of embodiment 92 wherein the amine-containing monomer is a linear amine possessing at least two reactive amine moieties to participate in the substitution polymerization reaction.

Embodiment 94. The method of embodiment 92 or 93 wherein the amine-containing monomer is 1,3-Bis[bis(2-aminoethyl)amino]propane, 3-Amino-1-{[2-(bis{2-[bis(3-aminopropyl)amino]ethyl}amino)ethyl](3-aminopropyl) amino}propane, 2-[Bis(2-aminoethyl)amino]ethanamine, Tris(3-aminopropyl)amine, 1,4-Bis[bis(3-aminopropyl) amino]butane, 1,2-Ethanediamine, 2-Amino-1-(2-aminoethylamino)ethane, 1,2-Bis(2-aminoethylamino)ethane, 1,3-Propanediamine, 3,3'-Diaminodipropylamine, 2,2-dimethyl-1,3-propanediamine, 2-methyl-1,3-propanediamine, N,N'-dimethyl-1,3-propanediamine, N-methyl-1,3-diaminopropane, 3,3'-diamino-N-methyldipropylamine, 1,3-diaminopentane, 1,2-diamino-2-methylpropane, 2-methyl-1,5-diaminopentane, 1,2-diaminopropane, 1,10-diaminodecane, 1,8-diaminooctane, 1,9-diaminooctane, 1,7-diaminoheptane, 1,6-diaminohexane, 1,5-diaminopentane, 3-bromopropylamine hydrobromide, N,2-dimethyl-1,3-propanediamine, N-isopropyl-1,3-diaminopropane, N,N'-bis(2-aminoethyl)-1,3-propanediamine, N,N'-bis(3-aminopropyl) ethylenediamine, N,N'-bis(3-aminopropyl)-1,4-butanediamine tetrahydrochloride, 1,3-diamino-2-propanol, N-ethylethylenediamine, 2,2'-diamino-N-methyldiethylamine, N,N'-diethylethylenediamine, N-isopropylethylenediamine, N-methylethylenediamine, N,N'-di-tert-butylethylenediamine, N,N'-diisopropylethylenediamine, N,N'-dimethylethylenediamine, N-butylethylenediamine, 2-(2-aminoethylamino)ethanol, 1,4,7,10,13,16-hexaazacyclooctadecane, 1,4,7,10-tetraazacyclododecane, 1,4,7-triazacyclononane, N,N'-bis(2-hydroxyethyl)ethylenediamine, piperazine, bis(hexamethylene)triamine, N-(3-hydroxypropyl)ethylenediamine, N-(2-Aminoethyl)piperazine, 2-Methylpiperazine, Homopiperazine, 1,4,8,11-Tetraazacyclotetradecane, 1,4,8,12-Tetraazacyclopentadecane, 2-(Aminomethyl)piperidine, or 3-(Methylamino)pyrrolidino.

Embodiment 95. The method of any of embodiments 66, 68, 65 and 71 wherein the crosslinking agent is selected from the group consisting of dihaloalkanes, haloalkyloxiranes, alkyloxirane sulfonates, di(haloalkyl)amines, tri(haloalkyl) amines, diepoxides, triepoxides, tetraepoxides, bis (halomethyl)benzenes, tri(halomethyl)benzenes, tetra(halomethyl)benzenes, epihalohydrins such as epichlorohydrin and epibromohydrin poly(epichlorohydrin), (iodomethyl) oxirane, glycidyl tosylate, glycidyl 3-nitrobenzenesulfonate, 4-tosyloxy-1,2-epoxybutane, bromo-1,2-epoxybutane, 1,2-dibromoethane, 1,3-dichloropropane, 1,2-dichloroethane, 1-bromo-2-chloroethane, 1,3-dibromopropane, bis(2-chloroethyl)amine, tris(2-chloroethyl)amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, 1,2 ethanedioldiglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol digylcidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropy loxy)propane, 1,2-cyclohexanedicarboxylic acid diglycidyl ester, 2,2'-bis(glycidyloxy) diphenylmethane, bisphenol F diglycidyl ether, 1,4-bis(2',3'epoxypropyl)perfluoro-n-butane, 2,6-di(oxiran-2-ylmethyl)-1,2,3,5,6,7-hexahydropyrrolo[3,4-f]isoindol-1,3,5,7-tetraone, bisphenol A diglycidyl ether, ethyl 5-hydroxy-6,8-di(oxiran-2-ylmethyl)-4-oxo-4-h-chromene-2-carboxylate, bis[4-(2,3-epoxy-propylthio) phenyl]-sulfide, 1,3-bis(3-glycidoxypropyl) tetramethyldisiloxane, 9,9-bis[4-(glycidyloxy)phenyl]fluorine, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris[[3-(epoxypropoxy propyl]dimethylsilyloxy]-1,3,5,7,9,11,14-heptacyclopentyltricyclo [7,3,3,15, 11]heptasiloxane, 4,4'methylenebis(N, N-diglycidylaniline), bis(halomethyl)benzene, bis(halomethyl)biphenyl and bis(halomethyl)naphthalene, toluene diisocyanate, acrylol chloride, methyl acrylate, ethylene bisacrylamide, pyromellitic dianhydride, succinyl dichloride, dimethylsuccinate, 3-chloro-1-(3-chloropropylamino- 2-propanol, 1,2-bis(3-chloropropylamino)ethane, Bis(3-chloropropyl)amine, 1,3-Dichloro-2-propanol, 1,3-Dichloropropane, 1-chloro-2,3-epoxypropane, tris[(2-oxiranyl)methyl]amine, and combinations thereof.

Embodiment 96. The method of embodiment 89 wherein the preparation of the crosslinked amine polymer comprises radical polymerization of an amine monomer comprising at least one amine moiety or nitrogen containing moiety.

Embodiment 97. The method of any preceding embodiment wherein the nonabsorbable pharmaceutical composition comprises a crosslinked amine polymer having an equilibrium swelling ratio in deionized water of about 1.5 or less.

Embodiment 98. The method of any preceding embodiment wherein the nonabsorbable pharmaceutical composition comprises a crosslinked amine polymer having an equilibrium swelling ratio in deionized water of about 1 or less.

Embodiment 99. The method of any preceding embodiment wherein the nonabsorbable pharmaceutical composition comprises a crosslinked amine polymer having a chloride ion to phosphate ion binding molar ratio of at least 0.5:1, respectively, in an aqueous simulated small intestine inorganic buffer ("SIB") containing 36 mM NaCl, 20 mM $NaH_2PO_4$, and 50 mM 2-(N-morpholino)ethanesulfonic acid (MES) buffered to pH 5.5 and at 37° C.

Embodiment 100. The method of any preceding embodiment wherein the nonabsorbable pharmaceutical composition comprises a crosslinked amine polymer having a chloride ion to phosphate ion binding molar ratio of at least 1:1, respectively, in an aqueous simulated small intestine inorganic buffer ("SIB") containing 36 mM NaCl, 20 mM $NaH_2PO_4$, and 50 mM 2-(N-morpholino)ethanesulfonic acid (MES) buffered to pH 5.5 and at 37° C.

Embodiment 101. The method of any preceding embodiment wherein the nonabsorbable pharmaceutical composition comprises a crosslinked amine polymer having a chloride ion to phosphate ion binding molar ratio of at least 2:1, respectively, in an aqueous simulated small intestine inorganic buffer ("SIB") containing 36 mM NaCl, 20 mM $NaH_2PO_4$, and 50 mM 2-(N-morpholino)ethanesulfonic acid (MES) buffered to pH 5.5 and at 37° C.

Embodiment 102. The method of any preceding embodiment wherein the nonabsorbable pharmaceutical composition comprises a crosslinked amine polymer having a proton binding capacity of at least 10 mmol/g and a chloride ion binding capacity of at least 10 mmol/g in an aqueous simulated gastric fluid buffer ("SGF") containing 35 mM NaCl and 63 mM HCl at pH 1.2 and 37° C.

Embodiment 103. The method of any preceding embodiment wherein the nonabsorbable pharmaceutical composition comprises a crosslinked amine polymer having an equilibrium proton binding capacity of at least 12 mmol/g and a chloride ion binding capacity of at least 12 mmol/g in an aqueous simulated gastric fluid buffer ("SGF") containing 35 mM NaCl and 63 mM HCl at pH 1.2 and 37° C.

Embodiment 104. The method of any preceding embodiment wherein the nonabsorbable pharmaceutical composition comprises a crosslinked amine polymer having an equilibrium proton binding capacity of at least 14 mmol/g and a chloride ion binding capacity of at least 14 mmol/g in an aqueous simulated gastric fluid buffer ("SGF") containing 35 mM NaCl and 63 mM HCl at pH 1.2 and 37° C.

Embodiment 105. The method of any preceding embodiment wherein the nonabsorbable pharmaceutical composition comprises a crosslinked amine polymer having a chloride binding capacity of at least 1 mmol/g in an aqueous simulated small intestine organic and inorganic buffer ("SOB") containing 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM sodium taurocholate, buffered to pH 6.2 and at 37° C.

Embodiment 106. The method of any preceding embodiment wherein the nonabsorbable pharmaceutical composition comprises a crosslinked amine polymer having a chloride binding capacity of at least 2 mmol/g in an aqueous simulated small intestine organic and inorganic buffer ("SOB") containing 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM sodium taurocholate, buffered to pH 6.2 and at 37° C.

Embodiment 107. The method of any preceding embodiment wherein the nonabsorbable pharmaceutical composition comprises a crosslinked amine polymer having a chloride binding capacity of at least 3 mmol/g in an aqueous simulated small intestine organic and inorganic buffer ("SOB") containing 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM sodium taurocholate, buffered to pH 6.2 and at 37° C.

Embodiment 108. The method of any preceding embodiment wherein the nonabsorbable pharmaceutical composition comprises a crosslinked amine polymer having a chloride binding capacity of at least 4 mmol/g in an aqueous simulated small intestine organic and inorganic buffer ("SOB") containing 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM sodium taurocholate, buffered to pH 6.2 and at 37° C.

Embodiment 109. The method of any preceding embodiment wherein the nonabsorbable pharmaceutical composition comprises a crosslinked amine polymer having a chloride binding capacity of at least 5 mmol/g in an aqueous simulated small intestine organic and inorganic buffer ("SOB") containing 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM sodium taurocholate, buffered to pH 6.2 and at 37° C.

Embodiment 110. The method of any preceding embodiment wherein the percentage of quaternized amines in the crosslinked amine polymer is less than 40%.

Embodiment 111. The method of any preceding embodiment wherein the percentage of quaternized amines in the crosslinked amine polymer is less than 30%.

Embodiment 112. The method of any preceding embodiment wherein the percentage of quaternized amines in the crosslinked amine polymer is less than 20%.

Embodiment 113. The method of any preceding embodiment wherein the percentage of quaternized amines in the crosslinked amine polymer is less than 10%.

Embodiment 114. The method of any preceding embodiment wherein the percentage of quaternized amines in the crosslinked amine polymer is less than 5%.

Embodiment 115. The method of any preceding embodiment wherein the nonabsorbable pharmaceutical composition comprises a crosslinked amine polymer in form of a gel or a bead having a mean particle size of 40 to 180 micrometers.

Embodiment 116. The method of any preceding embodiment wherein the nonabsorbable pharmaceutical composition comprises a crosslinked amine polymer in the form of a gel or a bead having a mean particle size of 60 to 160 micrometers.

Embodiment 117. The method of any preceding embodiment wherein the nonabsorbable pharmaceutical composition comprises a crosslinked amine polymer in the form of a gel or a bead having a mean particle size of 80 to 140 micrometers.

Embodiment 118. The method of any one of embodiments 115-117 wherein less than about 0.5 volume percent of the particles have a diameter of less than about 10 micrometers.

Embodiment 119. The method of any one of embodiments 115-117 wherein less than about 5 volume percent of the particles have a diameter of less than about 20 micrometers.

Embodiment 120. The method of any one of embodiments 115-117 wherein less than about 0.5 volume percent of the particles have a diameter of less than about 20 micrometers.

Embodiment 121. The method of any one of embodiments 115-117 wherein less than about 5 volume percent of the particles have a diameter of less than about 30 micrometers.

Embodiment 122. The method of any preceding embodiment wherein the pharmaceutical composition is in a dosage unit form.

Embodiment 123. The method of embodiment 122 wherein the dosage unit form is a capsule, tablet or sachet dosage form.

Embodiment 124. The method of any preceding embodiment wherein the pharmaceutical composition comprises a pharmaceutically acceptable carrier, excipient, or diluent.

Embodiment 125. The method of treatment of any preceding embodiment wherein less than 1 g of sodium or potassium is administered per day.

Embodiment 126. The method of any preceding embodiment wherein less than 0.5 g of sodium or potassium is administered per day.

Embodiment 127. The method of any preceding embodiment wherein less than 0.1 g of sodium or potassium is administered per day.

Embodiment 128. The method of any preceding embodiment wherein no sodium or potassium is administered.

Embodiment 129. The method according to any preceding embodiment, wherein in said treatment 0.1-50 g of said nonabsorbable pharmaceutical composition is administered to the patient per day.

Embodiment 130. The method according to any preceding embodiment, wherein in said treatment 0.1-40 g of said nonabsorbable pharmaceutical composition is administered to the patient per day.

Embodiment 131. The method according to any preceding embodiment, wherein in said treatment 0.1-30 g of said nonabsorbable pharmaceutical composition is administered to the patient per day.

Embodiment 132. The method according to any preceding embodiment, wherein in said treatment 0.1-20 g of said nonabsorbable pharmaceutical composition is administered to the patient per day.

Embodiment 133. The method according to any preceding embodiment, wherein in said treatment more than 1 g of said nonabsorbable pharmaceutical composition is administered to the patient per day.

Embodiment 134. The method according to any preceding embodiment, wherein in said treatment more than 5 g of said nonabsorbable pharmaceutical composition is administered to the patient per day.

Embodiment 135. The method according to any preceding embodiment, wherein in said treatment more than 10 g of said nonabsorbable pharmaceutical composition is administered to the patient per day.

Embodiment 136. The method according to any preceding embodiment, wherein in said treatment 0.1-12 g of said nonabsorbable pharmaceutical composition is administered to the patient per day.

Embodiment 137. The method according to according to any preceding embodiment, wherein in said treatment 1-11 g of said nonabsorbable pharmaceutical composition is administered to the patient per day.

Embodiment 138. The method according to according to any preceding embodiment, wherein in said treatment 2-10 g of said nonabsorbable pharmaceutical composition is administered to the patient per day.

Embodiment 139. The method according to according to any preceding embodiment, wherein in said treatment 3-9 g of said nonabsorbable pharmaceutical composition is administered to the patient per day.

Embodiment 140. The method according to according to any preceding embodiment, wherein in said treatment 3-8 g of said nonabsorbable pharmaceutical composition is administered to the patient per day.

Embodiment 141. The method according to according to any preceding embodiment, wherein in said treatment 3-7 g of said nonabsorbable pharmaceutical composition is administered to the patient per day.

Embodiment 142. The method according to according to any preceding embodiment, wherein in said treatment 3-6 g of said nonabsorbable pharmaceutical composition is administered to the patient per day.

Embodiment 143. The method according to according to any preceding embodiment, wherein in said treatment 3.5-5.5 g of said nonabsorbable pharmaceutical composition is administered to the patient per day.

Embodiment 144. The method according to according to any preceding embodiment, wherein in said treatment 4-5 g of said nonabsorbable pharmaceutical composition is administered to the patient per day.

Embodiment 145. The method according to according to any preceding embodiment, wherein in said treatment 1-3 g of said nonabsorbable pharmaceutical composition is administered to the patient per day.

Embodiment 146. The method according to according to any preceding embodiment, wherein in said treatment 0.1-2 g of said nonabsorbable pharmaceutical composition is administered to the patient per day.

Embodiment 147. The method according to according to any preceding embodiment, wherein in said treatment 0.5-1 g of said nonabsorbable pharmaceutical composition is administered to the patient per day.

Embodiment 148. The method according to any preceding embodiment, wherein about 0.5 g of the composition is administered to the patient per day.

Embodiment 149. The method according to any preceding embodiment, wherein about 1 g of the composition is administered to the patient per day.

Embodiment 150. The method according to any preceding embodiment, wherein about 1.5 g of the composition is administered to the patient per day.

Embodiment 151. The method according to any preceding embodiment, wherein about 2 g of the composition is administered to the patient per day.

Embodiment 152. The method according to any preceding embodiment, wherein about 2.5 g of the composition is administered to the patient per day.

Embodiment 153. The method according to any preceding embodiment, wherein about 3 g of the composition is administered to the patient per day.

Embodiment 154. The method according to any preceding embodiment, wherein about 3.5 g of the composition is administered to the patient per day.

Embodiment 155. The method according to any preceding embodiment, wherein about 4.0 g of the composition is administered to the patient per day.

Embodiment 156. The method according to any preceding embodiment, wherein about 4.5 g of the composition is administered to the patient per day.

Embodiment 157. The method according to any preceding embodiment, wherein about 5.0 g of the composition is administered to the patient per day.

Embodiment 158. The method of any preceding embodiment wherein the daily dose is administered once a day.

Embodiment 159. The method of any preceding embodiment wherein the daily dose is administered twice a day.

Embodiment 160. The method of any preceding embodiment wherein the daily dose is administered three times a day.

Embodiment 161. The method of any preceding embodiment wherein the patient's serum bicarbonate levels increase by less than 1.5 mEq/L during the treatment.

Embodiment 162. The method of treatment of any preceding embodiment wherein the daily dose results in a sustained serum bicarbonate increase of 1.0 mEq/L.

Embodiment 163. The method of any preceding embodiment wherein the daily dose results in a sustained serum bicarbonate increase of mEq/L.

Embodiment 164. The method of any preceding embodiment wherein the daily dose results in a sustained serum bicarbonate increase of mEq/L.

Embodiment 165. The method of any preceding embodiment wherein the crosslinked amine polymer retains 1 mmol/g chloride through the GI tract.

Embodiment 166. The method of any preceding embodiment wherein the crosslinked amine polymer retains 2 mmol/g chloride through the GI tract.

Embodiment 167. The method of any preceding embodiment wherein the crosslinked amine polymer retains 4 mmol/g chloride through the GI tract.

Embodiment 168. The method of any preceding embodiment wherein the crosslinked amine polymer retains 8 mmol/g chloride through the GI tract.

Embodiment 169. The method of any preceding embodiment wherein a dose of the pharmaceutical composition is titrated based on the serum bicarbonate values of a patient in need of treatment.

Embodiment 170. The method of any preceding embodiment, wherein the patient's serum bicarbonate level prior to the treatment is in the range of 22 mEq/L-about 24 mEq/L.

Embodiment 171. The method of any preceding embodiment, wherein the patient's serum bicarbonate level prior to the treatment is in the range of 22 mEq/L-about 23 mEq/L.

Embodiment 172. The method of any preceding embodiment, wherein the patient's serum bicarbonate level prior to the treatment is at least 22 mEq/L.

Embodiment 173. The method of any preceding embodiment wherein the method increases the patient's serum bicarbonate level.

Embodiment 174. The method of embodiment 160 wherein the patient's serum bicarbonate level increases to greater than 28 mEq/L.

Embodiment 175. The method of embodiment 160 wherein the patient's serum bicarbonate level increases to greater than 27 mEq/L.

Embodiment 176. The method of embodiment 160 wherein the patient's serum bicarbonate level increases to greater than 26 mEq/L.

Embodiment 177. The method of embodiment 160 wherein the patient's serum bicarbonate level increases to greater than 25 mEq/L.

Embodiment 178. The method of embodiment 160 wherein the patient's serum bicarbonate level increases to greater than 24 mEq/L.

Embodiment 179. The method of any preceding embodiment wherein the patient's serum bicarbonate level increases to be within the range 24-26 mEq.

Embodiment 180. The method of any preceding embodiment wherein the patient's serum bicarbonate level increases to be within the range 25-26 mEq.

Embodiment 181. The method of any preceding embodiment wherein the patient's serum bicarbonate level increases to be within the range 25-26 mEq.

Embodiment 182. The method of any preceding embodiment wherein the patient's serum bicarbonate level increases to be within the range 25-27 mEq.

Embodiment 183. The method of any preceding embodiment wherein the patient's serum bicarbonate level increases to be within the range 25-28 mEq.

Embodiment 184. The method of any preceding embodiment wherein the patient's serum bicarbonate level increases to be within the range 25-29 mEq.

Embodiment 185. The method of any preceding embodiment wherein the patient's increase in serum bicarbonate level is achieved within a treatment period of 2 weeks.

Embodiment 186. The method of any preceding embodiment wherein the patient's increase in serum bicarbonate level is achieved within a treatment period of 1 month.

Embodiment 187. The method of any preceding embodiment wherein the serum bicarbonate level is measured using the mean value of at least two serum bicarbonate values for measurements taken on non-consecutive days.

Embodiment 188. The method of embodiment 187 wherein the non-consecutive days are separated by at least two days.

Embodiment 189. The method of embodiment 187 wherein the non-consecutive days are separated by at least one week.

Embodiment 190. The method of embodiment 187 wherein the non-consecutive days are separated by at least two weeks.

Embodiment 191. The method of embodiment 187 wherein the non-consecutive days are separated by at least three weeks.

Embodiment 192. The method of any preceding embodiment wherein a dose of the pharmaceutical composition is titrated based on the urine citrate excretion of a patient in need of treatment.

Embodiment 193. The method of any preceding embodiment wherein the patient or the eubicarbonatemic metabolic acidosis is characterized by baseline urine citrate excretion values below about 640 mg/day.

Embodiment 194. The method of any preceding embodiment wherein the patient or the eubicarbonatemic metabolic acidosis is characterized by baseline urine citrate excretion values below about 400 mg/day.

Embodiment 195. The method of any preceding embodiment wherein the patient or the eubicarbonatemic metabolic acidosis is characterized by baseline urine citrate excretion values in the range of about 180-about 370 mg/day.

Embodiment 196. The method of any preceding embodiment wherein the method increases the patient's urine citrate excretion value relative to the patient's baseline urine citrate excretion value prior to treatment.

Embodiment 197. The method of any preceding embodiment wherein the patient's urine citrate excretion value is increased to at least about 450 mq/day.

Embodiment 198. The method of any preceding embodiment wherein the patient's urine citrate excretion value is increased to at least about 500 mq/day.

Embodiment 199. The method of any preceding embodiment wherein the patient's urine citrate excretion value is increased to at least about 550 mq/day.

Embodiment 200. The method of any preceding embodiment wherein the patient's urine citrate excretion value is increased to at least about 600 mq/day.

Embodiment 201. The method of any preceding embodiment wherein the patient's urine citrate excretion is increased by at least 10 mq/day relative to the patient's baseline urine citrate excretion value prior to treatment.

Embodiment 202. The method of any preceding embodiment wherein the patient's urine citrate excretion is increased by at least 20 mq/day relative to the patient's baseline urine citrate excretion value prior to treatment.

Embodiment 203. The method of any preceding embodiment wherein the patient's urine citrate excretion is increased by at least 30 mq/day relative to the patient's baseline urine citrate excretion value prior to treatment.

Embodiment 204. The method of any preceding embodiment wherein the patient's urine citrate excretion is increased by at least 40 mq/day relative to the patient's baseline urine citrate excretion value prior to treatment.

Embodiment 205. The method of any preceding embodiment wherein the patient's urine citrate excretion is increased by at least 50 mq/day relative to the patient's baseline urine citrate excretion value prior to treatment.

Embodiment 206. The method of any preceding embodiment wherein the patient's urine citrate excretion is increased by at least 60 mq/day relative to the patient's baseline urine citrate excretion value prior to treatment.

Embodiment 207. The method of any preceding embodiment wherein the patient's urine citrate excretion is increased by at least 70 mq/day relative to the patient's baseline urine citrate excretion value prior to treatment.

Embodiment 208. The method of any preceding embodiment wherein the patient's increase in urine citrate excretion is achieved within a treatment period of 2 weeks.

Embodiment 209. The method of any preceding embodiment wherein the patient's increase in urine citrate excretion is achieved within a treatment period of 1 month.

Embodiment 210. The method of any preceding embodiment wherein patient's increase in urine citrate excretion is achieved within a treatment period of 6 months.

Embodiment 211. The method of any preceding embodiment wherein the patient's increase in urine citrate excretion is achieved within a treatment period of 1 year.

Embodiment 212. The method of any preceding embodiment wherein the urine citrate excretion is measured using the mean value of at least two urine citrate excretion values for urine samples given on non-consecutive days.

Embodiment 213. The method of embodiment 212 wherein the non-consecutive days are separated by at least two days.

Embodiment 214. The method of embodiment 212 wherein the non-consecutive days are separated by at least one week.

Embodiment 215. The method of embodiment 212 wherein the non-consecutive days are separated by at least two weeks.

Embodiment 216. The method of embodiment 212 wherein the non-consecutive days are separated by at least three weeks.

Embodiment 217. The method of any preceding embodiment wherein a dose of the pharmaceutical composition is titrated based on the urine ammonium excretion of a patient in need of treatment.

Embodiment 218. The method of any preceding embodiment wherein the patient or the eubicarbonatemic metabolic acidosis is characterized by a baseline urine ammonium excretion above about 40 mEq/day.

Embodiment 219. The method of any preceding embodiment wherein the patient or the eubicarbonatemic metabolic acidosis is characterized by a baseline urine ammonium excretion above about 100 mEq/day.

Embodiment 220. The method of any preceding embodiment wherein the patient or the eubicarbonatemic metabolic acidosis is characterized by a baseline urine ammonium excretion above about 200 mEq/day.

Embodiment 221. The method of any preceding embodiment wherein the patient's urine ammonium excretion value decreases relative to the patient's baseline urine ammonium excretion value prior to treatment.

Embodiment 222. The method of any preceding embodiment wherein the patient's baseline urine ammonium excretion value decreases to 150 mEq/day or less.

Embodiment 223. The method of any preceding embodiment wherein the patient's baseline urine ammonium excretion value decreases to 80 mEq/day or less.

Embodiment 224. The method of any preceding embodiment wherein the patient's baseline urine ammonium excretion value decreases to 40 mEq/day or less.

Embodiment 225. The method of any preceding embodiment wherein the patient's urine ammonium excretion decreases by at least 10 mEq/day, relative to the patient's urine ammonium excretion prior to treatment.

Embodiment 226. The method of any preceding embodiment wherein the patient's urine ammonium excretion decreases by at least 20 mEq/day, relative to the patient's urine ammonium excretion prior to treatment.

Embodiment 227. The method of any preceding embodiment wherein the patient's urine ammonium excretion decreases by at least 30 mEq/day, relative to the patient's urine ammonium excretion prior to treatment.

Embodiment 228. The method of any preceding embodiment wherein the patient's urine ammonium excretion decreases by at least 40 mEq/day, relative to the patient's urine ammonium excretion prior to treatment.

Embodiment 229. The method of any preceding embodiment the patient's urine ammonium excretion decreases by at least 50 mEq/day, relative to the patient's urine ammonium excretion prior to treatment.

Embodiment 230. The method of any preceding embodiment wherein the decrease in urine ammonium excretion is achieved within a treatment period of 2 weeks.

Embodiment 231. The method of any preceding embodiment wherein the decrease in urine ammonium excretion is achieved within a treatment period of 1 month.

Embodiment 232. The method of any preceding embodiment wherein the decrease in urine ammonium excretion is achieved within a treatment period of 6 months.

Embodiment 233. The method of any preceding embodiment wherein the decrease in urine ammonium excretion is achieved within a treatment period of 1 year.

Embodiment 234. The method of any preceding embodiment wherein the serum bicarbonate value is measured using the mean value of at least two urine ammonium excretion values for urine samples given on non-consecutive days.

Embodiment 235. The method of embodiment 234 wherein the non-consecutive days are separated by at least two days.

Embodiment 236. The method of embodiment 234 wherein the non-consecutive days are separated by at least one week.

Embodiment 237. The method of embodiment 234 wherein the non-consecutive days are separated by at least two weeks.

Embodiment 238. The method of embodiment 234 wherein the non-consecutive days are separated by at least three weeks.

Embodiment 239. The method of any preceding embodiment wherein a dose of the pharmaceutical composition is titrated based on the net acid excretion (NAE) of a patient in need of treatment.

Embodiment 240. The method of any preceding embodiment wherein the patient or the eubicarbonatemic metabolic acidosis is characterized by baseline net acid excretion (NAE) values below about 60 mEq/day.

Embodiment 241. The method of any preceding embodiment wherein the patient or the eubicarbonatemic metabolic acidosis is characterized by baseline net acid excretion (NAE) values below about 50 mEq/day Embodiment 242. The method of any preceding embodiment wherein the patient or the eubicarbonatemic metabolic acidosis is characterized by baseline net acid excretion (NAE) values below about 40 mEq/day Embodiment 243. The method of any preceding embodiment wherein the patient or the eubicarbonatemic metabolic acidosis is characterized by baseline net acid excretion (NAE) values below about 30 mEq/day Embodiment 244. The method of any preceding embodiment wherein the patient or the eubicarbonatemic metabolic acidosis is characterized by baseline net acid excretion (NAE) values below about 20 mEq/day Embodiment 245. The method of any preceding embodiment wherein the method increases the patient's net acid excretion (NAE) value relative to the patient's baseline net acid excretion (NAE) value prior to treatment.

Embodiment 246. The method of any preceding embodiment wherein the patient's net acid excretion (NAE) is increased to at least about 60 mEq/day.

Embodiment 247. The method of any preceding embodiment wherein the patient's net acid excretion (NAE) is increased to at least about 100 mEq/day.

Embodiment 248. The method of any preceding embodiment wherein the patient's net acid excretion (NAE) is increased to at least about 150 mEq/day.

Embodiment 249. The method of any preceding embodiment wherein the patient's net acid excretion (NAE) is increased to at least about 200 mEq/day.

Embodiment 250. The method of any preceding embodiment wherein the patient's net acid excretion (NAE) is increased to at least about 300 mEq/day.

Embodiment 251. The method of any preceding embodiment wherein the patient's net acid excretion (NAE) is increased by at least 2 mEq/day relative to the patient's baseline net acid excretion (NAE) value prior to treatment.

Embodiment 252. The method of any preceding embodiment wherein the patient's net acid excretion (NAE) is increased by at least 4 mEq/day relative to the patient's baseline net acid excretion (NAE) value prior to treatment.

Embodiment 253. The method of any preceding embodiment wherein the patient's net acid excretion (NAE) is increased by at least 8 mEq/day relative to the patient's baseline net acid excretion (NAE) value prior to treatment.

Embodiment 254. The method of any preceding embodiment wherein the patient's net acid excretion (NAE) is increased by at least 20 mEq/day relative to the patient's baseline net acid excretion (NAE) value prior to treatment.

Embodiment 255. The method of any preceding embodiment wherein the patient's net acid excretion (NAE) is increased by at least 50 mEq/day relative to the patient's baseline net acid excretion (NAE) value prior to treatment.

Embodiment 256. The method of any preceding embodiment wherein the patient's net acid excretion (NAE) is increased by at least 100 mEq/day relative to the patient's baseline net acid excretion (NAE) value prior to treatment.

Embodiment 257. The method of any preceding embodiment wherein the patient's increase in net acid excretion (NAE) is achieved within a treatment period of 2 weeks.

Embodiment 258. The method of any preceding embodiment wherein the patient's increase in net acid excretion (NAE) is achieved within a treatment period of 1 month.

Embodiment 259. The method of any preceding embodiment wherein the patient's increase in net acid excretion (NAE) is achieved within a treatment period of 6 months.

Embodiment 260. The method of any preceding embodiment wherein the patient's increase in net acid excretion (NAE) is achieved within a treatment period of 1 year.

Embodiment 261. The method of any preceding embodiment wherein the net acid excretion (NAE) is measured using the mean value of at least two net acid excretion (NAE) values for urine samples given on non-consecutive days.

Embodiment 262. The method of embodiment 261 wherein the non-consecutive days are separated by at least two days.

Embodiment 263. The method of embodiment 261 wherein the non-consecutive days are separated by at least one week.

Embodiment 264. The method of embodiment 261 wherein the non-consecutive days are separated by at least two weeks.

Embodiment 265. The method of embodiment 261 wherein the non-consecutive days are separated by at least three weeks.

Embodiment 266. The method of any preceding embodiment wherein a dose of the pharmaceutical composition is titrated based on the plasma Endothelin 1 (ET-1) levels of a patient in need of treatment.

Embodiment 267. The method of any preceding embodiment wherein the patient or the eubicarbonatemic metabolic acidosis is characterized by baseline plasma Endothelin 1 (ET-1) levels above about 2.0 pg/mL.

Embodiment 268. The method of any preceding embodiment wherein the patient or the eubicarbonatemic metabolic acidosis is characterized by baseline plasma Endothelin 1 (ET-1) levels below above 3.0 pg/mL.

Embodiment 269. The method of any preceding embodiment wherein the patient or the eubicarbonatemic metabolic acidosis is characterized by baseline plasma Endothelin 1 (ET-1) levels above about 4.0 pg/mL.

Embodiment 270. The method of any preceding embodiment wherein the patient or the eubicarbonatemic metabolic acidosis is characterized by baseline plasma Endothelin 1 (ET-1) levels in the range of 2.0-5.0 pg/mL.

Embodiment 271. The method of any preceding embodiment wherein the patient or the eubicarbonatemic metabolic acidosis is characterized by baseline plasma Endothelin 1 (ET-1) levels in the range of 2.0-4.0 pg/mL.

Embodiment 272. The method of any preceding embodiment wherein the method decreases the patient's plasma Endothelin 1 (ET-1) level relative to the patient's baseline plasma Endothelin 1 (ET-1) levels prior to treatment.

Embodiment 273. The method of any preceding embodiment wherein the patient's plasma Endothelin 1 (ET-1) level is decreased to less than 2.0 pg/mL.

Embodiment 274. The method of any preceding embodiment wherein the patient's plasma Endothelin 1 (ET-1) level is decreased to less than 1.5 pg/mL.

Embodiment 275. The method of any preceding embodiment wherein the patient's plasma Endothelin 1 (ET-1) level is decreased to less than 1.0 pg/mL.

Embodiment 276. The method of any preceding embodiment wherein the patient's plasma Endothelin 1 (ET-1) level is decreased to 0.91-1.91 pg/mL.

Embodiment 277. The method of any preceding embodiment wherein the patient's plasma Endothelin 1 (ET-1) level is decreased to 1.2-1.6 pg/mL.

Embodiment 278. The method of any preceding embodiment wherein the patient's plasma Endothelin 1 (ET-1) level is decreased by at least 0.2 pg/mL relative to the patient's baseline plasma Endothelin 1 (ET-1) level prior to treatment.

Embodiment 279. The method of any preceding embodiment wherein the patient's plasma Endothelin 1 (ET-1) level is decreased by at least 0.5 pg/mL relative to the patient's baseline plasma Endothelin 1 (ET-1) level prior to treatment.

Embodiment 280. The method of any preceding embodiment wherein the patient's plasma Endothelin 1 (ET-1) level is decreased by at least 1.0 pg/mL relative to the patient's baseline plasma Endothelin 1 (ET-1) level prior to treatment.

Embodiment 281. The method of any preceding embodiment wherein the patient's plasma Endothelin 1 (ET-1) level is decreased by at least 1.5 pg/mL relative to the patient's baseline plasma Endothelin 1 (ET-1) level prior to treatment.

Embodiment 282. The method of any preceding embodiment wherein the patient's plasma Endothelin 1 (ET-1) level is decreased by at least 2.0 pg/mL relative to the patient's baseline plasma Endothelin 1 (ET-1) level prior to treatment.

Embodiment 283. The method of any preceding embodiment wherein the patient's plasma Endothelin 1 (ET-1) level is decreased by at least 2.5 pg/mL relative to the patient's baseline plasma Endothelin 1 (ET-1) level prior to treatment.

Embodiment 284. The method of any preceding embodiment wherein the patient's decrease in plasma Endothelin 1 (ET-1) level is achieved within a treatment period of 2 weeks.

Embodiment 285. The method of any preceding embodiment wherein the patient's decrease in plasma Endothelin 1 (ET-1) level is achieved within a treatment period of 1 month.

Embodiment 286. The method of any preceding embodiment wherein the patient's decrease in plasma Endothelin 1 (ET-1) level is achieved within a treatment period of 6 months.

Embodiment 287. The method of any preceding embodiment wherein the patient's decrease in plasma Endothelin 1 (ET-1) level is achieved within a treatment period of 1 year.

Embodiment 288. The method of any preceding embodiment wherein the plasma Endothelin 1 (ET-1) level is measured using the mean value of at least two plasma Endothelin 1 (ET-1) levels for blood samples.

Embodiment 289. The method of any preceding embodiment wherein the plasma Endothelin 1 (ET-1) level is measured using the mean value of at least two plasma Endothelin 1 (ET-1) levels for blood samples given on non-consecutive days.

Embodiment 290. The method of embodiment 289 wherein the non-consecutive days are separated by at least two days.

Embodiment 291. The method of embodiment 289 wherein the non-consecutive days are separated by at least one week.

Embodiment 292. The method of embodiment 289 wherein the non-consecutive days are separated by at least two weeks.

Embodiment 293. The method of embodiment 289 wherein the non-consecutive days are separated by at least three weeks.

Embodiment 294. The method of any preceding embodiment wherein a dose of the pharmaceutical composition is titrated based on the urine Endothelin 1 (ET-1) levels of a patient in need of treatment.

Embodiment 295. The method of any preceding embodiment wherein the patient or the eubicarbonatemic metabolic acidosis is characterized by baseline urine Endothelin 1 (ET-1) levels as a ratio of creatinine (ET-1/creatinine) of greater than 4.0.

Embodiment 296. The method of any preceding embodiment wherein the patient or the eubicarbonatemic metabolic acidosis is characterized by baseline urine Endothelin 1 (ET-1) levels as a ratio of creatinine (ET-1/creatinine) of greater than 4.2.

Embodiment 297. The method of any preceding embodiment wherein the patient or the eubicarbonatemic metabolic acidosis is characterized by baseline urine Endothelin 1 (ET-1) levels as a ratio of creatinine (ET-1/creatinine) of greater than 4.5.

Embodiment 298. The method of any preceding embodiment wherein the patient or the eubicarbonatemic metabolic acidosis is characterized by baseline urine Endothelin 1 (ET-1) levels as a ratio of creatinine (ET-1/creatinine) of greater than 4.7.

Embodiment 299. The method of any preceding embodiment wherein the patient or the eubicarbonatemic metabolic acidosis is characterized by baseline urine Endothelin 1 (ET-1) levels as a ratio of creatinine (ET-1/creatinine) of greater than 5.

Embodiment 300. The method of any preceding embodiment wherein the method decreases the patient's urine Endothelin 1 (ET-1) level as a ratio of creatinine (ET-1/creatinine) relative to the patient's ratio prior to treatment.

Embodiment 301. The method of any preceding embodiment wherein the patient's urine Endothelin 1 (ET-1) level as a ratio of creatinine (ET-1/creatinine) is decreased to less than 3.5.

Embodiment 302. The method of any preceding embodiment wherein the patient's urine Endothelin 1 (ET-1) level as a ratio of creatinine (ET-1/creatinine) is decreased to less than 3.4.

Embodiment 303. The method of any preceding embodiment wherein the patient's urine Endothelin 1 (ET-1) level as a ratio of creatinine (ET-1/creatinine) is decreased to less than 3.3.

Embodiment 304. The method of any preceding embodiment wherein the patient's urine Endothelin 1 (ET-1) level as a ratio of creatinine (ET-1/creatinine) is decreased to less than 3.2.

Embodiment 305. The method of any preceding embodiment wherein the patient's urine Endothelin 1 (ET-1) level as a ratio of creatinine (ET-1/creatinine) is decreased to less than 3.1.

Embodiment 306. The method of any preceding embodiment wherein the patient's urine Endothelin 1 (ET-1) level as a ratio of creatinine (ET-1/creatinine) is decreased by at least 0.2 relative to the patient's ratio prior to treatment.

Embodiment 307. The method of any preceding embodiment wherein the patient's urine Endothelin 1 (ET-1) level as a ratio of creatinine (ET-1/creatinine) is decreased by at least 0.4 relative to the patient's ratio prior to treatment.

Embodiment 308. The method of any preceding embodiment wherein the patient's urine Endothelin 1 (ET-1) level as a ratio of creatinine (ET-1/creatinine) is decreased by at least 0.6 relative to the patient's ratio prior to treatment.

Embodiment 309. The method of any preceding embodiment wherein the patient's urine Endothelin 1 (ET-1) level as a ratio of creatinine (ET-1/creatinine) is decreased by at least 0.8 relative to the patient's ratio prior to treatment.

Embodiment 310. The method of any preceding embodiment wherein the patient's urine Endothelin 1 (ET-1) level as a ratio of creatinine (ET-1/creatinine) is decreased by at least 1 relative to the patient's ratio prior to treatment.

Embodiment 311. The method of any preceding embodiment wherein the patient's urine Endothelin 1 (ET-1) level as a ratio of creatinine (ET-1/creatinine) is decreased by at least 1.5 relative to the patient's ratio prior to treatment.

Embodiment 312. The method of any preceding embodiment wherein the patient's decrease in urine Endothelin 1 (ET-1) level is achieved within a treatment period of 2 weeks.

Embodiment 313. The method of any preceding embodiment wherein the patient's decrease in urine Endothelin 1 (ET-1) level is achieved within a treatment period of 1 month.

Embodiment 314. The method of any preceding embodiment wherein the patient's decrease in urine Endothelin 1 (ET-1) level is achieved within a treatment period of 6 months.

Embodiment 315. The method of any preceding embodiment wherein the patient's decrease in urine Endothelin 1 (ET-1) level is achieved within a treatment period of 1 year.

Embodiment 316. The method of any preceding embodiment wherein the urine Endothelin 1 (ET-1) level is measured using the mean value of at least two urine Endothelin 1 (ET-1) levels for samples given on non-consecutive days.

Embodiment 317. The method of embodiment 316 wherein the non-consecutive days are separated by at least two days.

Embodiment 318. The method of embodiment 316 wherein the non-consecutive days are separated by at least one week.

Embodiment 319. The method of embodiment 316 wherein the non-consecutive days are separated by at least two weeks.

Embodiment 320. The method of embodiment 316 wherein the non-consecutive days are separated by at least three weeks.

Embodiment 321. The method of any preceding embodiment wherein a dose of the pharmaceutical composition is titrated based on the plasma aldosterone levels of a patient in need of treatment.

Embodiment 322. The method of any preceding embodiment wherein the patient or the eubicarbonatemic metabolic acidosis is characterized by baseline plasma aldosterone values above about 16 ng/dL when measured lying down.

Embodiment 323. The method of any preceding embodiment wherein the patient or the eubicarbonatemic metabolic acidosis is characterized by baseline plasma aldosterone values above about 30 ng/dL when measured lying down.

Embodiment 324. The method of any preceding embodiment wherein the patient or the eubicarbonatemic metabolic acidosis is characterized by baseline plasma aldosterone values in the range of about 40-64 ng/gL when measured lying down.

Embodiment 325. The method of any preceding embodiment wherein the method decreases the patient's plasma aldosterone value relative to the patient's baseline plasma aldosterone value prior to treatment.

Embodiment 326. The method of any preceding embodiment wherein the patient's plasma aldosterone value is decreased to less than about 50 ng/dL when measured lying down.

Embodiment 327. The method of any preceding embodiment wherein the patient's plasma aldosterone value is decreased to less than about 40 ng/dL when measured lying down.

Embodiment 328. The method of any preceding embodiment wherein the patient's plasma aldosterone value is decreased to less than about 30 ng/dL when measured lying down.

Embodiment 329. The method of any preceding embodiment wherein the patient's plasma aldosterone value is decreased to less than about 20 ng/dL when measured lying down.

Embodiment 330. The method of any preceding embodiment wherein the patient's plasma aldosterone value is decreased to less than about 16 ng/dL when measured lying down.

Embodiment 331. The method of any preceding embodiment wherein the patient's plasma aldosterone value is decreased by at least 2 ng/dL when measured lying down relative to the patient's baseline plasma aldosterone value prior to treatment when measured lying down.

Embodiment 332. The method of any preceding embodiment wherein the patient's plasma aldosterone value is decreased by at least 4 ng/dL when measured lying down relative to the patient's baseline plasma aldosterone value prior to treatment when measured lying down.

Embodiment 333. The method of any preceding embodiment wherein the patient's plasma aldosterone value is decreased by at least 6 ng/dL when measured lying down relative to the patient's baseline plasma aldosterone value prior to treatment when measured lying down.

Embodiment 334. The method of any preceding embodiment wherein the patient's plasma aldosterone value is decreased by at least 8 ng/dL when measured lying down relative to the patient's baseline plasma aldosterone value prior to treatment when measured lying down.

Embodiment 335. The method of any preceding embodiment wherein the patient's plasma aldosterone value is decreased by at least 10 ng/dL when measured lying down relative to the patient's baseline plasma aldosterone value prior to treatment when measured lying down.

Embodiment 336. The method of any preceding embodiment wherein the patient's plasma aldosterone value is decreased by at least 12 ng/dL when measured lying down relative to the patient's baseline plasma aldosterone value prior to treatment.

Embodiment 337. The method of any preceding embodiment wherein the patient's plasma aldosterone value is decreased by at least 16 ng/dL when measured lying down relative to the patient's baseline plasma aldosterone value prior to treatment when measured lying down.

Embodiment 338. The method of any preceding embodiment wherein the patient's plasma aldosterone value is decreased by at least 30 ng/dL when measured lying down relative to the patient's baseline plasma aldosterone value prior to treatment when measured lying down.

Embodiment 339. The method of any preceding embodiment wherein the patient's decrease in plasma aldosterone value is achieved within a treatment period of 2 weeks.

Embodiment 340. The method of any preceding embodiment wherein the patient's decrease in plasma aldosterone value is achieved within a treatment period of 1 month.

Embodiment 341. The method of any preceding embodiment wherein the patient's decrease in plasma aldosterone value is achieved within a treatment period of 6 months.

Embodiment 342. The method of any preceding embodiment wherein the patient's decrease in plasma aldosterone value is achieved within a treatment period of 1 year.

Embodiment 343. The method of any preceding embodiment wherein the plasma aldosterone value is measured using the mean value of at least two plasma aldosterone values for samples given on non-consecutive days.

Embodiment 344. The method of embodiment 343 wherein the non-consecutive days are separated by at least two days.

Embodiment 345. The method of embodiment 343 wherein the non-consecutive days are separated by at least one week.

Embodiment 346. The method of embodiment 343 wherein the non-consecutive days are separated by at least two weeks.

Embodiment 347. The method of embodiment 343 wherein the non-consecutive days are separated by at least three weeks.

Embodiment 348. The method of any preceding embodiment wherein the oral administration is as frequent as at least weekly, at least semi-weekly, or daily within the treatment period.

Embodiment 349. The method of any preceding embodiment wherein the oral administration is as frequent as at least weekly within the treatment period.

Embodiment 350. The method of any preceding embodiment wherein the oral administration is as frequent as at least semi-weekly within the treatment period.

Embodiment 351. The method of any preceding embodiment wherein the oral administration is as frequent as at least daily within the treatment period.

Embodiment 352. The method of any preceding embodiment wherein, upon cessation of the treatment, the individual's serum bicarbonate value decreases by at least 2 mEq/l within 1 month of the cessation of treatment.

Embodiment 353. The method of any preceding embodiment wherein the serum bicarbonate value is the mean value of at least two serum bicarbonate concentrations for serum samples drawn on non-consecutive days.

Embodiment 354. The method of embodiment 353 wherein the non-consecutive days are separated by at least two days.

Embodiment 355. The method of embodiment 353 wherein the non-consecutive days are separated by at least one week.

Embodiment 356. The method of embodiment 353 wherein the non-consecutive days are separated by at least two weeks.

Embodiment 357. The method of embodiment 353 wherein the non-consecutive days are separated by at least three weeks Embodiment 358. The method of any preceding embodiment wherein the daily dose has the capacity to remove at least 0.5 mEq of a target species as it transits the digestive system.

Embodiment 359. The method of any preceding embodiment wherein the daily dose has the capacity to remove at least 2.5 mEq of a target species as it transits the digestive system.

Embodiment 360. The method of any preceding embodiment wherein the daily dose has the capacity to remove at least 5.0 mEq of a target species as it transits the digestive system.

Embodiment 361. The method of any preceding embodiment wherein the daily dose has the capacity to remove at least 7.5 mEq of a target species as it transits the digestive system.

Embodiment 362. The method of any preceding embodiment wherein the daily dose has the capacity to remove at least 15 mEq of a target species as it transits the digestive system.

Embodiment 363. The method of any preceding embodiment wherein the daily dose has the capacity to remove at least 25 mEq of a target species as it transits the digestive system.

Embodiment 364. The method of any preceding embodiment wherein the theoretical binding capacity of the non-absorbable pharmaceutical composition for the target species is the theoretical binding capacity as determined in a SGF assay.

Embodiment 365. The method of any preceding embodiment wherein the daily dose has the capacity to remove at least about 2 mEq/day of the target species.

Embodiment 366. The method of any preceding embodiment wherein the daily dose has the capacity to remove at least about 5 mEq/day of the target species.

Embodiment 367. The method of any preceding embodiment wherein the daily dose has the capacity to remove at least about 8 mEq/day of the target species.

Embodiment 368. The method of any preceding embodiment wherein the daily dose has the capacity to remove at least about 10 mEq/day of the target species.

Embodiment 369. The method of any preceding embodiment wherein the daily dose has the capacity to remove at least about 15 mEq/day of the target species.

Embodiment 370. The method of any preceding embodiment wherein the daily dose has the capacity to remove at least about 20 mEq/day of the target species.

Embodiment 371. The method of any preceding embodiment wherein the daily dose has the capacity to remove at least about 25 mEq/day of the target species.

Embodiment 372. The method of any preceding embodiment wherein the daily dose has the capacity to remove at least about 30 mEq/day of the target species.

Embodiment 373. The method of any preceding embodiment wherein the daily dose removes less than 50 mEq/day of the target species.

Embodiment 374. The method of any preceding embodiment wherein the daily dose removes less than 35 mEq/day of the target species.

Embodiment 375. The method of any preceding embodiment wherein the nonabsorbable pharmaceutical composition is a cation exchange material optionally containing exchangeable sodium ions provided, however, that the amount of the sodium ions in a daily dose is insufficient to increase the patient's serum sodium ion concentration to a value outside the range of 135 to 145 mEq/l.

Embodiment 376. The method of any preceding embodiment wherein the nonabsorbable pharmaceutical composition is a cation exchange material containing exchangeable sodium ions and the composition contains less than 1% by weight sodium.

Embodiment 377. The method of any preceding embodiment wherein the nonabsorbable pharmaceutical composition is an anion exchange material having the capacity to induce an increase in the individual's serum bicarbonate value, at least in part, by delivering a physiologically significant amount of hydroxide, carbonate, citrate or other bicarbonate equivalent, or a combination thereof.

Embodiment 378. The method of any preceding embodiment wherein the nonabsorbable pharmaceutical composition is an anion exchange material comprising at least 1 mEq/g of an anion selected from the group consisting of hydroxide, carbonate, citrate or other bicarbonate equivalent anion, or a combination thereof.

Embodiment 379. The method of any preceding embodiments wherein the nonabsorbable pharmaceutical composition is an anion exchange material comprising less than 1 mEq/g of an anion selected from the group consisting of hydroxide, carbonate, citrate or other bicarbonate equivalent anion.

Embodiment 380. The method of any preceding embodiment wherein the nonabsorbable pharmaceutical composition is characterized by a chloride ion binding capacity of at least 1 mEq/g in a SIB assay.

Embodiment 381. The method of any preceding embodiment wherein the nonabsorbable pharmaceutical composition is characterized by a chloride ion binding capacity of at least 1.5 mEq/g in a SIB assay.

Embodiment 382. The method of any preceding embodiment wherein the nonabsorbable pharmaceutical composition is characterized by a chloride ion binding capacity of at least 2 mEq/g in a SIB assay.

Embodiment 383. The method of any preceding embodiment wherein the ratio of the amount of bound chloride to bound phosphate in a SIB assay is at least 0.25:1, respectively.

Embodiment 384. The method of any preceding embodiment wherein the ratio of the amount of bound chloride to bound phosphate in a SIB assay is at least 0.5:1, respectively.

Embodiment 385. The method of any preceding embodiment wherein the ratio of the amount of bound chloride to bound phosphate in a SIB assay is at least 1:1, respectively.

Embodiment 386. The method of any preceding embodiment wherein the nonabsorbable pharmaceutical composition is a neutral composition having the capacity to bind both protons and anions.

Embodiment 387. The method of any preceding embodiment wherein the nonabsorbable pharmaceutical composition (i) removes more chloride ions than bicarbonate equivalent anions (ii) removes more chloride ions than phosphate anions, and (iii) remove more chloride ions than the conjugate bases of bile and fatty acids.

Embodiment 388. The method of any preceding embodiment wherein the treatment with the nonabsorbable pharmaceutical composition does not have a clinically significant impact upon the serum or colon levels of a metabolically relevant species.

Embodiment 389. The method of any preceding embodiment wherein the treatment with the nonabsorbable pharmaceutical composition does not have a clinically significant impact upon the serum or colon levels of a metabolically relevant cationic species.

Embodiment 390. The method of any preceding embodiment wherein the treatment with the nonabsorbable pharmaceutical composition does not have a clinically significant impact upon the serum or colon levels of a metabolically relevant anionic species.

Embodiment 391. The method of any preceding embodiment wherein the treatment with the nonabsorbable pharmaceutical composition does not have a clinically significant impact upon the serum potassium levels of a statistically significant number of individuals.

Embodiment 392. The method of any preceding embodiment wherein the treatment with the nonabsorbable pharmaceutical composition does not have a clinically significant impact upon the serum phosphate levels of a statistically significant number of individuals.

Embodiment 393. The method of any preceding embodiment wherein the treatment with the nonabsorbable pharmaceutical composition does not have a clinically significant impact upon the serum low density lipoprotein (LDL) levels of a statistically significant number of individuals.

Embodiment 394. The method of any preceding embodiment, wherein the subject has nephrolithiasis.

Embodiment 395. The method of any preceding embodiment, wherein the subject has bone loss.

Embodiment 396. The method of any preceding embodiment, wherein the subject has renal hypertrophy.

Embodiment 397. The method of any preceding embodiment wherein the patient is treated for at least one week.

Embodiment 398. The method of any preceding embodiment wherein the patient is treated for at least one month.

Embodiment 399. The method of any preceding embodiment wherein the patient is treated for at least several months.

Embodiment 400. The method of any preceding embodiment wherein the patient is treated for at least six months.

Embodiment 401. The method of any preceding embodiment wherein the patient is treated for at least one year.

Embodiment 402. The method of any preceding embodiment wherein the patient is an adult.

Embodiment 403. A composition for use in a method of treating eubicarbonatemic metabolic acidosis, wherein the method of treatment (and/or composition) is as defined in any preceding embodiment.

Embodiment 404. A composition for use in a method of treating a patient with chronic kidney disease, wherein the patient has a serum bicarbonate value of at least 22 mEq/l wherein the method of treatment (and/or composition) is as defined in any preceding embodiment.

EXAMPLES

Exemplary Synthetic Approaches for the Preparation of Nonabsorbed Polymers for the Treatment of Acid-Base Imbalance (Reproduced from WO2016/094685 A1)

Exemplary Synthesis A

Step 1: Two aqueous stock solutions of monomer (50% w/w) were prepared by independently dissolving 43.83 g allylamine hydrochloride and 45.60 g diallylpropyldiamine ("DAPDA") in water. A 3-neck, 2 L round bottom flask with four side baffles equipped with an overhead stirrer (stirring at 180 rpm), Dean-Stark apparatus and condenser, and nitrogen inlet, was charged with 12 g surfactant (Stepan Sulfonic 100) dissolved in 1,200 g of a heptane/chlorobenzene solution (26/74 v/v), followed by the aqueous stock solutions, and an additional portion of water (59.14 g). In a separate vessel, a 15 wt % solution of initiator 2,2'-azobis (2-methylpropionamidine)-dihydrochloride ("V-50") (9.08 g) in water was prepared. The two mixtures were independently sparged with nitrogen while the reaction vessel was brought to 67° C. in an oil bath (approximately 30 min). Under inert atmosphere, the initiator solution was added to the reaction mixture, and subsequently heated at 67° C. for 16 hours. A second aliquot of initiator solution (equal to the first) and the reaction mixture, were sparged with nitrogen for 30 minutes and combined before increasing the temperature to 115° C. for a final dehydration step (Dean-Stark). The reaction was held at 115° C. until water stopped collecting in the Dean-Stark trap (6 h, 235 mL removed, >90% of total water, $T_{internal}$>99° C.). The reaction was allowed to cool to room temperature, and the stirring stopped to allow the beads to settle. The organic phase was removed from the bead cake by decanting. The beads were purified by washing (MeOH two times, $H_2O$ once, 1N HCl two times, $H_2O$ once, 1N NaOH three times, and then $H_2O$ until the pH of solution after washing was 7) and dried by lyophilization.

Step 2: Dry preformed amine polymer beads (15.00 g) prepared in accordance with Step 1 were added to a 250 mL round bottom flask equipped with a stir paddle and nitrogen gas inlet. To the beads was added 1,2-dichloroethane (DCE) (90 mL, resulting in a 1:6 bead to DCE (g/mL) ratio). The beads were dispersed in the DCE using mechanical agitation (~150 rpm stirring). Water (3.75 mL, resulting in a 0.25:1 water to bead mass ratio) was added directly to the dispersion, and stirring was continued for 30 minutes. After 30 minutes, the flask was immersed into an oil bath held at 70° C. The reaction was held in the oil bath and agitated using mechanical stirring under a nitrogen atmosphere for 16 hours. Methanol (100 mL) was added to the reaction and, solvent was removed by decanting. The beads were then filtered, and then purified by washing (MeOH two times, $H_2O$ once, 1N HCl two times, $H_2O$ once, 1N NaOH three times, and then $H_2O$ until the pH of solution after washing was 7). The purified beads were then dried by lyophilization for 48 hours. Swelling ratio, particle size, chloride binding capacity in SGF and chloride binding capacity (SIB—Cl) and phosphate binding capacity (SIB—P) in SIB are presented in Table S-1 for the resulting polymers.

TABLE S-1

| Unique ID | Water: Bead | Swelling | Particle Size (microns) | | | Binding (mmol/g dry weight) | | |
|---|---|---|---|---|---|---|---|---|
| | | | D10 | D50 | D90 | SGF | SIB-Cl | SIB-P |
| Averaged from 019069-A1 FA pooled batch* | — | 5.0 | 79 | 129 | 209 | 13.9 | 2.0 | 6.0 |
| 030008-A1 FA | 0.00 | 1.9 | NM | NM | NM | 11.8 | 2.4 | 4.0 |
| 019070-A1 FA | 0.05 | 1.5 | 64 | 99 | 155 | 11.1 | 2.4 | 3.5 |
| 019070-A2 FA | 0.15 | 1.1 | 64 | 97 | 147 | 11.0 | 3.3 | 2.5 |
| 019070-A3 FA | 0.25 | 1.2 | 63 | 102 | 168 | 10.4 | 4.4 | 1.4 |
| 019070-A4 FA | 0.35 | 0.7 | 59 | 91 | 140 | 10.7 | 4.5 | 1.3 |
| 019070-A5 FA | 0.45 | 1.6 | 63 | 105 | 184 | 11.1 | 3.7 | 2.5 |

*Averaged data from 4 batches of preformed polyamine bead

Exemplary Syntheses B-E

Step 1 Exemplary Synthesis B: To a 500 mL round bottom flask, polyallylamine (14 g, 15 kDa), and water (28 mL) were added. The solution was purged with nitrogen and stirred overhead at 220 rpm for 1 hour to completely dissolve the polymer. Next, 30 wt % aqueous NaOH (7 mL) was added and stirred for 5 minutes. A premade solution of DCE (175 mL), n-heptane (105 mL), and Span 80 (2.8 g) was added to the aqueous solution. The solution was heated to 70° C. and stirred for 16 hours. The Dean-Stark step was initiated by adding cyclohexane (100 mL) and heating the reaction to 95° C. to remove the water (>90%) from the beads. Swelling ratio, chloride binding capacity in SGF and chloride binding capacity (SIB—Cl) and phosphate binding capacity (SIB—P) in SIB are presented in Table S-2 (entries 018013-A1 FA and 015026-A1 FA) for the resulting polymer with SGF, SIB—Cl and SIB—P values expressed in mmol/g dry bead.

Step 1 Exemplary Synthesis C: To a 100 mL round bottom flask, DCP (31 mL), n-heptane (19 mL), and Span 80 (0.5 g) were added. A separate aqueous stock solution of polyallylamine (2.3 g, 900 kDa), Aq NaOH (1 mL, 30 wt %), and water (4 mL) was prepared. The aqueous stock solution was added to the organic solution in the round bottom flask. The solution was purged with nitrogen for 15 minutes, heated to 70° C., and stirred for 16 hours. Methanol (30 mL) was added to the reaction mixture and the organic solvent removed by decanting. The resulting beads were purified and isolated by washing the beads using, MeOH, HCl, aqueous sodium hydroxide, and water. The beads were dried using lyophilization techniques. Swelling ratio, chloride binding capacity in SGF and chloride binding capacity (SIB—Cl) and phosphate binding capacity (SIB—P) in SIB are presented in Table S-2 (018001-A2b FA) for the resulting polymer with SGF, SIB—Cl and SIB—P values expressed in mmol/g dry bead.

Step 1 Exemplary Synthesis D: Polyallylamine 15 kDa (3.0 g) and water (9.05 g) were dissolved in a conical flask. Sodium hydroxide (0.71 g) was added to the solution and the mixture was stirred for 30 minutes. To a 100 mL round bottom flask, equipped side arm and overhead stirrer was added 0.38 g of sorbitan sesquioleate and 37.9 g of toluene. The overhead stirrer was switched on to provide agitation to the reaction solution. Dichloropropanol (0.41 g) was added directly to the polyallylamine solution while stirring. The resulting aqueous polyallylamine solution was added to the toluene solution in the 100 mL flask. The reaction was heated to 50° C. for 16 hours. After this time, the reaction was heated to 80° C. for 1 hour and then cooled to room temperature. The resulting beads were purified and isolated by washing the beads using, MeOH, HCl, aqueous sodium hydroxide, and water. The beads were dried using lyophilization techniques. Swelling ratio, chloride binding capacity in SGF and chloride binding capacity (SIB—Cl) and phosphate binding capacity (SIB—P) in SIB are presented in Table S-2 (entries 002054-A3 FA and 011021-A6 FA) for the resulting polymer with SGF, SIB—Cl and SIB—P values expressed in mmol/g dry bead.

Step 1 Exemplary Synthesis E: Polyallylamine 15 kDa (3.1 g) and water (9.35 g) were dissolved in a conical flask. Sodium hydroxide (0.73 g) was added to the solution and the mixture was stirred for 30 minutes. To a 100 mL round bottom flask, equipped side arm and overhead stirrer was added 0.31 g of sorbitan trioleate and 39.25 g of toluene. The overhead stirrer was switched on to provide agitation to the reaction solution. The aqueous polyallylamine solution was added to the toluene solution in the 100 mL flask. Epichlorohydrin (0.30 g) was added directly to the reaction mixture using a syringe. The reaction was heated to 50° C. for 16 hours. After this time the reaction was heated to 80° C. for 1 hour and then cooled to room temperature. The resulting beads were purified and isolated by washing the beads using, MeOH, HCl, aqueous sodium hydroxide, and water. The beads were dried using lyophilization techniques. Swelling ratio, chloride binding capacity in SGF and chloride binding capacity (SIB—Cl) and phosphate binding capacity (SIB—P) in SIB are presented in Table S-2 (entries 002050-A1 FA and 002050-A2 FA) for the resulting polymer with SGF, SIB—Cl and SIB—P values expressed in mmol/g dry bead.

TABLE S-2

| Unique ID | Crosslinker | Swelling | Binding (mmol/g dry weight) | | |
|---|---|---|---|---|---|
| | | | SGF | SIB-Cl | SIB-P |
| 018013-A1 FA | DCE | 6.1 | 16.9 | 2.2 | 7.3 |
| 015026-A1 FA | DCE | 5.9 | 16.6 | 2.0 | 7.2 |
| 018001-A2b FA | DCP | 4.6 | 15.9 | 1.9 | 7.1 |
| 002054-A3 FA | DC2OH | 6.5 | 14.3 | 1.6 | 7.1 |
| 011021-A6 FA | DC2OH | 3.0 | 14.3 | 1.5 | 6.1 |
| 002050-A1 FA | ECH | 8.3 | 14.4 | 1.7 | 7.0 |
| 002050-A2 FA | ECH | 8.8 | 14.2 | 1.6 | 7.1 |

Step 1 polymers selected from Exemplary Synthesis B and D were subjected to Step 2 crosslinking according to the following general procedure. Dry preformed amine polymer beads were added to a reactor vessel equipped with a stir paddle and nitrogen gas inlet. To the beads was added 1,2-dichloroethane (DCE). The beads were dispersed in the DCE using mechanical agitation. Water was added directly to the dispersion, and stirring was continued. The flask was immersed into an oil bath held at a chosen temperature. The reaction was held in the oil bath and agitated using mechanical stirring under a nitrogen atmosphere for a chosen amount of time. Methanol was added to the reaction and, solvent was removed by decanting. The beads were then filtered, and then purified by washing. Swelling ratio, chloride binding capacity in SGF and chloride binding capacity (SIB—Cl) and phosphate binding capacity (SIB—P) in SIB are presented in Table S-3.

TABLE S-3

| Unique ID | Preformed amine polymer | Step 1 xlinker | Swelling | Binding (mmol/g dry weight) | | |
|---|---|---|---|---|---|---|
| | | | | SGF | SIB-Cl | SIB-P |
| 018022-A2 FA | 018013-A1 FA | DCE | 1.7 | 14.9 | 4.0 | 4.6 |
| 015032-A1 FA | 015026-A1 FA | DCE | 1.4 | 13.2 | 6.1 | 1.5 |
| 015032-B2 FA | 015026-A1 FA | DCE | 1.2 | 13.0 | 6.1 | 1.5 |
| 002064-B4 FA | 002054-A3 FA | DC2OH | 3.1 | 12.1 | 1.7 | 5.6 |
| 002064-B5 FA | 002054-A3 FA | DC2OH | 2.7 | 12.3 | 1.7 | 5.5 |

Exemplary Synthesis F

Step 2 Exemplary Synthesis F: Dry preformed amine polymer beads (3.00 g) (prepared as described in Step 1 of Exemplary Synthesis A) were added to a 100 mL round bottom flask equipped with a stir paddle and nitrogen gas inlet. To the beads was added DCP (4.30 mL) and DCE (13.70 mL), resulting in a 1:6 bead to DCE mass/volume ratio). The beads were dispersed in the DCE using mechanical agitation (~150 rpm stirring). Water (3.00 mL, resulting in a 1:1 water to bead mass ratio) was added directly to the dispersion, and stirring was continued for 30 minutes. After 30 minutes, the flask was immersed into an oil bath held at 70° C. The reaction was held in the oil bath and agitated using mechanical stirring under a nitrogen atmosphere for 16 hours. Methanol (60 mL) was added to the reaction and, solvent was removed by decanting. The beads were then filtered, and then purified by washing (MeOH two times, $H_2O$ once, 1N HCl two times, $H_2O$ once, 1N NaOH three times, and then $H_2O$ until the pH of solution after washing was 7). The purified beads were then dried by lyophilization for 48. Swelling ratio, chloride binding capacity in SGF and chloride binding capacity (SIB—Cl) and phosphate binding capacity (SIB—P) in SIB are presented in Table S-4.

TABLE S-4

| Unique ID | Vol % DCE | Swelling | Binding (mmol/g dry weight) | | |
|---|---|---|---|---|---|
| | | | SGF | SIB-Cl | SIB-P |
| 019031-B1 FA | 100 | 1.1 | 11.3 | 5.2 | 1.3 |
| 019031-B2 FA | 92 | 1.0 | 11.2 | 5.2 | 1.4 |
| 019031-B3 FA | 84 | 0.9 | 11.3 | 4.9 | 1.7 |
| 019031-B4 FA | 76 | 1.0 | 11.3 | 4.8 | 1.8 |
| 019031-B5 FA | 68 | 1.0 | 11.4 | 4.6 | 1.9 |
| 019031-B6 FA | 0 | 1.1 | 11.2 | 3.1 | 3.5 |

Exemplary Synthesis G

Polyallylamine hydrochloride is dissolved in water. Sodium hydroxide is added to partially deprotonate the polyallylamine hydrochloride (preferably 50 mol %). The aqueous phase generated has a water content (by weight) 2.42 times the weight of the polyallyamine hydrochloride. A baffled 3 necked flask, equipped with an overhead mechanical stirrer, nitrogen inlet, Dean Stark apparatus with condenser is set up to conduct the suspension reaction. A dichloroethane heptane mixture is prepared, such that there is 3 times by weight dichloroethane to heptane. This dichloroethane, heptane mixed solvent is added to the baffled 3 neck flask. The aqueous solution is added to the flask, such that the ratio is 6.4 dichloroethane to one water by volume. The reaction mixture is stirred and heated to 70° C. for 16 hours. At this point beads are formed. The Dean Stark step is initiated to remove all the water from the beads, while returning the dichloromethane and heptane back to the reaction mixture. Once no more water is removed the reaction mixture is cooled. Water and sodium hydroxide is added back to the reaction mixture at a ratio of 0.25 water to polyallylamine and up to 1 equivalent of sodium hydroxide per chloride on allylamine added (both calculated from polyallylamine hydrochloride added at the beginning of the reaction). The reaction is heated for a further 16 hours at 70° C. The reaction is cooled to room temperature. The beads are purified using a filter frit with the following wash solvents; methanol, water, aqueous solution of HCl, water, aqueous solution of sodium hydroxide and 3 water washes or until the filtrate measures a pH of 7.

Example 1

Efficacy of TRC101 in the Treatment of Acidosis in an Adenine-Induced Model of Nephropathy in Rats The drug substance, TRC101, is a non-absorbed free-flowing powder composed of low-swelling, spherical beads, approximately 100 micrometers in diameter; each bead is a single crosslinked, high molecular weight molecule. TRC101 is a highly crosslinked aliphatic amine polymer that is synthesized by first copolymerizing two monomers, allylamine hydrochloride and N,N'-diallyl-1,3-diaminopropane dihydrochloride, followed by crosslinking the polymer with 1,2-dichloroethane as described in Exemplary Synthesis A and in WO2016/094685 A1. TRC101 is the polymer with unique ID 019070-A3 FA in Table S-1 of Exemplary Synthesis A.

TRC101 is administered as a free-amine polymer and contains no counterion. TRC101 is insoluble in aqueous and non-aqueous solvents. TRC101 has both high proton and chloride binding capacity and chloride binding selectivity. The high amine content of the polymer is responsible for the high proton and chloride binding capacity of TRC101; the polymer's extensive crosslinking provides size exclusion properties and selectivity over other potential interfering anions, such as phosphate, citrate, bile acids, and short-chain and long-chain fatty acids.

TRC101 was evaluated in vivo in an adenine-induced rat model of chronic kidney disease (CKD) and metabolic acidosis. The study was designed in two parts. In both parts, male Sprague-Dawley rats weighing 260-280 g (10 per group) were first administered adenine (0.75 wt % in casein diet) for 2 weeks to induce nephropathy. Study Part 1 investigated the effect of early treatment with TRC101 administered in a casein diet with 0.25 wt % adenine for the 4 weeks following the 2-week nephropathy induction period. In contrast, study Part 2 assessed the effect of TRC101 administered after animals had been kept on casein diet with 0.25 wt % adenine for 5 weeks following the induction period, before the 4-week TRC101 treatment period was started. The dose levels of TRC101 were 0, 1.5, 3.0, and 4.5 wt % in the diet. Both study parts assessed the effect of withdrawing TRC101 after the end of the Treatment Phase with a 2-week Withdrawal Phase, in which TRC101 was discontinued in the low (1.5 wt %) and high (4.5 wt %) TRC101 dose groups, while dosing of TRC101 was continued in the mid dose group (3.0 wt %). All animals received casein diet with 0.25 wt % adenine during the Withdrawal Phase.

In both study parts, blood samples were taken from the tail vein of animals before treatments started and weekly during the Treatment and Withdrawal Periods for measurement of blood bicarbonate (SBC) using a HESKA Element POC™ blood gas analyzer. Animals were randomized based on SBC levels at baseline (i.e., following adenine induction of nephropathy and before initiation of the dosing period) so that mean baseline SBC levels were comparable across all dose groups. In addition, 24-h fecal collections were performed for the untreated and 4.5 wt % TRC101 groups. Collected fecal samples were stored at −20° C. before drying in a lyophilizer for 3 days followed by homogenization with a mortar and pestle. Anions (Cl, $SO_4$, and $PO_4$) were extracted from lyophilized, homogenized fecal samples by incubating the samples with NaOH for 18 hours. Sample supernatants were analyzed for by ion chromatography (IC).

Figure 2:
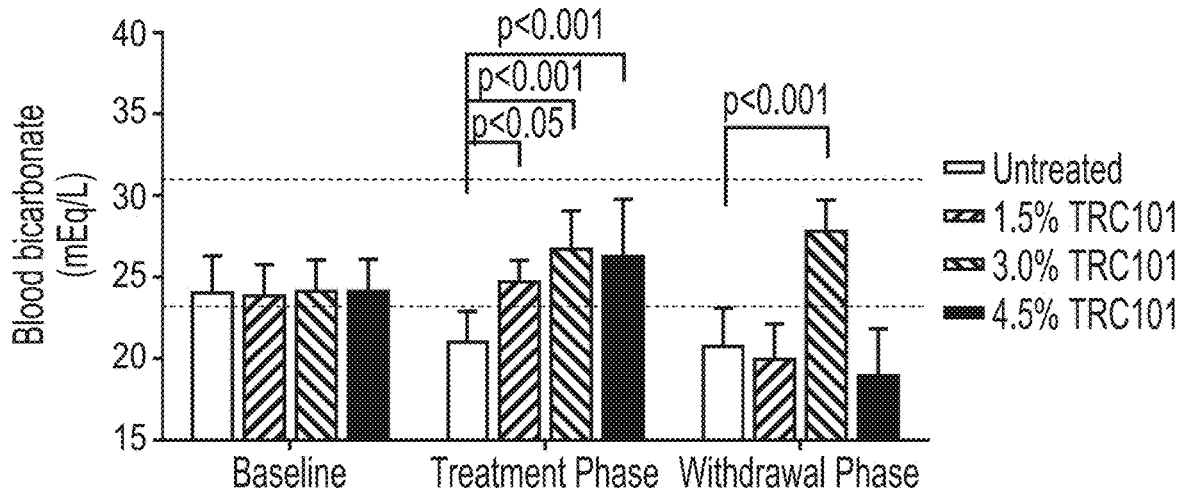
FIG. 2 is a graph of the effect of TRC101 on serum bicarbonate in a rat model of adenine-induced nephropathy and metabolic acidosis in Part 1 of the study described in Example 1.

In Part 1, early treatment with TRC101 resulted in a significant, dose-dependent increase in SBC in all treated groups, relative to the untreated controls (FIG. 2; statistical analysis: 2-way ANOVA with Dunnett's multiple comparisons test vs. untreated group; horizontal dotted lines marke the normal SBC range for male Sprague-Dawley rates of the same age). In contrast to the control group, which had a progressive decline in mean SBC due to adenine-induced renal insufficiency over the 4-week treatment period, mean SBC levels increased and remained in the normal range for low, mid and high treatment groups. Upon withdrawal of TRC101, mean SBC levels fell below the normal range in the low and high treatment groups and were similar to the untreated controls at the end of the withdrawal period; whereas, continued treatment with TRC101 (3.0 wt %) maintained SBC levels within the normal range, with the mean value significantly higher than that of the untreated controls.

Figures 3A, 3B, 3C:
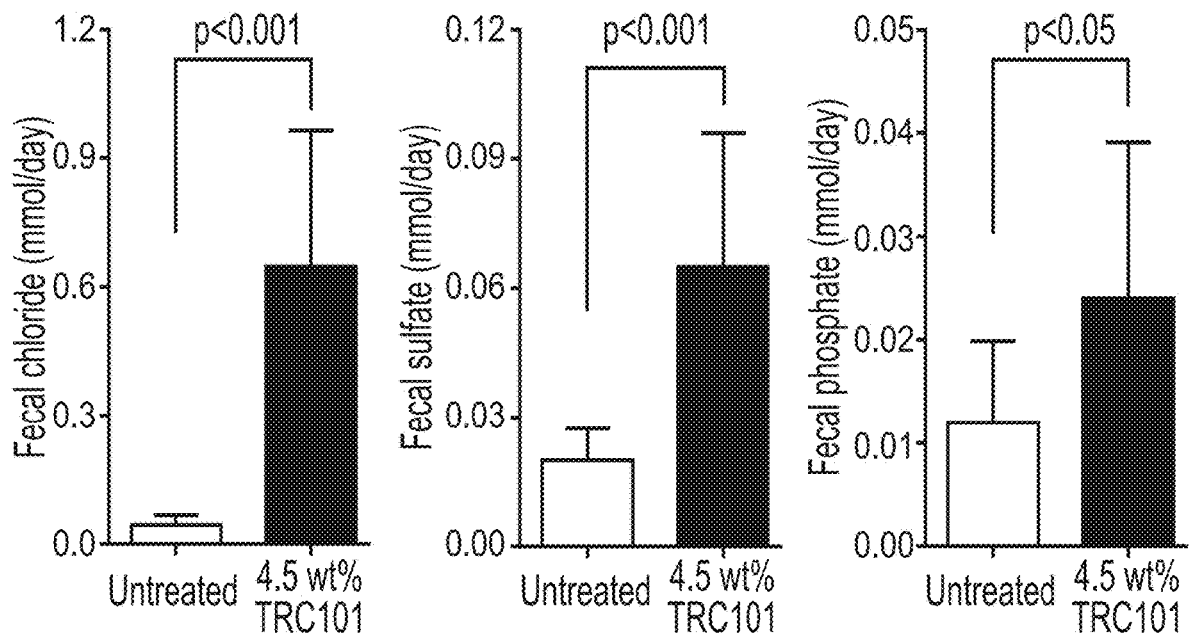
FIGS. 3A, 3B and 3C are graphs of the effect of TRC101 on fecal excretion of chloride (FIG. 3A), sulfate (FIG. 3B), and phosphate (FIG. 3C) in a rat model of adenine-induced nephropathy and metabolic acidosis in Part 1 of the study described in Example 1.

Consistent with the results observed on SBC, recovered fecal samples from animals treated with 4.5 wt % TRC101 in Part 1 of the study demonstrated a significant 15-fold increase in fecal Cl⁻ relative to untreated controls (FIGS. 3A-3C). TRC101 also significantly increased fecal $SO_4$ and $PO_4$ excretion, but the effect was much less (3- and 2-fold increase, respectively, compared to untreated controls) than that observed for Cl.

Figure 4:
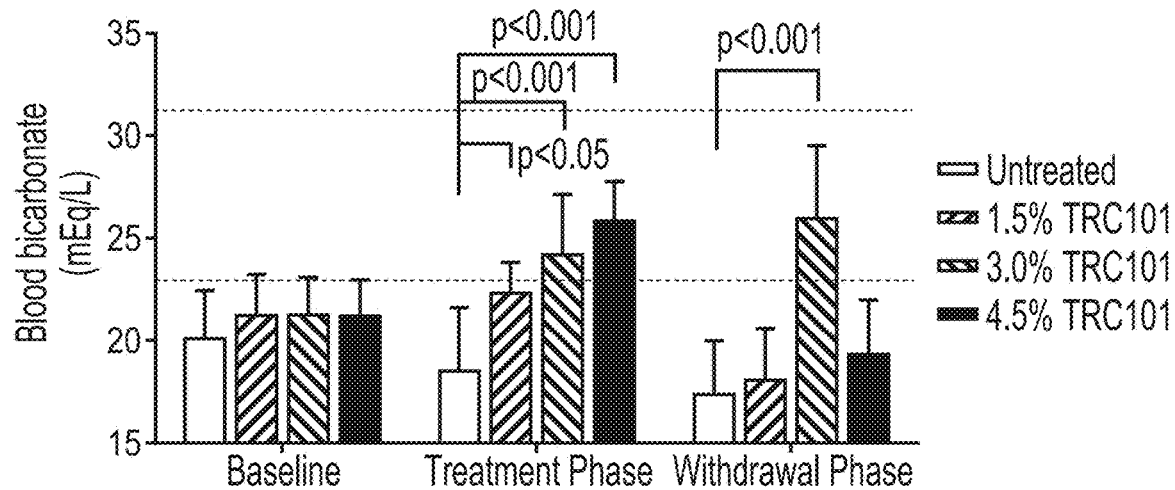
FIG. 4 is a graph of the effect of TRC101 on serum bicarbonate in a rat model of adenine-induced nephropathy and metabolic acidosis in Part 2 of the study described in Example 1.
Figures 5A, 5B, 5C:
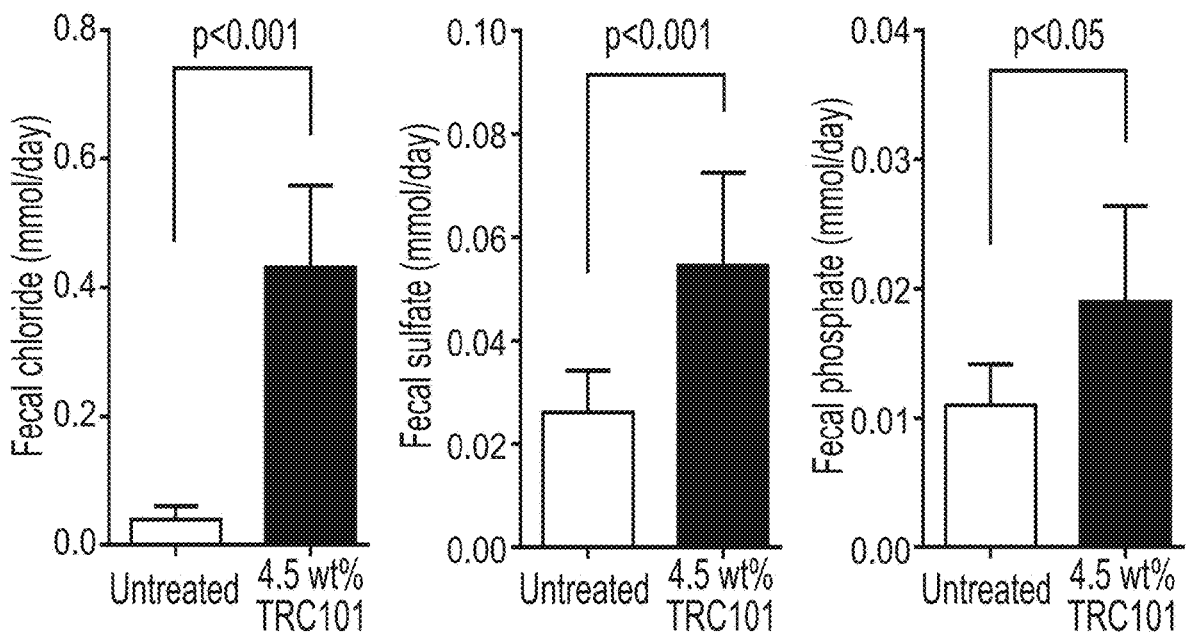
FIGS. 5A, 5B and 5C are graphs of the effect of TRC101 on fecal excretion of chloride (FIG. 5A), sulfate (FIG. 5B), and phosphate (FIG. 5C) in a rat model of adenine-induced nephropathy and metabolic acidosis in Part 2 of the study described in Example 1.

In Part 2 of the study, maintaining rats for a total of 7 weeks on adenine-containing diet prior to the start of the Treatment Phase resulted in mean baseline SBC values that were below the normal range in all treatment groups at a mean of approximately 20 to 21 mEq/L. Treatments with TRC101 resulted in a significant, dose-dependent increase in SBC in all treated groups, relative to the untreated controls. At the end of the 4-week treatment period, mean SBC levels in control animals remained below the normal range. The mean SBC level at the low dose (1.5 wt % TRC101) was only marginally below normal range. At the mid (3.0 wt %) and high (4.5 wt %) doses of TRC101, mean SBC values remained within the normal range (FIG. 4; 2-way ANOVA with Dunnett's multiple comparisons test vs. untreated group; horizontal dotted lines marke the normal SBC range for male Sprague-Dawley rates of the same age). Similar to the results observed in Part 1 of the study, withdrawal of TRC101 administration in Part 2 resulted in a decrease in mean SBC to below the normal range in the low and high doses treatment groups; whereas, continued treatment with 3.0 wt % TRC101 maintained mean SBC levels within the normal range (FIGS. 5A-5C). The mean SBC level in the 3.0 wt % TRC101 group remained significantly higher than that of the untreated control group throughout the study.

Consistent with the results observed on SBC, recovered fecal samples from animals treated with 4.5 wt % TRC101 in Part 2 of the study demonstrated a significant 10-fold increase in fecal Cl⁻ relative to controls, but only a 2-fold increase in fecal $SO_4$ and $PO_4$ excretion (FIGS. 5A-5C).

Example 2

In Vivo Anion Binding of Polymers in a Pig with Normal Renal Function

The anion binding capacities of TRC101 (as described in Example 1) was evaluated in vivo in a female Yorkshire pig with normal renal function. A comparative experiment was conducted using the free amine form of bixalomer (approved in Japan), an anion-binding resin designed to bind phosphate and available commercially to treat hyperphosphatemia. TRC101 and the free amine form of bixalomer were each individually sealed in nylon sachets (with a 64 micrometer mesh size and differentiated for each polymer by sachet shape), fed to a single pig at a total dose of 2 g for each polymer (i.e., 10 sachets each), and then the polymers were recovered from the sachets collected in the feces over a 10-day period (seven and six sachets were recovered from feces for bixalomer and TRC101, respectively). Bound anions were extracted from the polymers by incubating with NaOH for 18 hours. The anion concentrations in the samples were determined in supernatant by IC.

Figure 6A:
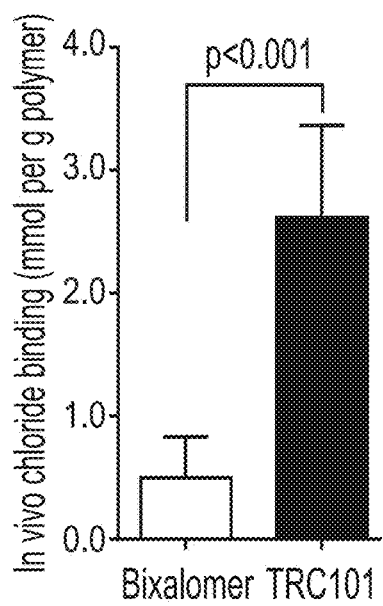
FIGS. 6A, 6B and 6C are graphs of the in vivo chloride (FIG. 6A), sulfate (FIG. 6B) and phosphate (FIG. 6C)
Figure 6B:
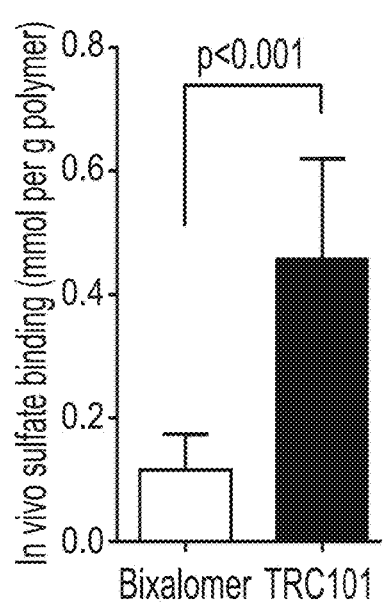
Figure 6C:
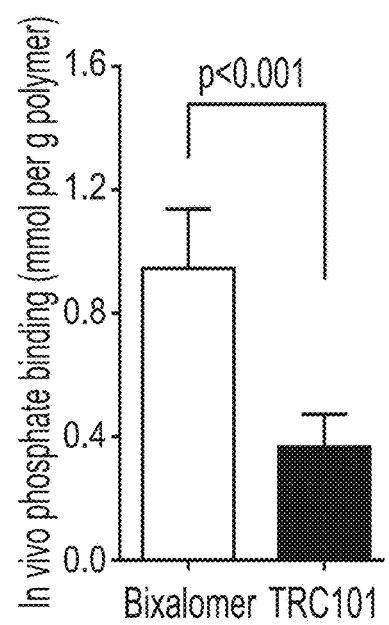

Analysis of the anions bound to the polymers after recovery from the feces revealed in vivo average binding of 2.62 and 0.50 mEq of chloride, 0.46 and 0.11 mmol of sulfate, and 0.37 and 0.95 mmol of phosphate per gram of TRC101 and bixalomer, respectively (FIGS. 6A-6C statistical analysis unpaired T test; Mean±standard deviation; N=7 and 6 sachests for Bixalomer and TRC101, respectively). Therefore, TRC101 removed 5- and 4-fold more chloride and sulfate, respectively, than bixalomer removed from the GI tract of the pig. On the other hand, bixalomer, a phosphate binder, removed 2.5-fold more phosphate than TRC101 removed from the GI tract of the pig.

Example 3

Efficacy of Trc101 in Subjects with Chronic Kidney Disease and Low Serum Bicarbonate Levels The following describes one example of a polymer as described herein being used to treat an acid/base disorder. In this example, the patients have chronic metabolic acidosis, which is shown to be treated by the increase in SBC caused by the administration of a proton binding polymer. However, based on this example, is it apparent that the polymer, and all the acid-binding polymers disclosed herein, are useful for the prevention or treatment of eubicarbonatemic metabolic acidosis. This is because the polymers reduce the amount of acid present in the patient, as illustrated in the following example by a chance in SBC. In patients with eubicarbonatemic metabolic acidosis, their SBC will not necessarily need to rise to achieve treatment (although it may rise). Instead, the successful reduction in acid load caused by the claimed polymers will result in less buffering being required by the bodies homeostatic mechanisms (e.g. by bone dissolving). Therefore, the following human trial in treating metabolic acidosis also supports the successful treatment of eubicarbonatemic metabolic acidosis.

Part 1

TRC101 (as described in Example 1) was studied in a double-blind, placebo-controlled, parallel-design, 4-arm, fixed dose study to evaluate the ability of TRC101 to control serum bicarbonate (SBC) in human subjects with marked metabolic acidosis. A total of 101 subjects with chronic kidney disease (CKD) and low SBC values were randomized into one of the four arms in an approximately 1:1:1:1 ratio (total daily doses of 3, 6 or 9 g/day TRC101 or 3 g/day placebo [microcrystalline cellulose], administered twice daily [BID]).

Subjects were eligible for inclusion in the study if they were 18 to 80 years of age, had Stage 3 or 4 CKD (estimated glomerular filtration rate [eGFR], 20 to <60 m L/min/1.73 $m^2$ of body surface area) and SBC levels of 12 to 20 mEq/L (inclusive) at both Screening and study Day-1, had systolic blood pressure (SBP) at Screening <170 mmHg, had a hemoglobin A1c (HbA1c) value of 9.0% and a fasting serum glucose (FSG) value of 250 mg/dL (13.9 mmol/L) at Screening. Key exclusion criteria were history of anuria, dialysis, acute kidney injury, acute renal insufficiency or >30% increase in serum creatinine or 30% decrease in eGFR in the past 3 month, severe comorbid conditions (other than CKD) such as congestive heart failure with maximum New York Heart Association (NYHA) Class III or IV symptoms, unstable angina or acute coronary syndrome, dementia, hypertensive urgency or emergency, transient ischemic attack, stroke, or use of home oxygen during the 6 months prior to Screening. Other exclusion criteria were serum potassium values of <3.8 mEq/L or >5.9 mEq/L at Screening, Type 1 diabetes or chronic obstructive pulmonary disease, history or current diagnosis of heart or kidney transplant, clinically significant diabetic gastroparesis, bariatric surgery, bowel obstruction, swallowing disorders, severe gastrointestinal disorders, severe recurrent diarrhea or severe recurrent constipation.

At the time of Screening, subjects who met all the entry criteria were admitted to the Clinical Research Unit (CRU) on Day-1 and placed on a study diet controlled for protein, caloric content, anions, cations and fiber, in accordance with dietary recommendations for patients with CKD (KDOQI, 2003). The potential renal acid load (i.e., PRAL value) (Scialla, 2013) was calculated for the daily meal plans to ensure that the study diet was neither acidic nor basic; PRAL values for the four daily meal plans ranged from −1.71 to +1.92 and averaged 0.82. The PRAL is calculated as follows:

$$PRAL(mEq/d)=(0.49*protein\ [g/d])+(0.037*phosphorus\ [mg/d])-(0.21*potassium\ [mg/d])-(0.26*magnesium\ [mg/d])-0.013*(calcium\ [mg/d])$$

Four detailed meal plans were developed that specified the foods (including measured quantities) provided at breakfast, lunch, dinner and two light snacks each day (Table S-5). Care was taken to ensure the diet closely approximated the subjects' typical diet so that perturbations in serum bicarbonate related to a sudden change in diet would be minimized. The dietary sources of protein were predominantly plant-based. Meat (i.e., pork, fish) was served once per day on two of the four meal plans. The sites rotated among the four daily meal plans over the course of the treatment period. The mean (±standard deviation) serum bicarbonate level in the placebo group was 17.6 (±1.43) mEq/L at baseline and remained constant during the 14-day treatment period (17.5 [±1.87] mEq/L at Day 15), demonstrating that the study diet did not change the level of serum bicarbonate.

TABLE S-5

Composition of Study Treatment Period Diet

| Parameter | Calories | Protein (g) | Ca (mg) | Mg (mg) | P (mg) | K (mg) | Na (mg) | Fiber (g) | PRAL |
|---|---|---|---|---|---|---|---|---|---|
| Mean | 2209.25 | 52.32 | 810 | 232.5 | 1008.125 | 2171.375 | 2249.5 | 27.022 | 0.82 |
| Range | 2129–2246 | 50.6–53.4 | 778–849 | 210–235 | 991–1060 | 2048–2277 | 2076–2370 | 22.9–32.1 | −1.71–+1.92 |

Ca = calcium;
K = potassium;
Mg = magnesium;
Na = sodium;
P = phosphate

Enrolled subjects were randomized to one of three TRC101 doses or placebo on Day −1 and dosing was initiated in the morning on Day 1 (next day) in accordance with the randomization assignment. 101 subjects were randomized in an approximately 1:1:1:1 ratio to one of the following groups: Group 1. 3 g/day of placebo administered in equally divided doses BID (twice daily) for 14 days (n=25); Group 2. 3 g/day of TRC101 administered in equally divided doses BID for 14 days (n=25); Group 3. 6 g/day of TRC101 administered in equally divided doses BID for 14 days (n=25); Group 4. 9 g/day of TRC101 administered in equally divided doses BID for 14 days (n=26). TRC101 or placebo were administered orally as an aqueous suspension BID, with breakfast and dinner. The first dose of study drug was taken with breakfast. One hour prior to the administration of the study drug, venous blood was drawn for a pre-dose SBC (contributing to the baseline SBC value) and safety laboratory measurements. Subjects remained in the CRU and continued BID dosing with study drug (at breakfast and dinner) for 14 days. On Day 15, subjects were discharged from the CRU. All subjects who completed the study had a discharge assessment on Day 15 and returned to the CRU on Day 17 and Day 21 for AE collection, blood draws and safety assessments. A subset of patients (n=41) also returned to the CRU on Day 28 for AE collection, blood draws and safety assessments.

No subject was withdrawn early from the study for any reason. The majority of subjects were male (65%), all subjects were white, and the median age was 61 years (range: 30 to 79 years).

Subjects in the study had Stage 3-4 CKD (39% with Stage 4) with a mean baseline eGFR of 36.4 mL/min/1.73 m$^2$ (range 19.0 to 66.0 mL/min/1.73 m$^2$) and metabolic acidosis characterized by a mean SBC level of 17.6 mEq/L (range 14.1-20.4 mEq/L). At baseline, 60% of subjects had an SBC value of 12-18 mEq/L and 40% had an SBC value of >18-20 mEq/L.

Subjects had baseline comorbidities common in CKD patients including hypertension (93%), diabetes (73%), left ventricular hypertrophy (30%), and congestive heart failure (21%). As would be expected in a CKD Stage 3-4 population, nearly all study subjects had indications for sodium restriction: hypertension (93%), congestive heart failure (21%), peripheral edema (15%) and use of diuretics (41%).

Over a 2-week treatment period, TRC101 significantly increased SBC levels in the study population of CKD patients with baseline SBC levels ranging from 14 to 20 mEq/L. At Day 15, all three doses tested (3, 6 and 9 g/day TRC101 BID) significantly (p<0.0001) increased mean SBC levels from baseline and each dose increased SBC levels to a significantly (p<0.0001) greater extent than placebo.

FIG. 7 illustrates the steady increase in mean SBC observed in all three TRC101 dose groups during the 14-day treatment period with a mean increase at the end of treatment of approximately 3-4 mEq/L across all three active dose groups. Serum bicarbonate levels in the placebo group remained essentially unchanged throughout the study, suggesting that the diet with a controlled protein and cation/anion content administered in the clinical research unit matched well with what the subjects ate at home and, therefore, had no significant impact on their SBC values.

TRC101 had a rapid onset of action (i.e., statistically significant increase in mean within group change from baseline in SBC; p<0.0001) within the first 24-48 hours following the initiation of treatment for all three TRC101 dose groups combined. The onset of action for between-group differences (active vs. placebo) appear to occur between 48-72 hours after the initiation of treatment with TRC101. At Day 4 (72 hours after the first dose of TRC101), the mean increase in SBC from baseline for each TRC101 group was 1-2 mEq/L: 3 g/day (p=0.0011); 6 g/day (p=0.0001); 9 g/day (p<0.0001).

Each of the TRC101 dose groups showed a statistically significant (p<0.0001) increase from baseline in SBC of approximately 3-4 mEq/L after 2 weeks of treatment (see Table 1).

TABLE 1

Change from Baseline in SBC at Day 15

|  | Placebo (N =25) | TRC101 3 g/d BID (N = 25) | TRC101 6 g/d BID (N = 25) | TRC101 9 g/d BID (N = 26) | TRC101 Combined (N = 76) |
|---|---|---|---|---|---|
| Baseline |  |  |  |  |  |
| n |  | 25 | 25 | 25 | 26 | 76 |
| Mean (SD) |  | 17.30 (1.338) | 18.02 (1.009) | 17.77 (1.212) | 17.48 (1.282) | 17.75 (1.180) |
| Median |  | 17.40 | 17.90 | 17.80 | 17.73 | 17.83 |
| Min, Max |  | 14.1, 19.6 | 15.6, 20.4 | 15.4, 19.9 | 14.5, 19.2 | 14.5, 20.4 |

TABLE 1-continued

Change from Baseline in SBC at Day 15

|  | Placebo (N =25) | TRC101 3 g/d BID (N = 25) | TRC101 6 g/d BID (N = 25) | TRC101 9 g/d BID (N = 26) | TRC101 Combined (N = 76) |
|---|---|---|---|---|---|
| Day 15 | | | | | |
| n | 25 | 25 | 25 | 26 | 76 |
| Mean (SD) | 17.35 (1.958) | 21.08 (1.960) | 20.72 (2.423) | 21.30 (2.977) | 21.04 (2.475) |
| Median | 17.00 | 21.30 | 20.50 | 21.45 | 21.20 |
| Min, Max | 14.1, 21.7 | 17.3, 24.8 | 15.4, 25.9 | 15.1, 27.0 | 15.1, 27.0 |
| Day 15 Change from Baseline (CFB) | | | | | |
| n | 25 | 25 | 25 | 26 | 76 |
| Mean (SD) | 0.05 (1.955) | 3.06 (2.209) | 2.95 (2.625) | 3.83 (2.372) | 3.29 (2.408) |
| Median | −0.10 | 3.55 | 2.40 | 3.23 | 3.07 |
| Min, Max | −3.5, 4.6 | −1.6, 7.5 | −1.5, 8.6 | −0.4, 9.2 | −1.6, 9.2 |
| Within Group CFB | | | | | |
| LS Mean (SEM) | −0.10 (0.414) | 3.21 (0.415) | 3.04 (0.414) | 3.74 (0.406) | 3.33 (0.237) |
| 95% CI of LS Mean | −0.91, 0.71 | 2.39, 4.02 | 2.23, 3.85 | 2.95, 4.54 | 2.86, 3.80 |
| p-value | 0.8109 | <.0001 | <.0001 | <.0001 | <.0001 |
| Between Group CFB Difference (TRC101 − Placebo) | | | | | |
| LS Mean (SEM) | NA | 3.31 (0.588) | 3.14 (0.587) | 3.84 (0.579) | 3.43 (0.478) |
| 95% CI of LS Mean | NA | 2.15, 4.46 | 1.99, 4.29 | 2.70, 4.98 | 2.49, 4.37 |
| p-value | NA | <.0001 | <.0001 | <.0001 | <.0001 |

Note:
baseline serum bicarbonate (SBC) is defined as an average of two SBC values from samples collected on Day −1 and at Day 1 pre-dose. Change from baseline (CFB) is defined as post-baseline value minus baseline value.
Note:
Least squares (LS) mean, standard error of LS mean (SEM), 95% CI of LS mean, and p-values are based on the mixed-effect repeated measures model with the CFB in SBC value as the dependent variable; treatment (placebo, 3 g/d BID, 6 g/d BID, and 9 g/d BID), time point (Days 2 through 15), and treatment by time point as fixed effects; subject as a random effect; and baseline estimated glomerular filtration rate (eGFR) and baseline SBC as continuous covariates. Within-subject correlations are modeled assuming a first-order autoregressive covariance structure.

There appeared to be little difference in efficacy between the 3 g/day and 6 g/day TRC101 doses; however, subjects in the 9 g/day TRC101 dose group demonstrated a more rapid and larger increase in SBC. For example, the mean increases in SBC at Day 8 were 1.82, 2.00, and 2.79 mEq/L in the 3, 6 and 9 g/day TRC101 dose groups respectively (i.e., ~0.8-1.0 mEq/L difference between the 9 g/day dose group and the other two TRC101 dose groups). At Day 15, the comparable SBC increases were 3.21, 3.04, and 3.74 mEq/L, respectively (i.e., ~0.5-0.7 mEq/L difference between the 9 g/day dose group and the other two TRC101 dose groups) (FIG. 8)).

Statistically significant between-group (active vs. placebo) differences in SBC change from baseline to Day 15 ranged from 3.14 to 3.84 mEq/L across the TRC101 treatment groups, with a combined mean difference of 3.43 mEq/L between TRC101 and placebo (p<0.0001) (see Table 1).

As shown in Table 2, after 2 weeks of treatment, SBC levels increased by mEq/L in over half of subjects (52.6%) in the combined TRC101 group compared to 8.0% of subjects in the placebo group (p<0.0001). In addition, 22.4% of all TRC101-treated subjects had increases in SBC mEq/L compared to 0 subjects in the placebo group.

TABLE 2

Change in SBC by Category over Time

| Subjects with Post Baseline SBC | Placebo N = 25 | TRC101 3 g/d N = 25 | TRC101 6 g/d N = 25 | TRC101 9 g/d N = 26 | TRC101 Combined N = 76 |
|---|---|---|---|---|---|
| Day 15 Increase from Baseline | | | | | |
| ≥2 mEq/L | 4 (16.0%) | 18 (72.0%) | 14 (56.0%) | 19 (73.1%) | 1 (67.1%) |
| ≥3 mEq/L | 2 (8.0%) | 14 (56.0%) | 10 (40.0%) | 16 (61.5%) | 40 (52.6%) |
| ≥4 mEq/L | 1 (4.0%) | 8 (32.0%) | 10 (40.0%) | 11 (42.3%) | 29 (38.2%) |
| ≥5 mEq/L | 0 | 3 (12.0%) | 6 (24.0%) | 8 (30.8%) | 17 (22.4%) |
| ≥6 mEq/L | 0 | 3 (12.0%) | 3 (12.0%) | 4 (15.4%) | 10 (13.2%) |
| ≥7 mEq/L | 0 | 1 (4.0%) | 2 (8.0%) | 2 (7.7%) | 5 (6.6%) |

In the combined TRC101 treatment group, 35.5% of subjects had their SBC corrected into the normal range (22-29 mEq/L) after 2 weeks of treatment, and at the end of the treatment period, 64.5% of TRC101-treated subjects had SBC levels that were above the upper limit of the baseline range (>20 mEq/L) (Table 3). The proportion of subjects achieving an SBC>22 mEq/L was similar in the 3, 6 and 9 g/day TRC101 dose groups (40.0%, 28.0%, and 38.5%, respectively). At Day 8 of the treatment period, only about half of the treatment effect was seen, again suggesting that the SBC increase has not yet plateaued by the end of the 2-week treatment period.

TABLE 3

Change in SBC by Category over Time

| Subjects with Post Baseline SBC | Placebo N = 25 | TRC101 3 g/d N = 25 | TRC101 6 g/d N = 25 | TRC101 9 g/d N = 26 | TRC101 Combined N = 76 |
|---|---|---|---|---|---|
| Day 8 SBC Values | | | | | |
| >20 mEq/L | 3 (12.0%) | 9 (36.0%) | 7 (28.0%) | 12 (46.2%) | 28 (36.8%) |
| >22 mEq/L | 2 (8.0%) | 2 (8.0%) | 5 (20.0%) | 6 (23.1%) | 13 (17.1%) |
| >27 mEq/L | 0 | 0 | 0 | 0 | 0 |
| >29 mEq/L | 0 | 0 | 0 | 0 | 0 |
| Day 15 SBC Values | | | | | |
| >20 mEq/L | 2 (8.0%) | 16 (64.0%) | 14 (56.0%) | 19 (73.1%) | 49 (64.5%) |
| >22 mEq/L | 0 | 10 (40.0%) | 7 (28.0%) | 10 (38.5%) | 27 (35.5%) |
| >27 mEq/L | 0 | 0 | 0 | 0 | 0 |
| >29 mEq/L | 0 | 0 | 0 | 0 | 0 |

The 2-week treatment period in the study was followed by a 2-week follow-up period in which subjects were off treatment. At the end of the 2-week follow-up period, a withdrawal effect of approximately 3 mEq/L was observed in the combined TRC101 group, with SBC levels returning nearly to baseline (FIG. 9). These results underscore the chronic nature of the underlying metabolic acidosis in these CKD patients, and suggest that continued treatment with TRC101 is needed to maintain elevated SBC levels.

There were no mean changes in serum parameters (sodium, calcium, potassium, phosphate, magnesium, low density lipoprotein) observed in the study that would indicate off-target effects of TRC101; there were also no mean changes in serum chloride.

Part 2

The double-blind, placebo-controlled, parallel-design, fixed dose study of Part 1 was extended by the introduction of two additional arms: a total of 34 subjects with chronic (CKD) and low SBC values were randomized into one of two additional arms: total daily dose of 6 g/day TRC101 (28 subjects) or 3 g/day placebo (6 subjects) [microcrystalline cellulose], administered once daily [QD]). All subjects who completed Part 2 of the study had a discharge assessment on Day 15 and returned to the CRU on Day 17, Day 21, and Day 28 for AE collection, blood draws and safety assessments. Part 2 of the study was otherwise unchanged from Part 1.

Discussion of Part 1 and Part 2 Study Results

There were no significant differences between the TRC101 and placebo treatment groups with respect to demographics, baseline eGFR or serum bicarbonate, or comorbidities (Table 4). Patients had a mean baseline eGFR of 34.8 mL/min/1.73 m2 and a mean baseline serum bicarbonate level of 17.7 mEq/L. Study participants had conditions common to CKD patients, including patients with hypertension (93.3%), diabetes (69.6%), left ventricular hypertrophy (28.9%), congestive heart failure (21.5%), peripheral edema (14.1%) and stable diuretic use (42.2%).

Analysis of the mean serum bicarbonate level in the placebo group over the course of the in-unit treatment period and out-patient follow-up period demonstrated that the study diet did not change the level of serum bicarbonate. The mean (±standard deviation) serum bicarbonate level in the placebo group was 17.6 (±1.43) mEq/L at baseline and remained constant during the 14-day treatment period (17.5 [±1.87] mEq/L at Day 15).

There was a significant increase in mean serum bicarbonate in all groups treated with TRC101 within the first 24-48 hours compared to placebo (FIGS. 10 & 11). Within 72 hours after the first dose of TRC101, the mean increase in serum bicarbonate from baseline for each TRC101 group was 1-2 mEq/L Over the 2-week treatment period, TRC101 increased serum bicarbonate values over the respective baseline values for each group, while placebo-treated patients had no change in serum bicarbonate (FIGS. 10 & 11). At day 15, the between group difference of serum bicarbonate versus placebo was 3.31 mEq/L (95% CI of LS mean 2.15 to 4.46; $p<0.0001$), 3.14 mEq/L (95% CI⁻ of LS mean 1.99 to 4.29; $p<0.0001$), 3.84 mEq/L (95% CI⁻ of LS mean 2.70 to 4.98; $p<0.0001$), and 3.72 mEq/L (95% CI⁻ of LS mean 2.70 to 4.74; $p<0.0001$), for TRC101 dose groups 1.5 g, 3.0 g, 4.5 g BID and 6 g QD, respectively. By comparison, the placebo within group change from baseline to day 15 was −0.21 mEq/L (95% CI⁻ of LS mean −0.91 to 0.49; $p=0.56$). The mean increase in the combined TRC101 dose groups was 3.57 mEq/L higher than in the placebo group at the end of the 14-day treatment period (95% CI⁻ of LS mean 2.75 to 4.38; $p<0.0001$). At day 15 there was no significant difference in the mean serum bicarbonate increase when TRC101 was given as a dose of 6.0 g once daily versus 3.0 g twice daily (−0.53 mEq/L; 95% CI⁻ of LS mean −1.61 to 0.56; $p=0.34$).

Treatment with TRC101 caused a steady increase in mean serum bicarbonate in all TRC101 dose groups during the 14-day treatment period. The slope of serum bicarbonate increase remained constant, with no evidence of a plateau at the end of treatment, indicating that the maximal increase in serum bicarbonate using the study doses of TRC101 was not established. The change in serum bicarbonate was similar in all groups treated with TRC101 at the end of the treatment period (FIGS. 10 & 11).

After 2 weeks of treatment with TRC101, serum bicarbonate increased by mEq/L in over half of the patients (51.9%) in the combined TRC101 dose group, compared to 6.5% of patients in the placebo group (Table 5). In addition, 38.5% and 22.1% of all TRC101-treated patients, compared to 3.2% and 0% of placebo-treated patients, had increases in serum bicarbonate of ≥4 mEq/L and mEq/L, respectively.

At the end of TRC101 treatment, 34.6% of patients in the combined TRC101 group had a serum bicarbonate in the normal range (22-29 mEq/L) compared to no patients in the placebo group. At the end of TRC101 dosing, the proportion of patients with a normal serum bicarbonate was similar in the four TRC101 dose groups (40.0%, 28.0%, and 38.5%, 32.1% for 1.5 g BID, 3.0 g BID, 4.5 g BID, and 6.0 g QD, respectively) while none of the patients in the placebo group had a normal serum bicarbonate (Table 6).

At the end of the 2-week, off-treatment, follow-up period, a decrease in serum bicarbonate of approximately 3.0-3.5 mEq/L from the end-of-treatment value was observed in all TRC101 dose groups, with serum bicarbonate levels returning nearly to baseline value in each respective group (FIGS. 10, 11 and 12).

In contrast to serum bicarbonate, serum potassium, serum sodium and serum chloride levels did not significantly change over the course of the study (FIGS. 13A-13D), yielding a change in the serum anion gap in excess of 2 mEq/l (FIG. 14) over the course of the study.

All 135 randomized patients received TRC101 or placebo daily for 14 consecutive days and were included in the safety analysis population. No patients died during the study, or had any adverse events resulting in treatment discontinuation, and no patients suffered serious or severe adverse events. Gastrointestinal adverse events were the most commonly reported events in TRC101-treated patients, and all events were mild or moderate in severity (Table 7). Diarrhea was the most common adverse event; all diarrhea events were mild, self-limited, of short duration, and none required treatment. There were no trends suggesting an off-target effect of TRC101 on electrolytes (i.e., sodium, potassium, magnesium, calcium or phosphate). There were also no trends suggesting an effect of TRC101 on vital signs or ECG intervals. No subject experienced increases in serum bicarbonate that resulted in metabolic alkalosis (i.e., serum bicarbonate >29 mEq/L).

This two-part, double-blind, placebo-controlled, parallel-design, 6-arm, fixed dose clinical study demonstrates that ingestion of TRC101 highly significantly increases serum bicarbonate level in patients with Stage 3 or 4 CKD and low SBC as assessed both by change from baseline within group and by comparisons between active and placebo groups. The rapid onset of action (within 24-72 hours) and efficacy (>3.0 mEq/L increase in SBC) observed in the study suggests that TRC101 is an effective agent in controlling SBC level in the target patient population. Unlike sodium bicarbonate, TRC101 does not introduce cations, such as sodium or potassium, which are deleterious to sodium-sensitive patients with common CKD comorbidities (e.g. hypertension, edema and heart failure). Therefore, TRC101 is expected to provide a safe treatment to control SBC in CKD patients with low SBC, including those who are sodium-sensitive.

TABLE 4

Baseline demographics, dietary intake, renal function, serum bicarbonate and comorbidities ($^a$ median values)

| | Placebo Combined N = 31 | TRC101 1.5 g BID N = 25 | TRC101 3.0 g BID N = 25 | TRC101 6 g QD N = 28 | TRC101 4.5 g BID N = 26 | TRC101 Combined N = 104 | Total N = 135 |
|---|---|---|---|---|---|---|---|
| Age$^a$ (years) | 65.0 | 59.0 | 61.0 | 65.0 | 66.0 | 62.5 | 63.0 |
| Gender (Male/Female) | 19 (61.3%)/ 12 (38.7%) | 19 (76.0%)/ 6 (24.6%) | 17 (68.0%)/ 8 (32.0%) | 16 (57.1%)/ 12 (42.9%) | 15 (57.7%)/ 11 (42.3%) | 68 (65.4%)/ 36 (34.6%) | 87 (64.4%)/ 48 (35.6%) |
| Weight$^a$, kg | 81.0 | 80.0 | 84.70 | 84.2 | 81.2 | 83.0 | 82.0 |
| Average Daily Protein Intake$^a$, g/kg/d | 0.64 | 0.65 | 0.61 | 0.62 | 0.64 | 0.63 | 0.63 |
| Diabetes Mellitus (Yes/No) | 20 (64.5%)/ 11 (35.5%) | 18 (72.0%)/ 7 (28.0%) | 20 (80.0%)/ 5 (20.0%) | 17 (60.7%)/ 11 (39.3%) | 19 (73.1%)/ 7 (26.9%) | 74 (71.2%)/ 30 (28.8%) | 94 (69.6%)/ 41 (30.4%) |
| Hypertension (Yes/No) | 30 (96.8%)/ 1 (3.2%) | 24 (96.0%)/ 1 (4.0%) | 23 (92.0%)/ 2 (8.0%) | 26 (92.9%)/ 2 (7.1%) | 23 (88.5%)/ 3 (11.5%) | 96 (92.3%)/ 8 (7.7%) | 126 (93.3%)/ 9 (6.7%) |
| Heart Failure (Yes/No) | 7 (22.6%)/ 24 (77.4%) | 5 (20.0%)/ 20 (80.0%) | 7 (28.0%)/ 18 (72.0%) | 5 (17.9%)/ 23 (82.1%) | 5 (19.2%)/ 21 (80.8%) | 22 (21.1%)/ 82 (78.9%) | 29 (21.5%)/ 106 (78.5%) |
| Left Ventricular Hypertrophy (Yes/No) | 8 (25.8%)/ 23 (74.2%) | 7 (28.0%)/ 18 (72.0%) | 7 (28.0%)/ 18 (72.0%) | 8 (28.6%)/ 20 (71.4%) | 9 (34.6%)/ 17 (65.4%) | 31 (29.8%)/ 73 (70.2%) | 39 (28.9%)/ 96 (71.1%) |
| Peripheral Edema (Yes/No) | 4 (12.9%)/ 27 (87.1%) | 3 (12.0%)/ 22 (88.0%) | 4 (16.0%)/ 21 (84.0%) | 4 (14.3%)/ 24 (85.7%) | 4 (15.4%)/ 22 (84.6%) | 15 (14.4%)/ 89 (85.6%) | 19 (14.1%)/ 116 (85.9%) |
| SBP$^a$, mmHg | 128.00 | 132.00 | 133.00 | 130.00 | 128.50 | 131.50 | 130.00 |
| eGFR$^a$, m$^2$/min/1.73 m$^2$ | 29.0 | 34.0 | 35.0 | 28.0 | 34.0 | 33.0 | 32.0 |
| SBC$^a$, mEq/L | 17.6 | 17.9 | 17.8 | 17.7 | 17.7 | 17.8 | 17.7 |

TABLE 5

Proportion of Patients by Serum Bicarbonate Increase Category at Day 15

| Patients with Post-baseline Serum Bicarbonate | Pooled Placebo N = 31 | TRC101 1.5 g BID N = 25 | TRC101 6 g QD N = 28 | TRC101 3.0 g BID N = 25 | TRC101 4.5 g BID N = 26 | TRC101 Combined N = 104 |
|---|---|---|---|---|---|---|
| ≥2 mEq/L | 4 (12.9%) | 18 (72.0%) | 23 (82.1%) | 14 (56.0%) | 19 (73.1%) | 74 (71.2%) |
| ≥3 mEq/L | 2 (6.5%) | 14 (56.0%) | 14 (50.0%) | 10 (40.0%) | 16 (61.5%) | 54 (51.9%) |
| ≥4 mEq/L | 1 (3.2%) | 8 (32.0%) | 11 (39.3%) | 10 (40.0%) | 11 (42.3%) | 40 (38.5%) |
| ≥5 mEq/L | 0 | 3 (12.0%) | 6 (21.4%) | 6 (24.0%) | 8 (30.8%) | 23 (22.1%) |
| ≥6 mEq/L | 0 | 3 (12.0%) | 5 (17.9%) | 3 (12.0%) | 4 (15.4%) | 15 (14.4%) |
| ≥7 mEq/L | 0 | 1 (4.0%) | 1 (3.6%) | 2 (8.0%) | 2 (7.7%) | 6 (5.8%) |

TABLE 6

Proportion of Patients by Serum Bicarbonate Category (Days 8 and 15)

| Patients with Post-baseline Serum Bicarbonate | Pooled Placebo N = 31 | TRC101 1.5 g BID N = 25 | TRC101 6 g QD N = 28 | TRC101 3.0 g BID N = 25 | TRC101 4.5 g BID N = 26 | TRC101 Combined N = 104 |
|---|---|---|---|---|---|---|
| Day 8 Serum Bicarbonate Values | | | | | | |
| >20 mEq/L | 5 (16.1%) | 9 (36.0%) | 16 (57.1%) | 7 (28.0%) | 12 (46.2%) | 44 (42.3%) |
| >22 mEq/L | 2 (6.5%) | 2 (8.0%) | 5 (17.9%) | 5 (20.0%) | 6 (23.1%) | 18 (17.3%) |
| >27 mEq/L | 0 | 0 | 0 | 0 | 0 | 0 |
| >29 mEq/L | 0 | 0 | 0 | 0 | 0 | 0 |
| Day 15 Serum Bicarbonate Values | | | | | | |
| >20 mEq/L | 2 (6.5%) | 16 (64.0%) | 17 (60.7%) | 14 (56.0%) | 19 (73.1%) | 69 (66.3%) |
| >22 mEq/L | 0 | 10 (40.0%) | 9 (32.1%) | 7 (28.0%) | 10 (38.5%) | 36 (34.6%) |
| >27 mEq/L | 0 | 0 | 0 | 0 | 0 | 0 |
| >29 mEq/L | 0 | 0 | 0 | 0 | 0 | 0 |

TABLE 7

Treatment-Emergent Adverse Events Occurring in >5% of Patients in any Treatment Group (Safety Analysis Set)

| Preferred Term | Pooled Placebo (N = 31) n (%) | 1.5 g BID (N = 25) n (%) | TRC101 6 g QD (N = 28) n (%) | 3.0 g BID (N = 25) n (%) | 4.5 g BID (N = 26) n (%) | TRC101 Combined (N = 104) n (%) | Study Total (N = 135) n (%) |
|---|---|---|---|---|---|---|---|
| Patients reporting any TEAE | 14 (45.2) | 13 (52.0) | 17 (60.7) | 9 (36.0) | 17 (65.4) | 56 (53.8) | 70 (51.9) |
| Diarrhea | 4 (12.9) | 9 (36.0) | 3 (10.7) | 3 (12.0) | 6 (23.1) | 21 (20.2) | 25 (18.5) |
| Headache | 1 (3.2) | 4 (16.0) | 1 (3.6) | 1 (4.0) | 2 (7.7) | 8 (7.7) | 9 (6.7) |
| Constipation | 0 | 1 (4.0) | 3 (10.7) | 1 (4.0) | 2 (7.7) | 7 (6.7) | 7 (5.2) |
| Hyperglycemia | 0 | 0 | 3 (10.7) | 2 (8.0) | 2 (7.7) | 7 (6.7) | 7 (5.2) |
| Hypoglycemia | 2 (6.5) | 2 (8.0) | 0 | 1 (4.0) | 2 (7.7) | 5 (4.8) | 7 (5.2) |
| Hypertension | 1 (3.2) | 1 (4.0) | 2 (7.1) | 0 | 2 (7.7) | 5 (4.8) | 6 (4.4) |
| Glomerular filtration rate decreased | 2 (6.5) | 2 (8.0) | 0 | 1 (4.0) | 1 (3.8) | 4 (3.8) | 6 (4.4) |
| Blood glucose increased | 2 (6.5) | 1 (4.0) | 1 (3.6) | 0 | 0 | 2 (1.9) | 4 (3.0) |

BID = twice daily;
GFR = glomerular filtration rate;
QD = once daily;
TEAE = treatment-emergent adverse event.

Example 4

Retrospective Analysis of the Benefit of Elevated Serum Bicarbonate Levels

The dataset used for this analysis is an extract of the Optum de-identified Electronic Health Record dataset (2007-2013), which contained longitudinal electronic health records for >22 million unique patient lives. The source of the information in the database was approximately three dozen US health systems in 43 states covering approximately 200 hospitals and 1,800 outpatient clinics. The extract included patients with a documented diagnosis code or clinical evidence of Stage 3, 4, or 5 CKD (based on the Ninth Revision, International Classification of Diseases [ICD-9] code 585.4, 585.5) or an estimated glomerular filtration rate (eGFR) <30 mL/min/1.73 m² at the start of the data period and with at least one serum bicarbonate ($HCO_3$) test result. The data period of the electronic health records is from January 2007 to July 2013. To exclude erroneous values, only serum bicarbonate values in the range 10 to 40 mEq/L and serum creatinine values in the range 0 to 20 mg/dL were included in the analysis dataset.

To assess the quantitative relationship between a death, dialysis or egfr decline of at least 40% (a "DD40" endpoint) and serum bicarbonate level, an analysis population was first defined that included only CKD patients with an eGFR value in the range of 15 to <45 mL/min/1.73 m² and and a serum bicarbonate level in the range of 12 to 29 mEq/L. Evidence of a Baseline Period of 1 to 2 years duration during which the patient had stable serum bicarbonate and eGFR values, prior to an up to 6.5-year Observation Period during which renal outcomes were assessed.

For inclusion in the analysis population, patients were required to have consistent evidence of the status of their acidosis by remaining in the same serum bicarbonate stratum (i.e., low [12 to 20 mEq/L], borderline [>20 to <22 mEq/L] or normal [22 to 29 mEq/L]) at the following three timepoints (with slightly wider ranges allowed for the second and third values to account for measurement variability):

1. Baseline serum bicarbonate value, defined as the average of serum bicarbonate results collected within 30 days of the first date of collection from the records with serum bicarbonate results between 10 and 40 mEq/L;
2. First recorded serum bicarbonate value occurring at least 1 year but not more than 2 years after the Baseline HCO3 Date; and
3. Last recorded serum bicarbonate value.

Patients were required to have remained in the same serum bicarbonate stratum to which they were assigned at the beginning of the Baseline Period both at the end of the 1- to 2-year Baseline Period as well as at the end of the Observation Period. This approach was chosen to ensure that DD40 endpoints recorded during the Observation Period could be reliably associated with a particular serum bicarbonate stratum. One drawback of this approach is that the analysis population is likely to be somewhat healthier than the population that will be enrolled in the post-marketing study, TRCA-303. Since this is not expected to exaggerate differences in DD40 event rates observed between strata, the approach is considered reasonable.

Requirements for inclusion in the analysis population also mandated that the patient's eGFR must have remained in the target range of 15 to <45 mL/min/1.73 m² at the beginning, and a target range of 10 to <50 mL/min/1.73 m² at the end, of the 1- to 2-year Baseline Period. The eGFR at the end of the Baseline Period was used as the eGFR Baseline Value from which reductions in eGFR were calculated for the purposes of DD40 endpoint assessment. For a reduction in eGFR from the eGFR Baseline Value to have counted toward the DD40 endpoint, it must have been supported by a confirmatory eGFR value also occurring during the Observation Period that also represented at least a 40% reduction from Baseline.

The requirements for inclusion in the analysis population, and the resulting size of the analysis population after each requirement was implemented, are summarized in FIGS. 15 and 16, respectively.

Baseline Characteristics for the Analysis Population

The analysis population contained 7,181 CKD patients, which were divided into three strata based on their baseline serum bicarbonate level (FIGS. 15 and 16): 351 patients with low bicarbonate levels (12 to 20 mEq/L), 295 patients with borderline acidosis (>20 to <22 mEq/L) and 6,535 patients with normal serum bicarbonate (22 to 29 mEq/L). Demographic and baseline information for the analysis population by serum bicarbonate stratum is provided in Table 400.

The analysis population was approximately 60% female, with an average age of approximately 74 years. Two-thirds (67%) of patients had a diagnosis of hypertension and 32% had a diagnosis of diabetes. A smaller proportion of patients (12%) had a history of cerebrovascular disease. Renin angiotensin aldosterone system (RAAS) inhibitor use prior to the beginning of the Observation Period was common in the analysis population (~42% of patients).

Demographic and baseline characteristics were similar among the three serum bicarbonate strata, with the following exceptions: patients in the low serum bicarbonate stratum (12 to 20 mEq/L) were younger, had lower baseline eGFR, and were more often male than patients in the normal serum bicarbonate stratum (22 to 29 mEq/L).

At the time of the first qualifying eGFR value (i.e., at the beginning of the Baseline Period), the majority (79%) of patients in the analysis population had CKD stage 3b, with the remainder having more severe disease (CKD stage 4). The lowest serum bicarbonate stratum had a greater proportion of patients with CKD stage 4 (44%) than did the borderline acidotic and normal serum bicarbonate strata (26% and 20%, respectively).

TABLE 400

Demographics and Baseline Characteristics of the Analysis Population

| | Serum Bicarbonate Stratum | | | | |
| --- | --- | --- | --- | --- | --- |
| | 12 to 20 mEq/L (N = 351) | >20 to <22 mEq/L (N = 295) | 22 to 29 mEq/L (N = 6,535) | Total (N = 7,181) | p-value |
| Age (years)[a] | | | | | <0.0001 |
| N | 351 | 295 | 6535 | 7181 | |
| Mean (SD) | 69.4 (11.88) | 72.9 (9.31) | 74.1 (8.01) | 73.9 (8.36) | |
| Median | 73.0 | 77.0 | 78.0 | 78.0 | |
| Min, Max | 13, 83 | 22, 83 | 13, 83 | 13, 83 | |
| <18 years | 1 (0.3%) | 0 | 2 (<0.1%) | 3 (<0.1%) | |
| 18 to <65 years | 94 (26.8%) | 49 (16.6%) | 774 (11.8%) | 917 (12.8%) | |
| ≥65 years | 256 (72.9%) | 246 (83.4%) | 5759 (88.1%) | 6261 (87.2%) | |
| Sex | | | | | 0.0015 |
| Male | 155 (44.2%) | 145 (49.2%) | 2590 (39.6%) | 2890 (40.2%) | |
| Female | 196 (55.8%) | 150 (50.8%) | 3945 (60.4%) | 4291 (59.8%) | |
| Hypertension | | | | | 0.3615 |
| Yes | 225 (64.1%) | 190 (64.4%) | 4379 (67.0%) | 4794 (66.8%) | |
| No | 126 (35.9%) | 105 (35.6%) | 2156 (33.0%) | 2387 (33.2%) | |
| Cerebrovascular disease | | | | | 0.1622 |
| Yes | 40 (11.4%) | 25 (8.5%) | 791 (12.1%) | 856 (11.9%) | |
| No | 311 (88.6%) | 270 (91.5%) | 5744 (87.9%) | 6325 (88.1%) | |
| Diabetes | | | | | 0.0655 |
| Yes | 118 (33.6%) | 110 (37.3%) | 2042 (31.2%) | 2270 (31.6%) | |
| No | 233 (66.4%) | 185 (62.7%) | 4493 (68.8%) | 4911 (68.4%) | |
| Baseline ACEi or ARB Use | | | | | 0.1582 |
| Yes | 162 (46.2%) | 135 (45.8%) | 2704 (41.4%) | 3001 (41.8%) | |
| No | 150 (42.7%) | 118 (40.0%) | 2961 (45.3%) | 3229 (45.0%) | |
| Missing | 39 (11.1%) | 42 (14.2%) | 870 (13.3%) | 951 (13.2%) | |
| Baseline Serum Bicarbonate (HCO3) (mEq/L)[b] | | | | | <0.0001 |

TABLE 400-continued

Demographics and Baseline Characteristics of the Analysis Population

| | Serum Bicarbonate Stratum | | | | |
| --- | --- | --- | --- | --- | --- |
| | 12 to 20 mEq/L (N = 351) | >20 to <22 mEq/L (N = 295) | 22 to 29 mEq/L (N = 6,535) | Total (N = 7,181) | p-value |
| N | 351 | 295 | 6535 | 7181 | |
| Mean (SD) | 18.3 (1.65) | 21.0 (0.26) | 25.3 (2.02) | 24.8 (2.59) | |
| Median | 19.0 | 21.0 | 25.0 | 25.0 | |
| Min, Max | 13, 20 | 20, 22 | 22, 29 | 13, 29 | |
| First Qualifying eGFR (mL/min/1.73 m$^2$) | | | | | <0.0001 |
| N | 351 | 295 | 6535 | 7181 | |
| Mean (SD) | 30.7 (7.86) | 33.7 (7.28) | 35.3 (6.56) | 35.0 (6.74) | |
| Median | 31.0 | 35.0 | 36.0 | 36.0 | |
| Min, Max | 15, 44 | 15, 44 | 15, 44 | 15, 44 | |
| Stage 3b Moderate CKD (30 to 44 mL/min/1.73 m$^2$) | 197 (56.1%) | 217 (73.6%) | 5260 (80.5%) | 5674 (79.0%) | |
| Stage 4 Severe CKD (15 to 29 mL/min/1.73 m$^2$) | 154 (43.9%) | 78 (26.4%) | 1275 (19.5%) | 1507 (21.0%) | |

ACEi = angiotensin converting enzyme inhibitor;
ARB = angiotensin receptor blocker;
CKD = chronic kidney disease;
eGFR = estimated glomerular filtration rate;
HCO3 = serum bicarbonate;
SD = standard deviation Note:
Race and urine albumin-to-creatinine ratio not included because >95% and >85% of patients, respectively, did not have this information recorded.
$^a$Age was calculated as the difference between date of birth and date of baseline bicarbonate, in years. All patients had their birth month and day set to June 1. Patients with no available birth date (i.e., no birth year) had their birth year set to the same year as the baseline serum bicarbonate measurement collection year (i.e., age = 0 years). Patients with birth year of 1928 or earlier had their birth year set to 1928 (i.e., age = 85 years).
$^b$Baseline serum bicarbonate calculated as average of all HCO$_3$ values within 30 days of first HCO$_3$ value.

Qualifying Serum Bicarbonate and eGFR Values for the Analysis Population

Because patients were required to remain in the same serum bicarbonate stratum to which they were assigned at the beginning of the Baseline Period, there was little difference in the mean serum bicarbonate values in a particular stratum over the course of the Baseline and Observation Periods. For example, patients in the low serum bicarbonate stratum had an average serum bicarbonate level of 18.3 mEq/L at the beginning of the Baseline Period, 18.5 mEq/L at the end of the Baseline Period (which is also the beginning of the Observation Period), and 18.5 mEq/L at the end of the Observation Period. Similarly, patients in the borderline and normal serum bicarbonate strata had serum bicarbonate values across the analysis periods that did not vary significantly (Table 500). The length of the Baseline Period varied among patients because it was determined by the time of the first serum bicarbonate record occurring at least 1 year but not more than 2 years after the patient's first recorded serum bicarbonate value. The average duration of the Baseline Period, determined by the second qualifying serum bicarbonate value, was 15.2 months in the analysis population overall, and it was similar among the three serum bicarbonate strata (Table 500).

To ensure that we were assessing the effects of various levels of acidosis in CKD patients who represent our intended TRCA-303 population, patients in the analysis population were required to have an eGFR value at least 1 year but not more than 2 years after the patient's first recorded serum bicarbonate value that was in the range between 10 and 50 mL/min/1.73 m$^2$. The patient's Baseline eGFR Value was calculated from the average of all serum creatinine values recorded in the 90 days prior to this second qualifying eGFR value. The mean Baseline eGFR Values were 29.6, 32.8 and 35.4 mL/min/1.73 m$^2$ in the low, borderline and normal serum bicarbonate groups, respectively. The duration of the Baseline Period, as defined by the time between the first and second qualifying eGFR values, was 15.06 months in the analysis population overall, and it was similar among the three serum bicarbonate strata (Table 500). A patient's Baseline eGFR Value was used for assessment of all DD40 endpoint events occurring during the Observation Period. Reductions in eGFR sufficiently large to contribute to the DD40 event rate (i.e., 40%) were calculated as reductions from this eGFR value, not the eGFR at the beginning of the Baseline Period. All reductions in eGFR contributing to the DD40 event rate were also confirmed by a second eGFR value that confirmed magnitude of the reduction.

The average duration of the Observation Period, as defined by the time from the Baseline eGFR Date to the last recorded patient contact, was 34.9 months in the analysis population overall, and ranged from 32.9 to 35.0 months among the three serum bicarbonate strata.

TABLE 500

Serum Bicarbonate and eGFR Values of the Analysis Population

| All Patients | Serum Bicarbonate Stratum | | | |
|---|---|---|---|---|
| | 12 to 20 mEq/L (N = 351) | >20 to <22 mEq/L (N = 295) | 22 to 29 mEq/L (N = 6,535) | Total (N = 7,181) |
| Baseline Serum Bicarbonate (mEq/L; First HCO3 Value) | | | | |
| Mean (SD) | 18.3 (1.65) | 21.0 (0.26) | 25.3 (2.02) | 24.8 (2.59) |
| Median (Min, Max) | 19.0 (13, 20) | 21.0 (20, 22) | 25.0 (22, 29) | 25.0 (13, 29) |
| First Qualifying eGFR (mL/min/1.73 m$^2$) | | | | |
| Mean (SD) | 30.7 (7.86) | 33.7 (7.28) | 35.3 (6.56) | 35.0 (6.74) |
| Median (Min, Max) | 31.0 (15, 44) | 35.0 (15, 44) | 36.0 (15, 44) | 36.0 (15, 44) |
| Second Qualifying Serum Bicarbonate (mEq/L; i.e. End of 1- to 2-year Baseline Period) | | | | |
| Mean (SD) | 18.5 (2.37) | 21.2 (1.50) | 25.0 (2.29) | 24.5 (2.75) |
| Median (Min, Max) | 19.0 (10, 22) | 21.0 (18, 24) | 25.0 (20, 29) | 25.0 (10, 29) |
| Baseline eGFR Value (mL/min/1.73 m$^2$; i.e., End of 1- to 2-year Baseline Period) | | | | |
| Mean (SD) | 29.6 (9.25) | 32.8 (8.93) | 35.4 (7.98) | 35.0 (8.20) |
| Median (Min, Max) | 30.0 (10, 49) | 34.0 (10, 49) | 36.0 (10, 49) | 36.0 (10, 49) |
| Last Serum Bicarbonate (mEq/L) | | | | |
| Mean (SD) | 18.5 (2.51) | 21.0 (1.61) | 24.9 (2.40) | 24.4 (2.85) |
| Median (Min, Max) | 19.0 (10, 22) | 21.0 (18, 24) | 25.0 (20, 29) | 25.0 (10, 29) |
| Time (months) from First HCO3 to Second Qualifying Serum Bicarbonate Value (i.e., length of Baseline Period) | | | | |
| Mean (SD) | 15.35 (3.283) | 14.95 (2.851) | 15.21 (3.149) | 15.20 (3.144) |
| Median (Min, Max) | 14.10 (12.0, 24.0) | 13.90 (12.0, 23.9) | 14.10 (12.0, 24.0) | 14.10 (12.0, 24.0) |
| Time (months) from First Qualifying eGFR to Baseline eGFR Date (i.e., length of Baseline Period) | | | | |
| Mean (SD) | 14.90 (3.016) | 14.83 (2.847) | 15.08 (3.081) | 15.06 (3.069) |
| Median (Min, Max) | 13.80 (12.0, 23.8) | 13.80 (12.0, 23.9) | 14.00 (12.0, 24.0) | 13.90 (12.0, 24.0) |
| Time (months) from Baseline eGFR Date to Last Contact Date (i.e., length of Observation Period) | | | | |
| Mean (SD) | 32.92 (19.80) | 34.74 (20.61) | 35.02 (19.47) | 34.90 (19.53) |
| Median (Min, Max) | 32.30 (0.0, 73.0) | 33.60 (0.4, 72.2) | 35.30 (0.0, 77.1) | 35.20 (0.0, 77.1) | eGFR = estimated glomerular filtration rate;
HCO$_3$ = serum bicarbonate;
SD = standard deviation Analysis Results Frequency of Endpoint Events by Serum Bicarbonate Stratum During the almost 6.5-year follow up of the 7,181 patients in the analysis population, 572 patients experienced the DD40 endpoint (Table 600). Of these patients, 50 died, 60 initiated dialysis or received renal transplantation and 462 had a 40% decline from baseline in eGFR. The incidence rate of each of the individual endpoint events, as well as of the DD40 composite endpoint, was 2.4- to 6.7-fold higher in the group of patients with low baseline serum bicarbonate than in the patients with normal serum bicarbonate.

TABLE 600

Frequency and Incidence Rates of Endpoint Events by Serum Bicarbonate Stratum

| Endpoint Event | 12 to 20 mEq/L (N = 351) | >20 to <22 mEq/L (N = 295) | 12 to <22 mEq/L (N = 646) | 22 to 24 mEq/L (N = 1,572) | 22 to 29 mEq/L (N = 6,535) | Total (N = 7,181) |
|---|---|---|---|---|---|---|
| DD40 | 71 (20.2%) | 35 (11.9%) | 106 (16.4%) | 110 (7.0%) | 466 (7.1%) | 572 (8.0%) |
| Death | 7 (2.0%) | 5 (1.7%) | 12 (1.9%) | 9 (0.6%) | 38 (0.6%) | 50 (0.7%) |
| Dialysis or kidney transplant | 14 (4.0%) | 6 (2.0%) | 20 (3.1%) | 9 (0.6%) | 40 (0.6%) | 60 (0.8%) |
| ≥40% decline from baseline in eGFR | 50 (14.2%) | 24 (8.1%) | 74 (11.5%) | 92 (5.9%) | 388 (5.9%) | 462 (6.4%) |

Number (%) of patients are reported.
DD40 = the composite of death, dialysis or kidney transplant, and ≥40% decline from baseline in eGFR;
eGFR = estimated glomerular filtration rate Cox Regression Analyses To understand the impact of each 1 mEq/L increase in serum bicarbonate on the hazard reduction of DD40, the benefit (i.e., reduction in hazard ratio of DD40) associated with different magnitudes of serum bicarbonate increase compared with the population of patients with serum bicarbonate 12 to 20 mEq was determined ("Analysis 3" in FIG. 17).

As shown in Table 700, the hazard ratio of the DD40 endpoint is reduced with both moderate and large increases in serum bicarbonate. This analysis used the low serum bicarbonate (12 to 20 mEq/L) stratum as Reference for comparison with two strata with higher average serum bicarbonate levels. The average baseline serum bicarbonate level in the Reference stratum was 18.3 mEq/L. The Test strata had average baseline serum bicarbonate levels of 21.0 and 23.1 mEq/L, representing increases in serum bicarbonate of approximately 3 and 5 mEq/L. A 3 mEq/L higher average serum bicarbonate level resulted in an adjusted hazard ratio of 0.60 (95% CI: 0.40, 0.91; p=0.0153), indicating that moderately higher serum bicarbonate levels significantly reduce the hazard of the DD40 endpoint. A 5 mEq/L higher average serum bicarbonate level resulted in an adjusted hazard ratio of 0.39 (95% CI: 0.29, 0.53; p<0.0001).

TABLE 700

Hazard Ratios and 95% Confidence Intervals for DD40 from Cox Model
($10 \leq$ Baseline eGFR $<50$ mL/min/1.73 m$^2$)
Patients[a] with Baseline SBC $\geq$=12 mEq/L and $\leq$=29 mEq/L and First Qualifying eGFR $\geq$=15 and $<45$ mL/min/1.73 m$^2$

| | Baseline Serum Bicarbonate | | | | | | |
|---|---|---|---|---|---|---|---|
| | >27-29 mEq/L (N = 612) | >24-27 mEq/L (N = 2413) | 22-24 mEq/L (N = 1572) | >20-<22 mEq/L (N = 295) | 12-20 mEq/L (N = 351) | Covariate | p-value[e] |
| | Baseline serum bicarbonate (mEq/L) | | | | | | |
| n | 612 | 2413 | 1572 | 295 | 351 | | |
| Mean (SD) | 28.4 (0.54) | 25.9 (0.82) | 23.1 (0.79) | 21.0 (0.26) | 18.3 (1.65) | | |
| Median | 28.0 | 26.0 | 23.0 | 21.0 | 19.0 | | |
| Min, Max | 27, 29 | 24, 27 | 22, 24 | 20, 22 | 13, 20 | | |
| | 1st qualifying estimated glomerular filtration rate (eGFR) (mL/min/1.73 m$^2$) | | | | | | |
| n | 612 | 2413 | 1572 | 295 | 351 | | |
| Mean (SD) | 36.7 (5.91) | 35.5 (6.44) | 34.9 (6.81) | 33.7 (7.28) | 30.7 (7.86) | | |
| Median | 38.0 | 36.0 | 36.0 | 35.0 | 31.0 | | |
| Min, Max | 17, 44 | 15, 44 | 15, 44 | 15, 44 | 15, 44 | | |
| | Length of observation period (months) | | | | | | |
| n | 612 | 2413 | 1572 | 295 | 351 | | |
| Mean (SD) | 33.25 (19.62) | 34.15 (19.67) | 34.54 (19.86) | 34.74 (20.61) | 32.92 (19.80) | | |
| Median | 33.02 | 33.91 | 34.30 | 33.58 | 32.30 | | |
| Min, Max | 0.1, 71.3 | 0.0, 77.1 | 0.1, 71.0 | 0.4, 72.2 | 0.0, 73.0 | | |
| | Number (%) patients | | | | | | |
| Had Event (New DD40 >1 Year (baseline eGFR date 1 to 2 years)) | 23 (3.8%) | 154 (6.4%) | 110 (7.0%) | 35 (11.9%) | 71 (20.2%) | | |
| Censored | 589 (96.2%) | 2259 (93.6%) | 1462 (93.0%) | 260 (88.1%) | 280 (79.8%) | | |
| | Model without adjustment[b] | | | | | | |
| Hazard Ratio (95% CI) | 0.17 (0.10, 0.27) | 0.28 (0.21, 0.37) | 0.31 (0.23, 0.42) | 0.54 (0.36, 0.81) | Reference | None | |
| p-value[c] | <.0001 | <.0001 | <.0001 | 0.0027 | Reference | | |
| | Model with adjustment[d] | | | | | | |
| Hazard Ratio (95% CI) | 0.25 (0.16, 0.41) | 0.41 (0.31, 0.55) | 0.43 (0.32, 0.59) | 0.66 (0.44, 0.99) | Reference | | |
| p-value[c] | <.0001 | <.0001 | <.0001 | 0.0452 | Reference | | |
| Age (>=65 years/<65 years) | | | | | | 0.69 (0.54, 0.89) | 0.0046 |
| Sex (Male/Female) | | | | | | 1.24 (1.01, 1.51) | 0.0367 |
| Diabetes (Yes/No) | | | | | | 1.68 (1.36, 2.06) | <.0001 |
| Cerebrovascular disease (Yes/No) | | | | | | 1.76 (1.35, 2.28) | <.0001 |
| Initial qualifying eGFR decreases of 1 (mL/min/1.73 m$^2$) | | | | | | 1.06 (1.04, 1.07) | <.0001 |

TABLE 700-continued

| | | |
|---|---|---|
| Baseline ACEi or ARB use | | 1.24 (1.01, 1.53) 0.0366 |

Note:
Events are counted when occurred >=365 days after the first recorded HCO3 value.
[a] Baseline serum bicarbonate was calculated as the average of measurements within 30 days of first measurement of HCO3 (between 10 and 40 mEq/L).
[b] Cox proportional hazard model stepwise selection for age (<65 or >=65), sex (Male or Female), hypertension (Yes, No), cerebrovascular disease (Yes, No), diabetes (Yes, No), initial qualifying eGFR value, and baseline ACEi/ARB use (Yes, No). The p-value for these covariates must be <0.3 to be included in the model.
[c] p-value is testing for the hazard ratio for eGFR deline >=40% in patients with a baseline SBC category over the reference category.
[d] Cox proportional hazard model stepwise selection for age (<65 or >=65), sex (Male or Female), hypertension (Yes, No), cerebrovascular disease (Yes, No), diabetes (Yes, No), initial qualifying eGFR value, baseline proteinuria (Moderate or Severe), baseline proteinuria (Servere), and baseline ACEi/ARB use (Yes, No). The p-value for these covariates must be <0.3 to be included in the model.
[e] The p-value is testing effect of covariates.

Conclusion

The subpopulations of patients that represent increases in serum bicarbonate of 2 to <4 mEq/L or 4 mEq/L in the acidotic (serum bicarbonate 12 to 20 mEq/L) population have a 40% and 61% reduced hazard of DD40, respectively. This result suggests that each 1 mEq/L increase of serum bicarbonate reduces hazard of DD40 by ~12 to 13%.

Example 5

Description and Analysis of Results from Clinical Trial

A double blind, randomized, placebo-controlled study that enrolled 217 subjects with Stage 3b or 4 CKD (an estimated glomerular filtration rate [eGFR] of 20 to 40 mL/min/1.73 m$^2$) and low blood bicarbonate levels (between 12 mEq/L and 20 mEq/L) was conducted. At the beginning of the 12-week treatment period, subjects were randomized in a 4:3 ratio to receive once-daily, or QD, a pharmaceutical composition according to the present invention, e.g., TRC101, or placebo. Subjects in the active group initially received a QD dose of 6 grams of TRC101 (2 sachets). After week 4, bi-directional blinded dose adjustments to 3 grams/day (1 sachet) or 9 grams/day (3 sachets) were allowed in order to maintain blood bicarbonate in the normal range. Subjects in the placebo group initially received 2 sachets of placebo, with the same ability for bi-directional dose adjustments after 4 weeks. The dose titration algorithm required down-titration at blood bicarbonate values of 27 to 30 mEq/L. Subjects with a blood bicarbonate level greater than 30 underwent an interruption of the study drug in accordance with the titration algorithm. Subjects were permitted to continue their existing oral alkali supplement during the trial, provided that dosing remained stable. The trial was conducted at 47 sites in the United States and Europe.

Eligible patients were aged 18 to 85 years and had systolic blood pressure <170 mmHg and hemoglobin A1c≤9%. During the up to 2-week Screening Period, three qualifying fasting serum bicarbonate values over 14 days were required to establish eligibility; the first two values and the average of all three were required to be within the range 12-20 mmol/L. Two qualifying eGFR values not different by >20% and in the range 20-40 mL/min/1.73 m$^2$ were required during screening. Patients were excluded if their serum bicarbonate level was low enough to need emergency intervention or evaluation for an acute acidotic process, or if in the 3 months prior to the first Screening Visit they had anuria, dialysis, or acute or chronic worsening renal function (e.g., 30% decline in eGFR). Patients with recent history of chronic obstructive pulmonary disease, heart failure with New York Heart Association Class IV symptoms, stroke, transient ischemic attack, cancer, cardiac event, diabetic gastroparesis, bariatric surgery, bowel obstruction, swallowing disorders, severe gastrointestinal disorders, or hospitalization other than for pre-planned diagnostic or minor invasive procedures, those who had a heart or kidney transplant, and those who planned initiation of renal replacement therapy within 12 weeks were also excluded. Eligible patients did not have liver enzyme levels >3 times the upper limit of normal, serum calcium levels mmol/L or serum potassium levels <3.8 mmol/L or >5.9 mmol/L. Concomitant medication requirements for study participation precluded use of any other investigational medication as well as other binder drugs (except for short-term use of potassium binders for treatment of hyperkalemia) and required stable doses (whenever possible) of the following if they were used: calcium-containing supplements; antacids; H2-blockers; proton pump inhibitors; oral alkali; diuretics; renin-angiotensin-aldosterone system inhibitors; and non-ophthalmic carbonic anhydrase inhibitors. Dosing of oral concomitant medications and study drug was separated by hours.

The starting study drug dose was 6 grams/day TRC101 (2 packets/day) or placebo (2 packets/day) administered orally as a suspension in water with lunch. The first dose was administered in the clinic on the day of randomisation, after which, patients self-administered the study drug for 12 weeks and recorded the dose in a diary, which was reviewed, together with used and unused study drug returned at each visit. Beginning at Week 4, the study drug dose was algorithmically titrated by the interactive response technology system in the range from 0-9 grams/day (or equivalent number of packets of placebo) to a target bicarbonate of 22-29 mmol/L based on the bicarbonate measurement at each visit. The dose was down-titrated if bicarbonate was high-normal (27-30 mmol/L) and interrupted if it was >30 mmol/L (Table 800).

TABLE 800

Dose Titration Algorithm

| Serum Bicarbonate (mmol/L) | Before Week 4 Visit | Week 4 through Week 11 |
|---|---|---|
| <12* | Evaluate for new acute acidotic process, contact Medical Monitor. Maintain dose pending discussion with Medical Monitor. | Evaluate for new acute acidotic process, contact Medical Monitor. Maintain dose pending discussion with Medical Monitor. |
| 12 to <22 | Maintain dose until next scheduled visit. | Increase the study drug dose by 1 packet/day (maximum dose is 3 packets/day). Only increase the dose if NO dose changes have been made during the previous 14 days. Retest serum bicarbonate at next scheduled visit. |
| 22 to <27 | Maintain dose until next scheduled visit. | |
| 27 to 30 | Decrease the study drug dose by 1 packet/day (minimum dose is 0 packets/day). Invite subject for a visit in approximately 1 week to retest serum bicarbonate. Only decrease the dose if NO dose changes have been made during the previous 14 days. | |
| >30* | Interrupt (hold) study drug. Invite subject for a visit in approximately 1 week to retest serum bicarbonate. If serum bicarbonate at that visit is: <27 mmol/L, restart study drug at a lower dose (1 packet/day less than before dose interruption). >27 mmol/L, continue to hold the dose and retest again in approximately 1 week. | |

*Serum bicarbonate value of <12 mmol/L or >30 mmol/L confirmed by a repeated measurement from a separate blood draw.

Comorbid conditions between treated and placebo subjects entering the trial were equally balanced and included: 97% with hypertension, 65% with type 2 diabetes, 44% with left ventricular hypertrophy, and 31% with congestive heart failure; during the three months prior to baseline, 12% of subjects had shortness of breath with exertion and 9% had recurrent or continuous signs/symptoms of edema or fluid overload. Nine percent of the total patient population in the trial reported the use of oral alkali therapy at baseline.

The blood bicarbonate levels of subjects were measured on day 1, week 1, week 2, and bi-weekly thereafter, up to and including week 14 (see, e.g., FIG. 18). The primary efficacy endpoint of the trial was an increase in blood bicarbonate level of at least 4 mEq/L or achieving a blood bicarbonate level in the normal range of 22 to 29 mEq/L at the end of the 12-week treatment period. The secondary efficacy endpoint of the trial was the change from baseline in blood bicarbonate at the end of treatment.

The study was conducted according to the principles of the Declaration of Helsinki and according to Good Clinical Practice guidelines. The study protocol was approved by each site's relevant institutional review board or ethics committee and appropriate competent authorities in accordance with applicable laws and regulations. Prior to enrollment, all patients provided written informed consent. An unblinded, independent Data Monitoring Committee performed scheduled reviews of safety data during the study.

Procedures

During the Screening Period, the Screening 1 and Screening 2 Visits were ≥5 days apart, and Screening 1 and Baseline Visits were 1.4 days apart. Following randomisation, patients attended scheduled visits at Weeks 1, 2, 4, 6, 8, 10, and 12 during which serum bicarbonate was measured using an i-STAT® Handheld Blood Analyzer (Abbott Point of Care) and safety assessments were conducted (FIG. 18: eGFR, estimated glomerular filtration rate; n, number of patients in each treatment group; QD, once daily; R, randomization; W, week).

Patients fasted for hours (other than water) prior to measurements of bicarbonate levels to reduce the indirect effect of food-induced secretion of bicarbonate into the bloodstream. Venous blood for bicarbonate measurement was drawn into a 2 mL lithium heparin tube and transferred with a mini-pipette as soon as possible (within 10 minutes) into an i-STAT G3+ cartridge for assessment of bicarbonate with the i-STAT device. Tubes were capped until blood was transferred into the cartridge, and strict adherence to blood drawing and transfer techniques were required. The i-STAT devices were calibrated prior to and during the study according to the manufacturer's recommendations. The Kidney Disease and Quality of Life (KDQOL) Short Form-36, Question 3 (Physical Functioning Domain) (FIG. 21) and standardized repeated chair stand test (FIGS. 22A & 22B) were administered at baseline and Week 12. The KDQOL was forward and backwards translated, linguistically validated, culturally adapted, reviewed by clinicians, and cognitively debriefed in CKD patients. Following completion of study treatment at Week 12, patients either rolled over into a 40-week extension study or underwent two follow-up visits (Week 13 and Week 14) after the last dose of study drug.

Serum Bicarbonate

A total of 71 of 120 (59%) TRC101-treated patients and 20 of 89 (22%) placebo-treated patients met the primary endpoint responder definition (p<0.0001 for the comparison), with a treatment difference (TRC101—placebo) of 37% (95% CI, 23%-49%). A similar placebo-subtracted treatment difference was observed for each of the two components of the primary endpoint. Compared with the placebo group, a higher percentage of patients in the TRC101 group had increases in serum bicarbonate at all pre-defined thresholds (≥2 through ≥7 mmol/L).

The serum bicarbonate curves for the TRC101 and placebo groups separated over time starting at Treatment Week 1 and maintained separation through the end of treatment (FIG. 19C). At Week 12, the mean change from baseline in the TRC101 and placebo groups was 4.5 (95% CI, 3.9 to 5.1) mmol/L and 1.7 (95% CI, 1.0 to 2.3) mmol/L, respectively (p<0.0001). The LS mean (SEM) change from baseline to Week 12, the secondary endpoint, was 4.4 (3.5) mmol/L and 1.8 (3.1) mmol/L in the TRC101 and placebo groups, respectively (p<0.0001). (FIGS. 19A-C: Change in Serum Bicarbonate—FIG. 19A: The composite primary endpoint, the placebo-subtracted percentage of patients achieving a ≥4 mmol/L increase from baseline in serum bicarbonate or a serum bicarbonate in the normal range (22-29 mmol/L) at Treatment Week 12 (37%, 95% CI: 23%, 49%), is depicted as the top line. The two lower lines depict each component of the primary endpoint. The individual primary endpoint component analyses were pre-specified but were not adjusted for multiple comparisons. P-values are for the difference in proportions between TRC101 and placebo groups (Fisher's exact test). FIG. 19B: The percentage of patients in the TRC101 (circles) and placebo (squares) groups whose serum bicarbonate level increased from baseline to Week 12 by pre-specified thresholds. Achieving a ≥4 mmol/L increase was a component of the primary endpoint. FIG. 19C: The baseline bicarbonate (Treatment Week 0), the mean of the Screening 1, Screening 2, and Baseline Day 1 values, was 17.3 mmol/L in both treatment groups. Values depicted are the means (±95% CI) change from baseline in serum bicarbonate (mmol/L). At Week 12, the mean serum bicarbonate increase was 4.5 (95% CI, 3.9 to 5.1) mmol/L in the TRC101 group (circles) vs. 1.7 (95% CI, 1.0 to 2.3) mmol/L in the placebo group (squares).

Results from post-hoc analyses using a rank-based model were consistent with those from the pre-specified MMRM model (p<0.0001 for treatment effect).

Other than in subgroups with <8 patients, the lower-bound of the 95% confidence interval for the treatment difference exceeded 0 within all pre-specified subgroups, including age, gender, geographical region, baseline bicarbonate, screening eGFR, and baseline alkali use. Other than in subgroups with <8 patients, the lower-bound of the 95% confidence interval for the treatment difference exceeded 0 within all pre-specified subgroups, including age, gender, geographical region, baseline alkali use, baseline bicarbonate and screening eGFR. P-values for the interaction between treatment and each subgroup were obtained from logistic regression models, where treatment, subgroup, and interaction of treatment×subgroup were included as predictors. However, these should be interpreted with caution given the post-hoc nature of the analysis and multiple comparisons.)

Physical Functioning

Metabolic acidosis has been implicated as an important factor contributing to reduced muscle mass, manifested in decreases in lean body mass and muscle strength as well as increased protein catabolic rate. Prior to a measurable decrease in blood bicarbonate, the body adapts, in part, to the increasing acid load by using intracellular buffers in muscle (primarily proteins and organic phosphates).

The two exploratory endpoints in this study were included to assess whether improvement in muscle function and patient quality of life could be demonstrated in the patient population through the treatment of metabolic acidosis. The first exploratory endpoint examined the effect of treatment with TRC101 on self-reported responses to the physical functioning subpart of the Kidney Disease and Quality of Life Short Form, or the KDQOL-SF, survey. The KDQOL-SF survey is a validated questionnaire designed to assess health-related quality of life, or HRQOL, in kidney disease patients. Subjects in the trial responded to 10 questions related to physical function during daily activities, or KDQOL-SF Physical Function Survey (Question 3) (see, e.g., FIG. 21). The score conversion for the Survey is as follows: 1 (limited a lot)=0; 2 (limited a little)=50; 3 (not limited)=100. Total score=sum of all 10, divided by 10. The second exploratory endpoint objectively measured physical function derived from a repeated chair stand test, or Repeated Chair Stand Test. In the Repeated Chair Stand Test, subjects were asked to fold their arms across their chests and to stand up from a sitting position once; if they successfully rose from the chair, they were asked to stand up and sit down five times as quickly as possible, and the time for these five repetitions was recorded (see, e.g., FIG. 22). The KDQOL-SF Physical Function Survey and Repeated Chair Stand Test were administered and scored in a blinded fashion, and a change in Physical Function Survey score and Repeated Chair Stand Test time from baseline at week 12 were pre-defined as exploratory endpoints.

At the end of 12 weeks of treatment, physical functioning, as measured by the KDQOL Physical Function Domain, which quantifies patients' self-reported degree of limitation in performing daily activities such as climbing stairs and walking (FIG. 21), increased significantly in TRC101-treated patients compared to placebo-treated patients (p=0.0122) (FIG. 20A). The LS mean (95% CI) change within the TRC101 group (6.3 [3.7, 8.9]) and the placebo-subtracted treatment effect (5.2 [1.1, 9.2]) both exceeded the minimal clinically important difference in KDQOL subscales as reported in the literature (Clement, F M et al., 2009, The Impact of Selecting a High Hemoglobin Target Level on Health-Related Quality of Life for Patients with Chronic Kidney Disease: A Systematic Review and Meta-Analysis, Arch. Intern. Med. 169 (12):

1104-1112; Collister, D et al., 2016, The Effect of Erythropoietin-Stimulating Agents on Health-Related Quality of Lide in Anemia of Chronic Kidney Disease: A Systematic Review and Meta-Analysis, Ann. Intern. Med. 164(7): 472-478; Leaf, D E et al., 2009, Interpretation and Review of Health-Related Quality of Life Data in CKD Patients Receiving Treatment for Anemia, Kidney Int. 75(1): 15-24; Samsa, G et al., Determining Clinically Important Differences in Health Status Measures: A General Approach with Illustration to the Health Utilities Index Mark II, Pharmacoeconomics, 15(2): 141-155). Physical function, as measured by the repeated chair stand test, numerically improved in the TRC101 group (p=0.0249) and numerically worsened (p=0.5727) in the placebo group: on average (LS mean [95% CI]), the chair stand time increased by 0.35 (−0.9, 1.6) seconds in the placebo group and declined by 1.17 (0.2, 2.2) seconds in the TRC101 group (FIG. 20B). The between-group difference was not statistically significant (p=0.0630). (FIGS. 20A-20B—Changes in Physical Functioning.) (FIG. 20A: Patients reported how limited they were on the 10 items of the Physical Functioning Domain of the Kidney Disease and Quality of Life (KDQOL) at Baseline and at Treatment Week 12 (see FIG. 21). The least squares mean and 95% Cl⁻ of the change from baseline to Week 12 in total score is presented for each group. The range for the minimal clinically important differences reported for the KDQOL subscales is 3-5 points.) (FIG. 20B: Patients were timed on the speed with which they could repeatedly stand from a chair five times at baseline and at Treatment Week 12. Least squares mean and 95% Cl⁻ of the change from baseline to Week 12 in the time to perform the repeated chair stand test is presented for each group. Not all patients were able to perform the test. Data are presented for patients who performed the test at both baseline and Week 12. (TRC101, n=109; Placebo, n=76).)

Post-hoc rank-based analyses of physical function showed consistent results for patient-reported physical function (p=0.0117) and a stronger association for the between-group difference in the time to complete the repeated chair stand test (p=00027), both favoring TRC101.

Safety

TRC101 was well-tolerated. In total, over 95% of subjects in each of the groups completed the trial. Overall treatment-related adverse events occurred in 9.7% of subjects in the placebo group and 13.7% of TRC101-treated subjects. The most common treatment-related adverse events were mild to moderate GI disorders, which occurred in 5.4% of subjects in the placebo group and 12.9% of TRC101-treated subjects. The GI adverse events that occurred in more than one subject in the trial included diarrhea, flatulence, nausea and constipation. The only other treatment-related adverse event that occurred in more than one subject was paresthesia (1.1% of subjects in the placebo group and 0.8% of TRC101-treated subjects). There were no apparent effects of TRC101 on serum parameters, such as sodium, calcium, potassium, phosphate, magnesium, or low-density lipoprotein observed in the trial that would indicate off-target effects of TRC101. A high blood bicarbonate level, defined as greater than 30 mEq/L, was observed transiently in 2 subjects, or 0.9%. Discontinuation of TRC101 per the protocol-defined dosing algorithm resulted in normalization of blood bicarbonate in these subjects.

There were no apparent effects of TRC101 on vital signs, ECG intervals, renal function, hematology parameters, liver function tests, lipids, or urinalyses (Table 806).

TABLE 806

Change from Baseline in Laboratory Parameters and Blood Pressure after 12 Weeks of Treatment

|  | Placebo (N = 93) | TRC101 (N = 124) |
|---|---|---|
| Blood urea nitrogen - mmol/L | | |
| no. | 89 | 120 |
| Mean (SD) | 0.65 (3.96) | −0.05 (4.02) |
| Median (IQR) | 0.36 (3.21) | 0.00 (3.75) |
| Serum creatinine - μmol/L | | |
| no. | 89 | 120 |
| Mean (SD) | 13.3 (49.4) | 11.1 (44.9) |
| Median (IQR) | 6.2 (37.1) | 6.6 (40.2) |
| Serum sodium - mmol/L | | |
| no. | 89 | 120 |
| Mean (SD) | 0.0 (2.9) | 0.3 (2.9) |
| Median (IQR) | 0.0 (4.0) | 0.5 (3.0) |
| Serum potassium - mmol/L | | |
| no. | 89 | 118 |
| Mean (SD) | 0.05 (0.63) | 0.03 (0.60) |
| Median (IQR) | 0.00 (0.80) | 0.00 (0.80) |
| Serum chloride - mmol/L | | |
| no. | 89 | 120 |
| Mean (SD) | −0.1 (3.4) | −0.2 (3.3) |
| Median (IQR) | 0.0 (4.0) | 0.0 (5.0) |
| Serum calcium - mmol/L | | |
| no. | 89 | 120 |
| Mean (SD) | −0.02 (0.13) | −0.02 (0.12) |
| Median (IQR) | −0.03 (0.13) | −0.01 (0.15) |
| Serum phosphate - mmol/L | | |
| no. | 89 | 120 |
| Mean (SD) | 0.03 (0.22) | 0.02 (0.19) |
| Median (IQR) | 0.03 (0.23) | 0.03 (0.19) |
| Serum magnesium - mmol/L | | |
| no. | 89 | 120 |
| Mean (SD) | 0.02 (0.09) | 0.02 (0.09) |
| Median (IQR) | 0.04 (0.12) | 0.00 (0.12) |
| Estimated glomerular filtration rate - mL/min/1.73 m² | | |
| no. | 89 | 120 |
| Mean (SD) | −0.8 (5.1) | −0.8 (6.0) |
| Median (IQR) | −1.0 (6.0) | −1.0 (5.0) |
| Venous blood pH | | |
| no. | 89 | 120 |
| Mean (SD) | 0.03 (0.12) | 0.05 (0.10) |
| Median (IQR) | 0.03 (0.10) | 0.05 (0.11) |
| Venous blood base excess - mmol/L | | |
| no. | 89 | 120 |
| Mean (SD) | 2.1 (4.2) | 5.3 (4.3) |
| Median (IQR) | 2.0 (6.0) | 5.0 (7.0) |
| Cholesterol (total) - mmol/L | | |
| no. | 89 | 120 |
| Mean (SD) | −0.16 (0.93) | 0.05 (0.99) |
| Median (IQR) | −0.08 (0.88) | 0.03 (1.03) |

TABLE 806-continued

Change from Baseline in Laboratory Parameters and Blood Pressure after 12 Weeks of Treatment

| | Placebo (N = 93) | TRC101 (N = 124) |
|---|---|---|
| Low-density lipoprotein cholesterol-mmol/L | | |
| no. | 87 | 115 |
| Mean (SD) | −0.06 (0.81) | 0.02 (0.84) |
| Median (IQR) | −0.05 (0.85) | −0.03 (0.93) |
| High-density lipoprotein cholesterol -mmol/L | | |
| no. | 89 | 120 |
| Mean (SD) | 0.02 (0.29) | 0.04 (0.34) |
| Median (IQR) | 0.03 (0.28) | 0.08 (0.25) |
| Systolic blood pressure- mmHg | | |
| no. | 89 | 120 |
| Mean (SD) | −1.1 (8.7) | −2.4 (7.6) |
| Median (IQR) | −1.0 (6.0) | −2.0 (7.5) |
| Diastolic blood pressure- mmHg | | |
| no. | 89 | 120 |
| Mean (SD) | −1.4 (7.4) | −1.5 (6.6) |
| Median (IQR) | −1.0 (7.0) | −1.0 (8.5) |

A high (>30 mmol/L) serum bicarbonate level was observed transiently in two patients but normalized following interruption of study drug per the protocol titration algorithm. There were no apparent effects on serum electrolytes that would indicate off-target effects of TRC101 (Table 806). The incidence of serum potassium ≥5.0 or ≥6.0 mmol/L (Table 807), and mean serum potassium over time, were similar in both groups.

TABLE 807

Proportion of Patients with Serum Potassium Exceeding Predefined Thresholds

| | Placebo (N = 93) | TRC101 (N = 124) |
|---|---|---|
| Baseline | | |
| no. | 92 | 124 |
| >5 mmol/L - no. (%) | 31 (34) | 41 (33) |
| >6 mmol/L - no. (%) | 2 (2) | 4 (3) |
| Week 1 | | |
| no. | 88 | 117 |
| >5 mmol/L - no. (%) | 39 (44) | 51 (44) |
| >6 mmol/L - no. (%) | 7 (8) | 5 (4) |
| Week 2 | | |
| no. | 87 | 115 |
| >5 mmol/L - no. (%) | 39 (45) | 46 (40) |
| >6 mmol/L - no. (%) | 3 (3) | 2 (2) |
| Week 4 | | |
| no. | 87 | 118 |
| >5 mmol/L - no. (%) | 46 (53) | 53 (45) |
| >6 mmol/L - no. (%) | 5 (6) | 7 (6) |
| Week 6 | | |
| no. | 91 | 120 |
| >5 mmol/L - no. (%) | 46 (51) | 52 (43) |
| >6 mmol/L - no. (%) | 6 (7) | 8 (7) |
| Week 8 | | |
| no. | 89 | 119 |
| >5 mmol/L - no. (%) | 40 (45) | 54 (45) |
| >6 mmol/L - no. (%) | 6 (7) | 8 (7) |

TABLE 807-continued

Proportion of Patients with Serum Potassium Exceeding Predefined Thresholds

| | Placebo (N = 93) | TRC101 (N = 124) |
|---|---|---|
| Week 10 | | |
| no. | 87 | 119 |
| >5 mmol/L - no. (%) | 40 (46) | 45 (38) |
| >6 mmol/L - no. (%) | 2 (2) | 7 (6) |
| Week 12 | | |
| no. | 89 | 118 |
| >5 mmol/L - no. (%) | 38 (43) | 43 (36) |
| >6 mmol/L - no. (%) | 5 (6) | 5 (4) |

Discussion

In non-dialysis-dependent patients with CKD and chronic metabolic acidosis (mean serum bicarbonate 17.3 mmol/L), 12 weeks of treatment with TRC101 significantly increased serum bicarbonate, with 50% of patients achieving normalization, 56% achieving a mmol/L increase, and 59% meeting the composite primary endpoint definition. The mean increase in serum bicarbonate at Week 12 in the TRC101 group was 4.5 mmol/L, and 39% and 26% of TRC101-treated patients had an increase in serum bicarbonate and mmol/L, respectively. The effect of TRC101 on serum bicarbonate was both rapid and sustained over 12 weeks in these outpatients whose dietary protein intake was not governed by the study protocol.

Accumulation of metabolically produced acid stimulates increases kidney production of endothelin, angiotensin II and aldosterone, substances that provide the short-term benefit of enhancing renal tubule acid excretion but are detrimental in the long term by promoting inflammation and fibrosis in the kidney interstitium that contributes to a progressive decline of kidney function. Similarly, in response to acid retention the kidney increases ammonia production per functioning nephron to facilitate acid excretion; however, the increased ammonia levels promote inflammation and activation of complement that also contributes to kidney fibrosis.

Metabolic acidosis in patients with CKD has traditionally been treated with sodium-based alkali supplements (sodium bicarbonate, sodium citrate) that enter the systemic circulation and neutralize accumulated acid. Potassium-based alkali therapies (e.g., potassium bicarbonate) are rarely used in patients with CKD because of the risk of life-threatening hyperkalemia. Alternative treatments for metabolic acidosis include vegetarian diets, but these limit patient choice and have low long-term adherence. An alternative treatment would remove, rather than neutralize, acid, without administering a sodium or potassium load. Removal of acid by binding to a non-absorbed polymer that is then excreted is a potential new mechanism for treating metabolic acidosis in patients with CKD.

The study described in this Example demonstrates that TRC101, a non-absorbed, counterion-free, polymeric drug that selectively binds and removes hydrochloric acid from the gastrointestinal tract, thus increasing systemic bicarbonate concentration, is effective in treating metabolic acidosis. These findings demonstrate that the effect of TRC101 on serum bicarbonate reaches a plateau after 4 to 8 weeks of treatment and the effect is sustained over 12 weeks in an outpatient CKD population eating a free choice diet.

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes can be made by those skilled in the art without departing from the spirit of this disclosure. Those skilled in the art will appreciate that the inventive principles can be practiced in other than the described embodiments, which are presented for purposes of illustration and not limitation.

The invention claimed is:

1. A method of treating a patient with chronic kidney disease and eubicarbonatemic metabolic acidosis, wherein the patient has a serum bicarbonate value of at least 22 mEq/l prior to the treatment, wherein the method comprises oral administration to the patient in need thereof of a proton-binding crosslinked amine polymer comprising the residue of an amine corresponding to Formula 2 or a salt thereof

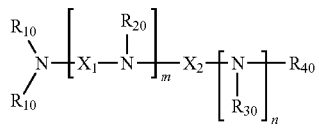

Formula 2 wherein
m and n are independently non-negative integers;
$R_{10}$, $R_{20}$, $R_{30}$, and $R_{40}$ are independently hydrogen, hydrocarbyl, or substituted hydrocarbyl;
$X_1$ is

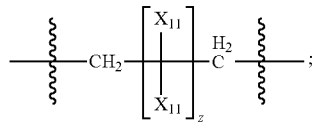

$X_2$ is hydrocarbyl or substituted hydrocarbyl;
each $X_{11}$ is independently hydrogen, hydrocarbyl, substituted hydrocarbyl, hydroxy, or amino;
z is a non-negative number,
the crosslinked amine polymer has an equilibrium swelling ratio in deionized water of 2 or less; and
the crosslinked amine polymer binds a molar ratio of chloride ions to interfering ions of at least 0.35:1, respectively, in an interfering ion buffer at 37° C. wherein the interfering ions are phosphate ions and the interfering ion buffer is a buffered solution at pH 5.5 of 36 mM chloride and 20 mM phosphate.

2. The method of claim 1 wherein the proton-binding crosslinked amine polymer has an equilibrium swelling ratio in deionized water of 1.5 or less.

3. The method of claim 1 wherein the patient is afflicted with eubicarbonatemic metabolic acidosis characterized by a marker of eubicarbonatemic metabolic acidosis selected from the group consisting of urine citrate excretion, urine ammonium excretion, net acid excretion, plasma Endothelin 1, urine Endothelin 1, and plasma aldosterone.

4. The method of claim 1 wherein the method comprises administering a dose of 1-11 grams of said proton-binding crosslinked amine polymer to the patient per day.

5. The method of claim 1 wherein the proton-binding crosslinked amine polymer is a crosslinked aliphatic amine polymer that has been synthesized by first copolymerizing allylamine hydrochloride and N,N'-diallyl-1,3-diaminopropane dihydrochloride to form a copolymer, followed by crosslinking the copolymer with 1,2-dichloroethane.

6. The method of claim 5 wherein the method comprises administering a dose of 1-11 grams of said proton-binding crosslinked amine polymer to the patient per day.

7. The method of claim 6 wherein the proton-binding crosslinked amine polymer has an equilibrium swelling ratio in deionized water of 1.5 or less.

* * * * *